(12) United States Patent
Thorpe et al.

(10) Patent No.: US 7,691,380 B2
(45) Date of Patent: *Apr. 6, 2010

(54) COMBINED METHODS FOR TUMOR COAGULATION AND TUMOR TREATMENT

(75) Inventors: Philip E. Thorpe, Cape Elizabeth, ME (US); Thomas S. Edgington, La Jolla, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 2047 days.

This patent is subject to a terminal disclaimer.

(21) Appl. No.: 10/375,716

(22) Filed: Feb. 27, 2003

(65) Prior Publication Data

US 2003/0219441 A1 Nov. 27, 2003

Related U.S. Application Data

(63) Continuation of application No. 09/483,679, filed on Jan. 14, 2000, now Pat. No. 6,749,853, which is a continuation of application No. 08/482,369, filed on Jun. 7, 1995, now Pat. No. 6,093,399, which is a continuation-in-part of application No. 08/273,567, filed on Jul. 11, 1994, now abandoned, which is a continuation-in-part of application No. 08/205,330, filed on Mar. 2, 1994, now Pat. No. 5,855,866, which is a continuation-in-part of application No. 07/846,349, filed on Mar. 5, 1992, now abandoned.

(51) Int. Cl.
*A61K 39/395* (2006.01)
*C12P 21/08* (2006.01)

(52) U.S. Cl. ................... 424/155.1; 530/388.8
(58) Field of Classification Search .............. 424/155.1; 530/388.8
See application file for complete search history.

(56) References Cited

U.S. PATENT DOCUMENTS

| 4,456,550 A | 6/1984 | Dvorak et al. ............ 260/112 R |
| 4,472,509 A | 9/1984 | Gansow et al. |
| 4,536,387 A | 8/1985 | Sakamoto et al. .............. 424/14 |
| 4,785,077 A | 11/1988 | Kornbluth et al. ............ 530/351 |
| 4,837,003 A | 6/1989 | Nicolotti .................... 424/1.53 |
| 4,925,922 A | 5/1990 | Byers et al. ................. 530/391 |
| 4,926,869 A | 5/1990 | Rubin et al. ................. 128/654 |
| 4,958,009 A | 9/1990 | Bjorn et al. .................. 530/389 |
| 4,975,369 A | 12/1990 | Beavers et al. ............. 435/69.1 |
| 4,980,457 A | 12/1990 | Jansen et al. ................ 530/391 |
| 4,981,953 A | 1/1991 | Barbieri et al. ............. 530/391 |
| 5,017,556 A | 5/1991 | O'Brien et al. ................. 514/2 |
| 5,021,236 A | 6/1991 | Gries et al. |
| 5,024,834 A | 6/1991 | Houston et al. ........... 424/85.91 |
| 5,057,313 A | 10/1991 | Shih et al. ................. 424/85.91 |
| 5,081,034 A | 1/1992 | Bevilacqua et al. |
| 5,110,730 A | 5/1992 | Edgington et al. ......... 435/69.6 |
| 5,147,638 A | 9/1992 | Esmon et al. ............... 424/85.8 |
| 5,183,756 A | 2/1993 | Schlom ................. 435/240.27 |
| 5,191,067 A | 3/1993 | Lappi et al. ................. 530/399 |
| 5,202,253 A | 4/1993 | Esmon et al. .......... 435/240.27 |
| 5,223,427 A | 6/1993 | Edgington et al. ..... 435/240.27 |
| 5,242,813 A | 9/1993 | Pastan et al. .............. 435/70.21 |
| 5,298,599 A | 3/1994 | Rezaie et al. ................ 530/350 |
| 5,308,622 A | 5/1994 | Casscells et al. ............ 424/422 |
| 5,314,695 A | 5/1994 | Brown ........................ 424/450 |
| 5,342,757 A | 8/1994 | Garin-Chesa et al. ....... 435/7.21 |
| 5,346,991 A | 9/1994 | Roy et al. .................... 530/350 |
| 5,354,778 A | 10/1994 | Ray et al. .................... 514/592 |
| 5,374,617 A | 12/1994 | Morrissey et al. .............. 514/8 |
| 5,399,346 A | 3/1995 | Anderson et al. ........ 424/93.21 |
| 5,403,713 A | 4/1995 | Bevilacqua et al. .......... 435/7.1 |
| 5,437,864 A | 8/1995 | Edgington et al. ........ 424/145.1 |
| 5,504,064 A | 4/1996 | Morrissey et al. .............. 514/8 |
| 5,504,067 A | 4/1996 | Morrissey et al. .............. 514/8 |
| 5,576,288 A | 11/1996 | Lappi et al. ..................... 514/2 |
| 5,587,297 A | 12/1996 | Jacobson et al. .............. 435/29 |
| 5,589,173 A | 12/1996 | O'Brien et al. ........... 424/145.1 |
| 5,589,363 A | 12/1996 | Roy et al. ................... 435/69.6 |
| 5,632,991 A | 5/1997 | Gimbrone, Jr. ........... 424/178.1 |
| 5,658,570 A | 8/1997 | Newman et al. ............. 424/184 |
| 5,659,013 A | 8/1997 | Senger et al. ................ 530/350 |
| 5,679,637 A | 10/1997 | Lappi et al. ..................... 514/2 |
| 5,719,120 A | 2/1998 | Letarte et al. ................... 514/2 |
| 5,725,856 A | 3/1998 | Hudziak et al. ........... 424/130.1 |
| 5,726,147 A | 3/1998 | Ruf et al. ........................ 514/2 |
| 5,739,101 A | 4/1998 | Roy et al. ....................... 514/2 |
| 5,741,658 A | 4/1998 | Morrissey ..................... 435/23 |
| 5,750,358 A | 5/1998 | Morrissey ..................... 435/13 |
| 5,830,448 A | 11/1998 | Vehar ........................ 424/85.2 |
| 5,830,847 A | 11/1998 | Letarte et al. .................. 514/2 |
| 5,866,127 A | 2/1999 | Senger et al. ............. 424/178.1 |
| 5,869,045 A | 2/1999 | Hellstrom et al. ........ 424/130.1 |
| 5,877,289 A | 3/1999 | Thorpe et al. ............. 530/387.1 |
| 5,922,688 A | 7/1999 | Hung et al. .................... 514/44 |
| 5,928,641 A | 7/1999 | Seon ........................ 424/130.1 |
| 5,942,602 A | 8/1999 | Wels et al. ............... 530/388.22 |
| 6,001,978 A | 12/1999 | Edgington et al. ........ 530/391.3 |
| 6,004,555 A * | 12/1999 | Thorpe et al. ............. 424/181.1 |
| 6,015,693 A | 1/2000 | Letarte et al. .............. 435/69.1 |
| 6,022,541 A | 2/2000 | Senger et al. ............. 424/172.1 |

(Continued)

FOREIGN PATENT DOCUMENTS

EP 0 255 424 A1 2/1988

(Continued)

OTHER PUBLICATIONS

Jain (Scientific American Jul. 1994).*

(Continued)

*Primary Examiner*—David J. Blanchard
*Assistant Examiner*—Lynn Bristol
(74) *Attorney, Agent, or Firm*—Shelley P. M. Fussey

(57) ABSTRACT

Disclosed are various compositions and methods for use in achieving specific blood coagulation. This is exemplified by the specific in vivo coagulation of tumor vasculature, causing tumor regression, through the site-specific delivery of a coagulant using a bispecific antibody.

69 Claims, 8 Drawing Sheets

U.S. PATENT DOCUMENTS

| | | | | |
|---|---|---|---|---|
| 6,036,955 | A | 3/2000 | Thorpe et al. | 424/136.1 |
| 6,037,329 | A | 3/2000 | Baird et al. | 514/44 |
| 6,093,399 | A | 7/2000 | Thorpe et al. | 424/182 |
| 6,107,090 | A | 8/2000 | Bander | 435/344 |
| 6,129,915 | A | 10/2000 | Wels et al. | 424/143.1 |
| 6,136,311 | A | 10/2000 | Bander | 424/155.1 |
| 6,150,508 | A | 11/2000 | Murphy et al. | 530/387.1 |
| 6,180,370 | B1 | 1/2001 | Queen et al. | 435/69.6 |
| 6,190,660 | B1 | 2/2001 | Seon | 424/130.1 |
| 6,200,566 | B1 | 3/2001 | Seon | 424/130.1 |
| 6,261,535 | B1 | 7/2001 | Thorpe et al. | 424/1.49 |
| 6,303,596 | B1 | 10/2001 | Morrissey et al. | 514/222.5 |
| 6,582,959 | B2 | 6/2003 | Kim | 435/346 |
| 6,749,853 | B1 | 6/2004 | Thorpe et al. | 424/182.1 |
| 6,824,780 | B1 | 11/2004 | Devaux et al. | 424/156.1 |
| 7,112,317 | B2 * | 9/2006 | Thorpe et al. | 424/1.49 |
| 7,125,541 | B2 * | 10/2006 | Thorpe et al. | 424/1.49 |
| 2002/0001566 | A1 | 1/2002 | Rajopadhye et al. | 424/1.69 |
| 2002/0098187 | A1 | 7/2002 | Ferrara et al. | 424/145.1 |
| 2003/0086919 | A1 | 5/2003 | Rosenblum et al. | 424/94.63 |
| 2003/0129223 | A1 | 7/2003 | Wartchow et al. | 424/450 |
| 2003/0133972 | A1 | 7/2003 | Danthi et al. | 424/450 |
| 2003/0180305 | A1 | 9/2003 | Rajopadhye et al. | 424/178.1 |
| 2003/0190317 | A1 | 10/2003 | Baca et al. | 424/142.1 |
| 2003/0194400 | A1 | 10/2003 | Liu et al. | 424/94.64 |
| 2003/0203409 | A1 | 10/2003 | Kim | 435/7.1 |
| 2003/0206899 | A1 | 11/2003 | Ferrara et al. | 424/133.1 |
| 2004/0013640 | A1 | 1/2004 | Zardi et al. | 424/85.1 |
| 2005/0281821 | A1 | 12/2005 | Pernasetti et al. | 424/145.1 |
| 2005/0287145 | A1 * | 12/2005 | Stewart et al. | 424/146.1 |
| 2006/0057146 | A1 | 3/2006 | Borsi et al. | 424/155.1 |

FOREIGN PATENT DOCUMENTS

| | | |
|---|---|---|
| EP | 0 260 148 | 3/1988 |
| EP | 0 266 993 | 5/1988 |
| EP | 0 458 878 | 9/1996 |
| EP | 0 484 401 B1 | 9/1996 |
| EP | 0 278 776 | 5/1997 |
| EP | 0 938 505 B1 | 3/2002 |
| WO | WO 81/01145 | 4/1981 |
| WO | WO 88/07543 | 10/1988 |
| WO | WO 90/03801 | 4/1990 |
| WO | WO 90/05539 | 5/1990 |
| WO | WO 90/12585 | 11/1990 |
| WO | WO 90/13300 | 11/1990 |
| WO | WO 90/13649 | 11/1990 |
| WO | WO 91/02058 | 2/1991 |
| WO | WO 91/05806 | 5/1991 |
| WO | WO 91/07941 | 6/1991 |
| WO | WO 92/01470 | 2/1992 |
| WO | WO 92/12729 | 8/1992 |
| WO | WO 92/14748 | 9/1992 |
| WO | WO 92/16558 | 10/1992 |
| WO | WO 92/19646 | 11/1992 |
| WO | WO 93/08210 | 4/1993 |
| WO | WO 93/08473 | 4/1993 |
| WO | WO 93/09803 | 5/1993 |
| WO | WO 93/17715 | 9/1993 |
| WO | WO 93/23074 | 11/1993 |
| WO | WO 94/05328 | 3/1994 |
| WO | WO 94/07515 | 4/1994 |
| WO | WO 94/10202 | 5/1994 |
| WO | WO 94/11499 | 5/1994 |
| WO | WO 94/28017 | 12/1994 |
| WO | WO 95/21868 | 8/1995 |
| WO | WO 96/01653 | 1/1996 |
| WO | WO 97/45544 | 12/1997 |
| WO | WO 99/58570 | 11/1999 |
| WO | WO/US00/34337 | 6/2000 |
| WO | WO 01/54723 A1 | 8/2001 |
| WO | WO 03/033514 A1 | 4/2003 |
| WO | WO 03/035688 A2 | 5/2003 |

OTHER PUBLICATIONS

Chatterjee et al (Cancer Immunol. Imunother., 1994).*
Dermer (Biotechnology 12: 320, 1994).*
Gura et al (Science vol. 278 Nov. 1997 1041-1042).*
Seaver (1994; Genetic Engineering vol. 14(14):pp. 10 and 21.*
Molema et al (J. Controlled Release 64:229-239 (2000)).*
Hagemeier et al. (Int. J. Canc. 38:481-488 (1986).*
Morrissey et al. (Thrombosis Research 52:247-261 (1988).*
Songsivilai et al. (Clin. Exp. Immunol. 79:315-321 (1990).*
Songsivilai et al. (Biochem. Biophys. Res. Comm 164:271-276 (1989).*
Wessels (Cancer Research 50(3 suppl):970s-973s (1990).*
Protein sequence search result for SEQ ID No. 23 (result 1).*
Spicer et al (PNAS, USA 84:5148-5152 (1987)).*
Wright (Critical reviews in Immunol. 125-168 (1992).*
Muller et al. (Biochemistry 33:10864-10870 (1994).*
Burgess et al. J. Cell Biol. 111:2129-2138 (1990).*
Lazar et al. Molec. and Cell. Biol. 8:1247-1252 (1988).*
Schwartz et al. Proc. Nat'l. Acad. Sci. USA 84:6408-6411 (1987).*
Lin et al. Biochem. 14:1559-1563 (1975).*
Imbragimova and Wade Biophys. J. 77:2191-2198 (1999).*
Nethersell (Ann Acad Med Singapore 19(2):223-34 (1990) (Abstract only).*
Webb et al. (Cancer Immunol. Immunother. 21:100-106 (1986).*
Osborn et al., "Leukocyte Adhesion to Endothelium in Inflammation," *Cell*, 62:3-6, 1990.
June et al., "Role of the CD28 Receptor in T-Cell Activation," *Immunology Today*, 11(6):211-216, 1990.
Denekamp, "Vascular Attack as a Therapeutic Strategy for Cancer," *Cancer and Metastasis Reviews*, 9:267-282, 1990.
Scott et al., "Anti-CD3 Antibody Induces Rapid Expression of Cytokine Genes In Vivo," *The Journal of Immunology*, 145(7):2183-2188, 1990.
O'Connell and Edidin, "A Mouse Lymphoid Endothelial Cell Line Immortalized by Simian Virus 40 Binds Lymphocytes and Retains Functional Characteristics of Normal Endothelial Cells," *The Journal of Immunology*, 144(2):521-525, 1990.
Ledbetter et al., "CD 28 Ligation in T-Cell Activation: Evidence for Two Signal Transduction," Abstract only, *Blood*, 75(7):1531-1539, 1990.
Watanabe et al., "Exogenous Expression of Mouse Interferon γ cDNA in Mouse Neuroblastoma C1300 Cells Results in Reduced Tumorigenicity by Augmented Anti-Tumor Immunity," *Proceedings of the National Academy of Scientists*, 86:9456-9460, 1989.
Schütt et al., "Human Monocyte Activation Induced by an Anti-CD14 Monoclonal Antibody," *Immunology Letters*, 19:321-328, 1988.
Thorpe et al., "Improved Antitumor Effects of Immunotoxins Prepared with Deglycosylated Ricin A-Chain and Hindered Disulfide Linkages," *Cancer Research*, 48:6396-6403, 1988.
Glennie et al., "Preparation and Performance of Bispecific (F(ab'γ)$_2$ Antibody Containing Thioether-Linked Fab'γ Fragments," *The Journal of Immunology*, 139(7):2367-2375, 1987.
Bevilacqua et al., "Identification of an Inducible Endothelial-Leukocyte Adhesion Molecule," *Proceedings of the National Academy of Scientists*, 84:9238-9242, 1987.
Cotran et al., "Induction and Detection of a Human Endothelial Activation Antigen In Vivo," Abstract only, *The Journal of Experimental Medicine*, 164(2):661-666, 1986.
Groenewegen et al., "Lymphokine Dependence of In Vivo Expression of MHC Class II Antigens by Endothelium," *Nature*, 316:361-263, 1985.
Moretta et al., Abstract only, *The Journal of Experimental Medicine*, 162(3):823-838, 1985.
Vaickus and Foon, "Overview of Monoclonal Antibodies in the Diagnosis and Therapy of Cancer," *Cancer Investigation*, 93(2):295-209, 1991.
Hagemeier et al., "A Monoclonal Antibody Reacting with Endothelial Cells of Budding Vessels in Tumors and Inflammatory Tissues, and Non-Reactive with Normal Adult Tissues," *International Journal of Cancer*, 38:481-488, 1986.

Duijvestijn et al., "Lymphoid Tissue- and Inflammation-Specific Endothelial Cell Differentiation defined by Monoclonal Antibodies," *The Journal of Immunology*, 138(3):713-719, 1987.

Murray et al., "Vascular Markers for Murine Tumours," *Radiotherapy and Oncology*, 16:221-234, 1989.

Schlingemann et al., "Monoclonal Antibody PAL-E Specific for Endothelium," *Laboratory Investigation*, 52(1):71-76, 1985.

Bruland et al., "New Monoclonal Antibodies Specific for Human Sarcomas," *International Journal of Cancer*, 38:27-31, 1986.

Reisfeld et al., "Human Tumor-Associated Antigens Defined by Monoclonal Antibodies," *CRC Critical Reviews in Immunology*, 5(1):27-53, 1984.

Schlom et al., "Monoclonal Antibodies Reactive with Breast Tumor-Associated Antigens," *Advances in Cancer Research*, 43:143-173, 1985.

Kaplan, "The Diagnostic and Therapeutic Use of Monoclonal Antibodies in Colorectal Cancer," *Hematology/Oncology Clinics of North American*, 3(1):125-134, 1989.

Smith and Teng, "Clinical Applications of Monoclonal Antibodies in Gynecologic Oncology," *Cancer*, 60:2068-2074, 1987.

Stavrou, "Monoclonal Antibodies in Neuro-Oncology," *Neurosurgery Review*, 13:7-18, 1990.

Shepard et al., "Monoclonal Antibody Therapy of Human Cancer: Taking the Her2 Protooncogene to the Clinic," *Journal of Clinical Immunology*, 11(3):117-127, 1991.

Szymendera, "Clinical Usefulness of Three Monoclonal Antibody-Defined Tumor Markers: CA 19-9, CA 50, and CA 125," *Tumour Biology*, 7:333-342, 1986.

Catane and Longo, "Monoclonal Antibodies for Cancer Therapy," *Israel Journal of Medical Sciences*, 24:471-476, 1988.

Greiner et al., "Applications of Monoclonal Antibodies and Recombinant Cytokines for the Treatment of Human Colorectal and Other Carcinomas," *Journal of Surgical Oncology Supplement*, 2:9-13, 1991.

Thor and Edgerton, "Monoclonal Antibodies Reactive with Human Breast or Ovarian Carcinoma: In Vivo Applications," *Seminars in Nuclear Medicine*, 19(4):295-308, 1989.

Thorpe et al., "Selective Killing of Proliferating Vascular Endothelial Cells by an Anti-Fibronectin Receptor Immunotoxin," *16th LH Gray Conference*, Sep. 17-21, 1990.

Ghose et al., "Preparation of Antibody-Linked Cytotoxic Agents," *Methods in Enzymology*, 93:280-333, 1983.

Thorpe et al., "Targeting to proliferating vascular endothelium," *Int. Symp. on Angio.*, Mar. 13-15, 1991.

Knowles and Thorpe, "Purification of Immunotoxins Containing Ricin A-Chain and Abrin A-Chain Using Blue Sepharose CL-6B," *Analytical Biochemistry*, 160:440-443, 1987.

Wang et al., "Photoreactive In-Cyclodextrin Inclusion Complex: a New Heterobifunctional Reagent for Antibody Labeling," *Nuclear Medicine and Biology*, 19(8):897-902, 1992.

PCT Search Report mailed Jun. 25, 1993.

Alvarez et al., "Localization of Basic Fibroblast Growth Factor and Vascular Endothelial Growth Factor in Human Glial Neoplasms," *Modern Pathology*, 5(3):303-307, 1992.

Brown et al., "Expression of Vascular Permeability Factor (Vascular Endothelial Growth Factor) and Its Receptors in Adenocarcinomas of the Gastrointestinal Tract," *Cancer Research*, 53:4727-4735, 1993.

Kim et al., "Inhibition of vascular endothelial growth factor-induced angiogenesis suppresses tumor growth in vivo," *Nature*, 362:841-843, 1993.

Dvorak et al., "Distribution of Vascular Permeability Factor (Vascular Endothelial Growth Factor) in Tumors: Concentration in Tumor Blood Vessels," *J. Exp. Med.*, 174:1275-1278, 1991.

Gerlach et al., "Enhanced Responsiveness of Endothelium in the Growing/Motile State to Tumor Necrosis Factor/Cachectin," *J. Exp. Med.*, 170:913-931, 1989.

Gougos et al., "Identification of distinct epitopes of endoglin, an RGD-containing glycoprotein of endothelial cells, leukemic cells, and syncytiotrophoblasts," *International Immunology*, 4(1):83-92, 1991.

Gougos et al., "Identification of a Human Endothelial Cell Antigen with Monoclonal Antibody 44G4 Produced Against a Pre-B Leukemic Cell Line," *The Journal of Immunology*, 141:1925-1933, 1988.

Gougos et al., "Biochemical Characterization of the 44G4 Antigen from the Hoon Pre-B Leukemic Cell Line," *The Journal of Immunology*, 141:1934-1940, 1988.

Hagemeier et al., "A Monoclonal Antibody Reacting with Endothelial Cells of Budding Vessels in Tumors and Inflammatory Tissues, and Non-Reactive with Normal Adult Tissues," *Int. J. Cancer*, 38:481-488, 1986.

Jakeman et al., "Binding Sites for Vascular Endothelial Growth Factor are Localized on Endothelial Cells in Adult Rat Tissues," *J. Clin. Invest.*, 89:244-253, 1992.

Nabel et al., "Recombinant fibroblast growth factor-1 promotes intimal hyperplasia and angiogenesis in arteries in vivo," *Nature*, 362:844, 1993.

O'Connell et al., "Endoglin: a 180-kD endothelial cell and macrophage restricted differentiation molecule," *Clin. Exp. Immunol.*, 90:154-159, 1992.

Plate et al., "Up-Regulation of Vascular Endothelial Growth Factor and Its Cognate Receptors in a Rat Glioma Model of Tumor Angiogenesis," *Cancer Research*, 53(23):5822-5827, 1993.

Plate et al., "Vascular endothelial growth factor is a potential tumour angiogenesis factor in human gliomas in vivo," *Nature*, 359:845-848, 1992.

Rettig et al., "Identification of endosialin, a cell surface glycoprotein of vascular endothelial cells in human cancer," *Proc. Natl. Acad. Sci. USA*, 89:10832-10836, 1992.

Sarma et al., "Cloning of a Novel Tumor Necrosis Factor-α-Inducible Primary Response Gene that is Differentially Expressed in Development and Capillary Tube-Like Formation in vitro," *The Journal of Immunology*, 148:3302-3312, 1992.

Senger et al., "Vascular permeability factor (VPF, VEGF) in tumor biology," *Cancer and Metatasts Reviews*, 12:303-324, 1993.

Shweiki et al., "Vascular endothelial growth factor induced by hypoxia may mediate hypoxia-initiated angiogenesis," *Nature*, 359:843-845, 1992.

Wang et al., "A Monoclonal Antibody Detects Heterogeneity in Vascular Endothelium of Tumours and Normal Tissues," *Int. J. Cancer*, 54:363-370, 1993.

Westphal et al., "A New 180-kDa Dermal Endothelial Cell Activation Antigen: In Vitro and In Situ Characteristics," *The Journal of Investigative Dermatology*, 100(1):27-34, 1993.

Yeo et al., "Vascular Permeability Factor (Vascular Endothelial Growth Factor) in Guinea Pig and Human Tumor and Inflammatory Effusions," *Cancer Research*, 53:2912-2918, 1993.

Büring et al., "Endoglin is expressed on a subpopulation of immature erythroid cells of normal human bone marrow," *Leukemia*, 5(10):841-847, 1991.

Dvorak et al., "Structure of Solid Tumors and Their Vasculature: Implications for Therapy with Monoclonal Antibodies," *Cancer Cells*, 3(3):77-85, 1991.

Gougos and Letarte, "Primary Structure of Endoglin, an RGD-containing Glycoprotein of Human Endothelial Cells," *The Journal of Biological Chemistry*, 265(15):8361-8364, 1990.

Bach et al., "Factor VII Binding to Tissue Factor in Reconstituted Phospholipid Vesicles: Induction of Cooperativity by Phosphatidylserine," *Biochemistry*, 25:4007-4020, 1986.

Brennan et al., "Preparation of Bispecific Antibodies by Chemical Recombination of Monoclonal Immunoglobulin GI Fragments," *Science*, 229:81-83, 1985.

Bruland et al., "Expression and Characteristics of a Novel Human Osteosarcoma-associated Cell Surface Antigen," *Cancer Res.*, 48:5302, 1983.

Burrows and Thorpe, "Eradication of Large Solid Tumors in Mice With an Immunotoxin Directed Against Tumor Vasculature," *Proc. Natl. Acad. Sci* (USA), 90:8996-9600, 1993.

Burrows et al., "A Murine Model for Antibody-Directed Targeting of Vascular Endothelial cells in solid tumors," *Cancer Res.*, 52:5954-5962, 1992.

Burrows et al., "Influence of Tumor-derived Interleukin-1 on Melanoma-endothelial Cell Interactions in Vitro," *Cancer Res.*, 51:4768-4775, 1991.

Carnemolla et al., "A Tumor-associated Fibronectin Isoform Generated by Alternative Splicing of Messenger RNA Precursors," *J. Cell. Biol.*, 108:1139, 1989.

Carnemolla et al., "The Inclusion of the Type III Repeat ED-B in the Fibronectin molecule Generates Conformational Modifications That Unmask a Cryptic Sequence," *Journal of Biological Chemistry*, 267(34):24689-24692, 1992.

Denekamp and Hobson, "Endothelial Cell Proliferation in Experimental Tumours." *Brit. J. Cancer*, 461:711-720, 1982.

Dewerchin et al., "Effect of Chemical Conjugation of Recombinant Single- Chain Urokinase-Type Plasminogen Activator With Monoclonal Antiplatelet Antibodies on Platelet Aggregation and on Plasma Clot Lysis In Vitro and In Vivo," *Blood*, 78(4):1005-1018, 1991.

Edgington et al., "The Structural Biology of Expression and Function of Tissue Factor," *Thrombosis and Haemostasis*, 66(1):67-79, 1991.

Epenetos et al., "Limitations of Radiolabeled Monoclonal Antibodies for Localization of Human Neoplasms," *Cancer Res.*, 46:3183-3191, 1986.

Fiore et al., "The biochemical basis for the apparent defect of soluble mutant tissue factor in enhancing the proteolytic activities of factor VIIa," *J. Biol. Chem.*, 269:143-149, 1994.

Fisher et al., "Cloning and Expression of Human Tissue Factor cDNA," *Thrombosis Research*, 48:89-99, 1987.

Folkman, Tumor Angiogenesis, *Adv. Cancer Res.*, 43:175-230, 1985.

Frelinger et al., "Monoclonal Antibodies to Ligand-occupied Conformers of Integrin $\alpha_{IIb}\beta_3$ (Glycoprotein IIb-IIIa) Alter Receptor Affinity, Specificity, and Function," *Journal of Biological Chemistry*, 266(26):17106-17111, 1991.

Frelinger et al., "Selective Inhibition of Integrin Function by Antibodies Specific for Ligand-occupied Receptor Conformers," *Journal of Biological Chemistry*, 265(11):6346-6352, 1990.

Hayward et al., "p-155, a Multimeric Platelet Protein That Is Expressed on Activated Platelets," *Journal of Biological Chemistry*, 266(11):7114-7120, 1991.

Heynen et al., "Absence of Ligands Bound to Glycoprotein IIB-IIIA on the Exposed Surface of a Thrombus May Limit Thrombus Growth in Flowing Blood," *J. Clin. Invest.*, 94:1098-1112, 1994.

Jain, Vascular and Interstitial Barriers to Delivery of Therapeutic Agents in Tumors. *Cancer Meta. Rev.*, 9(3):253-266, 1990.

Kim et al., "The Vascular Endothelial Growth Factor Proteins: Identification of Biologically Relevant Regions by Neutralizing Monoclonal Antibodies," *Growth Factors*, 7:53-64, 1992.

Kondo et al., "Significance of Vascular Endothelial Growth Factor/ Vascular Permeability Factor for Solid Tumor Growth, and Its Inhibition by the Antibody," *Biochemical and Biophysical Research Communications*, 194(3):1234-1241, 1993.

Krishnaswamy et al., "Role of the Membrane Surface in the Activation of Human Coagulation Factor X," *J. Biol. Chem.*, 267:26110-26120, 1992.

Martin et al., "Tissue factor: Molecular recognition and cofactor function," *Faseb J.*, 9:852..859, 1995.

Morrissey et al., "Molecular Cloning of the cDNA for Tissue Factor, the Cellular Receptor for the Initiation of the Coagulation Protease Cascade," *Cell*, 50:129-135, 1987.

Morrissey et al., "Monoclonal Antibody Analysis of Purified and Cell-Associated Tissue Factor," *Thrombosis Research*, 52:247-261, 1988.

Morrissey et al., "Quantitation of activated factor VII levels in plasma using a tissue factor mutant selectively deficient in promoting factor VII activation," *Blood*, 81:734-744, 1993.

Murray et al., "Tumor-derived Factors Which Induce Endothelial Tissue Factor and Enhance the Procoagulant Response to TNF," *Intl. J. Rad. Biology*, 60:273-277, 1991.

Nawroth et al., "Tumor necrosis factor/cachectin-induced intravascular fibrin formation in meth A fibrosarcomas," *J. Exp. Med.*, 168:637-647, 1988.

Nemerson, "Tissue Factor and Hemostasis," *Blood*, 71(1):1-8, 1988.

Neuenschwander and Morrissey, "Roles of the membrane-interactive regions of factor VIIa and tissue factor. The factor VIIaGla domain is dispensable for binding to tissue factor but important for activation of factor X," *J. Biol. Chem.*, 269:8007-8013, 1994.

Paborsky et al., "Lipid Association, but Not the Transmembrane Domain, Is Required for Tissue Factor Activity," *J. Biol. Chem.*, 266:21911-16, 1991.

Paborsky et al., "Purification of Recombinant Human Tissue Factor," *American Chemical Society*, 1989.

Rehemtulla et al., "High Level Expression of Recombinant Human Tissue Factor in Chinese Hamster Ovary Cells as a Human Thromboplastin," *Thrombosis and Haemostasis*, 65(5):521-527, 1991.

Rucco et al., "Cytokine Production (IL-a alpha, IL-1 beta, and TNF alpha) and Endothelial Cell Activation (ELAM-1 and HLA-DR) in Reactive Lymphadenits, Hodgkin's Disease, and in Non-Hodgkin's Lymphomas," *Am. J. Pathol.*, 137(5) 1163-1171, 1990.

Ruf and Edgington, "An Anti-Tissue Factor Monoclonal Antibody Which Inhibits TF-VIIa Complex is a Potent Anticoagulant in Plasma," *Thrombosis and Haemostasis*, 66(5):529-533, 1991.

Ruf and Edgington, "Structural biology of tissue factor, the initiator of thrombogenesis in vivo," *The FASEB Journal*, 8:385-390, 1994.

Ruf and Edgington, "Two sites in the tissue factor extracellular domain mediate the recognition of the ligand factor VIIa," *Proc. Natl. Acad. Sci. USA*, 88:8430-8434, 1991.

Ruf et al., "Phospholipid-independent and -dependent Interactions Required for Tissue Factor Receptor and Cofactor Function," *Journal of Biological Chemistry*, 266(4):2158-2166, 1991.

Ruf et al., "Tissue Factor Residues 157-167 are Required for Efficient Proteolytic Activation of Factor X and Factor VII," *Journal of Biological Chemistry*, 267(31):22206-22210, 1992.

Scarpati et al., "Human Tissue Factor: cDNA Sequence and Chromosome Localization of the Gene," *Biochemistry*, 26:5234-5238, 1987.

Schlingemann et al., "Leukocyte Antigen CD34 is Expressed by a Subset of Cultured Endothelial Cells and on Endothelial Albminal Microprocesses in the Tumor Stroma," *Laboratory Investigation*, 62:690-696, 1990.

Sioussat et al., "Inhibition of Vascular Permeability Factor (Vascular Endothelial Growth Factor) with Antipeptide Antibodies," *Archives of Biochemistry and Biophysics*, 301(1):15-20, 1993.

Spicer et al., "Isolation of cDNA clones coding for human tissue factor: Primary structure of the protein and cDNA," *Proc. Natl. Acad. Sci. USA*, 84:5148-5152, 1987.

ten Cate et al., "The activation of factor X and prothrombin by recombinant factor VIIa is mediated by tissue factor," *J. Clin. Invest.*, 92:1207-1212, 1993.

Thieme et al., "Comparative Analysis of Vascular Endothelial Growth Factor Receptors on Retinal and Aortic Vascular Endothelial Cells," *Diabetes*, 44:98, 1995.

Tomiyama et al., "The Arg-Gly-Asp (RGD) Recognition Site of Platelet Glycoprotein IIB-IIIA on Nonactivated Platelets is Accessible to High-Affinity Macromolecules," *Blood*, 79(9):2303-2312, 1992.

Ugarova et al., "Conformational Changes in Fibrinogen Elicited by its Interaction with Platelet Membrane Glycoprotein GPIIb-IIIa," *Journal of Biological Chemistry*, 268(28):21080-21087, 1993.

Zacharski et al., "Tumor Cell Procoagulant and Urokinase Expression in Carcinoma of the Ovary," *J. Nati Cancer Inst.*, 85:1225-1230, 1993.

Zamarron et al., "A Receptor-induced Binding Site in Fibrinogen Elicited by its Interaction with Platelet Membrane Glycoprotein IIb-IIIa," *Journal of Biological Chemistry*, 266(24)16193-16199, 1991.

UTSD:419; U.S. Appl. No. 08/273,567, filed Jul. 11, 1994; C.I.P. of UTSD:419.

UTSD:456; U.S. Appl. No. 08/485,482, filed Jun. 7, 1995; C.I.P. of UTSD:419.

UTSD:457; U.S. Appl. No. 08/487,427, filed Jun. 7, 1995; C.I.P. of UTSD:419.

UTSD:459; U.S. Appl. No. 08/479,733, filed Jun. 7, 1995; C.I.P. of UTSD:419.

UTSD:460; U.S. Appl. No. 08/472,631, filed Jun. 7, 1995; C.I.P. of UTSD:419.

UTSD:461; U.S. Appl. No. 08/479,727, filed Jun. 7, 1995; C.I.P. of UTSD:419.

UTSD:462; U.S. Appl. No. 08/481,904, filed Jun. 7, 1995; C.I.P. of UTSD:419.

Burrows and Thorpe, "Targeting the Vasculature of Solid Tumors," *Journal of Controlled Release*, 28:195-202, Jan. 1994.

Clauss et al., "A Polypeptide Factor Produced by Fibrosarcoma Cells That Induces Endothelial Tissue Factor and Enhances the Procoagulant Response to Tumor Necrosis Factor/Cachetin," *The Journal of Biological Chemistry*, 265(12):7078-7083, Apr. 1990.

Thorpe and Burrows, "Antibody-Directed Targeting of the Vasculature of Solid Tumors," *Breast Cancer Research and Treatment*, 36(2):237-251, 1995.

Yamazaki et al., "Bispecific Monoclonal Antibodies with Specificities for Activated Platelets and Thrombolytic Agents, Their Production and Use," Abstract for Canadian Patent Application CA 2039259; Chem Abstracts, 117(11), Abstract #109988.

International Search Report, Mailed Nov. 24, 1995.

Burgess et al., "Possible Dissociation of the Heparin-Binding and Mitogenic Activities of Heparin-Binding (Acidic Fibroblast) Growth Factor-1 from Its Receptor-Biding Activities by Site-Directed Mutagenesis of a Single Lysine Residue," *J. Cell Biol.*, 111:2129-2138, 1990.

Gillies and Wesolowski, "Antigen Binding and Biological Activities of Engineered Mutant Chimeric Antibodies with Human Tumor Specificities," *Hum. Antibod. Hybridomas*, 1(1):47-54, 1990.

Lapierre et al., "Three Distinct Classes of Regulatory Cytokines Control Endothelial Cell MHC Antigen Expression," *J. Exp. Med.*, 167:794-804, 1988.

Lazar et al., "Transforming Growth Factor α: Mutation of Aspartic Acid 47 and Leucine 48 Results in Different Biological Activities," *Mol. Cell Biol.*, 8(3):1247-1252, 1988.

Qian et al., "Human Peripheral Blood Lymphocytes Targeted with Bispecific Antibodies Release Cytokines That Are Essential for Inhibiting Tumor Growth," *J. Immunol.*, 146(9):3250-3256, 1991.

Tao and Morrison, "Studies of Aglycosylated Chimeric Mouse-Human IgG—Role of Carbohydrate in the Structure and Effector Functions Mediated by the Human IgG Constant Region," *J. Immunol.*, 143(8):2595-2601, 1989.

Waldman, Thomas A., "Monoclonal Antibodies in Diagnosis and Therapy," *Science*, 252: 1657-1662, 1991.

Wen et al., "Effects of γ-Interferon on Major Histocompatibility Complex Antigen Expression and Lymphocyte Infiltration in the 9L Gliosarcoma Brain Tumor Model: Implications for Strategies of Immunotherapy," *J. Neuroimmunol.*, 36:57-68, 1992.

Dermer, "Another Anniversary for the War on Cancer", *Bio/technology*, 12, 320 (1994).

Pober and Cotran, "What Can Be Learned From the Expression of Endothelial Adhesion Molecules in Tissues?", *Laboratory Investigation*, 64(3), 301-305 (1991).

Aoyagi, "Distribution of Plasma Fibronectin in the Metastatic Lesion of Cancer: Experimental Study by Autoradiography." *Thrombosis Research*, 49:265-75, 1988.

Balza et al., "Production and Characterization of Monoclonal Antibodies Specific for Different Epitopes of Human Tenascin," *FEBS* 332(1,2):39-43, 1993.

Bjorndahl, et al., "Human T Cell Activation: Differential Response to Anti-CD28 As Compared to Anti-CD3 Monoclonal Antibodies," *Eur. J. Immunol.*, 19:881-87, 1989.

Blanchard, et al., "Infiltration of Interleukin-2-Inducible Killer Cells in Ascitic Fluid and Pleural Effusions of Advanced Cancer Patients," *Cancer Research*, 48:6321-27, 1988.

Bohlen, et al., "Cytolysis of Leukemic B-Cells by T-Cells Activated via Two Bispecific Antibodies," *Cancer Research*, 53:4310-14, 1993.

Borsi, et al., "Expression of Different Tenascin Isoforms in Normal, Hyperplastic and Neoplastic Human Breast Tissues," *Int. J. Cancer*, 52:688-92, 1992.

Boyer, et al., "Differential Induction by Interferons of Major Histocompatibility Complex-Encoded and Non-Major Histocompatibility Complex-Encoded Antigens in Human Breast and Ovarian Carcinoma Cell Lines," *Cancer Research*, 49:2928-34, 1989.

Burton-Wurster, et al., "Expression of the Ed B Fibronectin Isoform in Adult Human Articular Cartilage," *Biochemical and Biophysical Research Communication* 165(2): 782-87, 1989.

Collins, et al., "Immune Interferon Activates Multiple Class II Major Histocompatibility Complex Genes and the Associated Invariant Chain Gene in Human Endothelial Cells and Dermal Fibroblasts," *Proc. Natl. Acad. Sci. USA*, 81:4917-21, 1984.

Carnemolla, et al., "A Tumor-associated Fibronectin Isoform Generated by Alternative Splicing of Messenger RNA Precursors," *The Journal of Cell Biology*, 108:1139-48, 1989.

Carnemolla et al., "The Inclusion of the Type III Repeat ED-B in the Fibronectin Molecule Generates Conformational Modifications that Unmask a Cryptic Sequence," *The Journal of Biological Chemistry*, 267(34):24589:92, 1992.

Carnemolla, et al., "Phage Antibodies with Pan-Species Recognition of the Oncofoetal Angiogenesis Marker Fibronectin ED-B Domain," *Int. J. Cancer* 68:397-405, 1996.

Castellani, et al., "The Fibronectin Isoform Containing the ED-B Oncofoetal Domain: A Marker of Angiogenesis," *Int. J. Cancer.* 59:612-18, 1994.

Conforti, et al., "Human Endothelial Cells Express Integrin Receptors on the Luminal Aspect of Their Membrane," *Blood* 80(2):437-46, 1992.

Diliman, "Monoclonal Antibodies for Treating Cancer," *Annals of Internal Medicine*, 111(7) 592-600, 1989.

Farnoud, et al., "Fibronectin Isoforms Are Differentially Expressed in Normal and Adenomatous Human Anterior Pituitaries," *Int. J. Cancer*, 61:27-34, 1995.

Garin-Chesa, et al., "Cell Surface Glycoprotein of Reactive Stromal Fibroblasts as a Potential Antibody Target in Human Epithelial Cancers," *Proc. Natl. Acad. Sci. USA*, 87:7235-39, 1990.

Groenewegen, et al., "Lymphokine Dependence of In Vivo Expression of MHC Class II Antigens by Endothelium," *Nature*, 316:361-63, 1985.

Harris and Emery, "Therapeutic Antibodies—The Coming of Age," *Btech*, 11:42-44, 1993.

June, et al., "T-Cell Proliferation Involving the CD28 Pathway Is Associated with Cyclosporine-Resistant Interleukin 2 Gene Expression," *Molecular and Cellular Biology* 7(12):4473-81, 1987.

Kaczmarek, et al., "Distribution of Oncofetal Fibronectin Isoforms in Normal Hyperplastic and Neoplastic Human Breast Tissues," *Int. J. Cancer*, 58:11-16, 1994.

Koulova et al., "The CD28 Ligand B7/BB1 Provides Costimulatory Signal for Alloactivation of CD4+ T Cells," *J. Exp. Med.* 173:759-62, 1991.

Kurosawa, et al., "Early Appearance and Activation of Natural Killer Cells in Tumor-Infiltrating Lymphoid Cells During Tumor Development," *Eur. J. Immunol.* 23:1029-33, 1993.

Lampugnani, et al., "The Role of Integrins in the Maintenance of Endothelial Monolayer Integrity," *The Journal of Cell Biology.* 112(3):479-90, 1991.

Linnala, et al., "Human Amnion Epithelial Cells Assemble Tenascins and Three Fibronectin Isoforms in the Extracellular Matrix," *FEBS*, 314(1,2):74-78, 1993.

Maeda, et al., "Production and Characterization of Tumor Infiltrating Lymphocyte Clones Derived from B16-F10 Murine Melanoma," *The Journal of Investigative Dermatology* 97(2):183-89, 1991.

Natali, et al., "Comparative Analysis of the Expression of the Extracellular Matrix Protein Tenascin in Normal Human Fetal, Adult and Tumor Tissues," *Int. J. Cancer*, 47:811-16, 1991.

Oyama, et al., "Coordinate Oncodevelopmental Modulation of Alternative Splicing of Fibronectin Pre-Messenger RNA at ED-A. ED-B and CS1 Regions in Human Liver Tumors," *Cancer Research* 53:2005-11, 1993.

Peters, et al., "Expression of the Alternatively Spliced E111B Segment of Fibronectin," *Cell Adhesion and Communication*, 3:67-89, 1995.

Pober et al., "Ia Expression by Vascular Endothelium Is Indcuible by Activated T Cells and by Human γ Interferon," *J. Exp. Med.* 157: 1339-53, 1983.

Pohl, et al., "CD30-Antigen-Specific Targeting and Activation of T Cells via Murine Bispecific Monoclonal Antiodies Against CD3 and CD28: Potential Use for the Treatment of Hodgkin's Lymphoma," *Int. J. Cancer*, 54:820-27, 1993.

Renner, et al., "Cure of Xenografted Human Tumors by Bispecific Monoclonal Antibodies and Human T Cells," *Science*, 264:833-35, 1994.

Rettig, et al., "Cell-Surface Glycoproteins of Human Sarcomas: Differential Expression in Normal and Malignant Tissues and Cultured Cells," *Proc. Natl. Acad. Sci. USA*, 85:3110-14, 1988.

Rettig, et al., Identification of Endosialin, A Cell Surface Glycoprotein of Vascular Endothelial Cells in Human Cancer, *Proc. Natl. Acad Sci. USA*, 89:10832-36, 1992.

Rosenberg, Steven, "Lymphokine-Activated Killer Cells: A New Approach to Immunotherapy of Cancer," *JNCI* 75(4):595-603, 1985.

Rosenberg, et al., "Observations of the Systemic Administration of Autologous Lymphokine-Activated Killer Cells and Recombinant Interleukin-2 to Patients with Metastatic Cancer," *The New England Journal of Medicine*, 313(23):1485-92, 1985.

Ruiter, et al., "Monoclonal Antibody-Defined Human Endothelial Antigens as Vascular Markers," *J. Investigative Dermatol.*, 93(2):25S-32S, 1989.

Saiki et al., "Anti-metastatic and Anti-invasive Effects of Polymeric Arg-Gly-Asp (RGD) Peptide, Poly(RGD), and Its Analogues," *Jpn. J. Cancer Res.* 81:660-67, 1990.

Saiki et al., "Inhibition of Tumor Angiogenesis by a Synthetic Cell-Adhesive Polypeptide Containing the Arg-Gly-Asp (RGD) Sequence of Fibronectin, Poly(RGD)," *Jpn. J. Cancer Res.* 81:668-75, 1990.

Schlingemann, et al.. "Differential Expression of Markers for Endothelial Cells, Pericytes, and Basal Lamina in the Microvasculature of Tumors and Granulation Tissue," *Am. J. Pathol.*, 138(6):1335-47, 1991.

Schwarzbauer, "Alternative Splicing of Fibronectin: Three Variants, Three Functions," *BioEssays* 13(10)527-33, 1991.

Siri, et al., "Human Tenascin: Primary Structure, Pre-mRNA Splicing Patterns and Localization of the Epitopes Recognized by Two Monoclonal Antibodies," *Nucleic Acids Research*, 19(3):525-31, 1991.

Steiniger, et al., "Interferon-γ in Vivo. Induction and Loss of Class II MHC Antigens and Immture Myelomonocytic Cells in Rat Organs," *Eur. J. Immunol.* 18:661-69, 1988.

Street, et al., "In Vivo Administration of Fab' Fragments of Anti-L3T4 (GK1.5) Antibody Inhibits the T Helper Cell Function of Murine Lymph Node Cells," *Cellular Immunology* 120:75-81, 1989.

Thompson, et al., "CD28 Activation Pathway Regulates the Production of Multiple T-Cell-Derived Lymphokines/Cytokines," *Proc. Natl. Acad. Sci. USA*, 86:1333-37, 1989.

Ueda, et al., "Selective Distribution of Fibronectin to a Tumor-Cell Line," *Cancer Letters* 31:261-65, 1986.

Vartio, et al., "Differential Expression of the ED Sequence-Containing Form of Cellular Fibronectin in Embryonic and Adult Human Tissues," *Journal of Cell Science*, 88:419-30, 1987.

Welt, et al., "Phase I Localization Study of $^{131}$I-monoclonal Antibody F19 Detecting an Activation Antigen of Neoplastic Stroma," *Proceedings of the American Association for Cancer Research*, 33:319, 1992, Abstract No. 1900.

Werb, et al., "Signal Transduction through the Fibronectin Receptor Induces Collagenase and Stromelysin Gene Expression," *The Journal of Cell Biology.*, 109:877-89, 1989.

Allowed Claims of U.S. Appl. No. 08/327,709, Dvorak.

Osband and Ross, "Problems in the Investigational Study and Clinical Use of Cancer Immunotherapy," *Immunotherapy*, 11:193-195, 1990.

Chatterjee, et al., "Idiotypic antibody immunotherapy of cancer," *Cancer Immunol. Immunotherapy*, 38:75-82, 1994.

European Application Serial No. 93 906 289.9 Office Action dated Sep. 25, 1997.

European Application Serial No. 93 923 817.1 Office Action dated Sep. 25, 1997.

Wellicome et al., A Monoclonal Antibody That Detects a Novel Antigen on Endothelial Cells That is Induced by Tumor Necrosis Factor, IL-1, Or Lipopolysaccharide, *J. Immunol.*, 144(7):2558-2565, Apr. 1, 1990.

Denekamp, "Vasculature as a Target for Tumour Therapy," *Prog. Appl. Microcirc.*, 4:28-38, 1984.

Klagsbrun and D'Amore, "Regulators of Angiogenesis," *Annu. Rev. Physiol.*, 53:217-239, 1991.

International Search Report for WO99/58570 (PCT/EP99/03210), republished Mar. 16, 2000.

Heimbrook et al., "Transforming growth factor α-*Pseudomonas* exotoxin fusion protein prolongs survival of nude mice bearing tumor xenografts," *Proc. Natl. Acad. Sci. USA*, 87:4697-4701, 1990.

Hirota et al., "Suppression of an epidermal growth factor receptor-hyperproducing tumor by an immunotoxin conjugate of gelonin and a monoclonal anti-epidermal growth factor receptor antibody," *Cancer Research*, 49:7106-7109, 1989.

Burrows and Thorpe, "Vascular Targeting—A New Approach to the Therapy of Solid Tumors," *Pharmac. Thera.*, 64:155-174, 1994.

Denekamp, "Endothelial Cell Attack as a Novel Approach to Cancer Therapy," *Cancer Topics*, 6:6-8, 1986.

Denekamp, The Current Status of Targeting Tumor Vasculature as a Means of Cancer Therapy: An Overview, *Int. J. Radiat. Biol.*, 60:401-408, 1991.

Murray et al., "Flavone Acetid Acid Potentiates the Induction of Endothelial Procagulant Activity by Tumor- Necrosis Factor," *Eur. J. Cancer*, 27:765-770, 1991.

Murray et al., "Selective Induction of Endothelial Cell Tissue Factor in the Presence of Tumor-Derived Mediator: A Potential Mechanism of Flavone Acetic Acit Action in Tumor Vasculature," *Int. J Cancer*, 49:254-259, 1991.

Riewald and Ruf, "Mechanistic Coupling of Protease Signaling and Initiation of Coagulation by Tissue Factor," *Proc. Natl. Acid. Sci. USA*, 98(14):7742-7747, 2001.

Tijburg et al. "Activation of the Coagulation Mechanism on Tumor Necrosis Factor-Stimulated Cultured Endothelial Cells and their Extracellular Matrix: The Role Flow and Factor IX/IXA," *J. Biol. Chem.*, 266:12067-12074, 1991.

Carson and Brozna, "The Role of Tissue Factor in the Production of Thrombin," *Blood Coagulation and Fibrinolysis*, 4:281-292, 1993.

Giles, "Functional, Biochemical, and Morphological Evaluations of Experimental Hemophilia Therapies in Animal Models," *Seminars in Hematology*, 31(2,4):56-59, 1994.

McCallum et al., "Issue Factor Positions and Maintains the Factor VIIa Active Site Far Above the Membrane Surface Even in the Absence of the Factor VIIa Gla Domain," *J. Biol. Chem.*, 272(48):30160-30166, 1997.

McCallum et al., "The Location of the Active Site of Blood Coagulation Factor VIIa above the Membrane Surface and Its Reorientation Upon Association with Tissue Factor," *J. Biol. Chem.*, 271(45):28168-28175, 1996.

Morrissey et al., "Factor VIIa-Tissue Factor: Functional Importance of Protein-Membrane Interactions," *Thrombosis Haemostasis*, 78(1):112-116, 1997.

Sakai and Kisiel, "Formation of Tissue Factor Activity Following Incubation of Recombinant Human tissue Factor Apoprotein with Plasma Lipoproteins," *Thrombosis Research*, 60:213-222, 1990/.

Giles et al., "A Combination of Factor Xa and Phosphatidylcholine-Phosphatidylserine Vesicles Bypasses Factor VIII In Vivo," *British Journal of Haematology*,69:491-497, 1988.

Ni and Giles, "Normalization of the Haemostatic Plugs of Dogs with Haemophilia A (Factor VIII Deficiency) Following the Infusion of a Combination of Factor Xa and Phosphatidylcholine/Phosphatidylserine Vesicles," *Thrombosis and Haemostasis*, 67(2):264-271, 1992.

Hornung et al., "Immunomodulation of Natural Killer Cell Activity by Flavone Acetic Acid: Occurrence Via Induction of Interferon α/β," *J. Natl. Cancer Inst.*,80:1226-1231, 1988.

Mace et al., Correlation Between In Vivo Induction of Cytokine Gene Expression by Flavone Acetic Acid and Strict Dose Dependency and Therapeutic Efficacy Against Murine Renal Cancer, *Cancer Res.*, 50:1742-1747, 1990.

Murray et al., "Flavone Acetic Acid Induces a Coagulopathy in Mice," *Br. J. Cancer*, 60:729-733, 1989.

Sandset et al., "Depletion of Extrinsic Pathway Inhibitor (EPI) Sensitizes Rabbits to Disseminated Intravascular Coagulation Induced with Tissue Factor: Evidence Supporting a Physiologic Role for EPI as a Natural Anticoagulant," *Proc. Natl. Acad. Sci. USA*, 88:708-712, 1991.

Thurston et al., "Anticoagulant Treatment Does Not Affect the Action of Flavone Acetic Acid in Tumour-Bearing Mice," *Br. J. Cancer*, 64:689-692, 1991.

Wiltrout and Hornung, "Natural Products as Antitumor Agents: Direct Versus Indirect Mechanisms of Activity of Flavonoids," *J. Natl. Cancer Inst.*, 80:1226-1231, 1988.

Wiltrout et al., "Flavone-8-Acetic Acid Augments Systemic Natural Killer Cell Activity and Synergizes with IL-2 for Treatment of Murine Renal Cancer," *J. Immunol.*, 140(9):3261-3265, 1988.

Bodey et al, "Failure of Cancer Vaccines: The Significant Limitations of this Approach to Immunotherapy," *Anticancer Res.*, 20:2665-2676, 2000.

Colman, "Effects of Amino Acid Sequence Changes on Antibody-Antigen Interactions," *In a Structural View of Immune Recognition by Antibodies*, 33-36, 1994.

Kuby et al., *Immunology, Second Edition*, 86-96, 1944.

Spitler, "Cancer Vaccines: The Interferon Analogy," *Cancer Biotherapy*, 10(1):1-3, 1995.

Abaza and Atassi, "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J. Protein Chemistry*, 11(5):433-444, 1992.

Attwood, "The Babel of Bioinformatics," *Science*, 290(5491):471-473, 2000.

Mikayama et al., "Molecular Cloning and Functional Expression of a cDNA Encoding Glycosylation-Inhibiting Factor," *Proc. Natl. Acad. Sci. USA*, 90:10056-10060, 1993.

Ngo et al., "Computational Complexity, Protein Structure Prediction, and the Levinthal Paradox," *In, The Protein Folding Problem and Tertiary Structure Prediction*, Eds., Merz & LeGrand, pp. 492-495, 1994.

Voet et al., "Chemical Evolution," *In, Biochemistry I*, Voet & Voet, pp. 126-234, 1990.

Connolly et al., "Human Vascular Permeability Factor," *J. Biol. Chem.*, 264(33):20017-20024, 1989.

Ferrara et al., "Molecular and Biological Properties of the Vascular Endothelial Growth Factor Family of Proteins," *Endocrine reviews*, 13(I):18-32, 1992.

Hori et al., "Suppression of Solid Tumor Growth by Immunoneutralizing Monoclonal Antibody Against Human Basic Fibroblast Growth Factor," *Cancer Res.*, 51:6180-6184, 1991.

Kim et al., "The Vascular Endothelial Growth Factor Proteins: Identification of Biologically relevant Regions by Neutralizing Monoclonal Antibodies," *Growth Factors*, 7:53-64, 1992.

Takahashi et al., "Inhibition of Cell Growth and Tumorigenesis of Human Glioblastoma Cells by a Neutralizing Antibody Against Human Basic Fibroblast Growth Factor," *FEBS Lett.*, 288(1,2):65-71, 1991.

Albrecht et al., "An ELISA for Tissue Factor Using Monoclonal Antibodies," *Blood Coagulation and Fibrinolysis*,3:263-270, 1992.

Gottstein et al., "Generation and Characterization of Recombinant Vascular Targeting Agents from Hybridoma Cell Lines," *BioTechniques*, 30(1):190-199, 2001.

Hu et al., "Comparison of Three Different Targeted Tissue Factor Fusion Proteins for Inducing Tumor Vessel Thrombosis," *Proc. Am. Assoc. Cancer Res.*, 43:912, #4519, 2002.

Hu et al., "Procoagulant Activity in Cancer Cells is Dependent on Tissue Factor Expression," *Oncology Res.*, 6(7):321-327, 1994.

Huang et al., "Tumor Infarction in Mice by Antibody-Directed Targeting of Tissue Factor to Tumor Vasculature," *Science*, 275:547-550, 1997.

Liu et al., "Prostate-Specific Membrane Antigen Directed Selective Thrombotic Infarction of Tumors," *Cancer Res.*, 62:5470-5475, 2002.

Mueller et al., "Expression of Tissue Factor by Melanoma Cells Promotes Efficient Hematogenous Metastasis," *Proc. Natl. Acad. Sci, USA.*, 89:11832-11836, 1992.

Nilsson et al., "Targeted Delivery of Tissue Factor to the ED-B Domain of Fibronectin, A Marker of Angiogenesis, Mediates the Infarction of Solid Tumors in Mice," *Cancer Res.*, 61:711-716, 2001.

Ran et al., "Infarction of Solid Hodgkin's Tumors in Mice by Antibody-Directed Targeting of Tissue Factor to Tumor Vasculature," *Cancer Res.*, 58:4646-4653, 1998.

Elias et al., "Phase I Study of High-Dose Ifosfamide, Carboplatin and Etoposide with Autologous Hematopoietic Stem Cell Support," *Bone Marrow Transplantation*, 15:373-379, 1995.

Greenberg et al., "A Clinical Trial of Antioxidant Vitamins to Prevent Colorectal Adenoma," *N. Engl. J. Med.*, 331:141-147, 1994.

Martin and Green, "Apoptosis as a Goal of Cancer Therapy," *Oncology*, 6:616-621, 1994.

Villikka and Pyrhonen, "Cytokine Therapy of Malignant Melanoma," *Annals of Medicine*, 28:227-233, 1996.

Zhang et al., "Tissue Factor Controls the Balance of Angiogenic and Antiangiogenic Properties of Tumor Cells in Mice," *J. Clin. Invest.*, 94:1320-1327, 1994.

Hardman et al., In Goodman & Gilman's the Pharmacological Basis of Therapeutics Ninth Edition, pp. 51 and 57-58, 1996.

Thorpe, "Vascular Targeting Agents as Cancer Therapeutics," *Clin. Can. Res.*, 10:415-427, 2004.

Fonsatti et al., "Emerging Role of Endoglin (CD105) as a Marker of Angiogenesis with Clinical Potential in Human Malignancies," *Current Cancer Drug Targets*, 3:429-434, 2003.

Haba et al., "Anti-Endoglin Monoclonal Antibody for Antiangiogenic Therapy: Comparison of IgG1 and IgG3 Human/Mouse Chimeric Antibodies and the Parental Monoclonal Antibody," *Proc. Assoc. Cancer Res.*, 42:823, Abstract #4422, 2001.

Haba et al., "Suppression of Metastases of Colon-26 Tumors by Anti-Endoglin (CD105) Monoclonal Antibodies and Detection of a Novel Epitope for Monitoring Micrometastases and Metastases," *Proc. Amer. Assoc. Cancer Res.*, 43:524-525, Abstract #2602, 2002.

Harada et al., "Antiangiogenic and Vascular Targeting Therapy of Established Tumors in Human Skin/SCID Mouse Chimeras by Anti-Endoglin (CD105) Monoclonal Antibody, Cyclophosphamide and Doxorubicin," *Proc. Amer. Assoc. Cancer Res.*, 44(2):602, Abstract #3032, 2003.

Harada et al., "Anti-Endoglin (CD105) Monoclonal/Antibody (mAb) for Antiangiogenic and Vascular Targeting Therapy of Cancer: Toxicity Testing of a Human/Mouse Chimeric Anti-Endoglin mAb in Non-Human Primates," *Proc. Amer. Assoc. Cancer Res.*, 44(2):600-601, Abstract #3027, 2003.

Li et al., "Both High Intratumoral Microvessel Density Determined Using CD105 Antibody and Elevated Plasma Levels of CD105 in Colorectal Cancer Patients Correlated with Poor Prognosis," *British J. Cancer*, 88:1424-1431, 2003.

Seon, "Expression of Endoglin (CD105) in Tumor Blood Vessels," *Int. J. Cancer*, 99:310-311, 2002.

She and Seon, "Epitope Mapping of Endoglin, a TGF-β Receptor, Using Recombinant Fragments and Twelve Monoclonal Antibodies," *Proc. Amer. Assoc. Cancer Research*, 42:825, Abstract #4430, 2001.

She et al., "Mechanisms of Antiangiogenic Activity of Anti-Endoglin (CD105) Monoclonal Antibodies," *Proc. Amer. Assoc. Cancer Research*, 43:30, Abstract #154, 2002.

She et al., "Synergy Between Anti-Endoglin (CD105) Monoclonal Antibodies and TGF-β in Suppression of Growth of Human Endothelial Cells," *Int. J. Cancer*, 108:251-257, 2004.

Shiozaki et al., "Anti-Endoglin (CD105) Monoclonal Antibody (mAb) for Antiangiogenic and Vascular Targeting Therapy of Cancer: Parmaodkinetics and Immunogenicity of Human/Mouse Chimeric Anti-Endoglin mAb in Non-Human Primates," *Proc. Amer. Assoc. Cancer Res.*, 44(2):600, Abstract #3026, 2003.

Tabata et al., "Antiangiogenic Radioimmunotherapy of Human Solid Tumors in SCID Mice Using $^{125}$I-Labeled Anti-Endoglin Monoclonal Antibodies," *Int. J. Cancer*, 82:737-742, 1999.

Takahashi et al., "Association of Serum Endoglin with Metastasis in Patients with Colorectal, Breast and Other Solid Tumors, and Suppressive Effect of Chemotherapy on the Serum Endoglin," *Proc. Amer. Assoc. Cancer Res.*, 42:721, Abstract #3874, 2001.

Ezzell et al., "Cancer "Vaccines": An Idea Whose Time Has come?," *J. NIH Research*, 7:46-49, 1995.

Skolnick and Fetrow, "From Genes to Protein Structure and Function: Novel Applications of Computational Approaches in the Genomic Era," *TIBTECH*, 18:34-39, 2000.

Wang et al., "The Effect of Antibody Against Vascular Endothelial Growth Factor on Tumor Growth and Metastasis," *J. Can. Res. Clin. Oncol.*, 124(11):615-620, 1998 (Abstract only).

Contag and Bachmann, "The Writing is on the Vessel Wall," *Nature*, 429:618-619, 2004.

Oh et al., "Subtractive Proteomic Mapping of the Endothelial Surface in Lung and Solid Tumours for Tissue-Specific Therapy," *Nature*, 429:629-635, 2004.

Aiello, "Suppression of Retinal Neovascularization In Vivo by Inhibition of Vascular Endothelial Growth Factor (VEGF) Using Soluble VEGF-Receptor Chimeric Proteins," *Proc. Natl. Acad. USA*, 92:10457-10461, 1995.

Alvarez et al., "Localization of Basic Fibroblast Growth Factor and Vascular Endothelial Growth Factor in Human Glial Neoplasms," *Modern Pathology*, 5(3):303-307, 1992.

Auerbach, "Vascular Endothelial Cell Differentiation: Organ-Specificity and Selective Affinities as the Basis for Developing Anti-Cancer Strategies," *Int. J. Radiat. Biol.*, 60(1/2):1-10, 1991.

Baird et al., "Immunoreactive Fibroblast Growth Factor (FGF) in a Transplantable Chondrosarcoma: Inhibition of Tumor Growth by Antibodies to FGF," *J. Cell. Biochem.*, 36:79-85, 1986.

Berse et al., "Vascular Permeability Factor (Vascular Endothelial Growth Factor) Gene is Expressed Differentially in Normal Tissues, Macrophages, and Tumors," *Molecular Biology Cell*, 3:211-220, 1992.

Berse et al., "Vascular Permeability Factor Vascular Endothelial Cell Growth Factor Expression in Normal Tissues and in Tumors," *J. Cell Biol.*, 115(3 part 2):421a, Abstract No. 2443, 1991.

Broadley et al., "Monospecific Antibodies Implicate Basic Fibroblast Growth Factor in Normal Wound Repair," *Lab. Invest.*, 61(5):571-575, 1989.

Brock et al., "Tumor-Secreted Vascular Permeability Factor Increases Cytosolic $Ca^{2+}$ and von Willebrand Factor Release in Human Endothelial Cells," *Am. J. Path.*, 138(1):213-221, 1991.

Brown et al., "Leaky Vessels, Fibrin Deposition, and Fibrosis: A Sequence of Events Common to Solid Tumors and to Many Types of Disease," *Am. Rev. Respir. Dis.*, 140:1104-1107, 1989.

Clauss et al., "Vascular Permeability Factor: A Tumor-Derived Polypeptide that Induces Endothelial Cell and Monocyte Procoagulant Activity, and Promotes Monocyte Migration," *J. Exp. Med.*, 172:1535-1545, 1990.

Conn et al., "Purification of a Glycoprotein Vascular Endothelial Cell Mitogen from a Rat Glioma-Derived Cell Line," *Proc. Nat. Acad. Sci. USA*, 87:1323-1327, 1990.

Conn et al., "Amino Acid and cDNA Sequences of a Vascular Endothelial Cell Mitogen that is Homologous to Platelet-Derived Growth Factor," *Proc. Natl. Acad. Sci. USA*, 87:2628-2632, 1990.

Connolly, "Vascular Permeability Factor: A Unique Regulator of Blood Vessel Function," *J. Cell Biochem.*, 47:219-223, 1991.

Connolly, "Tumor Vascular Permeability Factor Stimulates Endothelial Cell Growth and Angiogenesis," *J. Clin. Invest.*, 84:1470-1478, 1989.

Denekamp, "Vasculature as a Target for Tumour Therapy," *Prog. Appl. Microcirc.*, 4:28-38, 1984.

Dennis and Rifkin, "Studies on the Role of Basic Fibroblast Growth Factor In Vivo: Inability of Neutralizing Antibodies to Block Tumor Growth," *J. Cell. Physiol.*, 144:84-98, 1990.

Dvorak et al., "Vascular Permeability Factor, Fibrin, and the Pathogenesis of Tumor Stroma Formation," *Ann. N.Y. Acad. Sci.*, 667:101-111, 1992.

Dvorak, "Leaky Tumor Vessels: Consequences for Tumor Stroma Generation and for Solid Tumor Therapy," *Progress in Clinical and Bioilogical Research*, 354a: 317-330, 1990.

Dvorak, "Tumors: Wounds That Do Not Heal," *New Eng. J. Med.*, 315(26):1650-1659, 1986.

Dvorak et al, "Regulation of Extravascular Coagulation by Microvascular Permeability," *Science*, 227:1059-1061, 1985.

Dvorak et al., "Fibrin as a Component of the Tumor Stroma: Origins and Biological Significance," *Cancer Metastasis Reviews*, 2:41-73, 1983.

Ferrara et al., "Expression of Vascular Endothelial Growth Factor Does Not Promote Transformation but Confers a Growth Advantage In Vivo to Chinese Hamster Ovary Cells," *J. Clin. Invest.*, 91:160-170, 1993.

Ferrara et al., "The Vascular Endothelial Growth Factor Family of Polypeptides," *J. Cell. Biochem.*, 47:211-218, 1991.

Ferrara and Henzel, "Pituitary Follicular Cells Secrete a Novel Heparin Binding Growth Factor Specific for Vascular Endothelial Cells." *Biochem. Biophys. Res. Comm.*, 161(2):851-858, 1989.

Ferrara et al, "Molecular Characterization and Distribution of Vascular Endothelial Growth Factor," *J. Cell Biochem. Supp.*, 151(part F):p211, 1991, Abstract No. CF016.

Folkman and Ingber, "Inhibition of Angiogenesis," *Seminars in Cancer Biology*, 3:89-96, 1992.

Folkman and Shing, "Angiogenesis," *J. Biol. Chem.*, 267(16):10931-10934, 1992.

Folkman et al., "Induction of Angiogenesis During the Transition from Hyperplasia to Neoplasia," *Nature*, 339:58-61, 1989.

Folkman, "What is the Evidence that Tumors are Angiogenesis Dependent?," *J. Natl. Cancer Inst.*, 82(1):4-6, 1990.

Folkman and Klagsbrun, "Angiogenic Factors," *Science*, 235:442-447, 1987.

Gospodarowicz et al., "Isolation and Characterization of a Vascular Endothelial Cell Mitogen Produced by Pituitary-Derived Folliculo Stellate Cells," *Proc. Natl. Acad. Sci.*, 86:7311-7315, 1989.

Greenblatt and Shubi, "Tumor Angiogenesis: Transfilter Diffusion Studies in the Hamster by the Transparent Chamber Technique," *J. Natl. Cancer Inst.*, 41:111-124, 1968.

Houck et al., "The Vascular Endothelial Growth Factor Family: Identification of a Fourth Molecular Species and Characterization of Alternative Splicing of RNA," *Molecular Endocrinology*, 5:1806-1814, 1991.

Jain, "Haemodynamic and Transport Barriers to the Treatment of Solid Tumours," *Int. J. Radial. Biol.*, 60(1/2):85-100, 1991.

Jakeman et al., "Binding Sites for Vascular Endothelial Growth Factor are Localized on Endothelial Cells in Adult Rat Tissues," *J. Clin. Invest.*, 89:244-253, 1992.

Keck et al., "Vascular Permeability Factor, an Endothelial Cell Mitogen Related to PDGF," *Science*, 246:1309-1312, 1989.

Kerbel, "Inhibition of Tumor Angiogenesis as a Strategy to Circumvent Acquired Resistance to Anti-Cancer Therapeutic Agents," *BioEssays*, 13(I):31-36, 1991.

Leung et al., "Cloning, Expression During Development, and Evidence for release of a Trophic Factor for Ciliary Ganglion Neurons," *Neuron*, 8:1045-1053, 1992.

Leung et al., "Vascular Endothelial Growth Factor is a Secreted Angiogenic Mitogen," *Science*, 246:1306-1308, 1989.

Li et al., "Monoclonal Antibodies to Recombinant Human Vascular Endothelial Growth Factor (rHuVEGF)," *J. Cell. Biochem.*, Supp. 15F:251, Abstract CF417, 1991.

Pepper et al, "Potent Synergism Between Vascular Endothelial Growth Factor and Basic Fibroblast Growth Factor in the Induction of Angiogenesis In Vitro" *Biochem. Biophys. Res. Comm.*, 189(2):824-831, 1992.

Plouet et al., "Isolation and Characterization of a Newly Identified Endothelial cell Mitogen Produced by AtT-20 Cells," *EMBO*, 8(12):3801-3806, 1989.

Roberts and Palade, "Increased Microvascular Permeability and Endothelial Fenestration Induced by Vascular Endothelial Growth Factor," *J. Cell Sci.*, 108:2369-2379, 1995.

Senger et al., "A Highly Conserved Vascular Permeability Factor Secreted by a Variety of Human and Rodent Tumor Cell Lines," *Cancer Research*, 46:5629-5632, 1986.

Senger et al., "Purification and $NH_2$-Terminal Amino Acid Sequence of Guinea Pig Tumor-Secreted Vascular Permeability Factor," *Cancer Research*, 50:1774-1778, 1990.

Sioussat et al., "Anti-Peptide Antibodies to Vascular Permeability Factor," *J. Cell Biol.*, 115(3 part 2):p264A, Abstract No. 1528, 1991.

Tischer et al., "Vascular Endothelial Growth Factor: A New Member of the Platelet-Derived Growth Factor Gene Family," *Biochem. Biophys Res. Comm.*, 165(3): 1198-1206, 1989.

Van Brugen et al., "VEGF Antagonism Reduces Edema Formation and Tissue Damage After Ischemia/Reperfusion Injury in the Mouse Brain," *J. Clin. Invest.*, 104(11):1613-1620, 1999.

Weidner, "Tumor Angiogenesis and Metastasis-Correlation in Invasive Breast Carcinoma," *New. Eng. J. Med.*, 324(1):1-7, 1991.

Yeo et al., "Development of Time-Resolved Immunofluorometric Assay of Vascular Permeability," *Clin. Chem.*, 38(1):71-75, 1992.

Ben-Hur and Orenstein, "The Endothelium and Red Blood Cell as Potential Targets in PDT-Induced Vascular Stasis," *J. Radiat. Biol.*, 60(1/2):293-301, 1991.

Folkman, "Tumor Angiogenesis," *Adv. Cancer Res.*, 43:175-203, 1985.

Gschwind et al., "The Discovery of Receptor Tyrosine Kinases: Targets for Cancer Therapy," *Nature Reviews/Cancer*, 4:361-370, 2004.

Martiny-Baron and Marmé, "VEGF-Mediated Tumour Angiogenesis: A New Target for Cancer Therapy," *Curr. Opin. Biotech.*, 6:675-680, 1995.

McDonald and Baluk, "Significance of Blood Vessel Leakiness in Cancer," *Cancer Research*, 62:5381-5385, 2002.

Murata et al., "Immunohistochemical Detection of Extravasated Fibrinogen (Fibrin) in Human Diabetic Retina," *Graefe's Arch. Clin. Exp. Opthalmol.*, 230:428-431, 1992.

Risau, "What, if anything, is an Angiogenic Factor?" *Cancer Metastasis Rev.*, 15:149-151, 1996.

Senger et al., "Tumor Cells Secrete a Vascular Permeability Factor That Promotes Accumulation of Ascites Fluid," *Science*, 219:983-985, 1983.

Sioussat et al., "Inhibition of Vascular Permeability Factor (Vascular Endothelial Growth Factor) with Antipeptide Antibodies," *Arch. Biochem. Biophys.*, 301(1):15-20, 1993.

Wiig et al., "Interstitial Fluid Pressure in DMBA-Induced Rat Mammary Tumours," *Scand. J. Clin. Lab. Invest.*, 42:159-164, 1982.

Fishman et al., "Autoimmunity and Cancer—Beneficial Relationships: A New Concept for the Production of Human Monoclonal Antibodies (Review)," *Int. J. Oncol.*, 10:901-904, 1997.

Tschmelitsch et al., "Enhanced Antitumor Activity of Combination Radioimmunotherapy ($^{131}$I-Labeled Monoclonal Antibody A33) with chemotherapy (Fluorouracil)," *Cancer Res.*, 57:3181-3186, 1197, /lab/.

Storkebaum et al., "VEGF: Once Regarded as a Specific Angiogenic Factor, Now Implicated in Neuroprotection," *BioEssays*, 26:943-954, 2004.

Bicknell and Harris, "Anticancer Strategies Involving the Vasculature: Vascular Targeting and the Inhibition of Angiogenesis," *Seminars in Cancer Biology*, 3:399-407, 1992.

Bicknell and Harris, "Novel Growth Regulatory Factors and Tumour Angiogenesis," *Eur. J. Cancer*, 27(6):781-785, 1991.

Mansfield et al., "A Review of the Role of Radiation Therapy in the Treatment of Patients with Breast Cancer," *Seminars in Oncology*, 18(6):525-35, 1991.

Monyak & Levitt, "The Changing Role of Radiation Therapy in the Treatment of Primary Breast Cancer," *Investigative Radiology*, 24(6):483-94, 1989.

Bartelink et al., "Quality Assurance in Conservative Treatment of Early Brest Cancer. Report on a Consensus Meeting of the EORTC Radiotherapy and Breast Cancer Cooperative Groups and the EUSOMA (European Society of Mastology)," *Radiotherapy and Oncology*, 22(4):323-6, 1991.

Cox et al., "N$_2$ (Clinical) Non-Small Cell Carcinoma of the Lung: Prospective Trials of Radiation Therapy With Total Doses 60 GY by the Radiation Therapy Oncology Group," *International Journal of Radiation Oncology, Biology, Physics*, 20(1):169-71, 1991.

Kraft et al., "Role of Thoracic Radiotherapy Combined with Chemotherapy in Limited Stage Small Cell Lung Cancer (SCLC)," *Onkologie*, 13(4):253-8, 1990.

Rosenthal et al., "Randomized Trials of Adjuvant Radiation Therapy for Rectal Carcinoma: A Review," *Diseases of the Colon and Rectum*, 33(4):335-43, 1990.

Coia & Hanks, "The Role of Adjuvant Radiation in the Treatment of Rectal Cancer," *Seminars in Oncology*, 18(6):571-84, 1991.

Hanks, "Radiotherapy or Surgery for Prostate Cancer," *Acta Oncologica*, 30(2):231-37, 1991.

Lai et al., "The Effect of Overall Treatment Time on the Outcome of Definitive Radiotherapy for Localized Prostate Carcinoma: The Radiation Therapy Oncology Group 75-06 and 77-06 Experience," *Int. J. Radiation Oncology Biol. Phys.*, 21(4):925-33, 1991.

Krieger et al., "Fast Neutron Radiotherapy for Locally Advanced Prostate Cancer. Update of a Past Trial and Future Research Directions," *Urology*, 34(1):1-9, 1989.

Griffin et al., "Neutron Radiotherapy for Malignant Gliomas," *Am. J. Clin. Oncol.*, 12(4):311-5, 1989.

Shapiro et al., "Randomized trial of three chemotherapy regimens and two radiotherapy regimes in postoperative treatment of malignant glioma," *J. Neurosurgery*, 71(1):1-9, 1989.

Marcial et al., "Concomitant Cisplatin Chemotherapy and Radiotherapy in Advanced Mucosal Squamous Cell Carcinoma of the Head and Neck," *Cancer*, 66(9):1861-8; 1990.

Lee et al., "A Phase I/II Study of the Hypoxic Cell Sensitizer Misonidazole as an Adjunct to High Fractional Dose Radiotherapy in Patients with Unrespectable Squamous Cell Carcinoma of the Head and Neck: A RTOG Randomized Study (#79-04)," *Int. J. Radiation Oncology Biol. Phys.*, 16:465-70, 1989.

Moore, "Role of radiation therapy in ovarian cancer," *Current Opinion in Obstetrics & Gynecology*, 2(1):64-8, 1990.

Stehman et al., "Carcinoma of the Cervix Treated with Radiation Therapy I," *Cancer*, 67(11):2776-85, 1991.

Okawa et al., "Phase II Randomized Clinical Trial of LC9018 Concurrently Used with Radiation in the Treatment of Carcinoma of the Uterine Cervix. Its Effect on Tumor Reduction and Histology," *Cancer*, 64(9):1769-76, 1989.

Merrick et al., "Intraoperative Radiation Therapy for Pancreatic, Biliary and Gastric Carcinoma: The US Experience," *Frontiers of Radiation Therapy and Oncology*, 25:246-57, 1991.

Steel and Peckham, "Exploitable Mechanisms in Combined Radiotherapy-Chemotherapy: The Concept of Additivity," *Int. J. Radiation Oncology Biol. Phys.*, 5:85-91, 1979.

Thomas et al., "Concurrent Chemoradiation in Advanced Cervical Cancer," *Gynecologic Oncology*, 38(3):446-51, 1990.

Berek et al., "Concurrent Cisplatin and 5-Fluorouracil Chemotherapy and Radiation Therapy Advanced-Stage Squamous Carcinoma of the Vulva," *Gynecologic Oncology*, 42(3):197-201, 1991.

John et al., "Radiotherapy Alone and Chemoradiation for Nonmetastatic Esophageal Carcinoma. A Critical Review of Chemoradiation," *Cancer*, 63(12):2397-403, 1989.

MacFarlane et al., "Improved results of surgical treatment for esophageal and gastroesophageal junction carcinomas after preoperative combined chemotherapy and radiation," *J. Thoracic and Cardiovascular Surgery*, 95(3):415-22, 1988.

Lopez et al., "Squamous Cell Carcinoma of the Anal Canal," *American Journal of Surgery*, 162(6):580-4, 1991.

Nigro et al., "Dynamic management of squamous cell cancer of the anal canal," *Investigational New Drugs*, 7(1):83-9, 1989.

Brekken et al., "Vascular Endothelial Growth Factor as a Marker of Tumor Endothelium," *Cancer Res.*, 58(9):1952-1959, 1998.

Keyt et al., "Identification of Vascular Endothelial Growth Factor Determinants for Binding KDR and FLT-1 Receptors. Generation of Receptor-Selective VEGF Variants by Site-Directed Mutagenesis," *J. Biol. Chem.*, 271(10):5638-46, 1996.

Campbell, "General Properties and Applications of Monoclonal Antibodies" In 'Monoclonal Antibody Technology: The Production and Characterization of Rodent and Human Hybridomas', *Elsevier Science*, NY, 1986, pp. 1-33.

Freshney, In 'Culture of Animal Cells, A Manual of Basic Technique', *Alan R. Liss, Inc.*, New York, 1983, pp. 3-4.

Hillman et al., "Systemic Treatment with Interleukin-4 Induces Regression of Pulmonary Mctastases in a Murine Renal Cell Carcinoma Model," *Cell Immunol.*, 160:257-263, 1995.

Holash et al., "New Model of Tumor Angiogenesis: Dynamic Balance Between Vessel Regression and Growth Mediated by Angiopoietins and VEGF," *Oncogene*, 18:5356-5362, 1999.

Jain, "Barriers to Drug Delivery in Solid Tumors," *Scientific American*, 271(1):58-65, 1994.

Jordan et al., "Case Review: A 39-Year-Old-Man with Acute Hemolytic Crisis Secondary to Intravenous Injection of Hydrogen Peroxide," *J. Emergency Nursing*, 17:8-10, 1991.

Ran et al., "Increased Exposure of Anionic Phospholipids on the Surface of Tumor Blood Vessels," *Cancer Res.*, 62:6132-6140, 2002.

Symons et al., "Hydrogen Peroxide: A Potent Cytotoxic Agent Effective in Causing Cellular Damage and Used in the Possible Treatment for Certain Tumours," *Medical Hypotheses*, 57:56-58, 2001.

Weiner, "An Overview of Monoclonal Antibody Therapy of Cancer," *Seminars in Oncology*, 26(4):41-50, 1999.

Demur et al., "Effects of an Anti HLA-DR Immunotoxin on Leukaemia Cells and Hematopoietic Progenitors," *Leukemia Research*, 13(12):1047-1054, 1989.

Bregni et al., "Elimination of Clonogenic Tumor Cells from Human Bone Marrow Using a Combination of Monoclonal Antibody:Ricin A Chain Conjugates," *Cancer Research*, 46:1208-1213, 1986.

Lowe et al., "Studies on the Reappearance of MHC Class II Antigens on Cells of a Variant Human Lymphoblastoid Line," *Immunology Letters*, 12:263-269, 1986.

Nakahara et al., "The Effectiveness of Anti-Ia-Immunotoxins in the Suppression of MLR," *Transplantation*, 42(2):205-211, 1986.

Nakahara et al., "The Effectiveness of Anti-Ia-Immunotoxins in the Suppression of MLR," *Transplantation*, 40(1):62-67, 1985.

Thorpe et al., "Modification of the Carbohydrate in Ricin with Metaperiodate—Cyanoborohydride Mixtures," *Eur. J. Biochem.*, 147:197-206, 1985.

European Search Report for European Divisional Application No. 02024529.6, dated May 14, 2003.

Bach, American Heart Association. 7$^{th}$ National Conference on Thrombosis and Hemostasis, Nov. 17-20, 1986.

Broze et al., "Purification of Human Brain Tissue Factor," *J. Biol. Chem.*, 260:10917-10920, 1985.

Carson et al., "Monoclonal Antibodies Against Bovine Tissue Factor, Which Block Interaction With Factor VII," *Blood*, 66(1):152-156, 1985.

Giercksky, "The Procoagulant Activity of Adipose Tissue," *Scand J., Haematol.*, 19:385-395, 1977.

Guha et al., "Affinity Purification of Human Tissue Factor: Interaction of Factor VII and Tissue Factor in Detergent Micelles," *Proc. Natl. Acad. Sci. USA*, 83:299-302, 1986.

Morrissey et al., "Resolution of Monomeric and Heterodimeric Forms of Tissue Factor, the High-Affinity Cellular Receptor for Factor VII," *Throm. Res.*, 50:481-493, 1988.

Morrissey et al., American Heart Association. 7$^{th}$ National Conference on Thrombosis and Hemostasis, Nov. 17-20, 1986.

Neuenschwander and Morrissey, "Deletion of the Membrane Anchoring Region of Tissue Factor Abolishes Autoactivation of Factor VII but Not Cofactor Function," *J. Biol. Chem.*, 267:14477, 1992.

Scarpati et al., "Human Tissue Factor: cDNA Sequence and Chromosome Localization of the Gene," *Biochemistry*, 26:5234-5238, 1987.

Spicer et al., "Isolation of cDNA Clones Coding for Human Tissue Factor: Primary Structure of the Protein and cDNA," *Proc. Nat., Acad. Sci. USA*, 84:5148-5152, 1987.

Van der Besselaar and Bertina, "Interaction of Thromboplastin Apoprotein of Different Tissues with Concanavalin A—Evidence for Heterogeneous Glycosylation of the Human Apoprotein," *Throm. Haemostas*, 52:192-195, 1984.

Waxman et al., "Tissue Factor and Its Extracellular Soluble Domain: The Relationship Between Intermolecular Association with Factor VIIa and Enzymatic Activity of the Complex," *Biochemistry*, 31:3998-4003, 1992.

Wildgoose et al., "Measurement of Basal Levels of Factor VIIa in Hemophilia A and B Patients," *Blood*, 80:25, 1992.

Dienst et al., "Specific Occlusion of Murine and Human Tumor Vasculature by VCAM-1-Targeted Recombinant Fusion Proteins," *J. Natl. Cancer Inst.*, 97(10):733-746, 2005.

Narazaki, & Tosato, Targeting Coagulation to the Tumor Microvasculature: Perspectives and Therapeutic Implications From Preclinical Studies, *J. Natl. Cancer Inst.*, 97(10):705-707, 2005.

\* cited by examiner

Antibody-tTF

Antibody-ctTF and antibody-tTFC

A representative antibody, also including IgM, ScFv, Fab, etc.

n = 1-20 n = 1-20

Wherein
SC = selectively cleavable
including, e.g.
– disulfides
and
– peptide linkers Wherein —tTF— includes Wherein ⁀⁀⁀ is a membrane inserting moiety

COMBINED METHODS FOR TUMOR COAGULATION AND TUMOR TREATMENT

The present application is a continuation of U.S. patent application Ser. No. 09/483,679, filed Jan. 14, 2000, now issued as U.S. Pat. No. 6,749,853; which is a continuation of U.S. patent application Ser. No. 08/482,369, filed Jun. 7, 1995, now issued as U.S. Pat. No. 6,093,399; which is a continuation-in-part of U.S. patent application Ser. No. 08/273,567, filed Jul. 11, 1994 now abandoned; which is a continuation-in-part of U.S. patent application Ser. No. 08/205,330, filed Mar. 2, 1994, now issued as U.S. Pat. No. 5,855,866; which is a continuation-in-part of U.S. patent application Ser. No. 07/846,349, filed Mar. 5, 1992 now abandoned. The entire text and figures of the above-referenced disclosures are specifically incorporated herein by reference without disclaimer.

This invention was made with government support under Contract No. P01 HL 16411 by NIH. The U.S. government has certain rights in the invention.

BACKGROUND OF THE INVENTION

1. Field of the Invention

The present invention relates generally to the fields of blood vessels and of coagulation. More particularly, it provides a variety of growth factor-based and immunological reagents, including bispecific antibodies, for use in achieving specific coagulation.

2. Description of the Related Art

Advances in the chemotherapy of neoplastic disease have been realized during the last 30 years. This includes some progress in the development of new chemotherapeutic agents and, more particularly, the development of regimens for concurrent administration of drugs. A significant understanding of the neoplastic processes at the cellular and tissue level, and the mechanism of action of basic antineoplastic agents, has also allowed advances in the chemotherapy of a number of neoplastic diseases, including choriocarcinoma, Wilm's tumor, acute leukemia, rhabdomyosarcoma, retinoblastoma, Hodgkin's disease and Burkitt's lymphoma. Despite the advances that have been made in a few tumors, though, many of the most prevalent forms of human cancer still resist effective chemotherapeutic intervention.

A significant underlying problem that must be addressed in any treatment regimen is the concept of "total cell kill." This concept holds that in order to have an effective treatment regimen, whether it be a surgical or chemotherapeutic approach or both, there must be a total cell kill of all so-called "clonogenic" malignant cells, that is, cells that have the ability to grow uncontrolled and replace any tumor mass that might be removed. Due to the ultimate need to develop therapeutic agents and regimens that will achieve a total cell kill, certain types of tumors have been more amenable than others to therapy. For example, the soft tissue tumors (e.g., lymphomas), and tumors of the blood and blood-forming organs (e.g., leukemias) have generally been more responsive to chemotherapeutic therapy than have solid tumors such as carcinomas.

One reason for the susceptibility of soft and blood-based tumors to chemotherapy is the greater physical accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. Increasing the dose of chemotherapeutic agents most often results in toxic side effects, which generally limits the effectiveness of conventional anti-tumor agents.

The strategy to develop successful antitumor agents involves the design of agents that will selectively kill tumor cells, while exerting relatively little, if any, untoward effects against normal tissues. This goal has been elusive to achieve, though, in that there are few qualitative differences between neoplastic and normal tissues. Because of this, much research over the years has focused on identifying tumor-specific "marker antigens" that can serve as immunological targets both for chemotherapy and diagnosis. Many tumor-specific, or quasi-tumor-specific ("tumor-associated"), markers have been identified as tumor cell antigens that can be recognized by specific antibodies. Unfortunately, it is generally the case that tumor specific antibodies will not in and of themselves exert sufficient antitumor effects to make them useful in cancer therapy.

More recently, immunotoxins have been employed in an attempt to selectively target cancer cells. Immunotoxins are conjugates of a specific targeting agent, typically a tumor-directed antibody or fragment, with a cytotoxic agent, such as a toxin moiety. The targeting agent is designed to direct the toxin to cells carrying the targeted antigen and to kill such cells. "Second generation" immunotoxins have now been developed, for example, those that employ deglycosylated ricin A chain to prevent entrapment of the immunotoxin by the liver and reduce hepatotoxicity (Blakey et al., 1987a;b), and those with new crosslinkers to endow the immunotoxins with higher in vivo stability (Thorpe et al., 1988).

Immunotoxins have proven effective at treating lymphomas and leukemias in mice (Thorpe et al., 1988; Ghetie et al., 1991; Griffin et al., 1988a;b) and in man (Vitetta et al., 1991). However, lymphoid neoplasias are particularly amenable to immunotoxin therapy because the tumor cells are relatively accessible to blood-borne immunotoxins. Also, it is possible to target normal lymphoid antigens because the normal lymphocytes, which are killed along with the malignant cells during therapy, are rapidly regenerated from progenitors lacking the target antigens.

In contrast with their efficacy in lymphomas, immunotoxins have proved relatively ineffective in the treatment of solid tumors (Weiner et al., 1989; Byers et al., 1989). The principal reason for this is that solid tumors are generally impermeable to antibody-sized molecules: specific uptake values of less than 0.001% of the injected dose/g of tumor are not uncommon in human studies (Sands et al., 1988; Epenetos et al., 1986). Another significant problem is that antigen-deficient mutants can escape being killed by the immunotoxin and regrow (Thorpe et al., 1988).

Furthermore, antibodies that enter the tumor mass do not distribute evenly for several reasons. Firstly, the dense packing of tumor cells and fibrous tumor stromas present a formidable physical barrier to macromolecular transport and, combined with the absence of lymphatic drainage, create an elevated interstitial pressure in the tumor core which reduces extravasation and fluid convection (Baxter et al., 1991; Jain, 1990). Secondly, the distribution of blood vessels in most tumors is disorganized and heterogeneous, so some tumor cells are separated from extravasating antibody by large diffusion distances (Jain, 1990). Thirdly, all of the antibody entering the tumor may become adsorbed in perivascular regions by the first tumor cells encountered, leaving none to reach tumor cells at more distant sites (Baxter et al., 1991; Kennel et al., 1991).

Thus, it is quite clear that a significant need exists for the development of novel strategies for the treatment of solid tumors. One approach involves the targeting of agents to the vasculature of the tumor, rather than to tumor cells. Solid tumor growth is highly dependent on the vascularization of the tumor and the growth of tumor cells can only be maintained if the supply of oxygen, nutrients and other growth factors and the efflux of metabolic products are satisfactory. Indeed, it has been observed that many existing therapies may already have, as part of their action, a vascular-mediated mechanism of action (Denekamp, 1990).

The present inventors propose that targeting the vasculature will likely deprive the tumor of life sustaining events and result in reduced tumor growth rate or tumor cell death. This approach is contemplated to offer several advantages over direct targeting of tumor cells. Firstly, the target cells are directly accessible to intravenously administered therapeutic agents, permitting rapid localization of a high percentage of the injected dose (Kennel et al., 1991). Secondly, since each capillary provides oxygen and nutrients for thousands of cells in its surrounding 'cord' of tumor, even limited damage to the tumor vasculature could produce an avalanche of tumor cell death (Denekamp, 1990; Denekamp, 1984). Finally, the outgrowth of mutant endothelial cells, lacking a target antigen, is unlikely because they are normal cells.

At the present time, it is generally accepted that for tumor vascular targeting to succeed, antibodies are required that recognize tumor endothelial cells but not those in normal tissues. Although several antibodies have been raised (Duijvestijn et al., 1987; Hagemeier et al., 1986; Bruland et al., 1986; Murray et al., 1989; Schlingemann et al., 1985), none have shown a high degree of specificity. Also, there do not appear to be reports of any particular agents, other than the aforementioned toxins, that show promise as the second agent in a vascular targeted antibody conjugate. Thus, unfortunately, while vascular targeting presents certain theoretical advantages, effective strategies incorporating these advantages have yet to be developed.

SUMMARY OF THE INVENTION

The present invention overcomes the limitations of the prior art by providing novel compositions and methods for use in achieving specific coagulation, for example, coagulation in tumor vasculature, with limiting side-effects. The invention, in a general and overall sense, concerns various novel immunological and growth factor-based bispecific compositions capable of stimulating coagulation in disease-associated vasculature, and methods for their preparation and use. Provided are a series of novel approaches for the treatment and/or diagnosis (imaging) of vascularized tumors.

The invention provides binding ligands that may generally be described as "bispecific binding ligands". Such ligands comprise a "first binding region" that typically binds to a disease-related target cell, such as a tumor cell, or to a component associated with such a cell; to some component associated with disease-related vasculature, e.g., tumor vasculature; or to a component of, or associated with, disease-associated stroma. The first binding region is operatively associated with or linked to a "coagulating agent", which may be either a coagulation factor itself or may be a second binding region that is capable of binding to a coagulation factor.

The binding ligands of the invention are described as "bispecific" as they are "at least" bispecific, i.e., they comprise, at a minimum, two functionally distinct regions. Compositions and methods using other constructs, such as trispecific and mutlispecific binding ligands, are also included within the scope of the invention. Combined compositions, kits and methods of using the bispecific coagulating ligands described herein in conjunction with other effectors, such as other immunological- and growth-factor-based compositions, antigen-inducing agents, immunostimulants, immunosuppressants, chemotherapeutic drugs, and the like, are also contemplated.

The first binding regions, and any second binding regions, may be antibodies or fragments thereof. As used herein, the term "antibody" is intended to refer broadly to any immunologic binding agent such as IgG, IgM, IgA, IgD and IgE. Generally, IgG or IgM are preferred because they are the most common antibodies in the physiological situation and because they are most easily made in a laboratory setting. Monoclonal antibodies (MAbs) are recognized to have certain advantages, e.g., reproducibility and large-scale production, and their use is generally preferred. Engineered antibodies, such as recombinant antibodies and humanized antibodies, also fall within the scope of the invention.

Where antigen binding regions of antibodies are employed as the binding and targeting agent, a complete antibody molecule may be employed. Alternatively, a functional antigen binding region may be used, as exemplified by Fv, scFv (single chain Fv), Fab', Fab, Dab or F(ab')$_2$ fragment of an antibody. The techniques for preparing and using various antibody-based constructs are well known in the art and are further described herein.

The coagulation factor portion of the binding ligands is formed so that it maintains significant functional capacity, i.e., it is in a form so that, when delivered to the target region, it still retains its ability to promote blood coagulation or clotting. However, in certain embodiments, the coagulation factor portion of the binding ligands will be less active than, for example, the natural counterpart of the coagulant, and the factor will achieve the desired level of activity only upon delivery to the target area. One such example is a vitamin K-dependent coagulation factor that lacks the Gla modification, which will nonetheless achieve significant functional activity upon binding of the first binding region of the bispecific ligand to a membrane environment.

Where a second binding region is used to bind a coagulation factor, it is generally chosen so that it recognizes a site on the coagulation factor that does not significantly impair its ability to induce coagulation. Likewise, where a coagulation factor is covalently linked to a first binding agent, a site distinct from its functional coagulating site is generally used to join the molecules.

The "first binding region" of the bispecific ligands of the invention may be any component that binds to a designated target site, i.e., a site associated with a tumor region or other disease site in which coagulation is desired. The target molecule, in the case of tumor targeting, will generally be present at a higher concentration in the tumor site than in non-tumor sites. In certain preferred embodiments, the targeted molecules, whether associated with tumor cells, tumor vascular cells, tumor-associated stroma, or other components, will be restricted to such cells or other tumor-associated entities, however, this is not a requirement of the invention.

In this regard, it should be noted that tumor vasculature is 'prothrombotic' and is predisposed towards coagulation. It is thus contemplated that a targeted coagulant is likely to preferentially coagulate tumor vasculature while not coagulating normal tissue vasculature, even if other normal cells or body components, particularly, the normal endothelial cells or even stroma, express significant levels of the target molecule. This approach is therefore envisioned to be safer for use in humans, e.g., as a means of treating cancer, than that of targeting a toxin to tumor vasculature.

In certain embodiments, the first binding regions contemplated for use in this invention may be directed to a tumor cell component or to a component associated with a tumor cell. In targeting generally to a tumor cell, it is believed that the first binding ligand will cause the coagulation factor component of the bispecific binding ligand to concentrate on those perivascular tumor cells nearest to the blood vessel and thus trigger coagulation of tumor blood vessels, giving the bispecific binding ligand significant utility.

A first binding region may therefore be a component, such as an antibody or other agent, that binds to a tumor cell. Agents that "bind to a tumor cell" are defined herein as ligands that bind to any accessible component or components of a tumor cell, or that bind to a component that is itself bound to, or otherwise associated with, a tumor cell, as further described herein.

The majority of such tumor-binding ligands are contemplated to be agents, particularly antibodies, that bind toga cell surface tumor antigen or marker. Many such antigens are known, as are a variety of antibodies for use in antigen binding and tumor targeting. The invention thus includes first binding regions, such as antigen binding regions of antibodies, that bind to an identified tumor cell surface antigen, such as those listed in Table I, and first binding regions that preferentially or specifically bind to an intact tumor cell, such as binding to a tumor cell listed in Table II.

Currently preferred examples of tumor cell binding regions are those that comprise an antigen binding region of an antibody that binds to the cell surface tumor antigen $p185^{HER2}$, milk mucin core protein, TAG-72, Lewis a or carcinoembryonic antigen (CEA). Another group of currently preferred tumor cell binding regions are those that comprise an antigen binding region of an antibody that binds to a tumor-associated antigen that binds to the antibody 9.2.27, OV-TL3, MOv18, B3, KS1/4, 260F9 or D612.

The antibody 9.2.27 binds to high $M_r$ melanoma antigens, OV-TL3 and MOv18 both bind to ovarian-associated antigens, B3 and KS1/4 bind to carcinoma antigens, 260F9 binds to breast carcinoma and D612 binds to colorectal carcinoma. Antigen binding moieties that bind to the same antigen as D612, B3 or KS1/4 are particularly preferred. D612 is described in U.S. Pat. No. 5,183,756, and has ATCC Accession No. HB 9796; B3 is described in U.S. Pat. No. 5,242,813, and has ATCC Accession No. HB 10573; and recombinant and chimeric KS1/4 antibodies are described in U.S. Pat. No. 4,975,369; each incorporated herein by reference.

In tumor cell targeting, where the tumor marker is a component, such as a receptor, for which a biological ligand has been identified, the ligand itself may also be employed as the targeting agent, rather than an antibody. Active fragments or binding regions of such ligands may also be employed.

First binding regions for use in the invention may also be components that bind to a ligand that is associated with a tumor cell marker. For example, where the tumor antigen in question is a cell-surface receptor, tumor cells in vivo will have the corresponding biological ligand, e.g., hormone, cytokine or growth factor, bound to their surface and available as a target. This includes both circulating ligands and "paracrine-type" ligands that may be generated by the tumor cell and then bound to the cell surface.

The present invention thus further includes first binding regions, such as antibodies and fragments thereof, that bind to a ligand that binds to an identified tumor cell surface antigen, such as those listed in Table I, or that preferentially or specifically binds to one or more intact tumor cells. Additionally, the receptor itself, or preferably an engineered or otherwise soluble form of the receptor or receptor binding domain, could also be employed as the binding region of a bispecific coagulating ligand.

In further embodiments, the first binding region may be a component that binds to a target molecule that is specifically or preferentially expressed in a disease site other than a tumor site. Exemplary target molecules associated with other diseased cells include, for example, PSA associated with Benign Prostatic Hyperplasia (BPH) and FGF associated with proliferative diabetic retinopathy. It is believed that an animal or patient having one of the above diseases would benefit from the specific induction of coagulation in the disease site.

This is the meaning of "diseased cell" in the present context, i.e., it is a cell that is connected with a disease or disorder, which cell expresses, or is otherwise associated with, a targetable component that is present at a higher concentration in the disease sites and cells in comparison to its levels in non-diseased sites and cells. This includes targetable components that are associated with the vasculature in the disease sites.

Exemplary first binding regions for use in targeting and delivering a coagulant to other disease sites include antibodies, such as anti-PSA (BPH), and GF82, GF67 and 3H3 that bind to FGF. Biological binding ligands, such as FGF, that bind to the relevant receptor, in this case the FGF receptor, may also be used. Antibodies against vascular targets may also be employed, as described below. The targeting of the stroma or endothelial cells provides a powerful means of treating other diseases where the "diseased cell" itself may not be associated with a strong or unique marker antigen.

In further embodiments, the first binding regions of the invention will be components that are capable of binding to a component of disease-associated vasculature, i.e., a region of vasculature in which specific coagulation would be advantageous to the animal or patient. First binding regions capable of binding to a component specifically or preferentially associated with tumor vasculature are currently preferred. "Components of tumor vasculature" include both tumor vasculature endothelial cell surface molecules and any components, such as growth factors, that may be bound to these cell surface receptors or molecules. These include markers found, expressed, accessible to binding or otherwise localized on the cell surfaces of tumor-associated vascular endothelium as compared to normal vasculature.

Certain preferred binding ligands are antibodies, and fragments thereof, that bind to cell surface receptors and antibodies that bind to the corresponding biological ligands of these receptors. Exemplary antibodies are those that bind to MHC Class II proteins, VEGF/VPF receptors,. FGF receptors, TGFβ receptors, a TIE (tyrosine kinase-immunoglobulin-epidermal growth factor-like receptor, including TIE-1 and TIE-2), VCAM-1, P-selectin, E-selectin, $\alpha_v\beta_3$ integrin, pleiotropin, endosialin and endoglin.

First binding regions that comprise an antigen binding region of an antibody that binds to endoglin are one group of preferred agents. These are exemplified by antibodies and fragments that bind to the same epitope as the monoclonal antibody TEC-4 or the monoclonal antibody TEC-11, deposited Mar. 12, 1997 with the American Type Culture Collection (ATCC), 12301 Parklawn Drive, Rockville, Md. 20852, and given the ATCC Accession numbers ATCC HB-12312 and ATCC HB-12311, respectively. The present address of ATCC is 10801 University Blvd., Manassas, Va. 20110-2209.

Antigen binding region of antibodies that bind to the VEGF receptor are another group of preferred agents. These are particularly exemplified by antibodies and fragments that bind to the same epitope as the monoclonal antibody 3E11, 3E7, 5G6, 4D8, 10B10 or TEC-110. Anti-VEGF antibodies with binding specificities substantially the same as any one of the antibodies termed 1B4, 4B7, 1B8, 2C9, 7D9, 12D2, 12D7, 12E10, 5E5, 8E5, 5E11, 7E11, 3F5, 10F3, 1F4, 2F8, 2F9, 2F10, 1G6, 1G11, 3G9, 9G11, 10G9, GV97, GV39, GV97γ, GV39γ, GV59 or GV14 may also be used. Further suitable anti-VEGF antibodies include 4.6.1., A3.13.1, A4.3.1 and B2.6.2 (Kim et. al., 1992); SBS94.1 (Oncogene Science); G143-264 and G143-856 (Pharmingen).

Further useful antibodies are those that bind to a ligand that binds to a tumor vasculature cell surface receptor. Antibodies that bind to VEGF/VPF, FGF, TGFβ, a ligand that binds to a TIE, a tumor-associated fibronectin isoform, scatter factor, hepatocyte growth factor (HGF), platelet factor 4 (PF4), PDGF (including PDGFa and PDGFb) and TIMP (a tissue inhibitor of metalloproteinases, including TIMP-1, TIMP-2 and TIMP-3) are therefore useful in these embodiments, with antibodies that bind to VEGF/VPF, FGF, TGFβ, a ligand that binds to a TIE or a tumor-associated fibronectin isoform often being preferred.

In still further embodiments, it is contemplated that markers specific for tumor vasculature may be those that have been first induced, i.e., their expression specifically manipulated by the hand of man, allowing subsequent targeting using a binding ligand, such as an antibody.

Exemplary inducible antigens include those inducible by a cytokine, e.g., IL-1, IL-4, TNF-α, TNF-β or IFN-γ, as may be released by monocytes, macrophages, mast cells, helper T cells, CD8-positive T-cells, NK cells or even tumor cells. Examples of the induced targets are E-selectin, VCAM-1, ICAM-1, endoglin and MHC Class II antigens. When using MHC Class II induction, the suppression of MHC Class II in normal tissues is generally required, as may be achieved using a cyclosporin, such as Cyclosporin A (CsA), or a functionally equivalent agent.

Further inducible antigens include those inducible by a coagulant, such as by thrombin, Factor IX/IXa, Factor X/Xa, plasmin or a metalloproteinase (matrix metalloproteinase, MMP). Generally, antigens inducible by thrombin will be used. This group of antigens includes P-selectin, E-selectin, PDGF and ICAM-1, with the induction and targeting of P-selectin and/or E-selectin being generally preferred.

Antibodies that bind to epitopes that are present on ligand-receptor complexes, but absent from both the individual ligand and receptor may also be used. Such antibodies will recognize and bind to a ligand-receptor complex, as presented at the cell surface, but will not bind to the free ligand or uncomplexed receptor. A "ligand-receptor complex", as used herein, therefore refers to the resultant complex produced when a ligand, such as a growth factor, specifically binds to its receptor, such as a growth factor receptor. This is exemplified by the VEGF/VEGF, receptor complex.

It is envisioned that such ligand-receptor complexes will likely be present in a significantly higher number on tumor-associated endothelial cells than on non-tumor associated endothelial cells, and may thus be targeted by anti-complex antibodies. Anti-complex antibodies include those antibodies and fragments thereof that bind to the same epitope as the monoclonal antibody 2E5, 3E5 or 4E5.

In further embodiments, the first binding regions contemplated for use in this invention will bind to a component of disease-associated stroma, such as a component of tumor-associated stroma. This includes antigen binding regions of antibodies that bind to basement membrane components, activated platelets and inducible tumor stroma components, especially those inducible by a coagulant, such as thrombin. "Activated platelets" are herein defined as a component of tumor stroma, one reason for which being that they bind to the stroma when activated.

Preferred targetable elements of tumor-associated stroma are currently the tumor-associated fibronectin isoforms,.

Fibronectin isoforms are ligands that bind to the integrin family of receptors. Tumor-associated fibronectin isoforms are available, e.g., as recognized by the MAb BC-1. This Mab, and others of similar specificity, are therefore preferred agents for use in the present invention. Fibronectin isoforms, although stromal components, bind to endothelial cells and may thus be considered as a targetable vascular endothelial cell-bound ligand in the context of the invention.

Another group of preferred anti-stromal antibodies are those that bind to RIBS, the receptor-induced binding site, on fibrinogen. RIBS is a targetable antigen, the expression of which in stroma is dictated by activated platelets. Antibodies that bind to LIBS, the ligand-induced binding site, on activated platelets are also useful.

One further group of useful antibodies are those that bind to tenascin, a large molecular weight extracellular glycoprotein expressed in the stroma of various benign and malignant tumors. Antibodies such as those described by Shrestha et. al. (1994) and 143DB7C8, described by Tuominen & Kallioinen (1994), may thus be used as the binding portions of the coaguligands.

"Components of disease- and tumor-associated stroma" include various cell types, matrix components, effectors and other molecules or components that may be considered, by some, to be outside the narrowest definition of "stroma", but are nevertheless targetable entities that are preferentially associated with a disease region, such as a tumor.

Accordingly, the first binding region may be an antibody or ligand that binds to a smooth muscle cell, a pericyte, a fibroblast, a macrophage, an infiltrating lymphocyte or leucocyte. First binding regions may also bind to components of the connective tissue, and include antibodies and ligands that bind to, e.g., fibrin, proteoglycans, glycoproteins, collagens, and anionic polysaccharides such as heparin and heparin-like compounds.

In other preferred embodiments, the vasculature and stroma binding ligands of the invention will be binding regions that are themselves biological ligands, or portions thereof, rather than an antibody. "Biological ligands" in this sense will be those molecules that bind to or associate with cell surface molecules, such as receptors, that are accessible in the stroma or on vascular cells; as exemplified by cytokines, hormones, growth factors, and the like. Any such growth factor or ligand may be used so long as it binds to the disease-associated stroma or vasculature, e.g., to a specific biological receptor present on the surface of a tumor vasculature endothelial cell.

Suitable growth factors for use in these aspects of the invention include, for example, VEGF/VPF (vascular endothelial cell growth factor/vascular permeability factor), FGF (the fibroblast growth factor family of proteins), TGFβ (transforming growth factor B), a ligand that binds to a TIE, a tumor-associated fibronectin isoform, scatter factor, hepatocyte growth factor (HGF), platelet factor 4 (PF4), PDGF (platelet derived growth factor), TIMP or even IL-8, IL-6 or Factor XIIIa. VEGF/VPF and FGF will often be preferred.

Targeting an endothelial cell-bound component, e.g., a cytokine or growth factor, with a binding ligand construct based on a known receptor is also contemplated. Generally, where a receptor is used as a targeting component, a truncated or soluble form of the receptor will be employed. In such embodiments, it is particularly preferred that the targeted endothelial cell-bound component be a dimeric ligand, such as VEGF. This is preferred as one component of the dimer will already be bound to the cell surface receptor in situ, leaving the other component of the dimer available for binding the soluble receptor portion of the bispecific coagulating ligand.

The use of bispecific, or tri- or multi-specific, ligands that include at least one targeting region capable of binding to a component of disease-associated vasculature has the advantage that vascular endothelial cells, and disease-associated agents such as activated platelets, are similar in different diseases, and particularly in different tumors. This phenomenon makes it feasible to treat numerous diseases and types of cancer with one pharmaceutical, rather than having to tailor the agent to each individual disease or specific tumor type.

The compositions and methods of the present invention are thus suitable for use in treating both benign and malignant diseases that have a vascular component. Such vasculature-associated diseases include benign growths, such as BPH, diabetic retinopathy, vascular restenosis, arteriovenous malformations (AVM), meningioma, hemangioma, neovascular glaucoma and psoriasis. Also included within this group are synovitis, dermatitis, endometriosis, angiofibroma, rheumatoid arthritis, atherosclerotic plaques, corneal graft neovascularization, hemophilic joints, hypertrophic scars, osler-weber syndrome, pyogenic granuloma retrolental fibroplasia, scleroderma, trachoma, and vascular adhesions. Each of the above diseases are known to have a common angio-dependent pathology, it is thus contemplated that achieving coagulation in the disease site would prove beneficial.

The bispecific binding ligand-coagulation factor conjugates of the present invention may be conjugates in which the two or more components are covalently linked. For example, by using a biochemical or chemical crosslinker and, preferably, one that has reasonable stability in blood, as exemplified by SMPT. The components may also be linked using the well-known avidin (or streptavidin) and biotin combination. Various cross-linkers, avidin:biotin compositions and combinations, and techniques for preparing conjugates, are well known in the art and are further described herein.

Alternatively, such bispecific coagulating agents may be fusion proteins prepared by molecular biological techniques, i.e., by joining a gene (or cDNA) encoding a binding ligand or region to a gene (or cDNA) encoding a coagulation factor. This is well known in the art and is further described herein. Typically, an expression vector is prepared that comprises, in the same reading frame, a DNA segment encoding the first binding region operatively linked to a DNA segment encoding the coagulation factor and expressing the vector in a recombinant host cell so that it produces the encoded fusion protein.

Coagulation factors for use in the invention may comprise one of the vitamin K-dependent coagulant factors, such as Factor II/IIa, Factor VII/VIIa, Factor IX/IXa or Factor X/Xa. Factor V/Va, VIII/VIIIa, Factor XI/XIa, Factor XII/XIIa and Factor XIII/XIIIa may also be used.

Particular aspects concern the vitamin K-dependent coagulation factors that lack the Gla modification. Such factors may be prepared by expressing a vitamin K-dependent coagulation factor-encoding gene in a procaryotic host cell (which cells are unable to effect the Glu to Gla modification). The factors may also be prepared by making an engineered coagulation factor gene that encodes a vitamin K-dependent coagulation factor lacking the necessary or "corresponding" Glutamic acid residues, and then expressing the engineered gene in virtually any recombinant host cell. Equally, such a coagulation factor may be prepared by treating the vitamin K-dependent coagulation factor protein to remove or alter the corresponding Glutamic acid residues.

Preferred coagulation factors for use in the binding ligands of the invention are Tissue Factor and Tissue Factor derivatives. One group of useful Tissue Factors are those mutants deficient in the ability to activate Factor VII. A Tissue Factor may be rendered deficient in the ability to activate Factor VII by altering one or more amino acids from the region generally between about position 157 and about position 167 in the amino acid sequence. Exemplary mutants are those wherein Trp at position 158 is changed to Arg; wherein Ser at position 162 is changed to Ala; wherein Gly at position 164 is changed to Ala; and the double mutant wherein Trp at position 158 is changed to Arg and Ser at position 162 is changed to Ala.

Further preferred Tissue Factor derivatives are truncated Tissue Factors, dimeric or even polymeric Tissue Factors and dimeric, or even polymeric, truncated Tissue Factors.

The present invention further provides novel Tissue Factor constructs that comprise a Tissue Factor or derivative operatively linked to at least one other Tissue Factor or derivative. Truncated Tissue Factors are preferred, with truncated Tissue Factors that have been modified to comprise a hydrophobic membrane insertion moiety being particularly preferred.

"A hydrophobic membrane insertion moiety", as defined herein, is one or more units that direct the insertion or functional contact of the Tissue Factor with a membrane. The hydrophobic membrane insertion moieties of the invention are exemplified by stretches of substantially hydrophobic amino acids, such as between about 3 and about 20 hydrophobic amino acids; and also by fatty acids.

The hydrophobic amino acids may be located either at the N- or C-terminus of the truncated Tissue Factor, or appended at another point of the molecule. Where hydrophobic amino acids are used, they may be advantageously incorporated into the molecule by molecular biological techniques. Equally, hydrophobic amino acids or fatty acids may be added to the Tissue Factor using synthetic chemistry techniques.

In the Tissue Factor dimers, trimers and polymers of the present invention, each of the Tissue Factors or derivatives may be operatively linked via, e.g., a disulfide, thioether or peptide bond. In certain embodiments, the Tissue Factor units will be linked via a bond that is substantially stable in plasma, or in the physiological environment in which it is intended for use. This is based upon the inventors' concept that the dimeric form of Tissue Factor may prove to be the most biologically active. However, there is no requirement for a stable linkage as Tissue Factor monomers are known to be active in the methods of the invention.

One or more of the Tissue Factors or truncated Tissue Factors in the dimers and multimers may also be modified to contain a terminal cysteine residue or another moiety that is suitable for linking the Tissue Factor construct to a second agent, such as a binding region.

Tissue Factor monomers, truncated Tissue Factors, and Tissue Factor dimers and multimers that contain a peptide that includes a selectively-cleavable amino acid sequence therefore form another aspect of the invention. Peptide linkers that include a cleavage site for urokinase, plasmin, Thrombin, Factor IXa, Factor Xa or a metalloproteinase, such as an interstitial collagenase, a gelatinase or a stromelysin, are particularly preferred.

The Tissue Factor monomers, truncated Tissue Factors, Tissue Factor dimers and multimers, and indeed any coagulant, may therefore be linked to a second agent, such as an antibody, an antigen binding region of an antibody, a ligand or a receptor, via a biologically-releasable bond. The preference for peptide linkers that include a cleavage site for the above listed proteinases is based on the presence of such proteinases within, e.g., a tumor environment. The delivery of a bispecific agent or ligand to the tumor site is expected to result in cleavage, resulting in the relatively specific release of the coagulation factor.

Particular constructs of the invention are those comprising an operatively linked series of units in the sequence: a cysteine residue, a selectively cleavable peptide linker, a stretch of hydrophobic amino acids, a first truncated Tissue Factor and a second truncated Tissue Factor; or in the sequence: a first cysteine residue, a selectively cleavable peptide linker, a first stretch of hydrophobic amino acids, a first truncated Tissue Factor, a second truncated Tissue Factor and a second stretch of hydrophobic amino acids; wherein each construct may or not be linked to a second agent such as an antibody, ligand or receptor.

Other suitable coagulation factors are Russell's viper venom Factor X activator; platelet-activating compounds, such as thromboxane $A_2$ and thromboxane $A_2$ synthase; and inhibitors of fibrinolysis, such as $\alpha$2-antiplasmin.

Also encompassed by the invention are binding ligands in which the coagulation factor is not covalently linked to the conjugate, but is non-covalently bound thereto by means of binding to a second binding region that is operatively linked to the targeting agent of the construct. Suitable "second binding regions" include antigen combining sites of antibodies that have binding specificity for the coagulation factor, including functional portions of antibodies, such as scFv, Fv, Fab', Fab and F(ab')$_2$ fragments.

Binding ligands that contain antibodies, or fragments thereof, directed against the vitamin K-dependent coagulant Factor II/IIa, Factor VII/VIIa, Factor IX/IXa or Factor X/Xa; a vitamin K-dependent coagulation factor that lacks the Gla modification; Tissue Factor, a mutant Tissue Factor, a truncated Tissue Factor, a dimeric Tissue Factor, a polymeric Tissue Factor, a dimeric truncated Tissue Factor; Prekallikein; Factor V/Va, VIII/VIIIa, Factor XI/XIa, Factor XII/XIIa, Factor XIII/XIIIa; Russell's viper venom Factor X activator, thromboxane $A_2$ or $\alpha$2-antiplasmin are therefore contemplated.

The non-covalently bound coagulating agents may be bound to, or "precomplexed", with a coagulation factor, e.g., so that they may be used to deliver an exogenous coagulation factor to a disease site, e.g., the tumor vasculature, of an animal upon administration. Equally, binding ligands that comprise a second binding region that is specific for a coagulation factor may also be administered to an animal in an "uncomplexed" form and still function to achieve specific coagulation; in which instance, the agent would garner circulating (endogenous) coagulation factor and concentrate it within the disease or tumor site.

In terms of the "coagulation factors" or coagulating agents, these may be endogenous coagulation factors and derivatives thereof, or exogenously added version of such factors, including recombinant versions. Coagulants (in the present "coaguligands") have the distinct advantage over toxins (in immunotoxins) as they will not produce significant adverse side effects upon targeting to a marker that proves to be less than 100% disease-restricted. Furthermore, the coagulants used will most often be of human origin, and will therefore pose less immunogenicity problems than foreign toxins, such as ricin A chain.

Although not limited to such compositions, important examples of compositions in accordance with this invention are bispecific antibodies, which antibodies comprise a first antigen binding region that binds to a disease cell or component of disease-associated vasculature marker and a second antigen binding region that binds to a coagulation factor. The invention also provides scfv, Fv, Fab', Fab and F(ab')$_2$ fragments of such bispecific antibodies. One currently preferred example of such a bispecific antibody is an antibody comprising one binding site directed against an MHC Class II antigen and another binding site directed against Tissue Factor.

In further embodiments, the present invention provides pharmaceutical compositions of, and therapeutic kits comprising, any or a combination of the above binding ligands and bispecific antibodies in pharmacologically acceptable forms. This includes pharmaceutical compositions and kits where the binding ligand has a first binding region that is covalently linked to a coagulation factor, and also binding ligands in which the first binding region is covalently linked to a second binding region that, in turn, binds to the coagulation factor—whether binding occurs prior to, or subsequent to, administration to an animal.

Pharmaceutical compositions and therapeutic kits that include a combination of bispecific, trispecific or multispecific binding ligands in accordance with the invention are also contemplated. This includes combinations where one binding ligand is directed against a diseased cell or a tumor cell and where another is directed against a vasculature endothelial cell marker or component of disease-associated stroma. Other distinct components may also be included in the compositions and kits of the invention, such as antibodies, immunotoxins, immunoeffectors, chemotherapeutic agents, and the like.

The kits may also include an antigen suppressor, such as a cyclosporin, for use in suppressing antigen expression in endothelial cells of normal tissues; and/or an "inducing agent" for use in inducing disease-associated vascular endothelial cells or stroma to express a targetable antigen, such as E-selectin, P-selectin or an MHC Class II antigen. Exemplary inducing agents include T cell clones that bind disease or tumor antigens and that produce IFN-γ, although it is currently preferred that such clones be isolated from the animal to be treated using the kit.

Preferred inducing agents are bispecific antibodies that bind to disease or tumor cell antigens, or even stromal components, and to effector cells capable of producing cytokines, coagulants, or other factors, that induce expression of desired target antigens. Currently, one preferred group of bispecific antibodies are those that bind to a tumor antigen and to the activation antigens CD14 or CD16, to stimulate IL-1 production by monocytes, macrophages or mast cells; and those that bind to a tumor antigen and to the activation antigens CD2, CD3 or CD28, and preferably CD28, to stimulate IFN-γ production by NK cells or preferably by T cells.

A second preferred group of bispecific antibodies are those that bind to a tumor antigen or to a component of tumor stroma, and to Tissue Factor, a Tissue Factor derivative, prothrombin, Factor VII/VIIa, Factor IX/IXa, Factor X/Xa, Factor XI/XIa or Russell's viper venom Factor X activator, to stimulate thrombin production. Kits comprising such bispecific antibodies as a first "inducing" composition will generally include a second pharmaceutical composition that comprises a binding ligand that comprises a first binding region that binds to P-selectin or E-selectin.

The bispecific ligands of the invention, and other components as desired, may be conveniently aliquoted and packaged, using one or more suitable container means, and the separate containers dispensed in a single package. Pharmaceutical compositions and kits are further described herein.

Although the present invention has significant clinical utility in the delivery of coagulants and in disease treatment, it also has many in vitro uses. These include, for example, various assays based upon the binding ability of the particular antibody, ligand or receptor, of the bispecific compounds. The bispecific coagulating ligands of invention may thus be employed in standard binding assays and protocols, such as in immunoblots, Western blots, dot blots, RIAs, ELISAs, immunohistochemistry, fluorescent activated cell sorting (FACS), immunoprecipitation, affinity chromatography, and the like, as further described herein.

In still further embodiments, the invention concerns methods for delivering a coagulant to disease-associated vasculature, as may be used to treat diseases such as diabetic retinopathy, vascular restenosis, AVM, hemangioma, neovascular glaucoma, psoriasis and rheumatoid arthritis, and tumors that have a vascularized tumor component. Such methods generally comprise administering to an animal, including a human subject, with a disease that has a vascular component, a pharmaceutical composition comprising at least one bispecific binding ligand in accordance with those described above.

The compositions are administered in amounts and by routes effective to promote blood coagulation in the vasculature of the disease site, e.g., in the intratumoral vasculature of a solid tumor. Effective doses will be known to those of skill in the art in light of the present disclosure, such as the information in the Preferred Embodiments and Detailed Examples. Parenteral administration will often be suitable, as will other methods, such as, e.g., injection into a vascularized tumor site.

The methods of the invention provide for the delivery of exogenous coagulation factors, by means of both administering a binding ligand that comprises a covalently-bound coagulation factor and by means of administering a binding ligand that comprises a non-covalently bound coagulation factor that is complexed to a second binding region of the bispecific ligand or antibody.

Further methods of the invention include those that result in the delivery of an endogenous coagulation factor to disease or tumor vasculature. This is achieved by administering to the animal or patient a binding ligand that comprises a second binding region that binds to endogenous coagulation factor and concentrates the factor at the disease-associated or tumor vasculature.

In yet still further methodological embodiments, it is contemplated that markers of tumor vasculature or stroma may be specifically induced and then targeted using a binding ligand, such as an antibody. Exemplary inducible antigens include E-selectin, P-selectin, MHC Class II antigens, VCAM-1, ICAM-1, endoglin, ligands reactive with LAM-1, vascular addressins and other adhesion molecules, with E-selectin and MHC Class II antigens being currently preferred.

When inducing and subsequently targeting MHC Class II proteins, the suppression of MHC Class II in normal tissues is generally required. MHC Class II suppression may be achieved using a cyclosporin, or a functionally equivalent agent. MHC Class II molecules may then be induced in disease-associated vascular endothelial cells using cyclosporin-independent means, such as by exposing the disease-associated vasculature to an effector cell, generally a Helper T cell or NK cell, of the animal that releases the inducing cytokine IFN-γ.

Activated monocytes, macrophages and even mast cells are effector cells capable of producing cytokines (IL-1; TNF-α; TNF-β) that induce E-selectin; whereas Helper T cells, CD8-positive T cells and NK cells are capable of producing IFN-γ that induces MHC Class II. Activating monocyte/macrophages in the disease site to produce IL-1, or activating disease-associated Helper T cells or NK cells to produce IFN-γ, may be achieved by administering to the animal an activating antibody that binds to an effector cell surface activating antigen. Exemplary activating antigens include CD14 and CD16 (FcR for IgE) for monocytes/macrophages; and CD2, CD3 and CD28 for T cells; with CD14 and CD28, respectively, being preferred for use in certain embodiments.

To achieve specific activation and induction, one currently preferred method is to use a bispecific antibody that binds to both an effector cell activating antigen, such as CD14 or CD28, and to a disease or tumor cell antigen. These bispecific antibodies will localize to the disease or tumor site and activate monocyte/macrophages and T cells, respectively. The activated effector cells in the vicinity of the targeted disease or tumor component will produce inducing cytokines, in this case, IL-1 and IFN-γ, respectively.

MHC Class II suppression in normal tissues may also be achieved by administering to an animal an anti-CD4 antibody; this functions to suppress IFN-γ production by T cells of the animal resulting in inhibition of MHC Class II expression. MHC Class II molecules may again be specifically induced in disease-associated vascular endothelial cells by exposing only the disease site to IFN-γ. One means by which to achieve this is by administering to the animal an IFN-γ-producing T cell clone that binds to an antigen in the disease site. The IFN-γ-producing T cells will preferably be infiltrating leukocytes obtained from the disease site of the animal, such as tumor infiltrating leukocytes (TILs) expanded in vitro.

Methods using bispecific antibodies to induce coagulant, such as thrombin, production, only in a local environment, such as in a tumor site, are also provided. Again, this will generally be achieved by administering to an animal a pharmaceutical composition comprising a bispecific antibody that binds to a tumor cell or a component of tumor stroma and to Tissue Factor, a Tissue Factor derivative, prothrombin, Factor VII/VIIa, Factor IX/IXa, Factor X/Xa, Factor XI/XIa or Russell's viper venom Factor X activator. Antibodies that bind to E-selectin or P-selectin are then linked to a coagulation factor or a second binding region that binds to a coagulation factor and are introduced into the bloodstream of an animal.

More conventional combination treatment regimens are also possible where, for example, a tumor coagulating element of this invention is combined with an existing antitumor therapy, such as with radiotherapy or chemotherapy, or through the use of a second immunological reagent, such as an antitumor immunotoxin. The novel treatment methods for benign diseases can also be combined with other presently used therapies.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A; Before injection: blood vessels are intact and tumor cells are healthy. FIG. 3B; 0.5 hours: blood vessels throughout the tumor are thrombosed; tumor cells are healthy. FIG. 3C; 4 hours: dense thrombi are present in all tumor vessels and tumor cells are separating and developing pyknotic nuclei. Erythrocytes are visible in the tumor interstitium. FIG. 3D; 24 hours: advanced tumor necrosis throughout the tumor. Arrows indicate blood vessels.

DETAILED DESCRIPTION OF THE PREFERRED EMBODIMENTS

Figure 1:
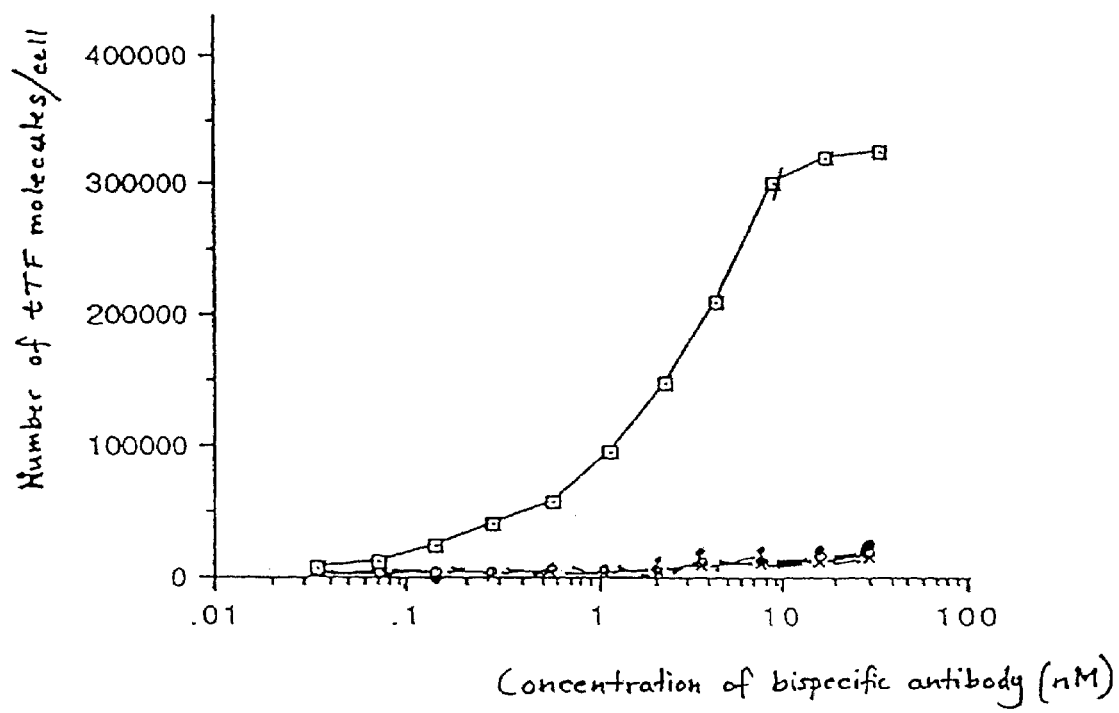
FIG. 1. Tethering of tTF to A20 cells via B21-2/10H10 bispecific antibody. A20 cells were incubated with varying concentrations of B21-2/10H10 (□), SFR8/10H10 (●) or B21-2/OX7 (○) plus an excess of $^{125}$I-tTF for 1 h at 4° C. in the presence of sodium azide. The number of $^{125}$I-tTF associated with the cells was determined as described in Example II.

Although they show great promise in the therapy of lymphomas and leukemias (Lowder et al., 1987; Vitetta et al., 1991), monoclonal antibodies (MAbs) and immunotoxins (ITs) have thus far proved relatively ineffective in clinical trials against carcinomas and other solid tumors (Byers & Baldwin, 1988; Abrams & Oldham, 1985), which account for more than 90% of all cancers in man (Shockley et al., 1991). A principal reason for this is that macromolecules do not readily extravasate into solid tumors (Sands, 1988; Epenetos et al., 1986) and, once within the tumor mass, fail to distribute evenly due to the presence of tight junctions between tumor cells (Dvorak et al., 1991), fibrous stroma (Baxter et al., 1991), interstitial pressure gradients (Jain, 1990) and binding site barriers (Juweid et al., 1992).

In developing new strategies for treating solid tumors, the methods that involve targeting the vasculature of the tumor, rather than the tumor cells themselves, therefore seem to offer certain advantages. Inducing a blockade of the blood flow through the tumor, e.g., through tumor vasculature specific fibrin formation, would interfere with the influx and efflux processes in a tumor site, thus resulting in anti-tumor effect. Arresting the blood supply to a tumor may be accomplished through shifting the procoagulant-fibrinolytic balance in the tumor-associated vessels in favour of the coagulating processes by specific exposure to coagulating agents.

The present invention provides various means for effecting specific blood coagulation, as exemplified by tumor-specific coagulation. This is achieved using bispecific or mutlispecific binding ligands in which at least one component is an immunological- or growth factor-based targeting component, and at least one other component is provided that is capable of directly, or indirectly, stimulating coagulation.

A. Targetable Disease Sites

The compositions and methods provided by this invention are broadly applicable to the treatment of any disease, such as a benign or malignant tumor, having a vascular component. Such vasculature-associated diseases include BPH, diabetic retinopathy, vascular restenosis, arteriovenous malformations (AVM), meningioma, hemangioma, neovascular glaucoma and psoriasis; and also angiofibroma, arthritis, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis and even endometriosis.

Typical vascularized tumors are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

One binding region of the bispecific agents of the invention will be a component that is capable of delivering the coagulating agent to the tumor region, i.e., capable of localizing within a tumor site, such as those described above. As somewhat wider distribution of the coagulating agent will not be associated with severe side effects, such as is known to occur with a toxin moiety, there is a less stringent requirement imposed on the targeting element of the bispecific ligand. The targeting agent may thus be directed to components of tumor cells; components of tumor vasculature; components that bind to, or are generally associated with, tumor cells; components that bind to, or are generally associated with, tumor vasculature; components of the tumor extracellular matrix or stroma; and even cell types found within the tumor vasculature.

The burden of very stringent targeting, e.g., as imposed when using immunotoxins, is also lessened due to the fact that tumor vasculature is 'prothrombotic' and is predisposed towards coagulation. Therefore, to achieve specific targeting means that coagulation is promoted in the tumor vasculature relative to the vasculature in non-tumor sites. Thus, specific targeting is a functional term rather than a purely physical term relating to the biodistribution properties of the targeting agent, and it is not unlikely that useful targets may be not be entirely tumor-restricted, and that targeting ligands which are effective to promote tumor-specific coagulation may nevertheless be found at other sites of the body following administration.

1. Tumor Cell Targets

The malignant cells that make up the tumor may be targeted using a bispecific ligand that has a region capable of binding to a relatively specific marker of the tumor cell. In that binding to tumor cells will localize the associated coagulating agent to the tumor, specific coagulation will be achieved. Furthermore, it is expected that this would be a particularly effective means of promoting coagulation as, due to the physical accessibility of perivascular tumor cells, the bispecific agents will likely be concentrated around the tumor cells that are nearest to a blood vessel.

Many so-called "tumor antigens" have been described, any one which could be employed as a target in connection with the present invention. A large number of exemplary solid tumor-associated antigens are listed herein in Table I. The preparation and use of antibodies against such antigens is well within the skill of the art, and exemplary antibodies are also listed in Table I.

Another means of defining a targetable tumor is in terms of the characteristics of a tumor cell itself, rather than describing the biochemical properties of an antigen expressed by the cell. Accordingly, Table II is provided for the purpose of exemplifying human tumor cell lines that are publically available (from ATCC Catalogue).

The information presented in Table II is by means of an example, and not intended to be limiting either by year or by scope. One may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature will thus readily reveal an appropriate choice of cell for any tumor cell type desired to be targeted.

TABLE I

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| A: Gynecological GY | 'CA 125' > 200 kD mucin GP | OC 125 | Kabawat et al., 1983; Szymendera, 1986 |
| ovarian | 80 Kd GP | OC 133 | Masuko et al, Cancer Res., 1984 |
| ovarian | 'SGA' 360 Kd GP | OMI | de Krester et al., 1986 |
| ovarian | High $M_r$ mucin | Mo v1 | Miotti et al, Cancer Res., 1985 |
| ovarian | High $M_r$ mucin/ glycolipid | Mo v2 | Miotti et al, Cancer Res., 1985 |
| ovarian | NS | 3C2 | Tsuji et al., Cancer Res., 1985 |
| ovarian | NS | 4C7 | Tsuji et al., Cancer Res., 1985 |
| ovarian | High $M_r$ mucin | $ID_3$ | Gangopadhyay et al., 1985 |
| ovarian | High $M_r$ mucin | DU-PAN-2 | Lan et al., 1985 |
| GY | 7700 Kd GP | F 36/22 | Croghan et al., 1984 |
| ovarian | 'gp 68' 48 Kd GP | $4F_7/7A_{10}$ | Bhattacharya et al., 1984 |
| GY | 40, 42 kD GP | OV-TL3 | Poels et al., 1986 |
| GY | 'TAG-72' High $M_r$ mucin | B72.3 | Thor et al., 1986 |
| ovarian | 300-400 Kd GP | $DF_3$ | Kufe et al., 1984 |
| ovarian | 60 Kd GP | $2C_8/2F_7$ | Bhattacharya et al., 1985 |
| GY | 105 Kd GP | MF 116 | Mattes et al., 1984 |
| ovarian | 38-40 kD GP | MOv18 | Miotti et al., 1987 |
| GY | 'CEA' 180 Kd GP | CEA 11-H5 | Wagener et al., 1984 |
| ovarian | CA 19-9 or GICA | CA 19-9 (1116NS 19-9) | Atkinson et al., 1982 |
| ovarian | 'PLAP' 67 Kd GP | H17-E2 | McDicken et al., 1985 |
| ovarian | 72 Kd | 791T/36 | Perkins et al., 1985 |
| ovarian | 69 Kd PLAP | $NDOG_2$ | Sunderland et al., 1984 |
| ovarian | unknown $M_r$ PLAP | H317 | Johnson et al., 1981 |
| ovarian | $p185^{HER2}$ | 4D5, 3H4, 7C2, 6E9, 2C4, 7F3, 2H11, 3E8, 5B8, 7D3, SB8 | Shepard et al., 1991 |
| uterus ovary | HMFG-2 | HMFG2 | Epenetos et al., 1982 |
| GY | HMFG-2 | 3.14.A3 | Burchell et al., 1983 |
| B: BREAST | 330-450 Kd GP | DF3 | Hayes et al., 1985 |
| | NS | NCRC-11 | Ellis et al., 1984 |
| | 37 kD | 3C6F9 | Mandeville et al., 1987 |
| | NS | MBE6 | Teramoto et al., 1982 |
| | NS | CLNH5 | Glassy et al., 1983 |
| | 47 Kd GP | MAC 40/43 | Kjeldsen et al., 1986 |
| | High $M_r$ GP | EMA | Sloane et al., 1981 |
| | High $M_r$ GP | HMFG1 HFMG2 | Arklie et al., 1981 |

TABLE I-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | NS | 3.15.C3 | Arklie et al., 1981 |
| | NS | M3, M8, M24 | Foster et al., 1982 |
| | 1 (Ma) blood group Ags | M18 | Foster et al., 1984 |
| | NS | 67-D-11 | Rasmussen et al., 1982 |
| | oestrogen receptor | D547Sp, D75P3, H222 | Kinsel et al., 1989 |
| | EGF Receptor | Anti-EGF | Sainsbury et al., 1985 |
| | Laminin Receptor | LR-3 | Horan Hand et al., 1985 |
| | erb B-2 p185 | TA1 | Gusterson et al., 1988 |
| | NS | H59 | Hendler et al., 1981 |
| | 126 Kd GP | 10-3D-2 | Soule et al., 1983 |
| | NS | HmABl, 2 | Imam et al., 1984; Schlom et al., 1985 |
| | NS | MBR 1, 2, 3 | Menard et al., 1983 |
| | 95 Kd | 24.17.1 | Thompson et al., 1983 |
| | 100 Kd | 24.17.2 (3E1.2) | Croghan et al., 1983 |
| | NS | F36/22.M7/105 | Croghan et al., 1984 |
| | 24 Kd | C11, G3, H7 | Adams et al., 1983 |
| | 90 Kd GP | B6.2 | Colcher et al., 1981 |
| | CEA & 180 Kd GP | B1.1 | Colcher et al., 1983 |
| | colonic & pancreatic mucin similar to Ca 19-9 | Cam 17.1 | Imperial Cancer Research Technology MAb listing |
| | milk mucin core protein | SM3 | Imperial Cancer Research Technology Mab listing |
| | milk mucin core protein | SM4 | Imperial Cancer Research Technology Mab listing |
| | affinity-purified milk mucin | C-Mul (566) | Imperial Cancer Research Technology Mab listing |
| | $p185^{HER2}$ | 4D5 3H4, 7C2, 6E9, 2C4, 7F3, 2H11, 3E8, 5B8, 7D3, 5B8 | Shepard et al., 1991 |
| | CA 125 > 200 Kd GP | OC 125 | Kabawat et al., 1985 |
| | High $M_r$ mucin/glycolipid | MO v2 | Miotti et al., 1985 |
| | High $M_r$ mucin | DU-PAN-2 | Lan et al., 1984 |
| | 'gp48' 48 Kd GP | $4F_7/7A_{10}$ | Bhattacharya et al., 1984 |
| | 300-400 Kd GP | $DF_3$ | Kufe et al., 1984 |
| | 'TAG-72' high $M_r$ mucin | B72.3 | Thor et al., 1986 |
| | 'CEA' 180 Kd GP | ccccCEA 11 | Wagener et al., 1984 |
| | 'PLAP' 67 Kd GP | H17-E2 | McDicken et al., 1985 |
| | HMFG-2 > 400 Kd GP | 3.14.A3 | Burchell et al., 1983 |
| | NS | FO23C5 | Riva et al., 1988 |
| C: COLORECTAL | TAG-72 High $M_r$ mucin | B72.3 | Colcher et al., 1987 |
| | GP37 | (17-1A) 1083-17-1A | Paul et al., 1986 |
| | Surface GP | CO17-1A | LoBuglio et al., 1988 |
| | CEA | ZCE-025 | Patt et al., 1988 |
| | CEA | AB2 | Griffin et al., 1988a |
| | cell surface AG | HT-29-15 | Cohn et al., 1987 |
| | secretory epithelium | 250-30.6 | Leydem et al., 1986 |
| | surface glycoprotein | 44X14 | Gallagher et al., 1986 |
| | NS | A7 | Takahashi et al., 1988 |
| | NS | GA73.3 | Munz et al., 1986 |
| | NS | 791T/36 | Farrans et al., 1982 |
| | cell membrane & cytoplasmic Ag | 28A32 | Smith et al., 1987 |
| | CEA & vindesine | 28.19.8 | Corvalen, 1987 |
| | gp72 | X MMCO-791 | Byers et al., 1987 |
| | high $M_r$ mucin | DU-PAN-2 | Lan et al., 1985 |
| | high $M_r$ mucin | $ID_3$ | Gangopadhyay et al., 1985 |
| | CEA 180 Kd GP | CEA 11-H5 | Wagener et al., 1984 |
| | 60 Kd GP | $2C_8/2F_7$ | Bhattacharya et al., 1985 |
| | CA-19-9 (or | CA-19-9 (1116NS 19-9) | Atkinson et al., 1982 |

TABLE I-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | GICA) | | |
| | Lewis a | PR5C5 | Imperial Cancer Research Technology Mab Listing |
| | Lewis a | PR4D2 | Imperial Cancer Research Technology Mab Listing |
| | colonic mucus | PR4D1 | Imperial Cancer Research Technology Mab Listing |
| D: MELANOMA | $p97^a$ | 4.1 | Woodbury et al., 1980 |
| | $p97^a$ | $8.2\ M_{17}$ | Brown, et al., 1981a |
| | $p97^b$ | 96.5 | Brown, et al., 1981a |
| | $p97^c$ | 118.1, 133.2, (113.2) | Brown, et al., 1981a |
| | $p97^c$ | $L_1, L_{10}, R_{10}(R_{19})$ | Brown et al., 1981b |
| | $p97^d$ | $I_{12}$ | Brown et al., 1981b |
| | $p97^e$ | $K_5$ | Brown et al., 1981b |
| | p155 | 6.1 | Loop et al., 1981 |
| | $G_{D3}$ disialoganglioside | R24 | Dippold et al., 1980 |
| | p210, p60, p250 | 5.1 | Loop et al., 1981 |
| | p280 p440 | 225.28S | Wilson et al., 1981 |
| | GP 94, 75, 70 & 25 | 465.12S | Wilson et al., 1981 |
| | P240-P250, P450 | 9.2.27 | Reisfeld et al., 1982 |
| | 100, 77, 75 Kd | F11 | Chee et al., 1982 |
| | 94 Kd | 376.96S | Imai et al., 1982 |
| | 4 GP chains | 465.12S | Imai et al., 1982; Wilson et al., 1981 |
| | GP 74 | 15.75 | Johnson & Reithmuller, 1982 |
| | GP 49 | 15.95 | Johnson & Reithmuller, 1982 |
| | 230 Kd | Mel-14 | Carrel et al., 1982 |
| | 92 Kd | Mel-12 | Carrel et al., 1982 |
| | 70 Kd | Me3-TB7 | Carrel et al., 1:387, 1982 |
| | HMW MAA similar to 9.2.27 AG | 225.28SD | Kantor et al., 1982 |
| | HMW MAA similar to 9.2.27 AG | 763.24TS | Kantor et al., 1982 |
| | GP95 similar to 376.96S 465.12S | 705F6 | Stuhlmiller et al., 1982 |
| | GP125 | 436910 | Saxton et al., 1982 |
| | CD41 | M148 | Imperial Cancer Research Technology Mab listing |
| E: GASTROINTESTINAL pancreas, stomach | high $M_r$ mucin | ID3 | Gangopadhyay et al., 1985 |
| gall bladder, pancreas, stomach | high $M_r$ mucin | DU-PAN-2 | Lan et al., 1985 |
| pancreas | NS | OV-TL3 | Poels et al., 1984 |
| pancreas, stomach, oesophagus | 'TAG-72' high $M_r$ mucin | B72.3 | Thor et al., 1986 |
| stomach | 'CEA' 180 Kd GP | CEA 11-H5 | Wagener et al., 1984 |
| pancreas | HMFG-2 > 400 Kd GP | 3.14.A3 | Burchell et al., 1983 |
| G.I. | NS | C COLI | Lemkin et al., 1984 |
| pancreas, stomach | CA 19-9 (or GICA) | CA-19-9 (1116NS 19-9) and CA50 | Szymendera, 1986 |
| pancreas | CA125 GP | OC125 | Szymendera, 1986 |
| F: LUNG non-small cell lung carcinoma | $p185^{HER2}$ | 4D5 3H4, 7C2, 6E9, 2C4, 7F3, 2H11, 3E8, 5B8, 7D3, SB8 | Shepard et al., 1991 |
| | high $M_r$ mucin/ glycolipid | MO v2 | Miotti et al., 1985 |
| | 'TAG-72' high $M_r$ mucin | B72.3 | Thor et al., 1986 |
| | high $M_r$ mucin | DU-PAN-2 | Lan et al., 1985 |
| | 'CEA' 180 kD GP | CEA 11-H5 | Wagener et al., 1984 |
| Malignant Gliomas | cytoplasmic antigen from 85HG-22 cells | MUC 8-22 | Stavrou, 1990 |
| | cell surface Ag from 85HG-63 cells | MUC 2-63 | Stavrou, 1990 |
| | cell surface Ag from 86HG-39 | MUC 2-39 | Stavrou, 1990 |

TABLE I-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | cells cell surface Ag from 86HG-39 cells | MUC 7-39 | Stavrou, 1990 |
| G: MISCELLANEOUS | p53 | PAb 240 PAb 246 PAb 1801 | Imperial Cancer Research Technology MaB Listing |
| small round cell tumors | neural cell adhesion molecule | ERIC.1 | Imperial Cancer Research Technology MaB Listing |
| medulloblastoma neuroblastoma rhabdomyosarcoma | | M148 | Imperial Cancer Research Technology MaB Listing |
| neuroblastoma | | FMH25 | Imperial Cancer Research Technology MaB Listing |
| renal cancer & glioblastomas | p155 | 6.1 | Loop et al., 1981 |
| bladder & laryngeal cancers | "Ca Antigen" 350-390 kD | CA1 | Ashall et al., 1982 |
| neuroblastoma | GD2 | 3F8 | Cheung et al., 1986 |
| Prostate | gp48 48 kD GP | $4F_7/7A_{10}$ | Bhattacharya et al., 1984 |
| Prostate | 60 kD GP | $2C_8/2F_7$ | Bhattacharya et al., 1985 |
| Thyroid | 'CEA' 180 kD GP | CEA 11-H5 | Wagener et al., 1984 | abbreviations:
Abs, antibodies;
Ags, antigens;
EGF, epidermal growth factor;
GI, gastrointestinal;
GICA, gastrointestinal-associated antigen;
GP, glycoprotein;
GY, gynecological;
HMFG, human milk fat globule;
Kd, kilodaltons;
Mabs, monoclonal antibodies;
$M_r$, molecular weight;
NS, not specified;
PLAP, placental alkaline phosphatase;
TAG, tumor-associated glycoprotein;
CEA, carcinoembryonic antigen.
footnotes:
the CA 19-9 Ag (GICA) is sialosylfucosyllactotetraosylceramide, also termed sialylated Lewis pentaglycosyl ceramide or sialyated lacto-N-fucopentaose II; p97 Ags are believed to be chondroitin sulphate proteoglycan; antigens reactive with Mab 9.2.27 are believed to be sialylated glycoproteins associated with chondroitin sulphate proteoglycan; unless specified, GY can include cancers of the cervix, endocervix, endometrium, fallopian tube, ovary, vagina or mixed Mullerian tumor; unless specified GI can include cancers of the liver, small intestine, spleen, pancreas, stomach and oesophagus.

TABLE II

HUMAN TUMOR CELL LINES AND SOURCES

| ATTC HTB NUMBER | CELL LINE | TUMOR TYPE |
|---|---|---|
| 1 | J82 | Transitional-cell carcinoma, bladder |
| 2 | RT4 | Transitional-cell papilloma, bladder |
| 3 | ScaBER | Squamous carcinoma, bladder |
| 4 | T24 | Transitional-cell carcinoma, bladder |
| 5 | TCCSUP | Transitional-cell carcinoma, bladder, primary grade IV |
| 9 | 5637 | Carcinoma, bladder, primary |
| 10 | SK-N-MC | Neuroblastoma, metastasis to supra-orbital area |
| 11 | SK-N-SH | Neuroblastoma, metastasis to bone marrow |
| 12 | SW 1088 | Astrocytoma |
| 13 | SW 1783 | Astrocytoma |
| 14 | U-87 MG | Glioblastoma, astrocytoma, grade III |
| 15 | U-118 MG | Glioblastoma |
| 16 | U-138 MG | Glioblastoma |
| 17 | U-373 MG | Glioblastoma, astrocytoma, grade III |
| 18 | Y79 | Retinoblastoma |
| 19 | BT-20 | Carcinoma, breast |

TABLE II-continued

HUMAN TUMOR CELL LINES AND SOURCES

| ATTC HTB NUMBER | CELL LINE | TUMOR TYPE |
|---|---|---|
| 20 | BT-474 | Ductal carcinoma, breast |
| 22 | MCF7 | Breast adenocarcinoma, pleural effusion |
| 23 | MDA-MB-134-VI | Breast, ductal carcinoma, pleural effusion |
| 24 | MDA-MD-157 | Breast medulla, carcinoma, pleural effusion |
| 25 | MDA-MB-175-VII | Breast, ductal carcinoma, pleural effusion |
| 27 | MDA-MB-361 | Adenocarcinoma, breast, metastasis to brain |
| 30 | SK-BR-3 | Adenocarcinoma, breast, malignant pleural effusion |
| 31 | C-33 A | Carcinoma, cervix |
| 32 | HT-3 | Carcinoma, cervix, metastasis to lymph node |
| 33 | ME-180 | Epidermoid carcinoma, cervix, metastasis to omentum |
| 34 | MS751 | Epidermoid carcinoma, cervix, metastasis to lymph node |
| 35 | SiHa | Squamous carcinoma, cervix |
| 36 | JEG-3 | Choriocarcinoma |
| 37 | Caco-2 | Adenocarcinoma, colon |
| 38 | HT-29 | Adenocarcinoma, colon, moderately well-differentiated grade II |
| 39 | SK-CO-1 | Adenocarcinoma, colon, ascites |
| 40 | HuTu 80 | Adenocarcinoma, duodenum |
| 41 | A-253 | Epidermoid carcinoma, submaxillary gland |
| 43 | FaDu | Squamous cell carcinoma, pharynx |
| 44 | A-498 | Carcinoma, kidney |
| 45 | A-704 | Adenocarcinoma, kidney |
| 46 | Caki-1 | Clear cell carcinoma, consistent with renal primary, metastasis to skin |
| 47 | Caki-2 | Clear cell carcinoma, consistent with renal primary |
| 48 | SK-NEP-1 | Wilms' tumor, pleural effusion |
| 49 | SW 839 | Adenocarcinoma, kidney |
| 52 | SK-HEP-1 | Adenocarcinoma, liver, ascites |
| 53 | A-427 | Carcinoma, lung |
| 54 | Calu-1 | Epidermoid carcinoma grade III, lung, metastasis to pleura |
| 55 | Calu-3 | Adenocarcinoma, lung, pleural effusion |
| 56 | Calu-6 | Anaplastic carcinoma, probably lung |
| 57 | SK-LU-1 | Adenocarcinoma, lung consistent with poorly differentiated, grade III |
| 58 | SK-MES-1 | Squamous carcinoma, lung, pleural effusion |
| 59 | SW 900 | Squamous cell carcinoma, lung |
| 60 | EB1 | Burkitt lymphoma, upper maxilla |
| 61 | EB2 | Burkitt lymphoma, ovary |
| 62 | P3HR-1 | Burkitt lymphoma, ascites |
| 63 | HT-144 | Malignant melanoma, metastasis to subcutaneous tissue |
| 64 | Malme-3M | Malignant melanoma, metastasis to lung |
| 66 | RPMI-7951 | Malignant melanoma, metastasis to lymph node |
| 67 | SK-MEL-1 | Malignant melanoma, metastasis to lymphatic system |
| 68 | SK-MEL-2 | Malignant melanoma, metastasis to skin of thigh |
| 69 | SK-MEL-3 | Malignant melanoma, metastasis to lymph node |
| 70 | SK-MEL-5 | Malignant melanoma, metastasis to axillary node |
| 71 | SK-MEL-24 | Malignant melanoma, metastasis to node |
| 72 | SK-MEL-28 | Malignant melanoma |
| 73 | SK-MEL-31 | Malignant melanoma |
| 75 | Caov-3 | Adenocarcinoma, ovary, consistent with primary |
| 76 | Caov-4 | Adenocarcinoma, ovary, metastasis to subserosa of fallopian tube |
| 77 | SK-OV-3 | Adenocarcinoma, ovary, malignant ascites |
| 78 | SW 626 | Adenocarcinoma, ovary |
| 79 | Capan-1 | Adenocarcinoma, pancreas, metastasis to liver |
| 80 | Capan-2 | Adenocarcinoma, pancrease |
| 81 | DU 145 | Carcinoma, prostate, metastasis to brain |
| 82 | A-204 | Rhabdomyosarcoma |
| 85 | Saos-2 | Osteogenic sarcoma, primary |
| 86 | SK-ES-1 | Anaplastic osteosarcoma versus Ewing sarcoma, bone |
| 88 | SK-LMS-1 | Leiomyosarcoma, vulva, primary |
| 91 | SW 684 | Fibrosarcoma |
| 92 | SW 872 | Liposarcoma |
| 93 | SW 982 | Axilla synovial sarcoma |

TABLE II-continued

HUMAN TUMOR CELL LINES AND SOURCES

| ATTC HTB NUMBER | CELL LINE | TUMOR TYPE |
|---|---|---|
| 94 | SW 1353 | Chondrosarcoma, humerus |
| 96 | U-2 OS | Osteogenic sarcoma, bone primary |
| 102 | Malme-3 | Skin fibroblast |
| 103 | KATO III | Gastric carcinoma |
| 104 | Cate-1B | Embryonal carcinoma, testis, metastasis to lymph node |
| 105 | Tera-1 | Embryonal carcinoma, malignancy consistent with metastasis to lung |
| 106 | Tera-2 | Embryonal carcinoma, malignancy consistent with, metastasis to lung |
| 107 | SW579 | Thyroid carcinoma |
| 111 | AN3 CA | Endometrial adenocarcinoma, metastatic |
| 112 | HEC-1-A | Endometrial adenocarcinoma |
| 113 | HEC-1-B | Endometrial adenocarcinoma |
| 114 | SK-UT-1 | Uterine, mixed mesodermal tumor, consistent with leiomyosarcoma grade III |
| 115 | SK-UT-1B | Uterine, mixed mesodermal tumor, consistent with leiomyosarcoma grade III |
| 117 | SW 954 | Squamous cell carcinoma, vulva |
| 118 | SW 962 | Carcinoma, vulva, lymph node metastasis |
| 119 | NCI-H69 | Small cell carcinoma, lung |
| 120 | NCI-H128 | Small cell carcinoma, lung |
| 121 | BT-483 | Ductal carcinoma, breast |
| 122 | BT-549 | Ductal carcinoma, breast |
| 123 | DU4475 | Metastatic cutaneous nodule, breast carcinoma |
| 124 | HBL-100 | Breast |
| 125 | Hs 578Bst | Breast, normal |
| 126 | Hs 578T | Ductal carcinoma, breast |
| 127 | MDA-MB-330 | Carcinoma, breast |
| 128 | MDA-MB-415 | Adenocarcinoma, breast |
| 129 | MDA-MB-435S | Ductal carcinoma, breast |
| 130 | MDA-MB-436 | Adenocarcinoma, breast |
| 131 | MDA-MB-453 | Carcinoma, breast |
| 132 | MDA-MB-468 | Adenocarcinoma, breast |
| 133 | T-47D | Ductal carcinoma, breast, pleural effusion |
| 134 | Hs 766T | Carcinoma, pancreas, metastatic to lymph node |
| 135 | Hs 746T | Carcinoma, stomach, metastatic to left leg |
| 137 | Hs 695T | Amelanotic melanoma, metastatic to lymph node |
| 138 | Hs 683 | Glioma |
| 140 | Hs 294T | Melanoma, metastatic to lymph node |
| 142 | Hs 602 | Lymphoma, cervical |
| 144 | JAR | Choriocarcinoma, placenta |
| 146 | Hs 445 | Lymphoid, Hodgkin's disease |
| 147 | Hs 700T | Adenocarcinoma, metastatic to pelvis |
| 148 | H4 | Neuroglioma, brain |
| 151 | Hs 696 | Adenocarcinoma primary, unknown, metastatic to bone-sacrum |
| 152 | Hs 913T | Fibrosarcoma, metastatic to lung |
| 153 | Hs 729 | Rhabdomyosarcoma, left leg |
| 157 | FHs 738Lu | Lung, normal fetus |
| 158 | FHs 173We | Whole embryo, normal |
| 160 | FHs 738Bl | Bladder, normal fetus |
| 161 | NIH: 0VCAR-3 | Ovary, adenocarcinoma |
| 163 | Hs 67 | Thymus, normal |
| 166 | RD-ES | Ewing's sarcoma |
| 168 | ChaGo K-1 | Bronchogenic carcinoma, subcutaneous metastasis, human |
| 169 | WERI-Rb-1 | Retinoblastoma |
| 171 | NCI-H446 | Small cell carcinoma, lung |
| 172 | NCI-H209 | Small cell carcinoma, lung |
| 173 | NCI-H146 | Small cell carcinoma, lung |
| 174 | NCI-H441 | Papillary adenocarcinoma, lung |
| 175 | NCI-H82 | Small cell carcinoma, lung |
| 176 | H9 | T-cell lymphoma |
| 177 | NCI-H460 | Large cell carcinoma, lung |
| 178 | NCI-H596 | Adenosquamous carcinoma, lung |
| 179 | NCI-H676B | Adenocarcinoma, lung |
| 180 | NCI-H345 | Small cell carcinoma, lung |
| 181 | NCI-H820 | Papillary adenocarcinoma, lung |
| 182 | NCI-H520 | Squamous cell carcinoma, lung |
| 183 | NCI-H661 | Large cell carcinoma, lung |
| 184 | NCI-H510A | Small cell carcinoma, extra-pulmonary origin, metastatic |
| 185 | D283 Med | Medulloblastoma |

TABLE II-continued

HUMAN TUMOR CELL LINES AND SOURCES

| ATTC HTB NUMBER | CELL LINE | TUMOR TYPE |
|---|---|---|
| 186 | Daoy | Medulloblastoma |
| 187 | D341 Med | Medulloblastoma |
| 188 | AML-193 | Acute monocyte leukemia |
| 189 | MV4-11 | Leukemia biphenotype |

(a) Anti-Tumor Cell Antibodies

A straightforward means of recognizing a tumor antigen target is through the use of an antibody that has binding affinity for the particular antigen. An extensive number of antibodies are known that are directed against solid tumor antigens. Certain useful anti-tumor antibodies are listed above in Table I. However, as will be instantly known to those of skill in the art, certain of the antibodies listed in Table I will not have the appropriate biochemical properties, or may not be of sufficient tumor specificity, to be of use therapeutically. An example is MUC8-22 that recognizes a cytoplasmic antigen. Antibodies such as these will generally be of use only in investigational embodiments, such as in model systems or screening assays.

Generally speaking, antibodies for use in these aspects of the present invention will preferably recognize antigens that are accessible on the cell-surface and that are preferentially, or specifically, expressed by tumor cells. Such antibodies will also preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity", as used herein, refers to an antibody or antibody fragment, that, when applied to the particular tissue under conditions suitable for immunohistochemistry, will elicit either no staining or negligible staining with only a few positive cells scattered among a field of mostly negative cells.

Particularly promising antibodies from Table I contemplated for use in the present invention are those having high selectivity for the solid tumor. For example, antibodies binding to TAG 72 and the HER-2 proto-oncogene protein, which are selectively found on the surfaces of many breast, lung and colorectal cancers (Thor et al., 1986; Colcher et al., 1987; Shepard et al., 1991); MOv18 and OV-TL3 and antibodies that bind to the milk mucin core protein and human milk fat globule (Miotti et al., 1985; Burchell et al., 1983); and the antibody 9.2.27 that binds to the high $M_r$ melanoma antigens (Reisfeld et al., 1982). Further useful antibodies are those against the folate-binding protein, which is known to be homogeneously expressed in almost all ovarian carcinomas; those against the erb family of oncogenes that are over-expressed in squamous cell carcinomas and the majority of gliomas; and other antibodies known to be the subject of ongoing pre-clinical and clinical evaluation.

The antibodies B3, KSI/4, CC49, 260F9, XMMCO-791, D612 and SM3 are believed to be particularly suitable for use in clinical embodiments, following the standard pre-clinical testing routinely practiced in the art. B3 (U.S. Pat. No. 5,242, 813; Brinkmann et al., 1991) has ATCC Accession No. HB 10573; KS1/4 can be made as described in U.S. Pat. No. 4,975,369; and D612 (U.S. Pat. No. 5,183,756) has ATCC Accession No. HB 9796.

Another means of defining a tumor-associated target is in terms of the characteristics of the tumor cell, rather than describing the biochemical properties of an antigen expressed by the cell. Accordingly, the inventors contemplate that any antibody that preferentially binds to a tumor cell listed in Table II may be used as the targeting component of a bispecific ligand. The preferential tumor cell binding is again based upon the antibody exhibiting high affinity for the tumor cell and not having significant reactivity with life-sustaining normal cells or tissues, as defined above.

The invention therefore provides several means for generating an antibody for use in the targeted coagulation methods described herein. To generate a tumor cell-specific antibody, one would immunize an animal with a composition comprising a tumor cell antigen and, as described more fully herein below, select a resultant antibody with appropriate specificity. The immunizing composition may contain a purified, or partially purified, preparation of any of the antigens in Table I; a composition, such as a membrane preparation, enriched for any of the antigens in Table I; any of the cells listed in Table II; or a mixture or population of cells that include any of the cell types listed in Table II.

Of course, regardless of the source of the antibody, in the practice of the invention in human treatment, one will prefer to ensure in advance that the clinically-targeted tumor expresses the antigen ultimately selected. This is achieved by means of a fairly straightforward assay, involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinity of antibodies from a "bank" of hybridomas are tested for reactivity against the tumor. Antibodies demonstrating appropriate tumor selectivity and affinity are then selected for the preparation of bispecific antibodies of the present invention.

Due to the well-known phenomenon of cross-reactivity, it is contemplated that useful antibodies may result from immunization protocols in which the antigens originally employed were derived from an animal, such as a mouse or a primate, in addition to those in which the original antigens were obtained from a human cell. Where antigens of human origin are used, they may be obtained from a human tumor cell line, or may be prepared by obtaining a biological sample from a particular patient in question. Indeed, methods for the development of antibodies that are "custom-tailored" to the patient's tumor are known (Stevenson et al., 1990) and are contemplated for use in connection with this invention.

(b) Further Tumor Cell Targets and Binding Ligands

In addition to the use of antibodies, other ligands could be employed to direct a coagulating agent to a tumor site by binding to a tumor cell antigen. For tumor antigens that are over-expressed receptors (oestrogen receptor, EGF receptor), or mutant receptors, the corresponding ligands could be used as targeting agents.

In an analogous manner to endothelial cell receptor ligands, there may be components that are specifically, or preferentially, bound to tumor cells. For example, if a tumor antigen is an over-expressed receptor, the tumor cell may be coated with a specific ligand in vivo. It seems that the ligand could then be targeted either with an antibody against the ligand, or with a form of the receptor itself. Specific examples of these type of targeting agents are antibodies against TIE-1 or TIE-2 ligands, antibodies against platelet factor 4, and leukocyte adhesion binding protein.

2. Other Disease Targets

In further embodiments, the first binding region may be a component that binds to a target molecule that is specifically or preferentially expressed in a disease site other than a tumor site.

Exemplary target molecules associated with other diseased cells include, for example, leukocyte adhesion molecules, that are associated with psoriasis; FGF, that is associated with proliferative diabetic retinopathy; platelet factor 4, that is associated with the activated endothelium of various diseases; and VEGF, that is associated with vascular proliferative disease. It is believed that an animal or patient having any one of the above diseases would benefit from the specific induction of coagulation in the disease site.

Diseases that are known to have a common angio-dependent pathology, as described in Klagsburn & Folkman (1990), may also be treated with bispecific ligand as described herein. In particular, a vascular endothelial cell-targeted ligand or a stroma-targeted ligand will be used to achieve coagulation in the disease site. The treatment of BPH, diabetic retinopathy, vascular restenosis, vascular adhesions, AVM, meningioma, hemangioma, neovascular glaucoma, rheumatoid arthritis and psoriasis are particularly contemplated at the present time.

3. Disease-Associated Vasculature Cell Targets

The cells of the vasculature are intended as targets for use in the present invention. In these cases, one binding region of the bispecific ligand will be capable of binding to an accessible marker preferentially expressed by disease-associated vasculature endothelial cells. The exploitation of the vascular markers is made possible due to the proximity of the vascular endothelial cells to the disease area and to the products of the local aberrant physiological processes. For example, tumor vascular endothelial cells are exposed to tumor cells and tumor-derived products that change the phenotypic profile of the endothelial cells.

Tumor cells are known to elaborate tumor-derived products, such as lymphokines, monokines, colony-stimulating factors, growth factors and angiogenic factors, that act on the nearby vascular endothelial cells (Kandel et al., 1991; Folkman, 1985a,b) and cytokines (Burrows et al., 1991; Ruco et al., 1990; Borden et al., 1990). The tumor products bind to the endothelial cells and serve to selectively induce expression of certain molecules. It is these induced molecules that may be targeted using the tumor endothelium-specific coagulant delivery provided by certain aspects of the present invention. Vascular endothelial cells in tumors proliferate at a rate 30-fold greater than those in miscellaneous normal tissues (Denekamp et al., 1982), suggesting that proliferation-linked determinants could also serve as markers for tumor vascular endothelial cells.

In certain embodiments of the invention, the targeting component of the bispecific ligands will be a component that has a relatively high degree of specificity for tumor vasculature. These targeting components may be defined as components that bind to molecules expressed on tumor endothelium, but that have little or no expression at the surface of normal endothelial cells. Such specificity may be assessed by the standard procedures of immunostaining of tissue sections, which are routine to those of skill in the art.

However, as stated above, an advantage of the present invention is that the requirement for selectivity is not as stringent as previously needed in the prior art methods, especially those employing immunotoxins, because any side effects associated with the mis-targeting of the coagulating agent will be minimal in comparison to those resulting from the mis-targeting of a toxin.

Therefore, it is generally proposed that the molecules to be targeted using the bispecific ligands or antibodies of this invention will be those that are expressed on tumor vasculature at a higher level than on normal endothelial cells.

(a) Vascular Endothelial Cell Markers in Disease

Molecules that are known to be preferentially expressed at the surface of vascular endothelial cells in a disease site or environment are herein termed "natural disease-associated vascular endothelial cell markers". This term is used for simplicity to refer to the endothelial cell components that are expressed in diseases connected with increased or inappropriate angiogenesis or endothelial cell proliferation. One particular example are the tumor endothelial cell components that are expressed in situ in response to tumor-derived factors. These components are also termed "naturally-induced tumor endothelial cell markers".

Both VEGF/VPF (vascular endothelial cell growth factor/vascular permeability factor) and components of the FGF (fibroblast growth factor) family are concentrated in or on tumor vasculature. The corresponding receptors therefore provide a potential target for attack on tumor vasculature. For example, VEGF receptors are known to be upregulated on tumor endothelial cells, as opposed to endothelial cells in normal tissues, both in rodents and man (Thieme et al., 1995). Possibly, this is a consequence of hypoxia—a characteristic of the tumor microenvironment (Leith et al., 1992). FGF receptors are also upregulated three-fold on endothelial cells exposed to hypoxia, and so are believed to be upregulated in tumors (Bicknell and Harris et al., 1992).

The TGFβ (transforming growth factor β) receptor (endoglin) on endothelial cells is upregulated on dividing cells, providing another target. One of the present inventors found that endoglin is upregulated on activated and dividing HUVEC in culture, and is strongly expressed in human tissues on endothelial cells at sites of neovascularization, including a broad range of solid tumors and fetal placenta. In contrast, endothelial cells in the majority of miscellaneous non-malignant adult tissues, including preneoplastic lesions, contain little or no endoglin. Importantly, endoglin expression is believed to correlate with neoplastic progression in the breast, as shown by benign fibroadenomas and early carcinomas binding low levels of TEC-4 and TEC-11 antibodies (ATCC HB-12312 and ATCC HB-12311, respectively), and late stage intraductal carcinomas and invasive carcinomas binding high levels of these antibodies.

(b) Cytokine-Inducible Vascular Endothelial Markers

Due to the nature of disease processes, which often result in localized dysfunction within the body, methods are available to manipulate the disease site whilst leaving other tissues relatively unaffected. This is particularly true in malignant and benign tumors, which exist as distinct entities within the body of an animal. For example, the tumor environment may be manipulated to create additional markers that are specific for tumor vascular endothelial cells. These methods generally mimic those that occur naturally in solid tumors, and also involve the local production of signalling agents, such as growth factors or cytokines, that induce the specific expression of certain molecules at the surface of the nearby vascular endothelial cells.

The group of molecules that may be artificially induced to be expressed at the surface of vascular endothelial cells in a disease or tumor environment are herein termed "inducible endothelial cell markers", or specifically, inducible tumor endothelial cell markers. This term is used to refer to those markers that are artificially induced, i.e., induced as a result of manipulation by the hand of man, rather than those that are induced as part of the disease or tumor development process in an animal. The term "inducible marker", as defined above, is chosen for simple reference in the context of the present application, notwithstanding the fact that "natural markers" are also induced, e.g., by tumor-derived agents.

Thus, although not required to practice the invention, techniques for the selective elicitation of vascular endothelial antigen targets on the surface of disease-associated vasculature are available that may, if desired, be used in conjunction with the invention. These techniques involve manipulating the antigenic expression, or cell surface presentation, such that a target antigen is expressed or rendered available on the surface of disease-associated vasculature and not expressed or otherwise rendered accessible or available for binding, or at least to a lesser extent, on the surface of normal endothelium.

Tumor endothelial markers can be induced by tumor-derived cytokines (Burrows et al., 1991; Ruco et al., 1990) and by angiogenic factors (Mignatti et al., 1991). Examples of cell surface markers that may be specifically induced in the tumor endothelium and then targeted using a bispecific coagulating ligand, as provided by the invention, include those listed in Table III (Bevilacqua et al., 1987; Dustin et al., 1986; Osborn et al., 1989; Collins et al., 1984).

The mechanisms for the induction of the proposed markers; the inducing, or "intermediate cytokine", such as IL-1 and IFN-γ; and the leukocyte cell type and associated cytokine-activating molecule, whose targeting will result in the release of the cytokine, are also set forth in Table III. In the induction of a specific marker, a bispecific "cytokine-inducing" or "antigen-inducing" antibody is generally required. This antibody will selectively induce the release of the appropriate cytokine in the locale of the tumor, thus selectively inducing the expression of the desired target antigen by the vascular endothelial cells. The bispecific antibody cross-links cells of the tumor mass and cytokine-producing leukocytes, thereby activating the leukocytes to release the cytokine.

The preparation and use of bispecific antibodies such as these is predicated in part on the fact that cross-linking antibodies recognizing CD3, CD14, CD16 and CD28 have previously been shown to elicit cytokine production selectively upon cross-linking with the second antigen (Qian et al., 1991). In the context of the present invention, since only successfully tumor cell-crosslinked leukocytes will be activated to release the cytokine, cytokine release will be restricted to the locale of the tumor. Thus, expression of the desired marker, such as E-selectin, will be similarly limited to the endothelium of the tumor vasculature.

TABLE III

POSSIBLE INDUCIBLE VASCULAR TARGETS

| INDUCIBLE ENDOTHELIAL CELL MOLECULES | ACRONYM | SUBTYPES/ALIASES (MOLECULAR FAMILY) | INDUCING CYTOKINES | LEUKOCYTES WHICH PRODUCE THOSE CYTOKINES | LEUKOCYTE MOLECULES WHICH, WHEN CROSSLINKED BY MONOCLONAL ANTIBODIES ACTIVATE THE CELLS TO PRODUCE CYTOKINES |
|---|---|---|---|---|---|
| Endothelial-Leukocyte Adhesion Molecule-1 | ELAM-1 E-selectin | — (Selectin) | IL-1, TNF-α, (TNF-β) (Bacterial Endotoxin) | monocytes macrophages mast cells | CD14 CD14 FcR for IgE |
| Vascular Cell Adhesion Molecule-1 | VCAM-1 | Inducible Cell Adhesion Molecule-110 (INCAM-110) (Immunoglobulin Family) | (Bacterial Endotoxin) IL-1, TNF-α TNF-β, IL-4 TNF | monocytes macrophages mast cells helper T cells NK cells | CD14 CD14 FcR for IgE CD2, CD3, CD28 FcR for IgG (CD16) |
| Intercellular Adhesion Molecule-1 | ICAM-1 | — (Immunoglobulin Family) | IL-1, TNFα (Bacterial Endotoxin) TNF-β, IFNγ | monocytes macrophages mast cells T helper cells NK cells | CD14 CD15 FcR for IgE CD2, CD3, CD28 FcR for IgG (CD16) |
| The Agent for Leukocyte Adhesion Molecule-1 | LAM-1 Agent | MEL-14 Agent (Mouse) | Il-1, TNFα (Bacterial Endotoxin) | monocytes macrophages mast cells | CD14 CD14 FcR for IgE |
| Major Histocompatability Complex Class II Antigen | MHC Class II | HLA-DR HLA-DP - Human HLA-DQ I-A - Mouse I-E | IFN-γ | helper T cells NK cells | CD2, CD3, CD28 FcR for IgG (CD16) |

It is important to note that, from the possible inducible markers listed in Table III, E-selectin and MHC Class II antigens, such as HLA-DR, HLA-DP and HLA-DQ (Collins et al., 1984), are by far the most preferred targets for use in connection with clinical embodiments. The other adhesion molecules of Table III appear to be expressed to varying degrees in normal tissues, generally in lymphoid organs and on endothelium, making their targeting perhaps appropriate only in animal models or in cases where their expression on normal tissues can be inhibited without significant side-effects. The targeting of E-selectin or an MHC Class II antigen is preferred as the expression of these antigens will likely be the most direct to promote selectively in tumor-associated endothelium.

E-Selectin

The targeting of an antigen that is not expressed on the surfaces of normal endothelium is the most straightforward form of the induction methods. E-selectin is an adhesion molecule that is not expressed in normal endothelial vasculature or other human cell types (Cotran et al., 1986), but can be induced on the surface of endothelial cells through the action of cytokines such as IL-1, TNF, lymphotoxin and bacterial endotoxin (Bevilacqua et al., 1987). It is not induced by IFN-γ (Wu et al., 1990). The expression of E-selectin may thus be selectively induced in tumor endothelium through the selective delivery of such a cytokine, or via the use of a composition that causes the selective release of such cytokines in the tumor environment.

Bispecific antibodies are one example of a composition capable of causing the selective release of one or more of the foregoing or other appropriate cytokines in the tumor site, but not elsewhere in the body. Such bispecific antibodies are herein termed "antigen-inducing antibodies" and are, of course, distinct from any bispecific antibodies of the invention that have targeting and coagulating components. Antigen-inducing antibodies are designed to cross-link cytokine effector cells, such as cells of monocyte/macrophage lineage, T cells and/or NK cells or mast cells, with tumor cells of the targeted solid tumor mass. This cross-linking would then effect a release of cytokine that is localized to the site of cross-linking, i.e., the tumor.

Effective antigen-inducing antibodies recognize a selected tumor cell surface antigen on the one hand (e.g., those in Table I) and, on the other hand, recognize a selected "cytokine activating" antigen on the surface of a selected leukocyte cell type. The term "cytokine activating" antigen is used to refer to any one of the various known molecules on the surfaces of leukocytes that, when bound by an effector molecule, such as an antibody or a fragment thereof or a naturally-occurring agent or synthetic analog thereof, be it a soluble factor or membrane-bound counter-receptor on another cell, promotes the release of a cytokine by the leukocyte cell. Examples of cytokine activating molecules include CD14 (the LPS receptor) and FcR for IgE, which will activate the release of IL-1 and TNFα; and CD16, CD2 or CD3 or CD28, which will activate the release of IFNγ and TNFβ, respectively.

Once introduced into the bloodstream of an animal bearing a tumor, such an antigen-inducing bispecific antibody will bind to tumor cells within the tumor, cross-link those tumor cells with effector cells, e.g., monocytes/macrophages, that have infiltrated the tumor, and thereafter effect the selective release of cytokine within the tumor. Importantly, however, without cross-linking of the tumor and leukocyte, the antigen-inducing antibody will not effect the release of cytokine. Thus, no cytokine release will occur in parts of the body removed from the tumor and, hence, expression of cytokine-induced molecules, e.g., E-selectin, will occur only within the tumor endothelium.

A number of useful "cytokine activating" antigens are known, which, when cross-linked with an appropriate bispecific antibody, will result in the release of cytokines by the cross-linked leukocyte. The generally preferred target for this purpose is CD14, which is found on the surface of monocytes and macrophages. When CD14 is cross linked it stimulates monocytes/macrophages to release IL-1 (Schutt et al., 1988; Chen et al., 1990), and possibly other cytokines, which, in turn stimulate the appearance of E-selectin on nearby vasculature. Other possible targets for cross-linking in connection with E-selectin induction and targeting include FcR for IgE, found on Mast cells; FcR for IgG (CD16), found on NK cells; as well as CD2, CD3 or CD28, found on the surfaces of T cells. Of these, CD14 targeting is generally preferred due to the relative prevalence of monocyte/macrophage infiltration of solid tumors as opposed to the other leukocyte cell types.

In an exemplary induction embodiment, an animal bearing a solid tumor is injected with bispecific (Fab'-Fab') anti-CD14/anti-tumor antibody (such as anti-CEA, 9.2.27 antibody against high Mr melanoma antigens OV-TL3 or MOv 18 antibodies against ovarian associated antigens). The antibody localizes in the tumor, by virtue of its tumor binding activity, and then activates monocytes and macrophages in the tumor by crosslinking their CD14 antigens (Schutt et. al., 1988; Chen et. al., 1990). The activated monocytes/macrophages have tumoricidal activity (Palleroni et. al., 1991) and release IL-1 and TNF which rapidly induce E-selectin antigens on the tumor vascular endothelial cells (Bevilacqua et. al., 1987; Pober et. al., 1991).

MHC Class II Antigens

The second preferred group of inducible markers contemplated for use with the present invention are the MHC Class II antigens (Collins et al., 1984), including HLA-DR, HLA-DP and HLA-DQ. Class II antigens are expressed on vascular endothelial cells in most normal tissues in several species, including man. Studies in vitro (Collins et al., 1984; Daar et al., 1984; O'Connell et al., 1990) and in vivo (Groenewegen et al., 1985) have shown that the expression of Class II antigens by vascular endothelial cells requires the continuous presence of IFN-γ which is elaborated by $T_{H1}$ cells and, to a lesser extent, by NK cells and $CD8^+$ T cells.

MHC Class II antigens are not unique to vascular endothelial cells, and are also expressed constitutively on B cells, activated T cells, cells of monocyte/macrophage linage and on certain epithelial cells, both in mice (Hammerling, 1976) and in man (Daar et al., 1984). Due to the expression of MHC Class II antigens on "normal" endothelium, their targeting is not quite so straightforward as E-selectin. However, the induction and targeting of MHC Class II antigens is made possible by using in conjunction with an immunosuppressant, such as Cyclosporin A (CsA), that has the ability to effectively inhibit the expression of Class II molecules in normal tissues (Groenewegen et al., 1985). The CsA acts by preventing the activation of T cells and NK cells (Groenewegen et al., 1985; DeFranco, 1991), thereby reducing the basal levels of IFN-γ below those needed to maintain Class II expression on endothelium.

There are various other cyclosporins related to CsA, including cyclosporins A, B, C, D, G, and the like, that also have immunosuppressive action and are likely to demonstrate an ability to suppress Class II expression. Other agents that might be similarly useful include FK506 and rapamycin.

Thus, the practice of the MHC Class II induction and targeting embodiment requires a pretreatment of the tumor-bearing animal with a dose of CsA or other Class II immunosuppressive agent that is effective to suppress Class II expression. In the case of CsA, this will typically be on the order of about 10 to about 30 mg/kg body weight. Once suppressed in normal tissues, Class II antigens can then be selectively induced in the tumor endothelium, again through the use of a bispecific antibody.

In this case, the antigen-inducing bispecific antibody will have specificity for a tumor cell marker and for an activating antigen found on the surface of an effector cell that is capable of inducing IFN-γ production. Such effector cells will generally be helper T cells ($T_H$) or Natural Killer (NK) cells. In these embodiments, it is necessary that T cells, or NK cells if CD16 is used, be present in the tumor to produce the cytokine intermediate in that Class II antigen expression is achieved using IFN-γ, but is not achieved with the other cytokines. Thus, for the practice of this aspect of the invention, one will desire to select CD2, CD3, CD28, or most preferably CD28, as the cytokine activating antigen for targeting by the antigen-inducing bispecific antibody.

The T cells that should be activated in the tumor are those adjacent to the vasculature since this is the region most accessible to cells and is also where the bispecific antibody will be most concentrated. The activated T cells should then secrete IFN-γ which induces Class II antigens on the adjacent tumor vasculature.

The use of a bispecific (Fab'-Fab') antibody having one arm directed against a tumor antigen and the other arm directed against CD28 is currently preferred. This antibody will crosslink CD28 antigens on T cells in the tumor which, when combined with a second signal (provided, for example, by IL-1 which is commonly secreted by tumor cells (Burrows et al., 1991; Ruco et al., 1990), has been shown to activate T cells through a $CA^{2+}$-independent non-CsA-inhibitable pathway (Hess et al., 1991; June et al., 1987; Bjorndahl et al., 1989).

The preparation of antibodies against various cytokine activating molecules is also well known in the art. For example, the preparation and use of anti-CD14 and anti-CD28 monoclonal antibodies having the ability to induce cytokine production by leukocytes has now been described by several laboratories (reviewed in Schutt et al., 1988; Chen et al., 1990, and June et al., 1990, respectively). Moreover, the preparation of monoclonal antibodies that will stimulate leukocyte release of cytokines through other mechanisms and other activating antigens is also known (Clark et al., 1986; Geppert et al., 1990).

In still further embodiments, the inventors contemplate an alternative approach for suppressing the expression of Class II molecules, and selectively eliciting Class II molecule expression in the locale of the tumor. This approach, which avoids the use of both CsA and a bispecific activating antibody, takes advantage of the fact that the expression of Class II molecules can be effectively inhibited by suppressing IFN-γ production by T cells, e.g., through use of an anti-CD4 antibody (Street et al., 1989). Using this embodiment, IFN-γ production is inhibited by administering anti-CD4, resulting in the general suppression of Class II expression. Class II is then induced only in the tumor site, e.g., using tumor-specific T cells which are only activatable within the tumor.

In this mode of treatment, one will generally pretreat an animal or human patient with a dose of anti-CD4 that is effective to suppress IFN-γ production and thereby suppress the expression of Class II molecules. Effective doses are contemplated to be, for example, on the order of about 4 to about 10 mg/kg body weight. After Class II expression is suppressed, one will then prepare and introduce into the bloodstream an IFN-γ-producing T cell clone (e.g., $T_h1$ or cytotoxic T lymphocyte, CTL) specific for an antigen expressed on the surface of the tumor cells. These T cells localizes to the tumor mass, due to their antigen recognition capability and, upon such recognition, then release IFN-γ. In this manner, cytokine release is again restricted to the tumor, thus limiting the expression of Class II molecules to the tumor vasculature.

The IFN-γ-producing T cell clone may be obtained from the peripheral blood (Mazzocchi et al., 1990), however, a preferred source is from within the tumor mass (Fox et al., 1990). The currently preferred means of preparing such a T cell clone is to remove a portion of the tumor mass from a patient; isolate cells, using collagenase digestion, where necessary; enrich for tumor infiltrating leukocytes using density gradient centrifugation, followed by depletion of other leukocyte subsets by, e.g., treatment with specific antibodies and complement; and then expand the tumor infiltrating leukocytes in vitro to provide the IFN-γ producing clone. This clone will necessarily be immunologically compatible with the patient, and therefore should be well tolerated by the patient.

It is proposed that particular benefits will be achieved by further selecting a high IFN-γ producing T cell clone from the expanded leukocytes by determining the cytokine secretion pattern of each individual clone every 14 days. To this end, rested clones will be mitogenically or antigenically-stimulated for about 24 hours and their culture supernatants assayed, e.g., using a specific sandwich ELISA technique (Cherwinski et al., 1989), for the presence of IL-2, IFN-γ, IL-4, IL-5 and IL-10. Those clones secreting high levels of IL-2 and IFN-γ, the characteristic cytokine secretion pattern of $T_{H1}$ clones, will be selected. Tumor specificity will be confirmed using proliferation assays.

Furthermore, one will prefer to employ as the anti-CD4 antibody an anti-CD4 Fab, because it will be eliminated from the body within 24 hours after injection and so will not cause suppression of the tumor-recognizing T-cell clones that are subsequently administered. The preparation of T cell clones having tumor specificity is generally known in the art, as exemplified by the production and characterization of T cell clones from lymphocytes infiltrating solid melanoma tumors (Maeda et al., 1991).

In using either of the MHC Class II suppression-induction methods, additional benefits will likely result from the fact that anti-Class II antibodies injected intravenously do not appear to reach the epithelial cells or the monocytes/macrophages in normal organs other than the liver and spleen. Presumably this is because the vascular endothelium in most normal organs is tight, not fenestrated as it is in the liver and spleen, and so the antibodies must diffuse across basement membranes to reach the Class II-positive cells. Also, any B cell elimination that may result, e.g., following cross-linking, is unlikely to pose a significant problem as these cells are replenished from Class II negative progenitors (Lowe et al., 1986). Even B cell killing, as occurs in B lymphoma patients, causes no obvious harm (Vitetta et al., 1991).

In summary, although the tumor coagulating compositions and antibodies of the present invention are elegantly simple, and do not require the induction of antigens for their operability, the combined use of an antigen-inducing bispecific antibody with this invention is also contemplated. Such antibodies would generally be administered prior to the bispecific coagulating ligands of this invention.

Generally speaking, the more "immunogenic" tumors would be more suitable for the MHC Class II approach involving, e.g., the cross-linking of T cells in the tumor through an anti-CD28/anti-tumor bispecific antibody, because these tumors are more likely to be infiltrated by T cells, a prerequisite for this method to be effective. Examples of immunogenic solid tumors include renal carcinomas, melanomas, a minority of breast and colon cancers, as well as possibly pancreatic, gastric, liver, lung and glial tumor cancers. These tumors are referred to as "immunogenic" because there is evidence that they elicit immune responses in the host and they have been found to be amenable to cellular immunotherapy (Yamaue et al., 1990). In the case of melanomas and large bowel cancers, the most preferred antibodies for use in these instances would be B72.3 (anti-TAG-72) and PRSC5/PR4C2 (anti-Lewis a) or 9.2.27 (anti-high Mr melanoma antigen).

For the majority of solid tumors of all origins, an anti-CD14 approach that employs a macrophage/monocyte intermediate would be more suitable. This is because most tumors are rich in macrophages. Examples of macrophage-rich tumors include most breast, colon and lung carcinomas. Examples of preferred anti-tumor antibodies for use in these instances would be anti-HER-2, B72.3, SM-3, HMFG-2, and SWA11 (Smith et al., 1989).

(c) Coagulant-Inducible Markers

Coagulants, such as thrombin, Factor IX/IXa, Factor X/Xa, plasmin and metalloproteinases, such as interstitial collagenases, stromelysins and gelatinases, also act to induce certain markers. In particular, E-selectin, P-selectin, PDGF and ICAM-1 are induced by thrombin (Sugama et. al., 1992; Shankar et. al., 1994).

Therefore, for this induction, an anti-coagulant/anti-tumor bispecific antibody will be utilized. The antibody will localize in the tumor via its tumor binding activity. The bispecific will then concentrate the coagulant, e.g., thrombin, in the tumor, resulting in induction of E-selectin and P-selectin on the tumor vascular endothelial cells (Sugama et. al., 1991; Shankar et. al., 1994).

Alternatively, targeting of truncated tissue factor to tumor cells or endothelium will induce thrombin deposition within the tumor. As the thrombin is deposited, E-selectin and P-selectin will be induced on the tumor vascular endothelial cells.

(d) Antibodies to Vascular Endothelial Cell Markers

A straightforward means of recognizing a disease-associated vasculature target, whether induced in the natural environment or by artificial means, is through the use of an antibody that has binding affinity for the particular cell surface receptor, molecule or antigen. These include antibodies directed against all cell surface components that are known to be present on, e.g., tumor vascular endothelial cells, those that are induced or over-expressed in response to tumor-derived factors, and those, that are induced following manipulation by the hand of man. Table IV and Table V summarize useful antibodies and their properties.

TABLE IV

SUMMARY OF VASCULATURE STAINING PATTERNS OF CERTAIN ANTIBODIES TO HUMAN TUMOR VASCULATURE

| Antibody | Antigen | Reference | % Tumor types stained | % tumor vessels stained | normal vessel reactivity |
|---|---|---|---|---|---|
| anti-vWF | VIII R Ag | | 100 | 100 | strong on all |
| FB5 | endosialin | Rettig & old | 30 | 10-20 | lymphoid organs |
| TP3 | 80 kDa osteosarcoma related antigen protein | Bruland | 50 | 10-30 | strong on small BV |
| BC-1 | fibronectin isoform | Zardi | 60 | 10-30 | none |
| TV-1 | fibronectin | Epstein | 100 | 100 | strong on all |
| LM 609 | $\alpha_v\beta_e$ vitronectin receptor | Cheneoh | 85 | 70-80 | medium on all |
| TEC 11 | endoglin | Thorpe; __ | 100 | 100 | weak on most |
| TEC 110 | VEGF | Thorpe; __ | 100 | 100 | weak on most |

TABLE V

COMPARISON OF ANTI-EC mAbs ON HUMAN TUMORS

| TUMOR TYPE | n | TEC 110 | TEC 11 | FB-5 | TP-3 | BC-1 | TV-1 | LM 609 |
|---|---|---|---|---|---|---|---|---|
| DIGESTIVE | | | | | | | | |
| Gastrointestinal | 9 | ++ | ++ | +-- | ++ | + | ++ | ++ |
| Parotid | 3 | ++ | ++ | − | ++ (SMALL) | − | ND | ND |
| REPRODUCTIVE | | | | | | | | |
| Breast | 1 | + | ++ | − | ND | ++ | ++ | − |
| Ovary | 4 | ++ | ++ | − | ++ (SMALL) | ++ | ++ | + |
| Uterus | 2 | ++ | ++ | − | | ++ | ++ | + |
| RESPIRATORY | | | | | | | | |
| Lung | 3 | ++ | ++ | + | ND | ++ | ++ | + |
| LYMPHOID | | | | | | | | |
| Hodgkins | 2 | ++ | ++ | − | + | − | +-++ | + |

Two further antibodies that may be used in this invention are those described by Rettig et al. (1992) and Wang et al. (1993) that are directed against unrelated antigens of unknown function expressed in the vasculature of human tumors, but not in most normal tissues.

The antibody described by Kim et. al. (1993) may also be used in this invention, particularly as this antibody inhibited angiogenesis and suppressed tumor growth in vivo.

Antibodies that have not previously been shown to be specific for human tumors may also be used. For example, Venkateswaran et al. (1992) described the production of anti-FGF MAbs. Xu et. al. (1992) developed and characterized a panel of 16 isoform and domain-specific polyclonal and monoclonal antibodies against FGF receptor (flg) isoforms. Massoglia et al. (1987) also reported MAbs against FGF.

(e) Generation of Antibodies to Disease Vasculature

In addition to utilizing a known antibody, such as those described above and others known and published in the scientific literature, one may also generate a novel antibody using standard immunization procedures, as described in more detail hereinbelow. To generate an antibody against a known disease-associated vascular marker antigen, one would immunize an animal with an immunogenic composition comprising the antigen. This may be a membrane preparation that includes, or is enriched for, the antigen; a relatively purified form of the antigen, as isolated from cells or membranes; a highly purified form of the antigen, as obtained by a variety of purification steps using, e.g., a native antigen extract or a recombinant form of the antigen obtained from a recombinant host cell.

The present invention also provides yet further methods for generating an antibody against an antigen present on disease-associated vasculature endothelial cells, which methods are suitable for use even where the biochemical identity of the antigen remains unknown. These methods are exemplified through the generation of an antibody against tumor vasculature endothelial cells. A first means of achieving antibody generation in this manner uses a preparation of vascular endothelial cells obtained from the tumor site of an animal or human patient. One simply immunizes an experimental animal with a preparation of such cells and collects the antibodies so produced. The most useful form of this method is that where specific antibodies are subsequently selected, as may be achieved using conventional hybridoma technology and screening against tumor vascular endothelial cells.

A development of the above method is that which mimics the tumor vasculature phenomenon in vitro, and where cell purification is not necessary. In using this method, endothelial cells are subjected to tumor-derived products, such as might be obtained from tumor-conditioned media, in cell culture rather than in an animal. This method generally involves stimulating endothelial cells with tumor-conditioned medium and employing the stimulated endothelial cells as immunogens to prepare a collection of antibodies. Again, specific antibodies should be selected, e.g., using conventional monoclonal antibody technology, or other techniques such as combinatorial immunoglobulin phagemid libraries prepared from RNA isolated from the spleen of the immunized animal. One would select a specific antibody that preferentially recognizes tumor-stimulated vascular endothelium and reacts more strongly with tumor-associated endothelial cells than with normal adult human tissues.

Stimulated endothelial cells contemplated to be of use in this regard include, for example, human umbilical vein endothelial cells (HUVE), human dermal microvascular endothelial cells (HDEMC), human saphenous vein endothelial cells, human omental fat endothelial cells, other human microvascular endothelial cells, human brain capillary endothelial cells, and the like. It is also contemplated that endothelial cells from another species may stimulated by tumor-conditioned media and employed as immunogens to generate hybridomas to produce an antibodies in accordance herewith, i.e., to produce antibodies that crossreact with tumor-stimulated human vascular endothelial cells, and/or antibodies for use in pre-clinical models.

"Tumor-conditioned medium or media" are defined herein as compositions or media, such as culture media, that contain one or more tumor-derived cytokines, lymphokines or other effector molecules. Most typically, tumor-conditioned medium is prepared from a culture medium in which selected tumor cells have been grown, and will therefore be enriched in such tumor-derived products. The type of medium is not believed to be particularly important, so long as it at least initially contains appropriate nutrients and conditions to support tumor cell growth. It is also, of course, possible to extract and even separate materials from tumor-conditioned media and employ one or more of the extracted products for application to the endothelial cells.

As for the type of tumor used for the preparation of the medium or media, one will, of course, prefer to employ tumors that mimic or resemble the tumor that will ultimately be subject to analysis or treatment using the present invention. Thus, for example, where one envisions the development of a protocol for the treatment of breast cancer, one will desire to employ breast cancer cells such as ZR-75-1, T47D, SKBR3, MDA-MB-231. In the case of colorectal tumors, one may mention by way of example the HT29 carcinoma, as well as DLD-1, HCT116 or even SW48 or SW122. In the case of lung tumors, one may mention by way of example NCI-H69, SW2, NCI H23, NCI H460, NCI H69, or NCI H82. In the case of melanoma, good examples are DX.3, A375, SKMEL-23, HMB-2, MJM, T8 or indeed VUP. In any of the above cases, it is further believed that one may even employ cells produced from the tumor that is to be treated, i.e., cells obtained from a biopsy.

Once prepared, the tumor-conditioned media is then employed to stimulate the appearance of tumor endothelium-specific marker(s) on the cell surfaces of endothelial cells, e.g., by culturing selected endothelial cells in the presence of the tumor-conditioned media (or products derived therefrom). Again, it is proposed that the type of endothelial cell that is employed is not of critical importance, so long as it is generally representative of the endothelium associated with the vasculature of the particular tumor that is ultimately to be treated or diagnosed. The inventors prefer to employ human umbilical vein endothelial cells (HUVE), or human dermal microvascular endothelial cells (HDMEC, Karasek, 1989), in that these cells are of human origin, respond to cytokine growth factors and angiogenic factors and are readily obtainable. However, it is proposed that any endothelial cell that is capable of being cultured in vitro may be employed in the practice of the invention and nevertheless achieve beneficial results. One may mention, by way of example, cells such as EA.hy9.26, ECV304, human saphenous vein endothelial cells, and the like.

Once stimulated using the tumor-derived products, the endothelial cells are then employed as immunogens in the preparation of monoclonal antibodies (MAbs). The technique for preparing MAbs against antigenic cell surface markers is quite straightforward, and may be readily carried out using techniques well known to those of skill in the art, as exemplified by the technique of Kohler & Milstein (1975), and further described hereinbelow.

Generally speaking, a preferred method of preparing MAbs using stimulated endothelial cells involves the following procedures: Cells or cell lines derived from human tumors are grown in tissue culture for ≧4 days. The tissue culture supernatant ('tumor-conditioned medium') is removed from the tumor cell cultures and added to cultures of HUVEC at a final concentration of 50% (v/v). After 2 days culture the HUVEC are harvested non-enzymatically and 1-2×10$^6$ cells injected intraperitoneally into mice. This process is repeated three times at two-weekly intervals, the final immunization being by the intravenous route. Three days later the spleen cells are harvested and fused with SP2/0 myeloma cells by standard protocols (Kohler & Milstein, 1975) and hybridomas producing antibodies with the appropriate reactivity are cloned by limiting dilution.

From the resultant collection of hybridomas, one will then desire to select one of more hybridomas that produce an antibody that recognizes the activated vascular endothelium to a greater extent than it recognizes non-activated vascular endothelium. One goal is the identification of antibodies having virtually no binding affinity for normal endothelium. However, in contrast to the prior art, in the present invention this property is not critical. In any event, one will generally identify suitable antibody-producing hybridomas by screening using, e.g., an ELISA, RIA, IRMA, IIF, or similar immunoassay, against one or more types of tumor-activated endothelial cells. Once candidates have been identified, one will desire to test for the absence of reactivity for non-activated or "normal" endothelium or other normal tissue or cell type. In this manner, hybridomas producing antibodies having an undesirably high level of normal cross-reactivity for the particular application envisioned may be excluded.

(f) Anti-Endoglin Antibodies

Using the technique described above, antibodies having relative specificity for tumor vascular endothelium have been prepared and isolated. In one particular example, HT29 carcinoma cells were employed to prepare the conditioned medium, which was then employed to stimulate HUVE cells in culture. The resultant HT29-activated HUVE cells were then employed as immunogens in the preparation of a hybridoma bank, which was ELISA-screened using HT29-activated HUVE cells and by immunohistologic analysis of sections of human tumors and normal tissues. From this bank, antibodies that recognized a tumor vascular endothelial cell antigen were selected.

The MAbs termed tumor endothelial cell antibody 4 and tumor endothelial cell antibody 11 (TEC4 and TEC11) were obtained using the above method. The antigen recognized by TEC4 and TEC11 was ultimately determined to be the molecule endoglin. The epitopes on endoglin recognized by TEC4 and TEC11 are present on the cell surface of stimulated HUVE cells, and only minimally present (or immunologically accessible) on the surface of non-stimulated cells. MAbs have previously been raised against endoglin. However, analyzing the reactivity with HUVEC or TCM-activated HUVEC cell surface determinants by FACS or indirect immunofluorescence shows the epitopes recognized by TEC-4 and TEC-11 to be distinct from those of a previous antibody termed 44G4 (Gougos & Letarte, 1988).

Although any of the known anti-endoglin antibodies (e.g., Gougos & Letarte, 1988; Gougos et al., 1992; O'Connell et al., 1992; Buhring et al., 1991) may be used in connection with the present invention, the TEC-4 and TEC-11 mAbs are envisioned to be particularly suitable. This is because they label capillary and venular endothelial cells moderately to strongly in a broad range of solid tumors (and in several chronic inflammatory conditions and fetal placenta), but display relatively weak staining of vessels in the majority of normal, healthy adult tissues. TEC-11 is particularly preferred as it shows virtually no reactivity with non-endothelial cells. Furthermore, both TEC-4 and TEC-11 are complement-fixing, which imparts to them the potential to also induce selective lysis of endothelial cells in the tumor vascular bed.

Antibodies that are cross-reactive with the MAbs TEC-4 and TEC-11, i.e., those that bind to endoglin at the same epitope as TEC-4 or TEC-11 (ATCC HB-12312 and ATCC HB-12311, respectively), are also contemplated to be of use in this invention. The identification of an antibody or antibodies that bind to endoglin at the same epitopes as TEC-4 or TEC-11 is a fairly straightforward matter. This can be readily determined using any one of variety of immunological screening assays in which antibody competition can be assessed. For example, where the test antibodies to be examined are obtained from a different source to that of TEC-4 or TEC-11, e.g., a rabbit, or are even of a different isotype, for example, IgG1 or IgG3, a competition ELISA may be employed. In one such embodiment of a competition ELISA one would pre-mix TEC-4 or TEC-11 with varying amounts of the test antibodies prior to applying to the antigen-coated wells in the ELISA plate. By using either anti-murine or anti-IgM secondary antibodies one will be able to detect only the bound TEC-4 or TEC-11 antibodies—the binding of which will be reduced by the presence of a test antibody that recognizes the same epitope as either TEC-4 or TEC-11.

To conduct an antibody competition study between TEC-4 or TEC-11 and any test antibody, one may first label TEC-4 or TEC-11 with a detectable label, such as, e.g., biotin or an enzymatic or radioactive label, to enable subsequent identification. In these cases, one would incubate the labelled antibodies with the test antibodies to be examined at various ratios (e.g., 1:1, 1:10 and 1:100) and, after a suitable period of time, one would then assay the reactivity of the labelled TEC-4 or TEC-11 antibodies and compare this with a control value in which no potentially competing antibody (test) was included in the incubation.

The assay may be any one of a range of immunological assays based upon antibody binding and the TEC-4 or TEC-11 antibodies would be detected by means of detecting their label, e.g., using streptavidin in the case of biotinylated antibodies or by using a chromogenic substrate in connection with an enzymatic label or by simply detecting the radiolabel. An antibody that binds to the same epitope as TEC-4 or TEC-11 will be able to effectively compete for binding and thus will significantly reduce TEC-4 or TEC-11 binding, as evidenced by a reduction in labelled antibody binding. In the present case, after mixing the labelled TEC-4 or TEC-11 antibodies with the test antibodies, suitable assays to determine the remaining reactivity include, e.g., ELISAs, RIAs or western blots using human endoglin; immunoprecipitation of endoglin; ELISAs, RIAs or immunofluorescent staining of recombinant cells expressing human endoglin; indirect immunofluorescent staining of tumor vasculature endothelial cells; reactivity with HUVEC or TCM-activated HUVEC cell surface determinants indirect immunofluorescence and FACS analysis. This latter method is most preferred and was employed to show that the epitopes recognized by TEC-4 and TEC-11 are distinct from that of 44G4 (Gougos & Letarte, 1988).

The reactivity of the labelled TEC-4 or TEC-11 antibodies in the absence of any test antibody is the control high value. The control low value is obtained by incubating the labelled antibodies with unlabelled antibodies of the same type, when competition would occur and reduce binding of the labelled antibodies. A significant reduction in labelled antibody reactivity in the presence of a test antibody is indicative of a test antibody that recognizes the same epitope, i.e., one that "cross-reacts" with the labelled antibody. A "significant reduction" in this aspect of the present application may be defined as a reproducible (i.e., consistently observed) reduction in binding of at least about 10-50% at a ratio of about 1:1, or more preferably, of equal to or greater than about 90% at a ratio of about 1:100.

The use of "cross-reactivity assays", as described above in the context of TEC-4 and TEC-11 antibodies, may be applied to any antibody for use in the present invention. Therefore, antibodies that bind to a component of a tumor cell, a component of tumor vasculature, a tumor cell-associated component, a tumor vasculature-associated component, a tumor extracellular matrix component, or to any cell type listed herein, at the same epitope as any of the antibodies listed herein, as determined by an antibody competition assay, will be an antibody that falls under the scope of this invention when combined with a coagulating agent to form a bispecific ligand.

(g) Use of Vascular Endothelial Cell Binding Ligands

Biological ligands that are known to bind or interact with endothelial cell surface molecules, such as growth factor receptors, may also be employed as a targeting component.

The growth factors or ligands contemplated to be useful as targets in this sense include VEGF/VPF, FGF, TGFβ, ligands that bind to a TIE, tumor-associated fibronectin isoforms, scatter factor, hepatocyte growth factor (HGF), platelet factor 4 (PF4), PDGF and TIMP.

Particularly preferred targets are VEGF/VPF, the FGF family of proteins and TGFβ. Abraham et al. (1986) cloned FGF, which is therefore available as a recombinant protein. As reported by Ferrara et al. (1991), four species of VEGF having 121, 165, 189, and 206 amino acids have been cloned.

(h) Targeting of Bound Ligands

Antibodies or specific targeting ligands may also be directed to any component that binds to the surface of vascular endothelial cells in a disease site, such as a tumor. Such components are exemplified by tumor-derived ligands and antigens, such as growth factors, that bind to specific cell surface receptors already present on the endothelial cells, or to receptors that have been induced, or over-expressed, on such cells in response to the tumor environment. Tumor vasculature-associated targets may also be termed tumor-derived endothelial cell binding factors.

A level of specificity required for successful disease targeting will be achieved partly because the local endothelial cells will be induced to express, or reveal, receptors that are not present, or are under-expressed or masked, on normal endothelial cells. With tumors, further specificity will result due to the fact that endothelial cells in the tumor will capture the tumor-derived factors, and bind them to the cell surface, reducing the amount of ligand available for other tissues. When combined with the further dilution of the factor or ligand by distribution in the blood and tissue fluid pool, endothelial cells in normal tissues will be expected to bind relatively little of such factors. Thus, operationally, cell-surface bound ligands or factors will be able to used as a tumor endothelial cell marker.

In addition to manufacture by the tumor cells themselves, tumor endothelial cell binding factors may also originate from other cell types, such as macrophages and mast cells, that have infiltrated tumors, or may be elaborated by platelets that become activated within the tumor.

Further growth factors or ligands contemplated to be useful as tumor vasculature-associated targets include EGF, FGF, VEGF, TGFβ, HGF (NaKamura, 1991), angiotropin, TGF-α, TNF-α, PD-ECGF and TIE binding ligands (Bicknell and Harris, 1992). The currently preferred targets are VEGF/VPF, the FGF family of proteins, transforming growth factor-β (TGF-β); TGF-α; tumor necrosis factor-α (TNF-α); angiotropin; platelet-derived endothelial cell growth factor (PD-ECGF); TIE binding ligands; pleiotropin.

Another aspect of the present invention is the use of targeting antibodies, or binding regions therefrom, that are specific for epitopes present only on ligand-receptor complexes, which epitopes are absent from both the individual (free) ligand and the receptor in its unbound form. These antibodies recognize and bind to the unique conformation that results when a ligand, such as a growth factor, binds to its receptor, such as a growth factor receptor, to form a specifically bound complex. Such epitopes are not present on the uncomplexed forms of the ligands or receptors.

The inventors contemplate that the ligand-receptor complexes to which these antibodies bind are present in significantly higher number on tumor-associated endothelial cells than on non-tumor associated endothelial cells. Such antibodies will therefore be useful as targeting agents and will serve to further increase the specificity of the bispecific coagulants of the invention.

(i) Receptor Constructs

Soluble binding domains of endothelial cell surface receptors are also contemplated for use as targeting ligands in the present invention. This concept is generally based upon the well-known sandwich binding phenomena that has been exploited in a variety of in vitro and in vivo binding protocols. Basically, as the endothelial cells express specific receptors, the cells bind to and adsorb the corresponding ligands, the ligands are then available for binding to further receptor constructs should they be introduced into the system.

A range of useful endothelial cell receptors has been identified in the foregoing sections, with VEGF/VPF, FGF, TGFβ, TIE-1 and TIE-2 being particularly preferred targets. Each of these receptors could be manipulated to form a soluble binding domain for use as a targeting ligand.

4. Disease-Associated Stromal Cell Targets (a) Extracellular Matrix/Stromal Targets The usefulness of the basement membrane markers in tumoral pathology was described by Birembaut et al. (1985). These studies showed that the distribution of basement membrane (BM) markers, type IV collagen, laminin (LM), heparan sulphate proteoglycan (HSP) and fibronectin (FN) were disrupted in tumoral pathology. Burtin et. al. (1983) also described alterations of the basement membrane and connective tissue antigens in human metastatic lymph nodes.

A preferred target for use with the invention is RIBS. Ugarova et al. (1993) reported that conformational changes occur in fibrinogen and are elicited by its interaction with the platelet membrane glycoprotein GPIIb-IIIa. The binding of fibrinogen to membrane glycoprotein GPIIb-IIIa on activated platelets leads to platelet aggregation. This interaction results in conformational changes in fibrinogen as evidenced by the expression of receptor-induced binding sites, RIBS:, epitopes which are expressed by the bound but not the free ligand.

Two RIBS epitopes have been localized by Ugarova et al. (1993). One sequence resides at γ112-119 and is recognized by MAb 9F9; the second is the RGDF sequence at Aα 95-98 and is recognized by mAb 155B16. These epitopes are also exposed by adsorption of fibrinogen onto a plastic surface and digestion of the molecule by plasmin. Proteolytic exposure of the epitopes coincides with cleavage of the carboxyl-terminal aspects of the Aα-chains to form fragment $x_2$. The inaccessibility of the RGDF sequence at Aα 95-98 in fibrinogen suggests that this sequence does not participate in the initial binding of the molecule to GPIIb-IIIa.

Binding of fibrinogen to its receptor alters the conformation of the carboxyl-terminal aspects of the Aα-chains, exposing the sequences which reside in the coiled-coil connector segments between the D and E domains of the molecule, generating the RIBS epitopes. In practical terms, the RIBS sequences are proposed as epitopes for use in targeting with a coaguligand. The MAbs 9F9 and 155B16 may thus be advantageously used, as may the antibodies described by Zamarron et al. (1991).

(b) Additional Cellular Targets

The present invention has the further advantage that it may be used to direct coagulants to disease-associated vasculature by targeting them to cell types found within the disease region.

Platelets participate in hemostasis and thrombosis by adhering to injured blood vessel walls and accumulating at the site of injury. Although platelet deposition at sites of blood vessel injury is responsible for the primary arrest of bleeding under physiologic conditions, it can lead to vascular occlusion with ensuing ischemic tissue damage and thrombus embolization under pathologic conditions.

Interactions of platelets with their environment and with each other represent complex processes that are initiated at the cell surface. The surface membrane, therefore, provides a reactive interface between the external medium, including components of the blood vessel wall and plasma, and the platelet interior.

p-155, a multimeric platelet protein that is expressed on activated platelets (Hayward et al., 1991), may be targeted using the invention. Platelets respond to a large number of stimuli by undergoing complex biochemical and morphological changes. These changes are involved in physiological processes including adhesion, aggregation, and coagulation. Platelet activation produces membrane alterations that can be recognized by monoclonal antibodies. The monoclonal antibody JS-1 (Hayward et al., 1991) is one such antibody contemplated for use as part of a coaguligand.

Ligand-induced binding sites (LIBS) are sites expressed on cell surface receptors only after ligand binding causes the receptor to change shape, mediate subsequent biological events. These may be seen as counterparts to RIBS and are also preferred targets for use with the present invention.

13 anti-LIBS antibodies have been developed by Frelinger et. al. (1990; 1991), any one of which may be used to deliver a coagulant to a disease or tumor site in accordance herewith. The murine monoclonal antiplatelet antibodies MA-TSPI-1 (directed against human thrombospondin) and MA-PMI-2, MA-PMI-1, and MA-LIBS-1 (directed against LIBS on human platelet glycoprotein IIb/IIIa) of Dewerchin et al. (1991) may also be used, as may RUU 2.41 and LIBS-1 of Heynen et al. (1994); OP-G2 of Tomiyama et al. (1992); and Ab-15.

Many other targets, such as antigens on smooth muscle cells, pericytes, fibroblasts, macrophages and infiltrating lymphocytes and leukocytes may also be used.

B. Coagulating Agents

The second arm or element of the bispecific agents of the invention will be a component that is capable of promoting coagulation. "Coagulation promoting agents" may be coagulation factors, factors that indirectly stimulate coagulation, or they may be in the form of a second binding region that is capable of binding and releasing a coagulation factor or factor that indirectly stimulates coagulation.

1. Coagulation Factors

A variety of coagulation factors may be used in connection with the present invention, as exemplified by the agents set forth below. Where a coagulation factor is covalently linked to a first binding agent, a site distinct from its functional coagulating site is used to join the molecules. Appropriate joining regions distinct from the active sites, or functional regions, of the coagulation factors are also described in each of the following sections.

(a) Tissue Factor

Tissue factor (TF) is one agent capable of initiating blood coagulation. TF is the activator of the extrinsic pathway of blood coagulation and is not in direct contact with the blood under physiologically normal conditions (Osterud et al., 1986; Nemerson, 1988; Broze, 1992; Ruf & Edington, 1994). In vascular damage or activation by certain cytokines or endotoxin, however, TF will be exposed to the blood, either by the (sub) endothelial cells (Weiss et al., 1989) or by certain blood cells (Warr et al., 1990). TF will then complex with factor VIIa, which under normal conditions circulates at low concentrations in the blood (Wildgoose et al., 1992), and the TF/factor VIIa complex will start the coagulation cascade through the activation of factor X into factor Xa. The cascade will ultimately result in the formation of fibrin.

For this sequence of events to occur, the TF:VIIa complex has to be associated with a phospholipid surface upon which the coagulation-initiation complexes with factors IX or X can assemble (Ruf et al., 1991; Paborsky et al., 1991; Bach et al., 1986). For this reason, truncated TF (or tTF), from which the transmembrane and cytoplasmic regions have been removed by truncating the gene, is a soluble protein having one hundred-thousandth of the factor X-activating activity of native TF (Ruf et al., 1991).

(b) Clotting Factors

Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may also be used in the present invention.

(c) Venom Coagulants

Russell's viper venom was shown to contain a coagulant protein by Williams and Esnouf in 1962. Kisiel (1979) isolated a venom glycoprotein that activates Factor V; and Di Scipio et al. (1977) showed that a protease from the venom activates human Factor X. The Factor X activator is the component contemplated for use in this invention.

Monoclonal antibodies specific for the Factor X activator present in Russell's viper venom have also been produced (e.g., MP1 of Pukrittayakamee et al., 1983), and could be used to deliver the agent to a specific target site within the body.

(d) Prostaglandins and Synthetic Enzymes

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation (Whittle et al., 1981).

Both thromboxane $A_2$ and active analogues thereof are contemplated for use in the present invention. A synthetic protocol for generating thromboxane $A_2$ is described by Bhagwat et al. (1985). The thromboxane $A_2$ analogues described by Ohuchida et. al. (1981) (especially compound 2) are particularly contemplated for use herewith.

It is possible that thromboxane synthase, and other enzymes that synthesize platelet-activating prostaglandins, may also be used as "coagulants" in the present context. Shen and Tai (1986a;b) describe monoclonal antibodies to, and immunoaffinity purification of, thromboxane synthase; and Wang et. al. (1991) report the cDNA for human thromboxane synthase.

(e) Inhibitors of Fibrinolysis

α2-antiplasmin, or α2-plasmin inhibitor, is a proteinase inhibitor naturally present in human plasma that functions to efficiently inhibit the lysis of fibrin clots induced by plasminogen activator (Moroi & Aoki, 1976). α2-antiplasmin is a particularly potent inhibitor, and is contemplated for use in the present invention.

α2-antiplasmin may be purified as first described by Moroi and Aoki (1976). Other purification schemes are also available, such as using affinity chromatography on plasminogen-Sepharose, ion-exchange chromatography on DEAE-Sephadex and chromatography on Concanavalin-A-Sepharose; or using affinity chromatography on a Sepharose column bearing an elastase-digested plasminogen formulation containing the three N-terminal triple-loop structures in the plasmin A-chain (LBSI), followed by gel filtration (Wiman & Collen, 1977; Wiman, 1980, respectively).

As the cDNA sequence for α2-antiplasmin is available (Tone et al., 1977), a preferred method for α2-antiplasmin production will be via recombinant expression.

Monoclonal antibodies against α2-antiplasmin are also available that may be used in the bispecific binding ligand embodiments of the invention. For example, Hattey et al. (1987) described two MAbs against α2-antiplasmin, MPW2AP and MPW3AP. As each of these MAbs were reported to react equally well with native α2-antiplasmin, they could both be used to deliver exogenous α2-antiplasmin to a target site or to garner endogenous α2-antiplasmin and concentrate it within the targeted region. Other antibodies, such as JTPI-2, described by Mimuro and colleagues, could also be used.

2. Agents that Bind Coagulation Factors

Another group of bispecific coagulating ligands of this invention are those in which the targeting region is not directly linked to a coagulation factor, but is linked to a second binding region that binds to a coagulating factor.

Where a second binding region is used to bind and deliver a coagulation factor, the binding region is chosen so that it recognizes a site on the coagulation factor that does not significantly impair its ability to induce coagulation. The regions of the coagulation factors suitable for binding in this manner will generally be the same as those regions that are suitable for covalent linking to the targeting region, as described in the previous sections.

However, in that bispecific ligands of this class may be expected to release the coagulation factor following delivery to the tumor site or region, there is more flexibility allowed in the regions of the coagulation factor suitable for binding to a second binding agent or antibody. Another advantage is that bispecific antibodies can be pre-localized before infusion of tTF which may reduce the amount of tTf required and hence toxicity.

Suitable second binding regions for use in this manner, will generally be antigen combining sites of antibodies that have binding specificity for the coagulation factor, including functional portions of antibodies, such as scFv, Fv, Fab', Fab and F(ab')$_2$ fragments.

Bispecific binding ligands that contain antibodies, or fragments thereof, directed against Tissue Factor, Thrombin, Prekallikein, Factor V/Va, Factor VIII/VIIIa, Factor IX/IXa, Factor X/Xa, Factor XI/XIa, Factor XII/XIIa, Factor XIII/XIIIa, Russell's viper venom, thromboxane $A_2$ or α2-antiplasmin are exemplary embodiments of this aspect of the invention.

C. Linkage Means

The first, targeting region and second, coagulating region will be operatively linked to allow each region to perform its intended function without significant impairment. Thus, the targeting region is capable of binding to the intended target, as selected from the range of tumor environment targets, and the coagulating region is capable of directly or indirectly, e.g., through the release of a bound factor, promoting blood coagulation or clotting.

To assess the targeting region binding function, all that is required is to conduct a binding assay to ensure that the bispecific ligand still binds to the targeted component in substantially the same manner as the uncomplexed first binding region. The suitable binding assays are of the type usually seen in immunological binding assays, where the first targeting region is an antibody, and/or other biochemical binding assays, e.g., those using $^{125}$Iodine labeled proteins or other radiolabeled components, as used to assess ligand-receptor binding, to generate Scatchard plots, and the like.

The target antigen or component in such assays may be provided in many forms, including proteins purified from natural or recombinant sources, membrane enriched preparations, intact cells and tissue sections. Generally, where protein compositions are used, they will immobilized on a solid support, such as a microtitre plate, a membrane, or even on a column matrix. It is also generally preferred to use a target composition that reflects the physiological target, therefore as the target will usually be cell-associated, the use of compositions that include intact cells, including tissues and the cells themselves, is also preferred.

The various immunological assays available to confirm the functional binding of a bispecific complex include, e.g., Western blots, ELISAS, ELISAs using fixed cells, immunohistochemistry, and fluorescent activated cell sorting (FACS). The execution of all such assays is generally known to those of skill in the art, and is further disclosed herein.

Assessing the targeting region binding function of a bispecific compound in any of the above or other binding assays is a straightforward matter, where the bispecific ligand and the uncomplexed first binding region will most usually be run in a parallel assay, under the same conditions, to enable ready comparison. Effective bispecific ligands will bind to the target without significant impairment, i.e., in substantially the same manner as the uncomplexed first binding region. Taking the uncomplexed binding region assay result as the 100% reference value, "substantial binding" of the bispecific ligand, as used herein, means that the bispecific ligand exhibits at least about 50% binding, and more preferably, between about 50% and about 80% binding, and most preferably, between about 80% and about 100% binding.

Where the bispecific ligand includes a second binding region that binds to a coagulant, e.g., it is a bispecific antibody, further useful assays are those of the type that allow the binding functions of both arms of the bispecific ligand to be assessed at the same time. For example, this may be achieved by assessing the binding of a radiolabeled coagulant to a target cell via bridging with the bispecific ligand or antibody. Such an assay is exemplified by the binding of tTF to target cells using the B21-2/10H10 bispecific antibody, as described in Example II.

Determining the coagulating agent function of the bispecific ligand is also a straightforward matter. All that is required here is to conduct a coagulation assay using the bispecific ligand and ensure that it functions to promote coagulation in substantially the same manner as the uncomplexed coagulating agent. This is true for "coagulating agents" that are both coagulation factors themselves and those that are second binding regions that bind to a coagulation factor. Naturally, in the latter case, in an in vitro or ex vivo assay, the bispecific ligand will be precomplexed with the coagulation factor to allow binding to the second binding region.

One suitable coagulation assay is that in which the bispecific ligands, pre-complexed with coagulant if necessary, are admixed with a plasma sample. The appearance of fibrin strands is indicative of coagulation in this assay. Effective bispecific ligands would thus be expected to reduce the time taken for fibrin strands to appear, and particularly, to significantly reduce the elapsed time in comparison to control levels.

A variation of the above assay involves first exposing appropriate target cells to the bispecific ligand under conditions effective, and for a time sufficient, to allow binding, washing the cells to remove non-specifically bound components and then resuspending the washed cells in plasma. Only cells effectively coated with the bispecific ligand would be expected to reduce the time taken for fibrin strands to appear in the assay. This type of assay is preferred in that it is, in itself, an assay that assesses both of the functions of the bispecific construct, i.e., initial targeting to the cell and subsequent localized coagulation.

To compare the coagulating function of a bispecific compound to that of an uncomplexed coagulating agent, parallel assays may again be conducted. Effective bispecific ligands will function to promote coagulation without significant impairment, i.e., will function in substantially the same manner as the uncomplexed coagulating agent. Taking the uncomplexed coagulant assay result as the 100% reference value, "substantial function", as used herein, means that the bispecific ligand exhibits at least about 50% coagulation, and more preferably, between about 50% and about 80% coagulation, and most preferably, between about 80% and about 100% coagulation.

The two functional regions of the bispecific ligands may be joined using synthetic chemistry techniques or recombinant DNA techniques. Each of these techniques are routinely employed and well known to those of skill in the art, and are further exemplified in Example I and by the details set forth below.

1. Biochemical Cross-Linkers

The joining of an antibody, or other targeting component, to a coagulating agent will generally employ the same technology as developed for the preparation of immunotoxins. However, considerable advantages are apparent in the present technology, as the consequences of a certain amount of uncomplexed coagulating agent becoming available physiologically are not contemplated to be particularly severe. Thus, the stability requirements for any cross-linkers are not so stringent as for linkers employed in other constructs, such as immunotoxins. Therefore, it can be considered as a general guideline that any biochemical crosslinker that is appropriate for use in an immunotoxin will also be of use in the present context, and additional linkers may also be considered.

In addition to toxins, a variety of other chemotherapeutic and pharmacological agents have been linked to antibodies to form conjugates that have been shown to function pharmacologically (see, e.g., Vaickus et al., 1991). Exemplary antineoplastic agents that have been investigated include doxorubicin, daunomycin, methotrexate and vinblastine, amongst others (Dillman et al., 1988; Pietersz et al., 1988). Moreover, the attachment of other agents such as neocarzinostatin (Kimura et al., 1983), macromycin (Manabe et al., 1984), trenimon (Ghose, 1982) and α-amanitin (Davis & Preston, 1981) has been described. The linking technology described in each of the foregoing scientific papers is also contemplated for use in connection with the present invention.

Cross-linking reagents are used to form molecular bridges that tie together functional groups of two different molecules, e.g., a binding and coagulating agent. To link two different proteins in a step-wise manner, heterobifunctional cross-linkers can be used that eliminate unwanted homopolymer formation (Table VI).

TABLE VI

HETEROBIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extended spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |

TABLE VI-continued

HETEROBIFUNCTIONAL CROSS-LINKERS

| linker | Reactive Toward | Advantages and Applications | Spacer Arm Length\after cross-linking |
|---|---|---|---|
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDC/Sulfo-NHS | Primary amines Carboxyl groups | Hapten-Carrier conjugation | 0 |
| ABH | Carbohydrates Nonselective | Reacts with sugar groups | 11.9 Å |

An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the coagulant).

It can therefore be seen that the preferred coagulants or coagulant binding regions will generally have, or be derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking. For a general overview of linking technology, one may wish to refer to Ghose & Blair (1987).

The spacer arm between the two reactive groups of a cross-linker may have various lengths and chemical compositions. A longer spacer arm allows a better flexibility of the conjugate components while some particular components in the bridge (e.g., benzene group) may lend extra stability to the reactive group or an increased resistance of the chemical link to the action of various agents (e.g., disulfide bond resistant to reducing agents). The use of peptide spacers, such as a four amino acid long peptide with alternating leucine and alanine residues, is also contemplated.

It is preferred that a cross-linker having reasonable stability in blood will be employed. Numerous types of disulfide-bond containing linkers are known that can be successfully employed to conjugate targeting and coagulating agents. Linkers that contain a disulfide bond that is sterically hindered may prove to give greater stability in vivo, preventing release of the coagulant prior to binding at the site of action. These linkers are thus one preferred group of linking agents.

One of the most preferred cross-linking reagents for use in immunotoxins is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific coagulating ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art.

Once conjugated, the bispecific agent will generally be purified to separate the conjugate from unconjugated targeting agents or coagulants and from other contaminants. It is important to remove unconjugated targeting agent to avoid the possibility of competition for the antigen between conjugated and unconjugated species. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

2. Recombinant Fusion Proteins

The bispecific targeted coagulants of the invention may also be fusion proteins prepared by molecular biological techniques. The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; and Ausubel et al., 1989).

In general, to prepare a fusion a protein one would join a DNA coding region, such as a gene or cDNA, encoding a binding ligand or other targeting region to a DNA coding region (i.e., gene or cDNA) encoding a coagulation factor or coagulant binding region. This typically involves preparing an expression vector that comprises, in the same reading frame, a first DNA segment encoding the first binding region operatively linked to a second DNA segment encoding the coagulation factor. The sequences are attached in a manner such that translation of the total nucleic acid yields the desired bispecific compounds of the invention. Expression vectors contain one or more promoters upstream of the inserted DNA regions that act to promote transcription of the DNA and to thus promote expression of the encoded recombinant protein. This is the meaning of "recombinant expression".

Should a particular binding region or coagulant be preferred, and the encoding DNA not instantly available, it may be obtained using the techniques of "molecular cloning" in which a DNA molecule encoding the desired protein is obtained from a DNA library (e.g., a cDNA or genomic library). In such procedures, an appropriate DNA library is screened, e.g., using an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (1989).

When produced via recombinant DNA techniques, the targeting agent/coagulating agent compounds of the invention are referred to as "fusion proteins". It is to be understood that such fusion proteins contain, at least, a targeting agent and a coagulating agent as defined in this invention, and that the agents are operatively attached. The fusion proteins may also include additional peptide sequences, such as peptide spacers which operatively attach the targeting agent and coagulating agent compounds, as long as such additional sequences do not appreciably affect the targeting or coagulating activities of the resultant fusion protein.

It will be understood that the recombinant bispecific protein ligands may differ from those bispecific constructs generated by chemically cross-linking the so-called naturally-produced proteins. In particular, the degree of post-translational modifications, such as, for example, glycosylation and phosphorylation may be different between recombinant fusions and chemical fusions of the same two proteins. This is not contemplated to be a significant problem, however, those of skill in the art will know to confirm that a recombinant fusion protein functions as intended, and expected from other data, before use in a clinical setting.

One advantage of recombinant expression is that the linking regions can be readily manipulated so that, e.g., their length and/or amino acid composition is readily variable. Non-cleavable peptide spacers may be provided to operatively attach the two agents of the invention, if desired. Equally, peptides with unique cleavage sites could be inserted between the two components.

If desired in a specific instance, it is possible to provide a peptide spacer operatively attaching the targeting agent and coagulating agent which is capable of folding into a disulfide-bonded loop structure. Proteolytic cleavage within the loop would then yield a heterodimeric polypeptide wherein the targeting agent and the coagulating agent are linked by only a single disulfide bond (see, for example, Lord et al., 1992).

Many standard techniques are available to construct expression vectors containing the appropriate nucleic acids and transcriptional/translational control sequences in order to achieve protein expression in a variety of host-expression systems. The cell types available for expression include, but are not limited to, microorganisms such as bacteria (e.g., *E. coli, B. subtilis*) transformed with recombinant bacteriophage DNA, plasmid DNA or cosmid DNA expression vectors containing targeting agent/coagulant coding sequences; yeast (e.g., Saccharomyces, Pichia) transformed with recombinant yeast expression vectors containing targeting agent/coagulating agent coding sequences; insect cell systems infected with recombinant virus expression vectors (e.g., baculovirus) containing the targeting agent/coagulating agent coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the targeting agent/coagulant coding sequence; and mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the targeting agent/coagulating agent construct being expressed. For example, when large quantities of bispecific agent are to be produced, vectors that direct the expression of high levels of fusion protein products that are readily purified may be desirable. Such vectors include, but are not limited to, the *E. coli* expression vector pUR278 (Ruther et al., 1983), in which the targeting agent/coagulating agent coding sequence may be ligated individually into the vector in frame with the lac Z coding region so that a fusion protein additionally containing a portion of the lac Z product is provided; pIN vectors (Inouye et al., 1985; Van Heeke et al., 1989); and the like. pGEX vectors may also be used to express foreign polypeptides, such as the targeting agent/coagulating agent combinations as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the binding agent/coagulant protein of the overall fusion protein can be released from the GST moiety.

In a useful insect system, *Autograph californica* nuclear polyhidrosis virus (AcNPV) is used as a vector to express foreign genes. The virus grows in *Spodoptera frugiperda* cells. The targeting agent/coagulating agent coding sequences may be cloned into non-essential regions (for example the polyhedrin gene) of the virus and placed under control of an AcNPV promoter (for example the polyhedrin promoter). Successful insertion of the bispecific ligand coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983; *U.S. Pat. No. 4,215,051, Smith).

In mammalian host cells, a number of viral based expression systems may be utilized. In cases where an adenovirus is used as an expression vector, the targeting agent/coagulating agent coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing bispecific proteins in infected hosts (e.g., see Logan et al., 1984).

Specific initiation signals may also be required for efficient translation of inserted targeting agent/coagulating agent coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in phase (or in-frame) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, etc.

For long-term, high-yield production of recombinant proteins, stable expression is preferred. For example, cell lines that stably express constructs encoding the targeting agent/coagulant ligands may be engineered. Rather than using expression vectors that contain viral origins of replication, host cells can be transformed with targeting agent/coagulant DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (Wigler et al., 1977), hypoxanthine-guanine phosphoribosyltransferase (Szybalska et al., 1962), and adenine phosphoribosyltransferase genes (Lowy et al., 1980) can be employed in tk-, hgprt- or aprt-cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin (Santerre et al., 1984).

D. Antibodies

Where antibodies are used as one or both portions of the bispecific ligand, the choice of antibody will generally be dependent on the type tumor and coagulating ligand chosen. However, certain advantages may be achieved through the application of particular types of antibodies. For example, while IgG based antibodies may be expected to exhibit better binding capability and slower blood clearance than their Fab' counterparts, Fab' fragment-based compositions will generally exhibit better tissue penetrating capability.

1. Monoclonal Antibodies

Means for preparing and characterizing antibodies are well known in the art (See, e.g., *Antibodies: A Laboratory Manual, Cold Spring Harbor Laboratory, 1988).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention, either with or without prior immunotolerizing, depending on the antigen composition and protocol being employed (e.g., tolerizing to a normal cell population and then immunizing with a tumor cell population), and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by is sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored, and/or the animal can be used to generate MAbs.

MAbs may be readily prepared through use of well-known techniques, such as those exemplified in *U.S. Pat. No. 4,196,265, incorporated herein by reference. Typically, this technique involves immunizing a suitable animal with a selected immunogen composition, e.g., a purified or partially purified tumor cell or vascular endothelial cell protein, polypeptide, peptide, or intact cell composition. The immunizing composition is administered in a manner effective to stimulate antibody producing cells. Rodents such as mice and rats are preferred animals, however, the use of rabbit, sheep frog cells is also possible. The use of rats may provide certain advantages (*Goding, 1986, pp. 60-61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (*Goding, pp. 65-66, 1986; *Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

One preferred murine myeloma cell is the A63-A68, 653 myeloma cell line, which is readily available from the ATCC. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate (*Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

The inventors also contemplate the use of a molecular cloning approach to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Where MAbs are employed in the present invention, they may be of human, murine, monkey, rat, hamster, chicken or even rabbit origin. The invention contemplates the use of human antibodies, "humanized" or chimeric antibodies from mouse, rat, or other species, bearing human constant and/or variable region domains, and other recombinant antibodies and fragments thereof. Of course, due to the ease of preparation and ready availability of reagents, murine monoclonal antibodies will typically be preferred.

2. Functional Antibody Binding Regions

The origin or derivation of the targeting agent antibody or antibody fragment (e.g., Fab', Fab, F(ab')$_2$, Fv or scFv) is not believed to be particularly crucial to the practice of the invention, so long as the antibody or fragment that is actually employed for the preparation of the bispecific ligand exhibits the desired binding properties.

It may be necessary to use antibody preparations in which the Fc portion has been removed. Fragmentation of immunoglobulin molecules can be achieved by controlled proteolysis, although the conditions will vary considerably with species and immunoglobulin class or subclass. Bivalent F(ab')$_2$ fragments are usually preferable over the univalent Fab or Fab' fragments.

Fab

Fab fragments can be obtained by proteolysis of the whole immunoglobulin by the non-specific thiol protease, papain. Papain must first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

F(ab')$_2$

The usual procedure for preparation of F(ab')$_2$ fragments from IgG of rabbit and human origin is limited proteolysis by the enzyme pepsin (Protocol 7.3.2). The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results.

Digestion of rat IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialysed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

3. Bispecific Antibodies

In general, the preparation of bispecific antibodies is also well known in the art, as exemplified by Glennie et al. (1987). Bispecific antibodies have been employed clinically, for example, to treat cancer patients (Bauer et al., 1991). One method for the preparation of bispecific antibodies involves the separate preparation of antibodies having specificity for the targeted tumor cell antigen, on the one hand, and the coagulating agent (or other desired target, such as an activating antigen) on the other.

Bispecific antibodies have also been developed particularly for use as immunotherapeutic agents. As mentioned earlier in conjunction with antigen-induction, certain of these antibodies were developed to cross-link lymphocytes and tumor antigens (Nelson, 1991; Segal et al., 1992). Examples include chimeric molecules that bind T cells, e.g., at CD3, and tumor antigens, and trigger lymphocyte-activation by physically cross-linking the TCR/CD3, complex in close proximity to the target cell (Staerz et al., 1985; Perez et al., 1985; 1986a; 1986b; Ting et al., 1988).

Indeed, tumor cells of carcinomas, lymphomas, leukemias and melanomas have been reported to be susceptible to bispecific antibody-mediated killing by T cells (Nelson, 1991; Segal et al., 1992; deLeij et al., 1991). These type of bispecific antibodies have also been used in several Phase I clinical trials against diverse tumor targets. Although they are not novel compositions in accordance with this invention, the combined use of bispecific cross-linking antibodies along with the bispecific coagulating ligands described herein is also contemplated. The bispecific cross-linking antibodies may be administered as described in references such as deLeij et al. (1991); Clark et al. (1991); Rivoltini et al. (1992); Bolhuis et al. (1992); and Nitta et al. (1990).

While numerous methods are known in the art for the preparation of bispecific antibodies, the Glennie et al. (1987) method involves the preparation of peptic F(ab'γ)$_2$ fragments from the two chosen antibodies, followed by reduction of each to provide separate Fab'γ$_{SH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'γ)$_2$ heteroconjugate.

Due to ease of preparation, high yield and reproducibility, the Glennie et al. (1987) method is often preferred for the preparation of bispecific antibodies, however, there are numerous other approaches that can be employed and that are envisioned by the inventors. For example, other techniques are known wherein crosslinking with SPDP or protein A is carried out, or a trispecific construct is prepared (Titus et al., 1987; Tutt et al., 1991).

Another method for producing bispecific antibodies is by the fusion of two hybridomas to form a quadroma (Flavell et al., 1991, 1992; Pimm et al., 1992; French et al., 1991; Embleton et al., 1991). As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen MAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1 \times 10^{-7}$M to $1 \times 10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques (Galfre et al., 1981), or by using the protocol described by Clark et al. (1988). Briefly, $4.5 \times 10^7$ HAT-sensitive first cells are mixed with $2.8 \times 10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. Bispecific antibody-containing cultures are identified using, for example, a solid phase isotype-specific ELISA and isotype-specific immunofluorescence staining.

In one identification embodiment to identify the bispecific antibody, the wells of microtiter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-anti-antibody conjugate added for 2 hours at room temperature. The plates are washed and a phosphatase substrate, e.g., P-Nitrophenyl phosphate (Sigma, St. Louis) is added to each well. Plates are incubated, 3N NaOH is added to each well to stop the reaction, and the $OD_{410}$ values determined using an ELISA reader.

In another identification embodiment, microtiter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation procedures, known to those skilled in the art of immunoglobulin purification. Means for preparing and characterizing antibodies are well known in the art (See, e.g., *Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

Furthermore, recombinant technology is now available for the preparation of antibodies in general, allowing the preparation of recombinant antibody genes encoding an antibody having the desired dual specificity (Van Duk et al., 1989). Thus, after selecting the monoclonal antibodies having the most preferred binding characteristics, the respective genes for these antibodies can be isolated, e.g., by immunological screening of a phage expression library (Oi & Morrison, 1986; Winter & Milstein, 1991). Then, through rearrangement of Fab coding domains, the appropriate chimeric construct can be readily obtained.

E. Binding Assays

Although the present invention has significant utility in animal and human treatment regimens, it also has many other practical uses. These uses are generally related to the specific binding ability of the bispecific compounds. In that all the compounds of the invention include at least one targeting and binding component, e.g., an antibody, ligand, receptor, or such like, the resultant bispecific construct may be used in virtually all of the binding embodiments that the original antibody, ligand or receptor, etc., may be used. The presence of the coagulant, or other binding regions, does not negate the utility of the first binding regions in any binding assay.

As such, the bispecific coagulating ligands may be employed in standard binding assays, such as in immunoblots, Western blots, and other assays in which an antigen is immobilized onto a solid support matrix, e.g., nitrocellulose, nylon or a combination thereof. They may be employed simply as an "antibody substitute" or may be used to provide a more-specific detection means for use in detecting antigens against which standard secondary reagents cause an unacceptably high background. This is especially useful when the antigens studied are themselves immunoglobulins or other antibodies are used in the procedure, as exemplified below in the case of ELISAs.

The bispecific binding ligands may also be used in conjunction with both fresh-frozen and formalin-fixed, paraffin-embedded tissue blocks in immunohistochemistry; in fluorescent activated cell sorting, flow cytometry or flow microfluorometry; in immunoprecipitation to separate a target antigen from a complex mixture, in which case, due to their potential to form molecular lattices, they may even achieve precipitation without a secondary matrix-coupled reagent; in antigen or cell purification embodiments, such as affinity chromatography, even including, in certain cases, the one-step rapid purification of one or more cell populations at the same time; and in many other binding assays that will be known to those of skill in the art given the information presented herein.

As an example, the bispecific ligands of the invention may be used in ELISA assays. Many types of ELISAs are known and routinely practiced in the art. The bispecific ligands may be employed in any of the binding steps, depending on the particular type of ELISA being performed and the "antigen" (component) to be detected. The ligands could therefore be used to coat the plate, to compete for binding sites, as an antigen to provide a standard curve, as a primary binding ligand, as a secondary binding ligand or even as a tertiary or other binding ligand. The many modes of conducting ELISAs will be known to those of skill in the art, in further light of the exemplary mode discussed below.

In one form of an ELISA, binding targets, generally antibodies themselves, are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

In these types of ELISAs, generally termed sandwich ELISAs, the plate-bound antibody is used to "trap" the antigen. After binding of the first antibody to the well, coating with a non-reactive material to reduce background, and washing to remove unbound material, the immobilizing surface is contacted with, in the present exemplary embodiment, a test sample containing the antigenic material to be detected and/or titered in a manner conducive to immune complex (antigen/antibody).formation. These embodiments are particularly useful for detecting ligands in clinical samples or biological extracts. The samples are preferably diluted with solutions of BSA, bovine gamma globulin (BGG) and phosphate buffered saline (PBS) and a detergent, e.g. Tween.

The layered antisera is then allowed to incubate for from 2 to 4 hours, at temperatures preferably on the order of 25° to 37° C. Following incubation, the antisera-contacted surface is washed so as to remove non-immunocomplexed material. A preferred washing procedure includes washing with a solution such as PBS/Tween, or borate buffer.

Following formation of specific immunocomplexes between the bound antigen and the test sample, and subsequent washing, the occurrence and amount of immunocomplex formation may be determined by subjecting same complex to a secondary specific binding component, which is generally an antibody-based component. In a particular embodiment, the bispecific ligands of the invention are proposed for use in this step. Further specific binding and washing steps are then conducted.

To provide a detecting means, in the present exemplary embodiment, a third antibody is used that is linked to a detectable label, such as an associated enzyme that will generate a color development upon incubating with an appropriate chromogenic substrate. The third, or tertiary, labeled antibody has binding affinity for a component of the bispecific ligand. The ultimate immunocomplex is determined, after appropriate binding and washing steps, by detecting the label, e.g., by incubating with a chromogenic substrate, such as urea and bromocresol purple or 2,2'-azino-di-(3-ethyl-benzthiazoline-6-sulfonic acid [ABTS] and $H_2O_2$. Quantification is then achieved by measuring the degree of color generation, e.g., using a visible spectra spectrophotometer.

Using a bispecific coagulating ligand as a secondary detection reagent in conjunction with the type of ELISA described above has distinct advantages. For example, it allows the use of a tertiary, labeled antibody that is specific for a portion of the bispecific ligand that is distinct from the typical antibody constant regions usually targeted. In particular, a tertiary binding ligand that is specific for the coagulant portion (or coagulant binding region) of the bispecific construct may be employed. This novel means of detecting immune complex formation imparts improved specificity, which is particularly useful in sandwich ELISAs where the tertiary antibody may cross-react with, and bind to, the original material used to coat the plate, i.e., the original antibody, rather than just binding to the intended secondary antibody. By directing the labelled tertiary component to an non-antibody portion, or even to a novel antigen combining region, of a bispecific ligand, the problem of non-specific binding, and unusually high background, will be avoided.

Further practical uses of the bispecific ligands are evident by exploiting their coagulating ability. As all of the proposed compounds are capable of inducing coagulation, they may be employed, e.g., as a control, in any assay that involves coagulation as a component. The presence of the targeting component does not negate the utility of the coagulant in such assays, as each component functions independently of the other.

F. Effective Use of Tissue Factor-Binding Bispecific Antibodies

As mentioned earlier, tissue factor (TF) is one agent capable of initiating blood coagulation. TF is exposed to the blood in vascular damage or following activation by certain cytokines. Available TF then complexes with factor VIIa to initiate the coagulation cascade that ultimately results in fibrin formation.

In one exemplary embodiment, the inventors have synthesized a bispecific antibody with specificity for antigens on tumor vasculature endothelial cells on one antigen combining site and specificity for the extracellular domains of human TF on the other antigen combining site. The antibody with specificity for human TF was previously shown to bind TF with high affinity without interfering with the factor VIIa complexing event or the TF/VIIa activity (Morrissey et al., 1988). Instead of using full length human TF, the inventors used a truncated form (tTF), which is devoid of the cytoplasmic as well as the transmembrane domain. Truncated TF lacks coagulation inducing activity, while still being able to complex factor VIIa, probably because it is not able to complex with a membrane surface upon which the coagulation-initiation complexes, including Factor X, could assemble.

The mouse model used for analyzing the effectiveness of this tumor vasculature endothelial cell specific targeting construct was a recently established model in which MHC class II antigens, that are absent from the vasculature of normal tissues, are expressed on the tumor vasculature through induction by IFN-γ that is secreted by the tumor cells (Burrows et al., 1992; Burrows & Thorpe, 1993). It has been demonstrated that anti-class II antibody administered intravenously localizes rapidly and strongly to the tumor vasculature (Burrows et al., 1992).

The present inventors herein demonstrate that, in a C1300 (Muγ) tumor bearing mouse, the anti-MHC Class II/anti-TF bispecific antibody is able to induce coagulation specifically in the vasculature of the tumor when administered together with tTF. Indeed, intravenous administration of the antibody: tTF complex induced rapid thrombosis of tumor vasculature and complete tumor regressions in 70% of animals. Neither the bispecific antibody alone, nor tTF alone, nor any of the isotype matched control antibodies in the presence or absence of tTF, was able to elicit the same effect. This indicates that the B21-2/10H10 bispecific antibody acts as a "coaguligand" that is capable of bridging target cells and tTF so that tTF can activate factor X and start the coagulation cascade. It also shows the evident success of the coaguligand in treating solid tumors.

G. Pharmaceutical Compositions and Kits

Pharmaceutical compositions of the present invention will generally comprise an effective amount of the bispecific coagulating ligand dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

1. Parenteral Formulations

The bispecific ligands of the present invention will often be formulated for parenteral administration, e.g., formulated for injection via the intravenous, intramuscular, sub-cutaneous or other such routes, including direct instillation into a tumor or disease site. The preparation of an aqueous composition that contains a tumor-targeted coagulant agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The bispecific ligands or antibodies can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of the bispecific ligand admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as shown in the studies detailed herein (see, e.g., Example III). Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in Example III, are widely used in pre-clinical testing.

The inventors have used mice with C1300 (Mo8) tumors to determine toxicity limits and working ranges of bispecific that give optimal anti-tumor effects with minimal toxicity.

It is currently proposed that effective doses for use in the treatment of cancer will be between about 0.1 mg/kg and about 2 mg/kg, and preferably, of between about 0.8 mg/kg and about 1.2 mg/kg, when administered via the IV route at a frequency of about 1 time per week. Some variation in dosage will necessarily occur depending on the condition of the subject being treated. The person responsible for administration will, in any event, determine the appropriate dose for the individual subject. Such optimization and adjustment is routinely carried out in the art and by no means reflects an undue amount of experimentation.

It should be remembered that one aspect of the present invention concerns the delivery of a coagulating agent to a tumor site by administering an uncomplexed bispecific binding ligand that garners an endogenous coagulation factor from the circulation and concentrates it within the tumor site. In these cases, the pharmaceutical compositions employed will contain a ligand having a targeting and coagulant binding region, but will otherwise generally be the same as those described above.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. For example, topical formulations that are appropriate for treating pathological conditions such as dermatitis and psoriasis; and ophthalmic formulations for diabetic retinopathy.

2. Ingestible Formulations

In certain embodiments, active compounds may be administered orally. This is contemplated for agents that are generally resistant, or have been rendered resistant, to proteolysis by digestive enzymes. Such compounds are contemplated to include chemically designed or modified agents; dextrorotatory peptidyl agents; liposomal formulations; and formulations in time release capsules to avoid peptidase and lipase degradation.

For oral administration, the active bispecific compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active bispecific coagulant. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

3. Liposomal Formulations

The bispecific coagulating ligands of the present invention may also be formulated in liposomal preparations if desired. The following information may be utilized in generating liposomal formulations incorporating the present coagulants. Phospholipids form liposomes when dispersed in water, depending on the molar ratio of lipid to water. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for use with the present invention will contain cholesterol, or even PEG.

The ability to trap solutes varies between different types of liposomes. For example, multilamellar vesicles (MLVs) are moderately efficient at trapping solutes, but small unilamellar vesicles (SUVs) are inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LLTs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior dictates that liposomes concentrate only in those organs and tissues accessible to their large size. As this clearly includes the blood, this is not a limitation to their combined use with the present invention.

In other embodiments, the bispecific components of the invention may be admixed with the liposome surface to direct the drug contents to the specific antigenic receptors located on the target cell surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

4. Topical Formulations

The formulation of bispecific coagulants for topical use, such as in creams, ointments and gels is also contemplated. The preparation of oleaginous or water-soluble ointment bases is also well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate.

Various water-soluble ointment bases may also be used, including glycol ethers and derivatives, polyethylene glycols, polyoxyl 40 stearate and polysorbates. Even delivery through the skin may be employed if desired, e.g., by using transdermal patches, iontophoresis or electrotransport.

5. Ophthalmic Formulations

The bispecific coagulating ligands of the present invention may also be formulated into pharmaceutical compositions suitable for use as ophthalmic solutions. Such ophthalmic solutions are of interest, for example, in the treatment of diabetic retinopathy. Thus, for the treatment of diabetic retinopathy a bispecific conjugate of this invention would be administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation will contain a novel bispecific coagulant or a pharmaceutically acceptable salt thereof in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.20%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

6. Therapeutic Kits

The present invention also provides therapeutic kits comprising the bispecific coagulating ligands described herein. Such kits will generally contain, in suitable container means, a pharmaceutically acceptable formulation of at least one bispecific ligand in accordance with the invention. The kits may also contain other pharmaceutically acceptable formulations, such as those containing additional bispecific coagulating ligands, generally those having a distinct targeting component; extra uncomplexed coagulation factors; bispecific antibodies, T cells, or other functional components for use in, e.g., antigen induction; components for use in antigen suppression, such as a cyclosporin; distinct anti-tumor site antibodies or immuntoxins; and any one or more of a range of chemotherapeutic drugs.

Preferred agents for use in combination kits are inducing agents capable of inducing disease-associated vascular endothelial cells to express a targetable antigen, such as E-selectin or an MHC Class II antigen. Inducing agents can include T cell clones that bind disease or tumor antigens and that produce IFN-γ. Preferred inducing agents include bispecific antibodies that bind to disease or tumor cell antigens and to effector cells capable of inducing target antigen expression through the elaboration of cytokines.

As such, the present invention further includes kits that comprise, in suitable container means, a first pharmaceutical composition comprising a bispecific antibody that binds to an activating antigen on an effector cell surface, i.e., a monocyte/macrophage, mast cell, T cell or NK cell, and to an antigen on the cell surface of disease cell; and a second pharmaceutical composition comprising a bispecific ligand that comprises a first binding region that binds to an endothelial cell antigen induced by an activated effector cell, or cytokine therefrom, where the first binding region is operatively linked to a coagulation factor or a second binding region that binds to a coagulation factor.

Kits including a first pharmaceutical composition that comprises a bispecific antibody that binds to the activating antigen CD14, CD16 (FcR for IgE), CD2, CD3, CD28 or the T-cell receptor antigen are preferred, with CD14 or CD28 binding bispecific antibodies being more preferred. Activation of monocyte/macrophages or mast cells via CD14 or CD16 binding results in IL-1 production that induces E-selectin; whereas activation of T cells via CD2, CD3 or CD28 binding results in IFN-γ production that induces MHC class II. Kits that include a second pharmaceutical composition that comprises a bispecific ligand that comprises a first binding region that binds to E-selectin or to an MHC Class II antigen are therefore also preferred.

The kits may have a single container means that contains the bispecific coagulating ligand, with or without any additional components, or they may have distinct container means for each desired agent. Kits comprising the separate components necessary to make a bispecific coagulating ligand are also contemplated.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means.

The container means of the kit will generally include at least one vial, test tube, flask, bottle, syringe or other container means, into which the bispecific coagulating ligand, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the bispecific ligand to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Synthesis of a Bispecific Coagulating Antibody

The present example describes the synthesis of a bispecific antibody capable of specifically directing a coagulant to a tumor site, i.e., a "coaguligand".

A. Materials and Methods

1. Reagents

Pepsin (A; EC 3.4.23.1), Ellmans reagent (ER; 5,5'-dithiobis(2-nitrobenzoic acid, DNTB), 2-mercaptoethanol (2-ME), sodium arsenite (NaAsO$_2$) and rabbit brain thromboplastin (acetone powder) were obtained from Sigma Chemical Co., St. Louis Mo. Sephadex G-25 and G-100 were obtained from Pharmacia LKB (Piscataway, N.J.).

2. Human Truncated Tissue Factor (tTF)

Recombinant human truncated TF (tTF) was prepared by one of two different methods.

Method I: Construction of the *E. coli* Expression Vector. The cDNA coding for tTF (residues 1-218) was amplified by PCR using the primers 5'-GAAGAAGGGATCCTGGT-GCCTCGTGGTTCTGGCACTACAAATACT-3' (5'-primer; SEQ ID NO:28) and 5'-CTGGCCTCAAGCT-TAACGGAATTCACCTTT-3' (3'-primer; SEQ ID NO:29) which allowed the addition of the coding sequence for a thrombin cleavage site upstream of the cDNA. The PCR products were cleaved using BamHI and HindIII and ligated between the BamHI and HindIII sites of the expression vector pTrcHisC (Invitrogen).

DH5α cells were transformed with the ligation mixture and recombinant plasmids were isolated after selection in the presence of ampicillin. The *E. coli* strain BL21 was transformed with the recombinant plasmid pTrcHisC-tTF and the resultant transformants were used for protein expression.

Method I: Expression, Refolding and Purification of tTF from *E. coli*. The poly(his)-tTF fusion protein was expressed using BL21 cells transformed with pTrc-HisC-tTF. Inoculant cultures (10 ml in LB medium) were grown overnight shaking at 37° C.

Inoculant cultures were added to growth medium which were then grown shaking at 37° C. When the optical density at 550 nm had reach ca. 0.5, 10 ml of 100 mM isopropyl-β-D-thiogalactopyranoside was added. Shaking was continued at 37° C. for ca. 20 h (to stationary phase).

The cells were harvested by centrifugation (10,000× g, 20 min.) and the inclusion bodies were isolated as follows (quantities of reagents are per gram of cell paste). The cell paste was suspended in 4 ml of 10 mM Tris, pH 7.5, 150 mM NaCl, 1 mM MgCl$_2$, 0.17 mg/ml PMSF, 2 mg/ml hen egg white lysozyme (Sigma). Benzonase (250 units, EM Science) was added the suspension was mixed gently at room temperature for 1.5 h then centrifuged at 12,000 g for 15 min.

The pellet was resuspended in 10 mM Tris, pH 7.5, 1 mM EDTA, 3% NP40 (2 ml), sonicated for 1 min at 50% power and centrifuged at 12,000× g for 20 min. The pellet was resuspended in water, sonicated for 20-30 seconds at 50% power and centrifuged at 12,000× g for 20 min. The water wash was repeated and the final pellet, highly enriched for the inclusion bodies, was suspended in 6 M guanidinium chloride, 0.5 M NaCl, 20 mM phosphate, 10 mM β-mercaptoethanol, pH 8.0 (9 ml per gram of inclusion bodies) by gentle mixing at room temperature overnight.

The suspension was centrifuged at 12,000× g for 20 min and the supernatant was loaded onto a nickel nitriloacetic acid (Ni-NTA, Qiagen) column. The column was washed successively with the same 6 M guanidinium chloride buffer at pH 8 then pH 7, then the protein was eluted by decreasing the pH to 4.

Ni-NTA column fractions containing the fusion protein were combined and dithiothreitol was added to 50 mM. The solution was held at room temperature overnight then diluted to a protein concentration of ca. 1 mg/ml in 6 M urea, 50 mM Tris, 0.02% sodium azide, pH 8.0 and dialyzed at 4° C. overnight against 10-20 volumes of the same buffer. The buffer was changed to 2 M urea, 50 mM Tris, 300 mM NaCl, 2.5 mM reduced glutathione, 0.5 mM oxidized glutathione, 0.02% sodium azide, pH 8.0 (folding buffer). Dialysis was continued for 2 more days, the buffer was replaced by fresh folding buffer and dialysis was continued for 2 more days.

The solution was then dialyzed extensively against 20 mM TEA (pH 7.5), removed from the dialysis bag, treated with human thrombin (ca. 1 part per 500 parts recombinant protein w/w) overnight at room temperature, and loaded onto a HR-10/10 mono-Q anion exchange column. tTF protein was eluted using a 20 mM TEA buffer containing NACl in a concentration increasing linearly from 0 to 150 mM over 30 minutes (flow rate 3 ml/min).

Method II: Preparation of tTF complimentary DNA (cDNA).
RNA from J-82 cells (human bladder carcinoma) was used for the cloning of tTF. Total RNA was isolated using the GlassMax™ RNA microisolation reagent (Gibco BRL). The RNA was reverse transcribed to cDNA using the Gene-Amp RNA PCR kit (Perkin Elmer). tTF cDNA was amplified using the same kit with the following two primers. The 5' primer is SEQ ID NO:3.

```
5' primer: 5'GTC ATG CCA TGG CCC TGG TGC CTC GTG CTT CTG GCA CTA CAA ATA CT    (SEQ ID NO:2)

3' primer: 5'TGA CAA GCT TAT TCT CTG AAT TCC CCT TTT CT
```

The underlined sequences codes for the N-terminus and C-terminus of tTF. The rest of the sequence in the 5' primer is the restriction site for NcoI allowing the cloning of tTF into the expression vector and codes for a cleavage site for thrombin. The sequence in the 3' primer is the HindIII site for cloning tTF into the expression vector. PCR amplification was performed as suggested by the manufacturer. Briefly, 75 µM dNTP; 0.6 µM primer, 1.5 mM $MgCl_2$ were used and 30 cycles of 30" at 95° C., 30" at 55° C. and 30" at 72° C. were performed.

Method II. Vector Constructs. *E. coli* expression vector $H_6$ pQE-60 was used for expressing tTF (Lee et. al., 1994). The PCR amplified tTF cDNA was inserted between the NcoI and HindIII site. $H_6$ pQE-60 has a built-in $(His)_6$ (SEQ ID NO:33) encoding sequence such that the expressed protein has the sequence of $(His)_6$ (SEQ ID NO:33) at the N-terminus, which can be purified on the Ni-NTA column.

Method II. tTF Purification. tTF containing $H_6$ pQE-60 DNA was transformed to *E. coli* TG-1 cells. The cells were grown to $OD_{600}$=0.5 and IPTG was added to 30 µM to induce the tTF production. The cells were harvested after shaking for 18 h at 30° C. The cell pellet was denatured in 6 M Gu-HCl and the lysate was loaded onto a Ni-NTA column (Qiagen). The bound tTF was washed with 6 M urea and tTF was refolded with a gradient of 6 M–1 M urea at room temperature for 16 h. The column was washed with wash buffer (0.05 Na $H_2 PO_4$, 0.3 M NaCl, 10% glycerol) and tTF was eluted with 0.2 M Imidozole in wash buffer.

The eluted tTF was concentrated and loaded onto a G-75 column. tTF monomers were collected and treated with thrombin to remove the $H_6$ peptide. This was done by adding 1 part of thrombin (Sigma) to 500 parts of tTF (w/w), and the cleavage was carried out at room temperature for 18 h. Thrombin was removed from tTF by passage of the mixture through a Benzamidine Sepharose 6B thrombin affinity column (Pharmacia).

The tTF had identical ability to recombinant tTF from yeast or Chinese hamster ovary cells to bind factor VIIa and to enhance the catalytic activity of VIIa (Ruf et al., 1991). When analyzed by polyacrylamide gel electrophoresis in sodium dodecyl sulfate, it ran as a single component having a molecular weight of approximately 24 kD.

3. Monoclonal Antibodies

B21-2 (TIB-229) hybridoma and SFR8-B6 hybridoma (HB-152, hereafter referred to as SFR8) were obtained from the ATCC. Both hybridomas secreted rat IgG2b antibodies, which were purified from culture supernatant by protein G affinity chromatography. The B21-2 antibody reacts with I-$A^d$ antigen expressed on A20 cells as well as on the vasculature of the C1300 (Muγ) transfectant tumors grown in BALB/c/nu/nu mice. SFR8 antibody is directed against the HLA-Bw6 epitope and serves as an isotype matched negative control for the B21-2 antibody.

TF9/10H10 (referred to as 10H10), a mouse IgG1, is reactive with human TF without interference of TF/factor VIIa activity and was produced as described by Morrissey et al. (1988).

The cell line MRC OX7 (referred to as OX7) was obtained from Dr. A. F. Williams (MRC Cellular Immunology Unit, University of Oxford, Oxford, England). It secretes the OX7 antibody, a mouse IgG1 antibody that recognizes the Thy 1.1 antigen on T lymphocytes. It was used as an isotype matched negative control for TF9/10H10.

All antibodies were purified from culture supernatant by protein G affinity chromatography.

4. Synthesis of Bispecific Antibodies $F(ab')_2$ fragments were obtained by digesting their respective IgGs with 2% (w/v) pepsin for 5-9 hrs at 37° C. and purification of the fragments by Sephadex G100 chromatography. Synthesis of the bispecific antibodies B21-2/10H10, SFR8/10H10 and B21-2/OX7 was carried out according to the method of Brennan et al. (1985) with minor modifications.

The bispecific antibodies B21-2/10H10, SFR8/10H10, OX7/10H10 and B21-2/OX7 were synthesized according to the method of Brennan et al. (1985) with minor modifications. In brief, $F(ab')_2$ fragments were obtained from the IgG antibodies by digestion with pepsin and were purified to homogeneity by chromatography Sephadex G100. $F(ab')_2$ fragments were reduced for 16 h at 20° C. with 5 mM 2-mercaptoethanol in 0.1 M sodium phosphate buffer, pH 6.8, containing 1 mM EDTA (PBSE buffer) and 9 mM $NaAsO_2$. Ellman's reagent (ER) was added to give a final concentration of 25 mM and, after 3 h at 20° C., the Ellman's-derivatized Fab' fragments (Fab'-ER) were separated from unreacted ER on columns of Sephadex G25 in PBSE.

To form the bispecific antibody, Fab'-ER derived from one antibody was concentrated to approximately 2.5 mg/ml in an ultrafiltration cell and was reduced with 10 mM 2-mercaptoethanol for 1 h at 20° C. The resulting Fab'-SH was filtered through a column of Sephadex G25 in PBSE and was mixed with equal molar quantities of Fab'-ER prepared from the second antibody. The mixtures were concentrated by ultrafiltration to approximately 3 mg/ml and were stirred for 16 h at 20° C. The products of the reaction were fractionated on columns of Sephadex G100 and the fractions containing the bispecific antibody (110 kDa) were concentrated to 1 mg/ml, and were stored at 4° C. in 0.02% sodium azide.

B. Results

1. Analysis of Bispecific Antibodies

The molecular weight of the $F(ab')_2$ fragments and bispecific preparations were determined by SDS-Page electrophoresis with 4-15% gradient gels using the Pharmacia LKB-Phastsystem (Pharmacia LKB, Piscataway, N.J.). Bispecificity as well as the percentage of heterodimer vs homodimer was determined by FACS analysis (Example II).

Analysis of the bispecific antibodies by SDS-Page electrophoresis (and by FACS, Example II) demonstrated that the B21-2/10H10 bispecific contained less than 4% homodimer of either origin and <10% fragments with a molecular weight of 140 kD or 55 kD. Approximately 10% of the preparation consisted of 140 kD fragments, probably being a $F(ab')_2$ construct with an extra light chain (of either origin) attached.

EXAMPLE II

Coagulating Antibody Binding and Function In Vitro

The present example shows the bispecificity of the coagulating antibody (coaguligand) and demonstrates that specific binding, cellular delivery and coagulation is achieved in vitro using the coaguligand.

A. Materials and Methods

1. Cells

The A20 cell line, which is an I-$A^d$ positive BALB/c B-cell lymphoma, was purchased from the American Type Culture Collection (ATCC; Rockville, Md.; TIB-208). A20 cells were grown in DMEM supplemented with 10% (v/v) fetal calf serum (FCS), 0.2 mM L-glutamine, 200 units/ml penicillin and 100 µg/ml streptomycin, 18 mM Hepes, 0.1 mM nonessential amino acids mix and 1 mM sodium pyruvate (medium hereafter referred to as complete DMEM; all reagents obtained from Life Technologies, Gaitherburg, Md.). 2-ME is added to complete DMEM to a final concentration of 0.064 mM for A20 cells. Cultures were maintained at 37° C. in a humidified atmosphere of 90% air/10% $CO_2$.

J82, a human gall bladder carcinoma expressing TF, was obtained from the ATCC (HTB-1). The cells grew adherently in complete DMEM.

The C1300 neuroblastoma cell line was established from a spontaneous tumor, which arose in an A/Jax mouse (Dunham & Stewart, 1953). The C1300 (Muγ) 12 line, hereafter referred to as C1300 (Muγ) was derived by transfection of C1300 neuroblastoma cells with the murine IFN-γ gene using the IFN-γ expression retrovirus pSVX (Muγ ΔAs) (Watanabe et al., 1989). The IFN-γ expression retrovirus was obtained from Dr. Y. Watanabe (Department of Molecular Microbiology, Kyoto University, Japan).

C1300(Muγ)12 cells were maintained in Dulbecco's modified Eagle Medium (DMEM) supplemented with 10% (v/v) fetal calf serum (FCS), 2.4 mM L-glutamine, 200 units/ml penicillin, 100 µg/ml streptomycin, 100 µM nonessential amino acids, 1 µM sodium pyruvate, 18 µM HEPES and 1 mg/ml G418 (Geneticin; Sigma). Cultures were maintained at 37° C. in a humidified atmosphere of 90% air/10% $CO_2$.

The Thy 1.1-expressing AKR-A mouse T lymphoma cell line was obtained from Prof. Dr. I. MacLennan (Department of Experimental Pathology, Birmingham University, Birmingham, England) and were grown in complete DMEM.

2. Indirect Immunofluorescence

A20 cells were resuspended in PBS/0.20% BSA/0.02% Na-azide (hereafter referred to as FACS buffer) at $4 \times 10^6$ cells/ml. J82 cells were released from the flask under mild conditions using PBS/EDTA (0.2 % w/v) and resuspended at $4 \times 10^6$ cells/ml in FACS buffer. 50 µl of cell suspension was added to 50 µl of optimal serial dilutions of the primary antibody in wells of a round-bottomed 96 well plate. After incubation at RT for 15 min, the cells were washed with FACS buffer 3 times. After removing the final supernatant, 50 µl of the secondary antibody conjugated to fluorescein isothiocyanate (FITC), in a 1 in 20 dilution in FACS buffer, was added to the cells. The cells were incubated for a further 15 min at RT and washed 3 times with FACS buffer. Cell associated fluorescence was measured on a FACScan (Becton Dickenson, Fullerton, Calif.). Data were analyzed using the Lysis II program. When FITC-anti-rat immunoglobulin was used as the secondary antibody, normal mouse serum (10% v/v) was added to block non-specific cross reactivity with the mouse cells.

3. Radiolabeling of Proteins

Proteins were labeled with $^{125}$Iodine according to the chloramine T protocol described by Mason & Williams (1980), (protocol 2). The iodinated product was purified on G25 and stored at −70° C. in the presence of 5% DMSO and 5 mg/ml bovine IgG in the case of the monoclonal fragments and 5% DMSO and 5 mg/ml BSA in the case of tTF. Specific activity ranged between 2.5 µCi/µg and 4.8 µCi/µg.

4. Binding Studies

Human tTF was labelled with $^{125}$I to a specific activity of 2.5-4.8 µCi/µg using the chloramine T procedure (Protocol 2) described by Mason and Williams (1980). A suspension of A20 cells at $2 \times 10^6$ cells/ml in PBS containing 2 mg/ml BSA and 0.02% sodium azide was distributed in 50 µl volumes into the wells of 96 well round-bottomed microtiter plates. To the wells were added 25 µl of bispecific antibodies prepared over a range of concentrations (8 to 0.02 µg/ml) in the same buffer.

25 µl of $^{125}$I-tTF at 8 µg/ml in the same buffer were added to each well, giving a molar excess of tTF. The plates were shaken and incubated for 1 hr at 4° C. The cells were then washed 3× in the plates with 0.9% (w/v) NaCl containing 2 mg/ml BSA. The contents of the wells were pipetted over a 10:11 (v/v) mixture of dibutyl phthalate and bis(2-ethylhexyl)phthalate oils in microcentrifuge tubes. The tubes were centrifuged for 1.5 min at 7500 g and were snap frozen in liquid nitrogen. The tips containing the cells were cut off. The radioactivity in the cell pellet and in the supernatant was measured in a gamma counter.

5. Coaculation Assay

An identical microplate to that used for the binding assay above was set up on the same occasion, except that non-labelled tTF was added instead of $^{125}$I-tTF. After the 1 h incubation at 4° C., the cells were washed 3× as before and were resuspended in 75 µl of 0.9% NaCl containing 2 mg/ml BSA and 12.5 mM $CaCl_2$. The contents of the wells were transferred to 5 ml clear plastic tubes and were warmed to 37° C. To each tube was added 30 µl of citrated mouse plasma at 37° C. The time for the first fibrin strands to form was recorded.

B. Results

1. Antibody Bispecificity

For SFR8/10H10 bispecificity was shown by FACS using J82 cells (TF positive) as target cells and FITC-anti-mouse immunoglobulin to demonstrate 10H10 presence. FITC-anti-rat immunoglobulin was used to demonstrate the presence of SFR8. The mean fluorescence intensity-versus-concentration curves were coincident for both stains, demonstrating that both the mouse and the rat arm are present in the bispecific preparation.

2. Antibody Binding

Binding studies with $^{125}$Iodine labeled B21-2 Fab' and SFR8 Fab' showed that the concentration at which saturation of binding of B21-2 Fab' to A20 cells is reached is 21.5 nM. The SFR8 Fab' bound non-specifically to A20 cells, with the number of molecules bound per cell being less than 50,000 at 21.5 nM versus 530,000 for B21-2 Fab'.

3. Coaculant Delivery and Tethering

To study the capability of bridging tTF to A20 cells through the B21-2/10H10 bispecific antibody as compared to the control bispecific antibodies, A20 cells were incubated with bispecific antibody and a $^{125}$I-tTF concentration range as indicated. Saturation was attained at concentrations of bispecific antibody of 10 nM (1 µg/ml) or more, when an average of 310,000 molecules of tTF were bound to each A20 cell. The binding was specific since no tTF binding was mediated by either of the isotype-matched control bispecific antibodies, SFR8/10H10 or B21-2/OX7, which had only one of the two specificities needed for tethering tTF (FIG. 1).

4. Coaculation

To investigate whether tTF bound to A20 cells through a bispecific antibody was able to induce coagulation, the inventors first incubated A20 cells with 21.5 nM bispecific antibody and 69 nM tTF. The resulting effect on the coagulation time is shown in Table VII. These first studies showed that A20 cells coated with a complex of B21-2/10H10 and tTF were capable of inducing fibrin formation: it shortened coagulation time from 140 sec (the time for mouse plasma in $CaCl_2$ to coagulate in the absence of added antibodies or TF under the specific conditions used) to 60 sec. In contrast, the control bispecific antibodies did not induce activation of coagulation: in these cases coagulation time was 140 sec.

Later studies confirmed and extended the initial results. Mouse plasma added to A20 cells to which tTF had been tethered with B21-2/10H10 coagulated rapidly. Fibrin strands were visible 36 seconds after adding the plasma as compared with 164 seconds in plasma added to untreated A20 cells (Table VII). Only when tTF had been tethered to the cells was coagulation induced: no effect on coagulation time was seen with cells incubated with of tTF alone, homodimeric $F(ab')_2$ Fab' fragments or bispecific antibodies having only one of the two specificities needed for tethering tTF.

Figure 2:
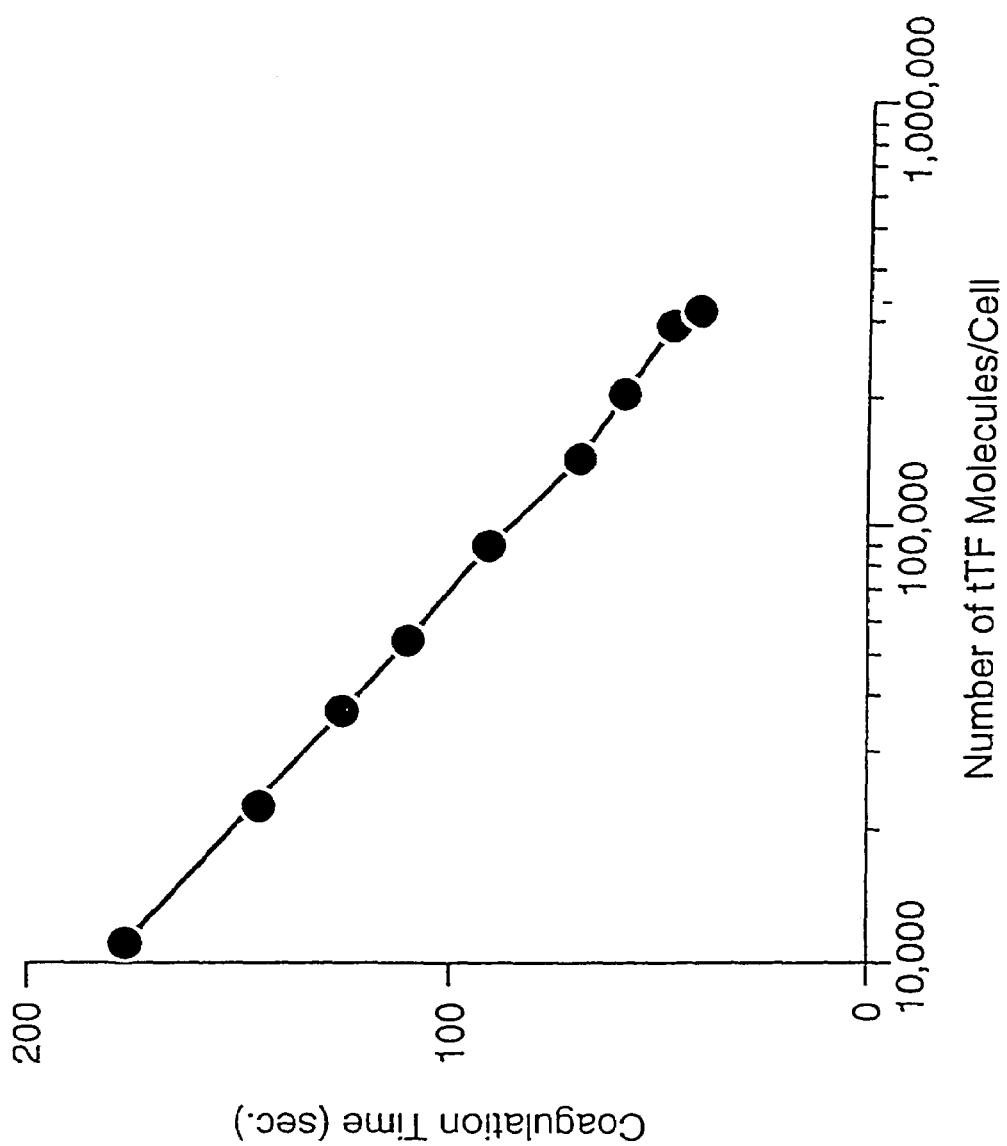
FIG. 2. Relationship between number of tethered tTF molecules per A20 cell and ability to induce coagulation of plasma. A20 cells were incubated with varying concentrations of B21-2/10H10 plus an excess of tTF for 1 h at 4° C. in the presence of sodium azide. The cells were washed, warmed to 37° C., calcium and mouse plasma were added and the time for the first fibrin strands to form was recorded (abscissa). An identical study was performed in which the A20 cells were incubated for 1 h at 4° C. with bispecific antibody plus $^{125}$I-tTF and the number of tTF specifically bound to the cells was determined as described in Example II (ordinate). Plasma added to untreated A20 cells (i.e. zero tTF molecules/cell) coagulated in 190 seconds.

A linear relationship existed between the logarithm of the average number of tTF molecules tethered to each A20 cell and the rapidity with which those cells induced coagulation of mouse plasma (FIG. 2). Cells bearing 300,000 molecules of tTF per cell induced coagulation in 40 secs but even with 20,000 molecules per cell coagulation was significantly faster (140 secs) than it was with untreated cells (190 secs).

TABLE VII

Coagulation of mouse plasma induced by tethering tTF to A20 cells with bispecific antibody.

| Reagents added[1] | Coagulation time[2] (sec) |
|---|---|
| None | 164 ± 4 |
| B21-2/10H10 + tTF | 36 ± 2 |
| B21-2/10H10 | 163 ± 2 |
| tTF | 163 ± 3 |
| B21-2/OX7 + tTF | 165 ± 4 |
| SFR8/10H10 + tTF | 154 ± 5 |
| 10H10 F(ab')$_2$ + tTF | 160 ± 3 |
| 10H10 Fab' + tTF | 162 ± 2 |
| B21-2 F(ab')$_2$ + tTF | 168 ± 4 |
| B21-2 Fab' + tTF | 165 ± 4 |

[1]Bispecific antibodies F(ab')$_2$ and Fab' fragments (0.33 μg/10$^5$ cells/100 μl) and tTF (0.17 μg/10$^5$ cells/100 μl) were incubated with A20 cells for 1 h at 4° C. in 0.2% w/v sodium azide. The cells were washed, warmed to 37° C., calcium and plasma were added and the time for the first fibrin strands to form was recorded.
[2]Arithmetic mean of triplicate determinations ± standard deviation

EXAMPLE III

Specific Tumor Vasculature Specific Coagulation In Vivo

The present example describes the specific coagulation of tumor vasculature in vivo that results following the administration of the bispecific antibody coaguligand as a delivery vehicle for human tissue factor.

A. Materials and Methods

1. Reagents

Mouse blood was obtained by heartpuncture and collected in 1/10 volume of 3.8%. buffered citrate. The blood was centrifuged for 10 min at 3000 g and the plasma snap frozen in small aliquots and stored at −70° C.

2. Animals

BALB/c nu/nu mice were obtained from Simonsen (Gilroy, Calif.) and maintained under SPF conditions.

3. C1300 (Muγ) Mouse Model and Treatment

The tumor model was as previously described (Burrows et al., 1992; Burrows & Thorpe, 1993) with three refinements. First, a different antibody, B21-2, was used. This antibody recognizes I-A$^d$ but not I-E$^d$, unlike the previously used M5/114 antibody which recognizes both molecules. The B21-2 antibody has an approximately 10-fold better affinity than M5/114. Second, a subline of the previously used C1300 (Muγ) 12 line was used which grew continuously in BALB/c nu/nu mice. The C1300(Muγ) 12 cells used previously had to be mixed with untransfected C1300 cells in order to form continuously growing tumors. The new subline, designated C1300(Muγ) t1P3, will be referred to hereafter as C1300 (Muγ). Third, it was unnecessary to add tetracycline to the mice's drinking water to prevent gut bacteria from inducing I-A$^d$ on the gastrointestinal epithelium. Unlike immunotoxins, coaguligands do not damage I-A$^d$-expressing intestinal epithelium.

For establishment of solid tumors, 1.5×10$^7$ C1300 (Muγ) cells were injected subcutaneously into the right anterior flank of BALB/c nu/nu mice. When the tumors had grown to 0.8 cm in diameter, mice were randomly assigned to different treatment groups each containing 7-8 mice.

Coaguligands were prepared by mixing bispecific antibodies (140 μg) and tTF (110 μg) in a total volume of 2.5 ml of 0.9% NaCl and leaving them at 4° C. for one hour. Mice then received intravenous injections of 0.25 ml of this mixture (i.e. 14 μg of bispecific antibody plus 11 μg of tTF). Other mice received 14 μg of bispecific antibodies or 11 μg of tTF alone. The injections were performed slowly into one of the tail veins over approximately 45 sec and were followed with a second injection of 200 μl of saline into the same vein. This injection procedure was adopted to prevent thrombosis of the tail vein which was seen if mice were rapidly injected (1-2 sec). Seven days later, the treatments were repeated.

Perpendicular tumor diameters were measured at regular intervals and tumor volumes were estimated according to the following equation:

volume=smaller diameter$^2$×larger diameter×π/6

Differences in tumor volume were tested for statistical significance using the Mann-Whitney-Wilcoxon nonparametric test for two independent samples (Gibbons, 1976).

For histopathological analyses, animals were anesthetized with metophane at various times after treatment and were exsanguinated by perfusion with heparinized saline. 500 IU of heparin were i.v. injected, the animal anesthetized with metofane and the systemic circulation perfused with PBS at a flow rate of 0.6 mls/min until the liver had been cleared of blood. The tumor and normal tissues were excised and formalin fixed (4% v/v). Paraffin sections of the tissues were cut and stained with the standard Martius Scarlet Blue (MSB) trichrome technique for detection of fibrin, and with hematoxylin and eosin stain for cell morphology.

B. Results

1. Improved Tumor Model

To improve the C1300 (Muγ) tumor model as described before (Burrows et al., 1992), the inventors subcloned the C1300 (Muγ) cell line into a cell line that can grow without being mixed with its parental cell, C1300, but still express the I-A$^d$ MHC Class II antigen on the endothelial cells of the tumor. The inventors used an anti-I-A$^d$ antibody (B21-2) that has a 5-10 fold higher affinity for its antigen than the initial anti-I-A$^d$ antibody (M5/114.15.2) used in this model as determined by FACS. In vivo distribution studies with this new anti-I-A$^d$ antibody showed the same tissue distribution pattern as did M5/114.15.2. Intense staining with B21-2 was seen in tumor vascular endothelium, light to moderate staining in Kuppfer cells in the liver, the marginal zones in the spleen and some areas in the small and large intestines. Vessels in other normal tissues were unstained.

2. Determination of Suitable In Vivo Doses

The maximum tolerated dose was 16 μg B21-2/10H10 plus 11 μg tTF injected intravenously into the tail vein of mice. At this dose, mice lost no weight and had normal appearance and activity levels. At a higher dose of 20 Ag B21-2/10H10 plus 16 μg tTF, two of ten mice developed localized dermal hemorrhages which eventually resolved. The lower dose was adopted for in vivo studies. Truncated TF itself was not toxic at 50 μg, given intravenously.

3. Specific Coagulation and Infarction in Tumor Vasculature

Figure 3B:
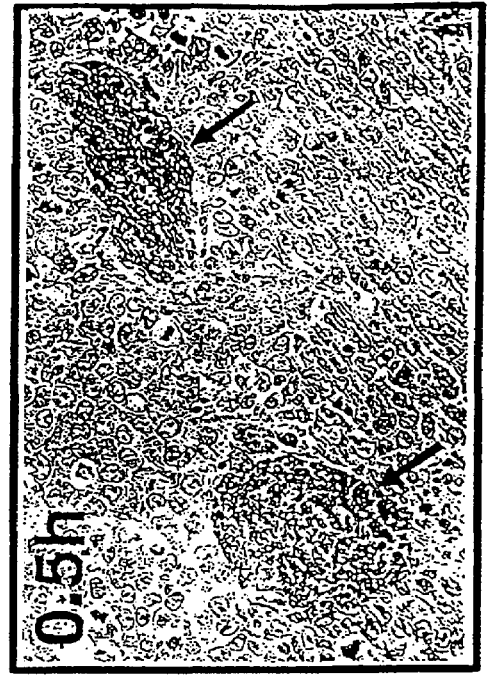
FIG. 3A, FIG. 3B, FIG. 3C and FIG. 3D. Time course of vascular thrombosis and tumor necrosis after administration of coaguligand. Groups of 3 mice bearing 0.8 cm diameter C1300 (Muγ) tumors were given an intravenous injection of a coaguligand composed of 14 μg B21-2/10H10 and 11 μg tTF.
Figure 3D:
Figure 3A:
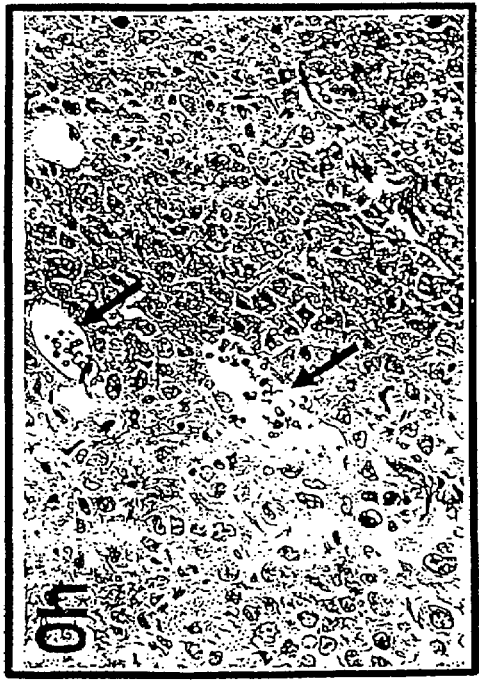

Intravenous administration of a coaguligand composed of B21-2/10H10 (20 μg) and tTF (16 μg) to mice bearing solid C1300 (Muγ) tumors caused tumors to assume a blackened, bruised appearance within 30 minutes. A histological study of the time course of events within the tumor revealed that 30 minutes after injection of coaguligand all vessels in all regions of the tumor were thrombosed (FIG. 3B). Vessels contained platelet aggregates, packed red cells and fibrin. At this time, tumor-cells were healthy, being indistinguishable morphologically from tumor cells in untreated mice (FIG. 3A).

Figure 3C:
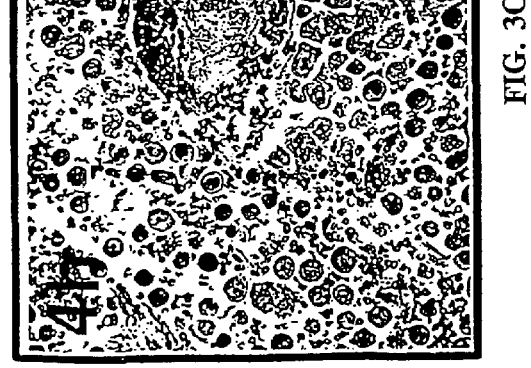

By 4 hours, signs of tumor cell distress were evident. The majority of tumor cells had begun to separate from one another and had developed pyknotic nuclei (FIG. 3C). Erythrocytes were commonly observed in the tumor interstitium. By 24 hours, advanced tumor necrosis was visible throughout the tumor (FIG. 3D). By 72 hours, the entire central region of the tumor had compacted into morphologically indistinct debris.

In one of three of the tumors examined, a viable rim of tumor cells 5-10 cell layers thick was visible on the outskirts of the tumor where it was infiltrating into surrounding normal tissues. Immunohistochemical examination of serial sections of the same tumor revealed that the vessels in the regions of tumor infiltration lacked class II antigens.

Tumors from control mice which had received B21-2/10H10 bispecific antibody (20 μg) alone 30 minutes or 24 hours earlier showed no signs of infarction. Tumors from mice which received tTF (16 μg), alone or in combination with B21-2/OX7 or SFR8/10H10, showed no signs of infarction 30 min after injection but 24 hours after injection, occasional vessels (about 20% of vessels overall) in the tumor were infarcted. These appeared to be most prevalent in the core of the tumor.

No thrombi or morphological abnormalities were visible in paraffin sections of liver, kidney, lung, intestine, heart, brain, adrenals, pancreas and spleen taken from tumor-bearing mice 30 minutes, 4 hours and 24 hours after administration of coaguligand or tTF.

4. Tumor Regressions of Solid Tumors

Figure 4:
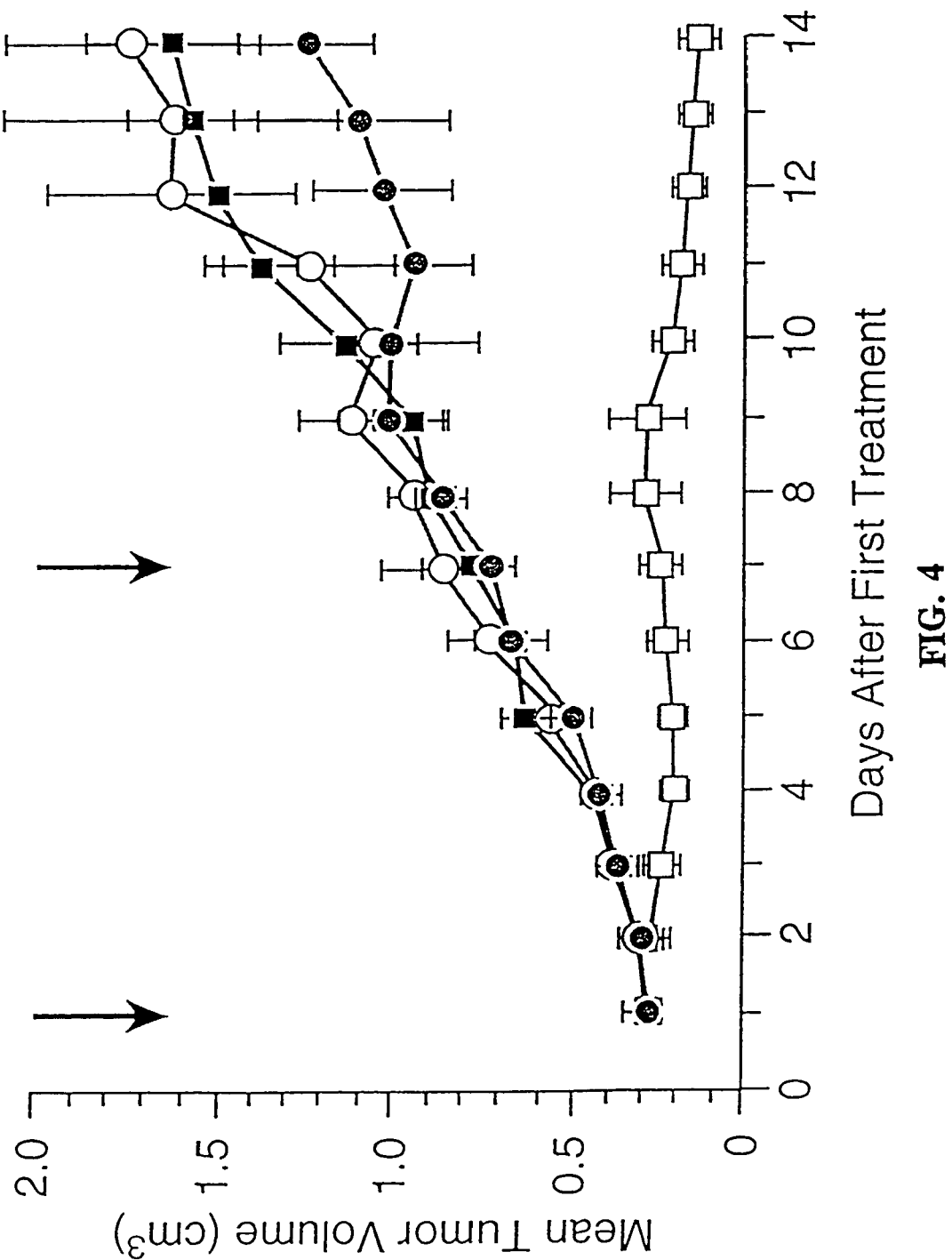
FIG. 4. Solid tumor regression induced by tumor-vasculature directed coaguligand therapy. Nu/nu mice bearing approximately 0.8 cm diameter C1300 (Muγ) tumors were given two intravenous injections of B21-2/10H10 (14 μg) mixed with tTF (11 μg) spaced 1 week apart (arrows) (□). Mice in control groups received equivalent doses of tTF alone (●), B21-2/10H10 alone (○) or diluent (■). Other control groups which received equivalent doses of isotype-matched control bispecific antibodies (SFR8/10H10, OX7/10H10 or B21-2/OX7) and tTF had similar tumor responses to those in animals receiving tTF alone. The number of mice per group was 7 or 8.

FIG. 4 shows the results of a representative anti-tumor study in which a coaguligand composed of B21-2/10H10 and tTF was administered to mice with 0.8 cm diameter tumors. The tumors regressed to approximately half their pretreatment size. Repeating the treatment on the 7th day caused the tumors to regress further, usually completely. In 5/7 animals, complete regressions were obtained. Two of the mice subsequently relapsed four and six months later. These anti-tumor effects are statistically highly significant ($P<0.001$) when compared with all other groups.

Tumors in mice treated with tTF alone or with tTF mixed with the isotype-matched control bispecific antibodies, SFR8/10H10 or B21-2/OX7, grew more slowly than those in groups receiving antibodies or diluent alone. These differences were statistically significant ($P<0.05$) on days 12-14. Thus, part of the anti-tumor effects seen with the B21-2/10H10 coaguligand are attributable to a slight non-specific action of tTF itself.

At the end of the study, two mice which had been treated with diluent alone and which had very large tumors of 2.0 cm$^3$ and 2.7 cm$^3$ (i.e. 10-15% of their body weight) were given coaguligand therapy. Both had complete remissions although their tumors later regrew at the original site of tumor growth.

C. Discussion

The present studies show that soluble human tTF, possessing. practically no ability to induce coagulation, became a powerful thrombogen for tumor vasculature when targeted by means of a bispecific antibody to tumor endothelial cells. In vitro coagulation studies showed that the restoration of thrombotic activity of tTF is mediated through its cross-linking to antigens on the cell surface.

tTF binds factors VII and VIIa with high affinity and enhances the catalytic activity of VIIa but does not induce coagulation of plasma because the tTF:VIIa complex has to be associated with a membrane surface for efficient activation of factors IX and X (Ruf et al., 1991; Krishnaswamy et al., 1992). Tethering of tTF:VIIa to the cell surface by means of a bispecific antibody restores its ability to induce coagulation by bringing the tTF:VIIa into close proximity to the membrane: the membrane phospholipid provides the surface on which the coagulation-initiation complexes with factors IX or X can assemble and efficiently produce intermediates in the clotting process.

Administration of a coaguligand directed against class II to mice having tumors with class II-expressing vasculature caused rapid thrombosis of blood vessels throughout the tumor. This was followed by infarction of the tumor and complete tumor regressions in a majority of animals. In those animals where complete regressions were not obtained, the tumors grew back from a surviving rim of tumor cells on the periphery of the tumor where it had infiltrated into the surrounding normal tissues. The vessels at the growing edge of the tumor lacked class II antigens, thus explaining the lack of thrombosis of these vessels by the coaguligand. It is likely that these surviving cells would have been killed by coadministering a drug acting on the tumor cells themselves, as was found previously (Burrows & Thorpe, 1993).

The anti-tumor effects of the coaguligand were similar in magnitude to those obtained in the same tumor model with an immunotoxin composed of anti-class II antibody and deglycosylated ricin A-chain (Burrows & Thorpe, 1993). One difference between the two agents is their rapidity of action. The coaguligand induced thrombosis of tumor vessels in less than 30 minutes whereas the immunotoxin took 6 hours to achieve the same effect. The immunotoxin acts more slowly because thrombosis is secondary to endothelial cell damage caused by the shutting down of protein syntheses.

A second and important difference between the immunotoxin and the coaguligand is that they have different toxic side effects. The immunotoxin caused a lethal destruction of class II-expressing gastrointestinal epithelium unless antibiotics were given to suppress class II induction by intestinal bacteria. The coaguligand caused no gastrointestinal damage, as expected because of the absence of clotting factors outside of the blood, but caused coagulopathies in occasional mice when administered at high dosage.

RNA was isolated using the GlassMax™ RNA microisolation reagent (Gibco BRL). The RNA was reverse transcribed to cDNA using the GeneAmp RNA PCR kit (Perkin Elmer). tTF cDNA was amplified using the same kit with the following two primers:

```
5' primer: 5' GTC ATG CCA TGG CCT CAG GCA CTA CAA          (SEQ ID NO:1)

3' Primer: 5' TGA CAA GCT TAT TCT CTG AAT TCC CCC TTT CT   (SEQ ID NO:2)
```

The findings described in this report demonstrate the therapeutic potential of targeting human coagulation-inducing proteins to tumor vasculature. For clinical application, antibodies or other ligands are needed that bind to molecules that are present on the surface of vascular endothelial cells in solid tumors but absent from endothelial cells in normal tissues. Tumor endothelial markers could be induced directly by tumor-derived angiogenesis factors (Folkman, 1985) or cytokines (Burrows et al., 1991; Ruco et al., 1990), or could relate to the rapid proliferation (Denekamp & Hobson, 1982) and migration (Folkman, 1985) of endothelial cells during neovascularization.

Several candidate antibodies have been described. The antibody TEC-11, against endoglin is a particular example that binds selectively to human tumor endothelial cells.

Other antibodies include FB5, against endosialin (Rettig et al., 1992), E-9, against an endoglin-like molecule (Wang et al., 1993), BC-1, against a fibronectin isoform (Carnemolla et al., 1989) and TP-1 and TP-3, against an osteosarcoma-related antigen (Bruland et al., 1988). CD34 has been reported to be upregulated on migrating endothelial cells and on the abluminal processes of budding capillaries in tumors and fetal tissues (Schlingemann et al., 1990). The receptors for vascular endothelial cell growth factor (VEGF) become upregulated in tumor blood vessels (Plate et al., 1993; Brown et al., 1993) probably in response to hypoxia (Thieme et al., 1995), and selectively concentrate VEGF in tumor vessels (Dvorak et al., 1991).

The induction of tumor infarction by targeting coagulation-inducing proteins to these and other tumor endothelial cell markers is proposed as a valuable new approach to the treatment of solid tumors. The coupling of human (or humanized) antibodies to human coagulation proteins to produce wholly human coaguligands is particularly contemplated, thus permitting repeated courses of treatment to be given to combat both the primary tumor and its metastases.

EXAMPLE IV

Synthesis of Truncated Tissue Factor (tTF) Constructs tTF is herein designated as the extracellular domain of the mature tissue factor protein (amino acid 1-219 of the mature protein; SEQ ID NO:23). SEQ ID NO:23 is encoded by, e.g., SEQ ID NO:22.

A. H$_6$[tTF]

H$_6$ Ala Met Ala [tTF]. The tTF complimentary DNA (cDNA) was prepared as follows: RNA from J-82 cells (human bladder carcinoma) was used for the cloning of tTF. Total The underlined sequences codes for the N-terminus of tTF. The rest of the sequence in the 5' primer is the restriction site for NcoI allowing the cloning of tTF into the expression vector. The sequence in the 3' primer is the HindIII site for cloning tTF into the expression vector. PCR amplification was performed as suggested by the manufacturer. Briefly, 75 µM dNTP; 0.6 µM primer, 1.5 mM MgCl$_2$ were used and 30 cycles of 30" at 95° C., 30" at 55° C. and 30" at 72° C. were performed.

The E. coli expression vector H$_6$ pQE-60 was used for expressing tTF (Lee et al., 1994). The PCR amplified tTF cDNA was inserted between the NcoI and Hind3 site. H$_6$ pQE-60 has a built-in (His)$_6$ encoding sequence such that the expressed protein has the sequence of (His)$_6$ at the N terminus, which can be purified on a Ni-NTA column.

To purify tTF, tTF containing H6 pQE-60 DNA was transformed to E. coli TG-1 cells. The cells were grown to OD$_{600}$=0.5 and IPTG was added to 30 µM to induce the tTF production. The cells were harvested after shaking for 18 h at 30° C. The cell pellet was denatured in 6 M Gu-HCl and the lysate was loaded onto a Ni-NTA column (Qiagen). The bound tTF was washed with 6 M urea and tTF was refolded with a gradient of 6 M-1 M urea at room temperature for 16 h. The column was washed with wash buffer (0.05 Na H$_2$ PO$_4$, 0.3 M Nacl, 10% glycerol) and tTF was eluted with 0.2 M Imidozole in wash buffer. The eluted tTF was concentrated and loaded onto a G-75 column. tTF monomers were collected.

B. tTF

Gly[tTF]. The GlytTF complimentary DNA (cDNA) was prepared the same way as described in the previous section except the 5' primer was replaced by the following primer in the PCR.

5' primer: 5' GTC ATG CCA TGG CCC TGG TGC CTC GTG CT<u>TCTGGCACTACAAATACT</u>(SEQ ID NO:3)

The underlined sequence codes for the N-terminus of tTF. The remaining sequence encodes a restriction site for NcoI and a cleavage site for thrombin.

The H$_6$ pQE60 expression vector and the procedure for protein purification is identical to that described above except that the final protein product was treated with thrombin to remove the H$_6$ peptide. This was done by adding 1 part of thrombin (Sigma) to 500 parts of tTF (w/w), and the cleavage was carried out at room temperature for 18 h. Thrombin was removed from tTF by passage of the mixture through a Benzamidine Sepharose 6B thrombin affinity column (Pharmacia).

C. Cysteine-Modified tTFS tTF constructs were modified with an N or C-terminal cysteine to allow for easier conjugation to derivatized antibody through a disulfide bond.

$H_6$ C[tTF]. (His)$_6$ Ala Met Ala Cys-[tTF] (SEQ ID NO:34). The DNA was made as described in the previous section except that the 5' primer was replaced by the following primer in the PCR.

5' primer: 5' GTC ATG CCA TGG CC TGCTCAGGCACTACAAATACTGTG(SEQ ID NO:4)

All of the procedures were the same as described above, except the N-terminal cys was protected with an exchangeable oxidizing/reducing reagent.

C[tTF]. Gly Ser Cys [tTF2-219]. The DNA was made as described in the previous section except that the 5' primer was replaced by the following primer in the PCR.

5' primer: 5' GTC ATG CCA TGG CCC TGG TGC CTC GTG GTT CTT GCG GCA CTA CAA ATA CT (SEQ ID NO:5)

The vector construct and protein purification is the same as described for the (His)$_6$ Ala Met Ala Cys [tTF] construct, except that thrombin treatment was used to remove the (His)$_6$ as described above.

$H_6$ [tTF]C. (His)$_6$ Ala Met Ala [tTF] Cys. The DNA was made the same way as described in the (His)$_6$ AMA [tTF] sections, except that the 3' primer was replaced by the following primer.

3' primer:5' TGA CAA GCT TAG CA TTCTCTGAATTCCCCCTTTCT (SEQ ID NO:6)

The underlined sequence encodes the C-terminus of tTF. The rest of the sequence contains the HindIII restriction site for cloning tTF in to the expression vector.

All of the procedures are the same as described in the tTF section except that 10 mM β-ME was used in the 6 M Gu-HCl denaturing solution and the C-terminal cysteine was protected with an exchangeable oxidizing/reducing reagent.

Other [tTF] Cys monomers, such as [tTF 1-220] Cys, [tTF 1-221] Cys and [tTF 1-222] Cys are also made (and conjugated) using the same methodology.

D. C Linker [tTF]

The C Linker [tTF], Gly-Ser-Cys-(Gly)$_4$-Ser-(Gly)$_4$-Ser-(Gly)$_4$-Ser-[tTF] (SEQ ID NO:35), was also constructed. The cDNA was made using a two step PCR procedure as follows:

PCR 1: amplification of linker DNA cDNA encoding the NcoI site, the thrombin cleavage site, cysteine, linker and the N-terminus of tTF was amplified using the following primers:

5' primer: 5'GTC ATG CCA TGG CCC TGG TGC CTC GTG GTT GC G GA GGC GGT GGA TCA GGC (SEQ ID NO:7)

3' primer: 5'AGT ATT TGT AGT GCC TGA GGA TCC GCC ACC TCC ACT (SEQ ID NO:8)

The underlined sequences encode the linker peptide. The DNA template used in the PCR was double strand DNA encoding the following linker.

Sequence: GGA GGC GGT GGA TCA GGC GGT GGA GGT AGT GGA GGT GGC GGA TCC (SEQ ID NO:9)

The same PCR conditions were used as described in the tTF section. The 95 b.p. amplified product was linked to tTF DNA in the PCR2.

PCR 2: Linking the Cys-linker DNA to tTF DNA. DNA templates used in the PCR were two overlapping DNA: The 95 b.p. DNA from PCR 1 as described above and tTF DNA. The primers used were the following:

5' primer: 5'GTC ATG CCA TGG CCC TG (SEQ ID NO:10)

3' primer: 5'TGA CAA GCT TAT TCT CTG AAT TCC CCC TTT CT (SEQ ID NO:11)

The final PCR product of 740 b.p. was digested with NcoI and HindIII and inserted into the H6 pQE 60 as described in the tTF section.

The vector constructs and protein purification procedures are all the same as described in the C[tTF] section.

EXAMPLE V

Synthesis of Dimeric Tissue Factor

The inventors' reasoned that tissue factor dimers may be more potent than monomers at initiating coagulation. It is possible that native tissue factor on the surface of J82 bladder carcinoma cells may exist as a dimer (Fair et al., 1987). The binding of one factor VII or VIIa molecule to one tissue factor molecule may also facilitate the binding of another factor VII or VIIa to another tissue factor (Fair et al., 1987; Bach et al., 1986). Furthermore, tissue factor shows structural homology to members of the cytokine receptor family (Edgington et al., 1991) some of which dimerize to form active receptors (Davies and Wlodawer, 1995). The inventors therefore synthesized TF dimers, as follows.

A. [tTF] Linker [tTF].

The Gly [tTF] Linker [tTF] with the structure Gly[tTF] (Gly)$_4$ Ser (Gly)$_4$ Ser (Gly)$_4$ Ser [tTF] (SEQ ID NO:36) was made. Two pieces of DNA were PCR amplified separately and were ligated and inserted into the vector as follows:

PCR 1: Preparation of tTF and the 5' half of the linker DNA. The primer sequences in the PCR are as follows:

```
5' primer:
5' GTC ATG CCA TGG CCC TGG TGC CTC GTG GTT CTT GCG GCA CTA CAA ATA CT      (SEQ ID NO:12)

3' primer:
5' CGC GGA TCC ACC GCC ACC AGA TCC ACC GCC TCC TTC TCT GAA TTC CCC TTT CT  (SEQ ID NO:13)
```

Gly[tTF] DNA was used as the DNA template. Further PCR conditions were as described in the tTF section.

PCR 2: Preparation of the 3' half of the linker DNA and tTF DNA. The primer sequences in the PCR were as follows:

```
5' primer:
5' CGC GGA TCC GGC GGT GGA GGC TCT TCA GGC ACT ACA AAT ACT GT   (SEQ ID NO:14)

3' primer:
5' TGA CAA GCT TAT TCT CTG AAT TCC CCT TTC T                    (SEQ ID NO:15)
``` tTF DNA was used as the template in the PCR. The product from PCR 1 was digested with NcoI and BamH. The product from PCR 2 was digested with HindIII and BamH1. The digested PCR1 and PCR2 DNA were ligated with NcoI and HindIII-digested $H_6$ pQE 60 DNA.

For the vector constructs and protein purification, the procedures were the same as described in the Gly [tTF] section.

B. Cys [tTF] Linker [tTF]

The Cys [tTF] Linker [tTF] with the structure Ser Gly Cys [tTF 2-219] $(Gly)_4$ Ser $(Gly)_4$ Ser$(Gly)_4$ Ser [tTF] (SEQ ID NO:37) was also constructed. DNA was made by PCR using the following primers were used:

```
5' primer:
5' GTC ATG CCA TGG CCC TGG TGC CTC GTG GTT CTT GCG GCA CTA CAA ATA CT   (SEQ ID NO:16)

3' primer:
5' TGA CAA GCT TAT TCT CTG AAT TCC CCT TTC T                            (SEQ ID NO:17)
```

[tTF] linker [tTF] DNA was used as the template. The remaining PCR conditions were the same as described in the tTF section. The vector constructs and protein purification were all as described in the purification of $H_6$C[tTF].

C. [tTF] Linker [tTF]cys

The [tTF] Linker [tTF]cys dimer with the protein structure [tTF] $(Gly)_4$ Ser $(Gly)_4$ Ser $(Gly)_4$ Ser [tTF] Cys (SEQ ID NO:38) was also made. The DNA was made by PCR using the following primers:

```
5' primer:
5' GTC ATG CCA TGG CCC TGG TGC CTC GTG GTT GCA CTA CAA ATA CT   (SEQ ID NO:18)

3' primer:
5' TGA CAA GCT TAG CAT TCT CTG AAT TCC CCT TTC T.               (SEQ ID NO:19)
```

[tTF] linker [tTF] DNA was used as the template. The remaining PCR conditions were the same as described in the tTF section. The vector constructs and protein purification were again performed as described in the purification of [tTF] cys section.

D. Chemically Conjugated Dimers

[tTF] Cys monomer are conjugated chemically to form [tTF] Cys-Cys [tTF] dimers. This is done by adding an equal molar amount of DTT to the protected [tTF] Cys at room temperature for 1 hr to deprotect and expose the cysteine at the C-terminus of [tTF] Cys. An equal molar amount of protected [tTF] Cys is added to the DTT/[tTF] Cys mixture and the incubation is continued for 18 h at room temperature. The dimers are purified on a G-75 gel filtration column.

The Cys [tTF] monomer is conjugated chemically to form dimers using the same method.

EXAMPLE VI

Synthesis of Tissue Factor Mutants

Two tTF mutants are described that lack the capacity to convert tTF-bound factor VII to factor VIIa. There is 300-fold less factor VIIa in the plasma compared with factor VII (Morrissey et al., 1993). Therefore, circulating mutant tTF should be less able to initiate coagulation and hence exhibit very low toxicity. In coaguligands, once the mutant tTF has localized through the attached antibody to the tumor site, Factor VIIa will be injected to exchange with the tTF-bound Factor VII. The mutants are active in the presence of factor VIIa.

A. [tTF]G164A

The "[tTF]G164A" has the mutant protein structure with the amino acid 164 (Gly) of tTF being replaced by Ala. The Chameleon double-stranded site directed mutagenesis kit (Stratagene) is used for generating the mutant. The DNA template is Gly[tTF] DNA and the sequence of the mutagenizing primer is:

5' CAA GTT CAG CCA AGA AAAC (SEQ ID NO:20)

The vector constructs and protein purification procedures described above are used in the purification of Gly[tTF].

B. [tTF] W158R S162A The [tTF]W158R S162A is a double mutant in which amino acid 158 (Trp) of tTF is replaced by Arg and amino acid 162 (Ser) is replaced by Ala. The same mutagenizing method is used as described for [tTF] G164A. The mutagenizing primer is:

5' ACA CTT TAT TAT CGG AAA TCT TCA GCT TCA GGA AAG (SEQ ID NO:21)

The foregoing vector constructs and protein purification procedures are used for purifying Gly[tTF].

EXAMPLE VII

Synthesis of Tissue Factor Conjugate

A. Chemical Derivatization and Antibody Conjugation

Figure 5:
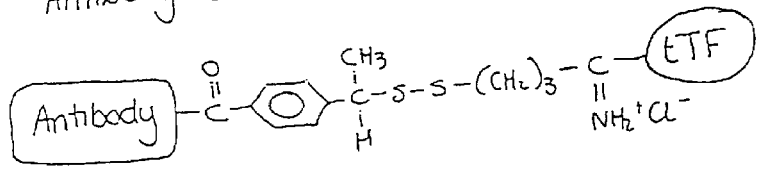
FIG. 5. Exemplary antibody-tTF constructs. This figure shows both the conjugates synthesized by the linkage of chemically derivatized antibody to chemically derivatized tTF via a disulfide bond, and also the linkage of various TF or TF dimers to antibodies and fragments thereof.
Figure 5:
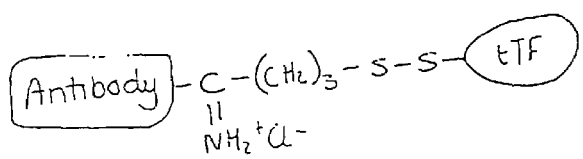
Figure 5:
Figure 5:
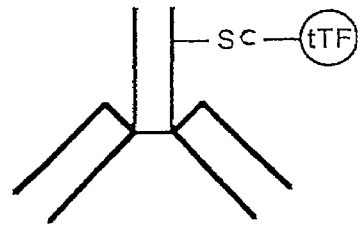
Figure 5:
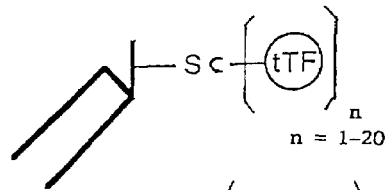
Figure 5:
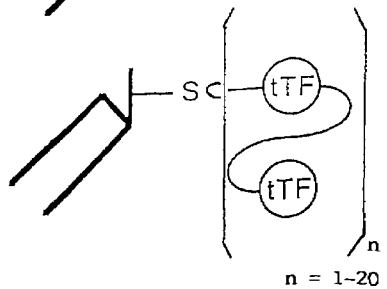

Antibody tTF conjugates were synthesized by the linkage of chemically derivatized antibody to chemically derivatized tTF via a disulfide bond (as exemplified in FIG. 5).

Antibody was reacted with a 5-fold molar excess of succinimidyl oxycarbonyl-α-methyl α-(2-pyridyldithio)toluene (SMPT) for 1 hour at room temperature to yield a derivatized antibody with an average of 2 pyridyldisulphide groups per antibody molecule. Derivatized antibody was purified by gel permeation chromatography.

A 2.5-fold molar excess of tTF over antibody was reacted with a 45-fold molar excess of 2-iminothiolane (2IT) for 1 hour at room temperature to yield tTF with an average of 1.5 sulfhydryl groups per tTF molecule. Derivatized tTF was also purified by gel permeation chromatography and immediately mixed with the derivatized antibody.

The mixture was left to react for 72 hours at room temperature and then applied to a Sephacryl S-300 column to separate the antibody-tTF conjugate from free tTF and released pyridine-2-thione. The conjugate was separated from free antibody by affinity chromatography on a anti-tTF column. The predominant molecular species of the final conjugate product was the singly substituted antibody-tTF conjugate (Mr approx. 176,000) with lesser amounts of multiply substituted conjugates (Mr≧approx. 202,000) as assessed by SDS-PAGE.

B. Conjugation of Cysteine-Modified tTF to Derivatized Antibody

Antibody-C[TF] and [tTF]C conjugates were synthesized by direct coupling of cysteine-modified tTF to chemically derivatized antibody via a disulfide bond (as exemplified in FIG. 5).

Antibody was reacted with a 12-fold molar excess of 2IT for 1 hour at room temperature to yield derivatized antibody with an average of 1.5 sulfhydryl groups per antibody molecule. Derivatized antibody was purified by gel permeation chromatography and immediately mixed with a 2-fold molar excess of cysteine-modified tTF. The mixture was left to react for 24 hours at room temperature and then the conjugate was purified by gel permeation and affinity chromatography as described above.

The predominant molecular species of the final conjugate was the singly substituted conjugate (Mr approx. 176,000) with lesser amounts of multiple substituted conjugates (Mr≧approx. 202,000) as assessed by SDS-PAGE.

C. Conjugation of Cysteine-Modified tTF to Fab' Fragments

Antibody Fab'-C[tTF] and [tTF]C conjugates are prepared. Such conjugates may be more potent in vivo because they should remain on the cell surface for longer than bivalent conjugates due to their limited internalization capacity. Fab' fragments are mixed with a 2-fold molar excess of cysteine-modified tTF for 24 hours and then the conjugate purified by gel permeation and affinity chromatography as described above.

D. Clotting Activity of tTF Conjugates tTF conjugates were prepared with the B21-2 monoclonal antibody which binds to Class II antigens expressed on the surface to A20 cells. The conjugates were prepared with chemically derivatized tTF and cysteine-modified tTF and the ability of the conjugates to clot mouse plasma in $CaCl_2$ was determined after their binding to the surface of A20 cells.

Figure 6:
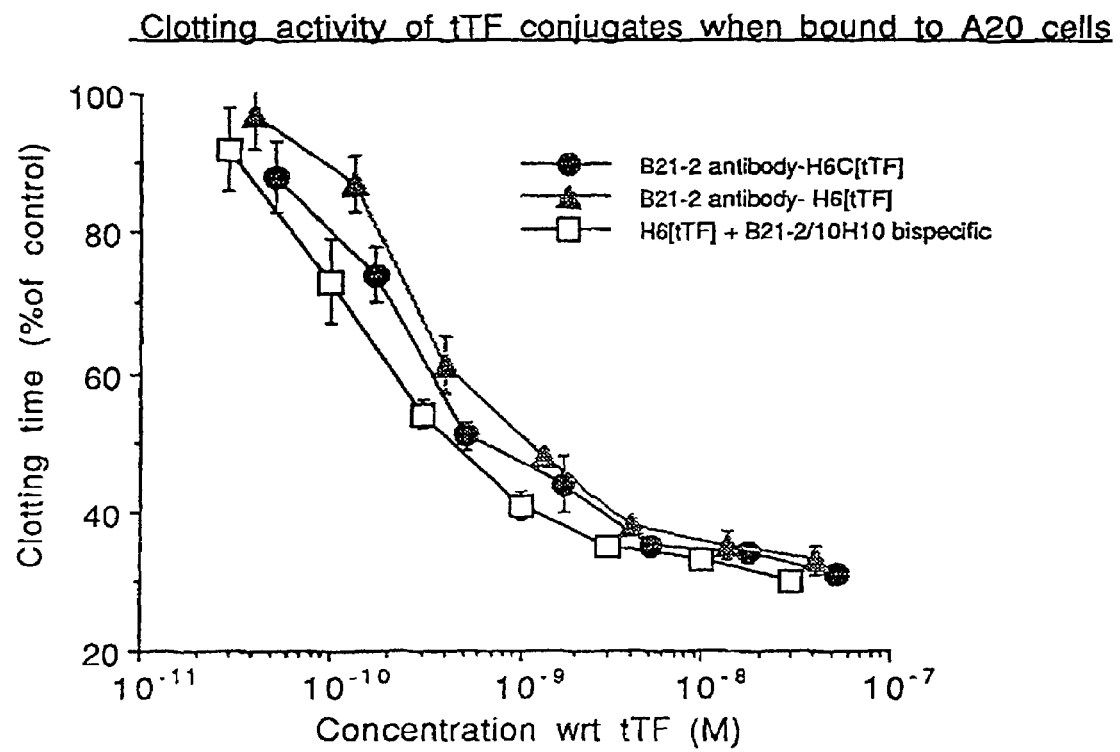
FIG. 6. Clotting activity of tTF conjugates when bound to A20 cells. A20 cells were incubated with varying concentrations of B21-2/10H10 bispecific+H$_6$[tTF] in a 1:1 molar ratio, premixed for one hour (□), B21-2 antibody-H$_6$ C[tTF] (●), and B21-2 antibody-H$_6$[tTF] (▲) for 1 hour at 4° C. in the presence of sodium azide. The cells were washed, warmed to 37° C., calcium and mouse plasma were added and the time for the first fibrin strands to form was recorded. The results are expressed as clotting time as a % of the clotting time in the absence of tTF.

Both B21-2 conjugates shortened the clotting time of mouse plasma in $CaCl_2$ (control) in a dose-dependent manner. The tTF conjugates displayed a similar enhancement in coagulation as occurred when tTF was tethered to the surface of A20 cells with the bispecific antibody B21-2/10H10 (FIG. 6).

E. Anti-tumor Cell tTF Conjugates

It has already been established that when tTF is targeted to tumor vascular endothelial cells it induces coagulation within the tumor vessels (Examples I through III). The inventors' contemplated that coagulation would be induced in tumor vessels if tTF was targeted to the surface of tumor cells.

Three anti-tumor cell antibodies, KS1/4, D612, and XMMCO-791, were conjugated to tTF as described in the "Preparation of tTF conjugates" section above. KS1/4 was obtained from Dr. R. Reisfeld at the Scripps Research Institute, Department of Immunology, La Jolla, Calif., and is also described in U.S. Pat. No. 4,975,369; D612 was obtained from Dr. J. Schlom at the NCI, Laboratory of Tumor Immunology and Biology, Bethesda, Maryland, is described in U.S. Pat. No. 5,183,756 and can be obtained from culture supernatants from the ATCC hybridoma cell line Accession No. HB 9796; XMMCO-791 was purified from tissue culture supernatant from the hybridoma cell line purchased from the ATCC.

The human colon carcinoma cell line Widr was used as a target cell for KS1/4. Widr cells were purchased from the ATCC and were maintained in DMEM supplemented with 10% (v/v) fetal calf serum, L-glutamine and antibiotics in an atmosphere of 10% (v/v) $CO_2$ in air. The human colon carcinoma cell line LS147T was used as a target cell for D612. LS147T cells were purchased from the ATCC and were maintained in RPMI supplemented with 10% (v/v) fetal calf serum, L-glutamine and antibiotics in an atmosphere of 5% (v/v) CO2 in air. The human non small cell lung cancer cell line H460 was used as a target cell for XMMCO-791. H460 cells were obtained from Dr. Adi Gazdar, Simmons Cancer Center, University of Texas Southwestern Medical Center, Dallas, Tex. and were maintained in DMEM supplemented with 10% (v/v) fetal calf serum, L-glutamine and antibiotics in an atmosphere of 10t (v/v) $CO_2$ in air. All three cell lines grew as adherent monolayers.

The conjugates were tested for their ability to enhance the clotting time of mouse plasma in $CaCl_2$ when bound to tumor cells expressing the relevant target antigens. Tumor cells were removed from tissue culture flasks with 0.05% (w/v) EDTA in PBS. The cells were preincubated with TF9-6B4 and TF8-5G9 antibodies to neutralize any native tissue factor activity (Morrisey et. al., 1988) and then the coagulation assay was performed as described for A20 cells.

Figure 7:
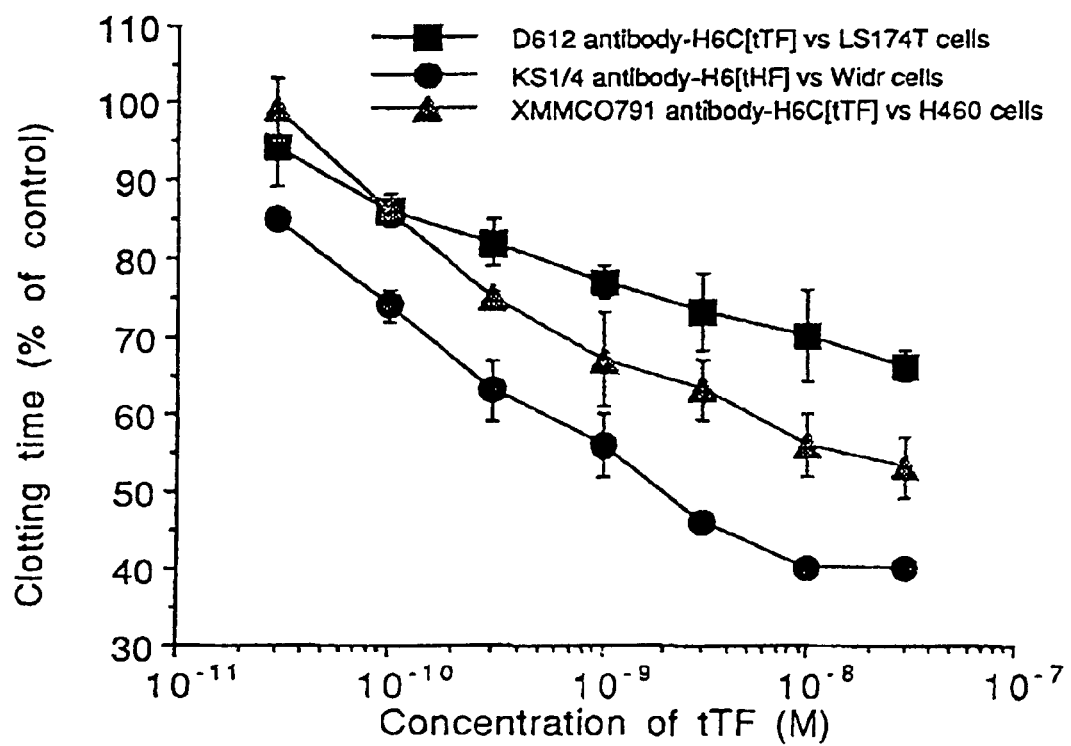
FIG. 7. Clotting activity of anti-tumor cell tTF conjugates. LS174T cells (■), Widr cells (●) and H460 cells (▲), preincubated with TF9-6B4 and TF8-5G9 antibodies, were incubated with varying concentrations of D612 antibody-H$_6$C [tTF] (■), KS1/4 antibody-H$_6$[tTF] (●), and XMMCO791 antibody-H$_6$[tTF] (▲) for 1 hour at 4° C. in the presence of sodium azide. The cells were washed, warmed to 37° C., calcium and mouse plasma were added and the time for the first fibrin strands to form was recorded. The results are expressed as clotting time as a % of the clotting time in the absence of tTF.

When bound to their target cell line, all three conjugates shortened the clotting time of mouse plasma in $CaCl_2$ (control) in a dose-dependent manner (FIG. 7), indicating that coagulation was accelerated at the surface of tumor cells when tTF was targeted to the cell surface.

EXAMPLE VIII

Synthesis of Tissue Factor Prodrugs

Exemplary tTF prodrugs have the following structures: $tTF_{1-219}$ $(X)_{n1}$ $(Y)_{n2}$ Z Ligand, where $tTF_{1-219}$ represents TF minus the cytosolic and transmembrane domains; X represents a hydrophobic transmembrane domain n1 amino acids (AA) in length (1-20 AA); Y represents a hydrophilic protease recognition sequence of n2 AA in length (sufficient AA to ensure appropriate protease recognition); Z represents a disulfide thioester or other linking group such as $(Cys)_{1-2}$; Ligand represents an antibody or other targeting moiety recognizing tumor-cells, tumor EC, connective tissue (stroma) or basal lamina markers The tTF prodrug is contemplated for injection intravenously allowing it to localize to diseased tissue (i.e. tumor). Once localized in the diseased tissue, endogenous proteases (i.e., metalloproteinases, thrombin, factor Xa, factor VIIa, factor IXa, plasmin) will cleave the hydrophilic protease recognition sequence from the prodrug which will allow the hydrophobic transmembrane sequence to insert into a local cell membrane. Once the tail has inserted into the membrane, the tTF will regain its coagulation-inducing properties resulting in clot formation in the vasculature of the diseased tissue.

EXAMPLE IX

Synthesis of Coagulation Factors Lacking the Gla Modification

The vitamin-K-dependent coagulation factors (Factor II/IIa, Factor VII/VIIa, Factor IX/IXa and Factor X/Xa) lacking the Gla (γ-carboxyglutamic acid) modification are contemplated to be useful for the formation of coaguligands. Coagulation factors lacking the Gla modification are poor coagulants because the unmodified factors associate inefficiently with lipid membranes: targeting the factor via a ligand to the vasculature of tumors or other sites should bring the factor back into proximity to the cell surface and enable coagulation to proceed in that site.

"Gla" is made post-translationally by modifying the existing Glu (Glutamic acid) residues. Vitamin-K-dependent coagulation factors (Factor II/IIa, Factor VII/VIIa, Factor IX/IXa and Factor X/Xa) lacking the Gla modification may be made by expressing the genes that encode them in a host, such as bacteria, that does not modify Glu to Gla. The DNA sequences encoding each of Factor II/IIa, Factor VII/VIIa, Factor IX/IXa and Factor X/Xa are included herein as SEQ ID NO:24, SEQ ID NO:25, SEQ ID NO:26 and SEQ ID NO:27, respectively. Procaryotic expression is therefore straightforward.

Such Gla-lacking factors may also be made by mutating any of the sequences described above (SEQ ID NO:24, SEQ ID NO:25, SEQ ID NO:26 and SEQ ID NO:27) to change the corresponding Glu residues to another amino acid before expressing the genes, this time in virtually any host cell. The codon to be changed is the GAG codon (GAA also encodes Glu and is to be avoided). Using Factor VII as an example, the Gla "domain" is located generally in the 216-325 region. The first Gla-encoding triplet occurs at 231 of SEQ ID NO:25, and the last extends through 318 of SEQ ID NO:25. The GAG codons may readily be changed using molecular biological techniques.

Figure 8:
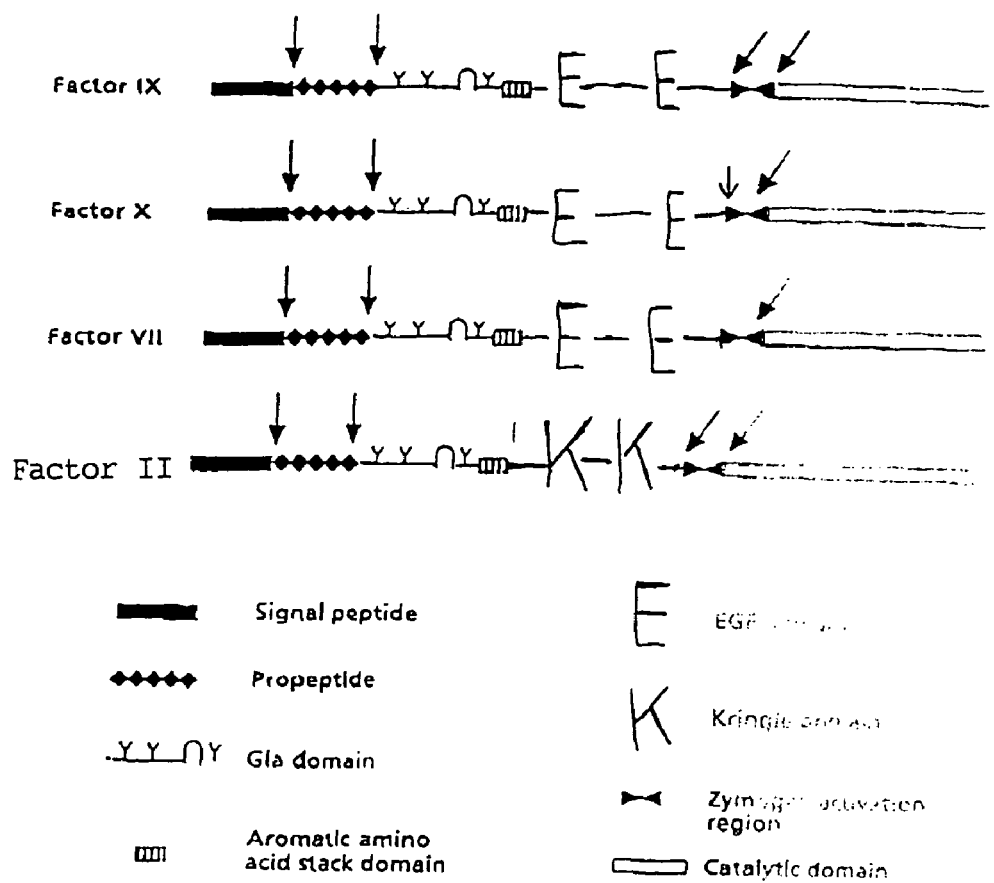
FIG. 8. Gla domains (γ-carboxyglutamic acid) of Factor II/IIa, Factor VII/IIa, Factor IX/IXa and Factor X/Xa. The arrows represent signal peptide and pro-peptide cleavage sites and activating cleavage sites (slanted arrows).

FIG. 8 shows that the Gla domains of each of the above vitamin-K-dependent coagulation factors lie in an analogous region. Therefore, mutation of the so-called "corresponding" Glu residues in any one of SEQ ID NO:24, SEQ ID NO:26 and SEQ ID NO:27 will also be straightforward.

The following Table of codons is provided to enable ready mutation choices to be made in modifying a given Gla-encoding codon or sequence.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Site-specific mutagenesis is the technique contemplated for use in the preparation of individual vitamin-K-dependent coagulation factors lacking the Gla modification, through specific mutagenesis of the underlying DNA and the introduction of one or more nucleotide sequence changes into the DNA.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by publications such as Adelman et al. (1983) and by the TF mutant studies described above. The technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the vitamin-K-dependent coagulation factor. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

EXAMPLE X

Further Anti-Tumor Vasculature Antibodies

This example describes the generation of antibodies directed against tumor-derived endothelial cell "binding factors" for use in distinguishing between tumor vasculature and the vasculature of normal tissues. Particularly described is the generation of antibodies directed against vascular permeability factor (VPF), also termed vascular endothelial cell growth factor (VEGF), and against bFGF (basic fibroblast growth factor).

For further details concerning FGF one may refer to Gomez-Pinilla and Cotman (1992); Nishikawa et al. (1992), that describe the localization of basic fibroblast growth factor; Xu et al. (1992), that relates to the expression and immunochemical analysis of FGF; Reilly et al. (1989), that concerns monoclonal antibodies; Dixon et al. (1989), that relates to FGF detection and characterization; Matsuzaki et al. (1989), that concerns monoclonal antibodies against heparin-binding growth factor; and Herblin and Gross (1992), that discuss the binding sites for bFGF on solid tumors associated with the vasculature.

In the present studies, rabbits were hyperimmunized with N-terminal peptides of human VEGF, mouse VEGF, guinea pig VEGF, human bFGF, mouse bFGF or guinea pig bFGF coupled to tuberculin (purified protein derivative, PPD) or thyroglobulin carriers. The peptides were 25 to 26 amino acids in length and were synthesized on a peptide synthesizer with cysteine as the C-terminal residue. Antisera were affinity purified on columns of the peptides coupled to Sephraose matrices.

Antibodies to VEGF were identified by ELISA and by their staining patterns on frozen sections of guinea pig tumors and normal tissues. Polyclonal antibodies to guinea pig VEGF and human VEGF reacted with the majority of vascular endothelial cells on frozen sections of guinea pig L10 tumors and a variety of human tumors (parotid, ovarian, mammary carcinomas) respectively. The anti-human VEGF antibody stained mesangial cells surrounding the endothelial cells in normal human kidney glomerulae and endothelial cells in the liver, but did not stain blood vessels in normal human stomach, leg muscle and spleen. The anti-guinea pig VEGF antibody did not stain endothelial cells in any normal tissues, including kidney, brain, spleen, heart, seminal vesicle, lung, large intestine, thymus, prostrate, liver, testicle and skeletal muscle.

Polyclonal antibodies to human FGF stained endothelial cells in parotid and ovarian carcinomas, but not those in mammary carcinomas. Anti-human FGF antibodies stained glomerular endothelial cells in human kidney, but not endothelial cells in normal stomach, leg muscle and spleen.

Monoclonal antibodies to guinea pig VEGF, human VEGF and guinea pig bFGF were prepared by immunizing BALB/c mice with the N-terminal sequence peptides (with cysteine at the C-terminus of the peptide) coupled to PPD or to thyroglobulin. The synthetic peptides immunogens of defined sequence are shown below and are represented by SEQ ID NO:30, SEQ ID NO:31 AND SEQ ID NO:32, respectively:

| guinea pig VEGF | A | P | M | A | E | G | E | Q | K | P | R | E | V | V | K | F | M | D | V | Y | K | R | S | Y | C |
| human VEGF | A | P | M | A | E | G | G | G | Q | N | H | H | E | V | V | K | F | M | D | V | Y | Q | R | S | Y | C |
| guinea pig bFGF | M | A | A | G | S | I | T | T | L | P | A | L | P | E | G | G | D | G | G | A | F | A | P | G | C |

The peptides were conjugated to thyroglobulin or to PPD by derivatizing the thyroglobulin with succimidyl 4-(N-maleimidomethyl)cyclohexane-1-carboxylate (SMCC) and reacting the derivative with the peptide. This yields a conjugate having one or more peptide sequences linked via a thioether bond to thyroglobulin.

Specifically, the generation of monoclonal antibodies against the above sequences was achieved using the following procedure: BALB/c mice were immunized by serial injections with peptide-PPD or peptide-thyroglobulin into several sites. Four or five days after the last injection, the spleens were removed and splenocytes were fused with P3xG3Ag8.653 myeloma cells using polyethyleneglycol according to the procedures published in Morrow, et al. (1991).

Individual hybridoma supernatants were screened as follows:

| First screen: | ELISA on peptide-thyroglobulin-coated plates. |
| Second screen: | ELISA on cysteine linked via SMCC to thyroglobulin. |
| Third screen: | Indirect immunoperoxidase staining of frozen sections of guinea pig line 10 tumor or human parotid carcinoma. |
| Fourth screen: | Indirect immunoperoxidase staining of frozen sections of miscellaneous malignant and normal guinea pig and human tissues. |

Antibodies were selected that bound to peptide-thyroglobulin but not to cysteine-thyroglobulin, and which bound to endothelial cells in malignant tumors more strongly than they did to endothelial cells in normal tissues (Table VIII).

TABLE VIII

Reactivity of Monoclonal Antibodies

| | | | Reactivity with Tumour Endothelium | | Tumour Reactivity |
|---|---|---|---|---|---|
| MoAB | Immunogen+ | Class | g. pig | human | Pattern* |
| GV14 | gp VEGF | IgM | + | + | BV + some tumor cells |
| GV35 | gp VEGF | IgM | ± | ± | Tumor cells, weak on BV |

TABLE VIII-continued

Reactivity of Monoclonal Antibodies

| MoAB | Immunogen+ | Class | Reactivity with Tumour Endothelium g. pig | Reactivity with Tumour Endothelium human | Tumour Reactivity Pattern* |
|---|---|---|---|---|---|
| GV39 | gp VEGF | IgM | + | + | BV and some tumor cells |
| GV59 | gp VEGF | IgM | + | + | BV and some tumor cells |
| GV97 | gp VEGF | IgM | + | + | BV, weak on tumor cells |
| HV55 | hu VEGF | IgG | ? | + | Basement membrane, some BV |
| GF67 | gp FGF | IgM | + | + | BV and tumor cells |
| GF82 | gp FGF | IgM | + | + | BV and tumor cells |

*BV = blood vessels
+gp = guinea pig
hu = human

A. GV97 Staining of Human and Guinea Pig Tissue Sections

The GV97 antibody against guinea pig VEGF N-terminus bound to endothelial cells in miscellaneous human malignant (Table IX) and normal (Table X) tissues. The GV39 and GV97 antibodies were deposited Dec. 12, 1997 with the American Type Culture Collection (ATCC), 12301 Parklawn Drive, Rockville, Md. 20852, U.S.A. and given the ATCC Accession numbers ATCC HB-12450 and ATCC HB-12451, respectively. The present address of ATCC is 10801 University Blvd., Manassas, Va. 20110-2209.

Binding to endothelial cells in malignant tumors tended to exceed that to endothelial cells in normal tissues.

The staining of endothelial cells in guinea pig tumor (line 10 hepatocellular carcinoma) and normal tissues was similar in distribution and intensity to that observed with human tissues (Table XI).

In the Tables, + indicates a positive, as opposed to a negative, result. The numbers 2+, 3+ and 4+ refer to a positive signal of increasing strength, as is routinely understood in this field of study.

TABLE IX

Anti-GPVEGF on Human Tumors

| Tumor TISSUE | Purified GV97 20 ug/ml | Purified GV97 10 ug/ml | Purified GV97 5 ug/ml | 1 ug/ml or 2 ug/ml | 0.5 ug/ml | GV97 supt. | GV14 | GV39 | GV59 supt. |
|---|---|---|---|---|---|---|---|---|---|
| DIGESTIVE TRACT | | | | | | | | | |
| 92-01-A073 esophagus carcinoma | | 2+ | 1+ | +/− | −ve | | | 4+ | 4+ |
| M4 Parotid | | | | | | 4+ | | | |
| 87-07-A134 Parotid carcinoma | | 3+ | 2+ | +/− | −ve | | | 3+ | 4+ |
| M5 Parotid | | | | | | 4+ | | | |
| 88-04-A010 parotid adenoca. | | 1-2+ | 1+ | −ve | −ve | | | | 1-3+ |
| 90-11-B319 Adeno. Ca. of colon to liver | | | | | | 3-4+ | | 3-4+ | |
| 94-02-B021C Adenocarcinoma of colon | | | | | | 3-4+ | | 3-4+ | |
| 93-10-A333 Adeno. Ca. of colon with normal | 4+ | 2-4+ | 1-4+ | −ve-1+ | | 4+ | | | 3+ |
| 93-02-B004 Villous and Adenomatous polyp of colon | 4+ | 3-4+ | 2-4+ | 1-2+ | | 3-4+ | | 2-3+ | |
| 93-02-A130 Leiomyosarcoma in colon | | 3+ | 2+ | +/−-1+ | −ve | 4+ | | 4+ | 3-4+ |
| 93-02-B020 Gastric Ca. | | 4+ | 2+ | 2-3+ | −ve-1+ | | | 1-2+ | 4+ |
| 93-04-A221 Pancreas Adenoca. | | 3-4+ | 2-3+ | 1-2+ | −ve-0.5+ | | | 4+ | 4+ |
| 94-04-A390 rectum adenoca. | | 4+ | 3+ | 1-2+ | 1+ | | | | 3+ |
| 93-12-A160 tongue carcinomaadenoca. | | 1-2+ | +/− | −ve | −ve | | | 3+ | 3+ |
| 101-84a Stomach signet ring Ca. (101-84b pair) | | 3+ | 2+ | −ve-1+ | −ve | most 1-2+ but a few 3-4+ | | | 3+ |
| 90-05-A172 Stomach Adenoca. | | 4+ | 3+ | 1-2+ | −ve-1+ | | | −ve | 3+ |
| REPRODUCTIVE TRACT | | | | | | | | | |
| 91-10-A115 Squam. cell Ca. of vulva | 1-4+ | 1-3+ | 1-2+ | 1-2+ | | 1-4+ | | | 1-3+ |
| 93-03-A343 Prostate Adenoca. | | +/−-3-4+ | +/− to 2-3+ | +/− to 1-2+ | +/− | | | 3-4+ | 3-4+ |

TABLE IX-continued

Anti-GPVEGF on Human Tumors

| Tumor TISSUE | Purified GV97 20 ug/ml | 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| MUSCLE | | | | | | | | | |
| IMMUNE SYSTEM | | | | | | | | | |
| URINARY SYSTEM | | | | | | | | | |
| 93-10-B002 Renal cell Ca. | | | | | | 2+ | | | 3+ |
| 90-01-A225 Renal cell Ca. | | 4+ | 4+ | 3-4+ of most | 1-3+ of some | 3-4+ | | 3+ | 3-4+ |
| 93-01-A257 Transit. cell Ca. of bladder | 3-4+ | 2-3+ | 1-2+ | +/− | | 2-3+ | | | 2-3+ |
| ENDOCRINE SYSTEM | | | | | | | | | |
| 94-01-A246 Pheochromocytoma of adrenal | 4+ | 4+ | 3-4+ | 3+ | | 4+ | | | 3-4+ |
| 93-11-A074 Adrenal Cort. Ca. | 3-4+ | 3-4+ | 2-3+ | 1+ | | 3-4+ | | | 4+ |
| RESPIRATORY SYSTEM | | | | | | | | | |
| 93-08-N009 Lung Adenoca. | | | | | | 3-4+ | | 3-4+ | 3-4+ |
| 92-10-A316 Sq. cell lung Ca. | | 4+ | 3-4+ | 1-2+ | −ve-0.5+ | | | 4+ | 4+ |
| 03-05-A065 Lung adenoca. | | 4+ | 3-4+ | −ve-1+ | 1+ | | | 3+ | 3+ |
| CENTRAL NERVOUS SYSTEM | | | | | | | | | |
| 94-01-A299 malig. metast. schwanoma to Lymph node | 4+ | 4+ | 4+ | 3-4+ | | 4+ | | | 3-4+ |
| 92-10-A139 Meningioma | 4+ | 3-4+ | 2-3+ | 1-2+ | | 4+ | | | 3-4+ |
| 91-12-A013 Meningioma | 4+ | 2-3+ | −ve-3+ | +/− | | 4+ | | | 3+ |
| 93-03-A361 Atypical meningioma | | 4+ | 4+ | 3+ | 2+ | 4+ | | | 3+ |
| INTEGUMENTARY SYSTEM | | | | | | | | | |
| 94-04-V037 Skin Sq. cell Ca. w/normal | | −ve to 4+ | −ve to 3+ | −ve to 1+ | −ve | | | 2-3+ | 2-3+ |
| 89-02-225 leg sarcoma | | 4+ | 3-4+ | 1+ | 1+ | | | 4+ | 2+ |
| MISC. TUMORS | | | | | | | | | |

TABLE X

Anti-GPVEGF on Human Normal Tissues

| Tumor TISSUE | Purified GV97 20 ug/ml | 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| DIGESTIVE SYSTEM | | | | | | | | | |
| 91-01-A128 Bladder w/ cystitis | | 3+ | 2+ | 1+ | −ve | | | 2-3+ | 2-3+ |
| 94-02-B020 uninvolved colon | | | | | | 2-3+ | | 2-3+ | |
| 92-01-A292 N. Colon | 4+ | 4+ | 4+ | 3-4+ | | 4+ | | | 3-4+ |
| 93-10-A116 N. Colon | Z-4+ | 1-4+ | 1-3+ | −ve-2+ | −ve | 3-4+ | | 2-3+ | 3-4+ |
| 90-06-A116 N. colon | | | | | | 3+ of many | | 2+ | |
| 93-02-A350 N. esophagus | | 3-4+ | 3+ | 1+ | +/− | | | 4+ | 4+ |
| 93-05-A503 N. Ileum | | | | | | 4+ | | | 4+ |
| 94-03-A244 N. Liver | | 4+ | 1-3+ | −ve-1+ | −ve | | | 4+ | 4+ |

TABLE X-continued

Anti-GPVEGF on Human Normal Tissues

| Tumor TISSUE | Purified GV97 20 ug/ml | 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| 90-02-B132 N. Liver | 1+ of a few | +/− | −ve | −ve | −ve | 1-3+ | 2-3+ | 2-3+ | 2-3+ |
| 94-01-A181 N. Pancreas | | 1-4+ | 1-3+ | 1-3+ of a few | −ve | | | | 3-4+ |
| 90-05-D008 N. Pancreas | | 2-4+ | 1-3+ | +/− | −ve | | | 2-3+ | 2-3+ |
| 93-05-A174 N. Parotid | | 2+ of a few | 1-2+ of a few | 1+ of a few | −ve | −ve | | 3+ of a few | 2-3+ |
| 94-04-A391 N. Small bowel | | 1-3+ | −ve-2+ | −ve | −ve | | | | 3+ |
| 88-06-107 N. Stomach | 3+ | 2+ | +/− | −ve | −ve | 3-4+ | | | 3+ |
| 101-84b N. Stomach (101=84a pair) | | 3-4+ in main and periphery | 2-3+ in main and 3-4+ in periphery | +/− in main and 2+ in periphery | −ve in main and 1+ in periphery | 3+ | | | 3-4+ |
| 90-11-B337 N. Stomach | | 2-3+ | +/−-1+ | −ve | −ve | | | 3+ | 3+ |
| REPRODUCTIVE TRACT | | | | | | | | | |
| 93-04-A041 N. Breast | | | | | | 4+ | | 3+ | |
| 94-02-A197 N. Breast w/fibrocystic change | | | | | | 4+ | | 3+ | |
| 93-02-A051 Breast w/fibrocystic change | | −ve-1+ | −ve | −ve | −ve | | | +/− | +/−-2+ |
| 93-02-A103 Breast w/fibrocyst. change | 4+ | 3+ | 2+ | 1+ | | | | | |
| 92-11-A006 N. ectocervix | 2+ of most | 1-2+ of most | 0.5+ | −ve | −ve | 1-2+ of some | | | 3+ of most |
| 91-03-A207 N. ectocervix | | 2.5+ | 1.5+ | 1+ | .5+ | | | | 2-3+ |
| 92-02-A139 N. ovary w/corp. lusteum | 1+ in most but 2+ in one area | −ve in most but 1+ in one area | −ve | −ve | | −ve in most but 3-4+ in one area | | | −ve in most bet 3-4 in one area |
| 93-06-A11B N. Prostate | | 1+ of a few | −ve | −ve | −ve | | | | 3+ |
| 93-11-A317d Prostate chip | | 3-4+ | 2-3+ | −ve-3+ | −ve-1+ | | | 3-4+ | 3-4+ |
| 93-02-A315 Seminal Vesicle | | 0.5-1+ | 0.5+ | −ve | −ve | | | 1+ | 1.2+ |
| 92-04-A069 N. testis | | 1+ | +/− | +/− | +/− | | | 1-2+ | |
| 91-04-A117 Ureter w/inflammation | | 1+ | +/− | −ve | −ve | | | +/−-1+ | 3-4+ |
| MUSCLE | | | | | | | | | |
| 94-01-A065 N. Heart | | 3-4+ | 2+ | +/− | −ve | | | 3-4+ | 4+ |
| 91-07-D007 N. skeletal muscle | 1-4+ | 1-3+ | 1-2+ | −ve | −ve | 1-3+ | | | 1-3+ |
| 95-03-A395 N. Skeletal muscle | | 4+ | 3-4+ | 1-2+ | 0.5-1+ | | | 4+ | 4+ |
| IMMUNE SYSTEM | | | | | | | | | |
| 90-01-A077 N. lymph node | 2-3+ | 2+ | 1+ of some | −ve | −ve | 2-3+ | | | 3-4+ |
| 90-08-A022 N. lymph node | | most 1+ but a few 4+ | most 0,5+ but a few 2+ | most −ve but a few 2+ | most −ve but a few 0.5-1+ | | | 3+ | 3+ |
| 91-03-A057 N. lymph node | | 2+ | 1+ | +/− | −ve | | | 3-4+ | 3-4+ |
| 91-09-B017E uninvolved lymph node | | 3+ | 2+ | +/−-1+ | −ve | | | 2-3+ | 2-3+ |
| 93-07-A236 N. Spicen | | 3-4+ | 3-4+ | −ve-3+ | −ve | | | | 2-4+ |

TABLE X-continued

Anti-GPVEGF on Human Normal Tissues

| Tumor TISSUE | 20 ug/ml | Purified GV97 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| 93-07-252 N. spicen | | 3+ | 1+ | +/− | −ve | | | 2-3+ | |
| ENDOCRINE SYSTEM | | | | | | | | | |
| 94-04-A252 N. adrenal w/ medulia and cortex | 4+ | 4+ | 3-4+ | 1-2+ | | 4+ | | | 3+ |
| 93-05-A086 N. Adrenal medulla | | most −ve a few 1-2+ | most −ve a few 1-2+ | −ve | −ve | | | 2-3+ | 3-4+ |
| 92-03-A157 Hyperplasic thyroid | | 1+ | +/− | +/− | −ve | | | 4+ | 4+ |
| 91-03-B019 N. Thyroid | | −ve-3+ | −ve-2+ | −ve-1+ | −ve | | | 2-3+ | 2-3+ |
| URINARY SYSTEM | | | | | | | | | |
| 93-09-A048 N. Kidney | | | | | | 4+ | | | 2-3+ |
| 91-11-A075 N. Kidney | | 4+ | 3+ | 2+ | 1+ | 4+ on glomeruli | | 4+ on gbomeruli | 4+ on glomeruli |
| 93-10-B001 N. Kidney | | 4+ | 3+ | +/− | −ve | 4+ on glomeruli | | 4+ on glomeruli | 4+ on glomeruli |
| INTEGUMENTARY SYSTEM | | | | | | | | | |
| 92-08-A029 N. Breast skin | | +/− to 4+ | +/− to 3+ | +/− to 1+ | +/− | | | 2+ | 2+ |
| 89-02-257 Cartiledge marches 2SS | | 4+ | 3-4+ | 2-3+ | 1-2+ | | | 1+ | 3-4+ |
| RESPIRATORY SYSTEM | | | | | | | | | |
| 93-05-A203 N. Lung | | −ve-2+ | −ve-1+ | +/− | −ve | | | 2+ | 3+ |
| 92-12-A263 N. Bronchus | | 2-3+ w/ducts staining 3-4+ | 1-2+ w/ ducts staining 2-3+ | −ve | −ve | | | | 2-3+ |

TABLE XI

Staining Pattern of 9F7 anti-VEGF by direct immunohistochemical staining on 6-8 week old GP tissues

| TISSUE | 20 ug/ml | Purified GV97 10 ug/ml | 5 ug/ml | 1 ug/ml or 2 ug/ml | 0.5 ug/ml | 9F7 supt. | 3F9 supt. | 5F9 supt. |
|---|---|---|---|---|---|---|---|---|
| DIGESTIVE SYSTEM | | | | | | | | |
| LIVER | | 2+ | 1-2+ | +/− | +/− | | 1-2+ | 1-2+ |
| INTESTINE | 4+ | 3+ | 2+ | 1+ | | | 4+m lymphoid, rest diff. than | 4+m lymphoid, rest diff. than |
| PANCREAS | 1+ of many and 3+ in islands of cells | | | | | | | |
| SMALL INTESTINE | 4+ of many and 4+ in lymphoid | 2-3+ of many and 4+ in lymphoid, rest diff. than fVIII | 1-2+ of many and 4+ in lymphoid, rest diff. than fVIII | +/− of many and 4+ in lymphoid, rest diff. than fVIII | | | 3+ of some and 4+ in lymphoid | 3+ of some and 4+ in lymphoid |
| STOMACH | 3-4+ | 1-2+ on most occasional 3+ | +/− on most occasional 2+ | +/− on most occasional 1+ | | | 3-4+ (some fVIII-ve) | 3-4+ (some fVIII-ve) |

TABLE XI-continued

Staining Pattern of 9F7 anti-VEGF by direct immunohistochemical staining on 6-8 week old GP tissues

| TISSUE | Purified GV97 20 ug/ml | 10 ug/ml | 5 ug/ml | 1 ug/ml or 2 ug/ml | 0.5 ug/ml | 9F7 supt. | 3F9 supt. | 5F9 supt. |
|---|---|---|---|---|---|---|---|---|
| REPRODUCTIVE SYSTEM | | | | | | | | |
| TESTIS | | | | | | | | |
| MUSCLE AND INTEGUMENTARY SYSTEM | | | | | | | | |
| HEART | −ve | −ve | −ve | −ve | | | 3-4+ (some fVIII−ve) | 3-4+ (some fVIII−ve) |
| MUSCLE | | | | | | | | |
| SKIN | 1-2+ in fatty layer and 3-4+ in cellular layer | 1+ in fatty layer and 3-4+ in cellular layer | +/− in fatty layer and 3-4+ of a few in cellular layer | +/− in fatty layer and 1-2+ of a few in cellular layer | | | 3+ | 3+ |
| IMMUNE SYSTEM | | | | | | | | |
| SPLEEN | 4+ | 3+ | 2+ | −ve | | | 4+ | 4+ |
| THYMUS | | | | | | | | |
| URINARY SYSTEM | | | | | | | | |
| KIDNEY | glomeruli 4+ | glomeruli 3-4+ | glomeruli 2-3+ | glomeruli 1-2+ | | | glomeruli 3-4+ | glomeruli 3-4+ |
| ENDOCRINE SYSTEM | | | | | | | | |
| ADRENAL | | | | | | | | |
| RESPIRATORY SYSTEM | | | | | | | | |
| LUNG | | | | | | | | |
| NERVOUS SYSTEM | | | | | | | | |
| CEREBELLUM | 4+ | 2+ | +/− of most and 1+ of a few | +/− of most and 1+ of a few | | | 4+ | 4+ |
| TUMORS | | | | | | | | |
| TUMOR | 4+ | 4+ | 3-4+ | 2-3+ (2) | | 4+ | | 3+ |

B. Lack of Reactivity of GV97 With Soluble Human VEGF

To identify antibodies that are specific for VEGF, the VEGF receptor (Flk-1) or VEGF bound (or complexed) to the receptor, an ELISA screening protocol was developed. The procedure is as follows:

Initially, a 96 well ELISA plate (round bottom) was coated (outside wells left blank) with 100 μl/well of FLK/seap at 10 μg/ml in sensitizing buffer. After overnight incubation, the plate was washed twice with PBS overnight at 4° C. Next the FLK/Seap coated plate was blocked with 250 μl/well of PBS+CAH (5%) solution for 1 h at 37° C. The blocking solution was removed and the plate was vigorously tapped on paper towels.

The blocked plates were then incubated with 100 μl/well of VEGF-165 (VEGF 165 aa form produced in yeast obtained from Dr. Ramakrishnan, University of Minnesota) at 2 μg/ml in binding plus 0.1 μg/ml heparin for 4 h at room temperature or overnight at 4° C. The VEGF solution was collected and the plate washed 2 times with PBS-tween (0.10%). Next, 100 μl/well of hybridoma fusion supernatant was added to the wells and incubated for 1 h at 32° C. Following this superna- tant incubation, the plate was washed 3 times with PBS tween and then incubated with 100 μl well of secondary antibody (KPL, Gt anti-mouse IgG at 1:1000 in PBS tween+CAH (5%) for 1 hour at 37° C.

Following secondary antibody incubation, the plates were washed 4 times with PBS tween, incubated with 100 μl/well of substrate (Substrate Sigma OPD dissolved in citrate buffer+$H_2O_2$) for 20 minutes and read at 490 nm on a Cambridge Technology Microplate Reader (Model 7520). Wells with an absorbance above appropriate control wells were selected as positives and further characterized.

It was found that GV97 did not bind to recombinant VEGF-coated ELISA plates, nor did recombinant human VEGF bind to GV97 coated ELISA plates. Soluble recombinant human VEGF did not block the binding of 5 μg/ml GV97 to tumor endothelium in histological sections even when added at 50 μg/ml.

These data suggest that GV97 recognizes an epitope of VEGF that is concealed in recombinant human VEGF but which becomes accessible when VEGF binds to its receptor on endothelial cells.

C. GV97 Localization in Line 10-Bearing Guinea Pigs

In contrast with staining data obtained from histological sections, GV97 antibody localized selectively to tumor endothelial cells after injection into line 10 tumor-bearing guinea pigs (Table XII). Staining of endothelial cells in the tumor was moderately strong whereas staining of normal endothelium in miscellaneous organs was undetectable.

D. Anti-bFGF Selectively Bind to Tumor Endothelial Cells

GF67 and GF82, which had been raised against guinea pig bFGF N-terminus, bound strongly to endothelial cells in frozen sections of guinea pig line 10 tumor and to endothelial cells in two types of human malignant tumors (Table XIII). By contrast, relatively weak staining of endothelial cells in miscellaneous guinea pig normal tissues was observed.

TABLE XII

GV97 injected into tumor bearing GP

| TISSUE | GV97 10 ug/ml | GV 97 20 ug/ml serum volume injected |
|---|---|---|
| DIGESTIVE SYSTEM | | |
| LIVER | 2+ | −ve |
| INTESTINE | 3+ | possible 0.5-1+ of a few |
| PANCREAS | +/− of many and 2+ in islands of cells | possible 0.5-1+ of a few |
| SMALL INTESTINE | 2-3+ of many and 4+ in lymphoid, rest diff. than fVIII | +/− |
| STOMACH | 1-2+ on most occasional 3+ | possibly 0.5+ of a few |
| REPRODUCTIVE SYSTEM | | |
| TESTIS | | +/− |
| MUSCLE AND INTEGUMENTARY SYSTEM | | |
| HEART | −ve | −ve |
| MUSCLE | | −ve |
| SKIN | 1+ in fatty layer and 3-4+ in cellular layer | |
| IMMUNE SYSTEM | | |
| SPLEEN | 3+ | Possibly a few 1+ |
| THYMUS | | |
| URINARY SYSTEM | | |
| KIDNEY | glomeruli 3-4+ | |
| ENDOCRINE SYSTEM | | |
| ADRENAL | 4+ | −ve |
| RESPIRATORY SYSTEM | | |
| LUNG | 2+ | −ve |
| NERVOUS SYSTEM | | |
| CEREBELLUM | 2+ | −ve |
| TUMORS | | |
| TUMOR | 4+ | 2-3+ |

TABLE XIII

Anti-GP FGF Antibody Staining on GP Tissues

| GP TISSUE | GF 67 | GF 82 |
|---|---|---|
| DIGESTIVE SYSTEM | | |
| LIVER | ND | ND |
| INTESTINE | +/− | +/− |
| PANCREAS | 2-3+ | 2+ |
| SMALL INTESTINE | +/− | +/− |
| STOMACH | ND | ND |
| REPRODUCTIVE SYSTEM | | |
| TESTIS | ND | ND |
| MUSCLE AND INTEGUMENTARY SYSTEM | | |
| HEART | 2-3+ | 1+ |
| MUSCLE | +/− | 1+ |
| SKIN | ND | ND |
| IMMUNE SYSTEM | | |
| SPLEEN | 3+ | −ve |
| THYMUS | | |
| URINARY SYSTEM | | |
| KIDNEY | 1-2+ | −ve |
| ENDOCRINE SYSTEM | | |
| ADRENAL | 1-2+ | +/− |
| RESPIRATORY SYSTEM | | |
| LUNG | 1-2+ | 2-3+ |
| NERVOUS SYSTEM | | |
| CEREBELLUM | 1+ | −1+ |
| TUMORS | | |
| LINE 1 TUMOR | 4+ | 4+ |
| HUMAN TUMORS | | |
| PHEOCHROMO CYTOMA | 4+ | 4+ |
| SCHWANOMA | 4+ | 4+ |

EXAMPLE XI

Human Treatment Protocols

This example is concerned with human treatment protocols using the bispecific binding and coagulating ligands of the invention. These ligands are contemplated for use in the clinical treatment of various human cancers and even other disorders, such as benign prostatic hyperplasia and rheumatoid arthritis, in which the intermediate or longer term arrest of blood flow would be advantageous.

The bispecific ligands are considered to be particularly useful tools in anti-tumor therapy. From the data presented herein, including the animal studies, and the knowledge in the art regarding treatment of Lymphoma (Glennie et al., 1988), T-Cell targeting (Nolan & Kennedy, 1990) and drug targeting (Paulus, 1985) appropriate doses and treatment regimens may be straightforwardly developed.

Naturally, before wide-spread use, further animal studies and clinical trials will be conducted. The various elements of conducting a clinical trial, including patient treatment and monitoring, will be known to those of skill in the art in light of the present disclosure. The following information is being presented as a general guideline for use in establishing such trials.

It is contemplated that patients chosen for the study would have failed to respond to at least one course of conventional therapy and had to have objectively measurable disease as determined by physical examination, laboratory techniques, or radiographic procedures. Where murine monoclonal antibody portions are employed, the patients should have no history of allergy to mouse immunoglobulin. Any chemotherapy should be stopped at least 2 weeks before entry into the study.

In regard to bispecific ligand administration, it is considered that certain advantages will be found in the use of an indwelling central venous catheter with a triple lumen port. The bispecific ligands should be filtered, for example, using a 0.22 μm filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87 to 99%, and adjustments for protein loss can then be accounted for.

The bispecific ligands may be administered over a period of approximately 4-24 hours, with each patient receiving 2-4 number of infusions at 2-7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses of bispecific coagulating ligands should be administered to groups of patients until approximately 60% of patients showed unacceptable Grade III or IV toxicity in any category. Doses that are ⅔ of this value could be defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the intact bispecific ligand or components thereof and antibodies against any or both portions of the ligand. Immunological analyses of sera, using any standard assay such as, for example, an ELISA or RIA, will allow the pharmacokinetics and clearance of the therapeutic agent to be evaluated.

To evaluate the anti-tumor responses, it is contemplated that the patients should be examined at 48 hours to 1 week and again at 30 days after the last infusion. When palpable disease was present, two perpendicular diameters of all masses should be measured daily during treatment, within 1 week after completion of therapy, and at 30 days. To measure non-palpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Abbassi et al., *J Clin Invest*, 92(6):2719-30, 1993.
Abraham et al., *Science*, 233:545-548, 1986.
Abrams & Oldham, *Monoclonal antibody therapy of human cancer*, Foon & Morgan (Eds.), Martinus Nijhoff Publishing, Boston, pp. 103-120, 1985.
Adams et al., *Cancer Res.*, 43:6297, 1983.
Adelman et al., *DNA* 2:183, 1983.
Alvarez et al., *Modern Pathology*, 5(3):303-307, 1992.
Antibodies: A Laboratory Manual, Cold Spring Harbor Laboratory, 1988.
Arklie et al., *Int. J. Cancer*, 28:23, 1981.
Ashall et al., *Lancet*, 2(8288):7-10, 1982.
Atkinson et al., *Cancer Res.*, 62:6820, 1982.
Ausubel et al., *Current Protocols in Molecular Biology*, Greene Publishing Associates and Wiley Interscience, N.Y., 1989.
Bach et al., *Biochemistry*, 25, 4007-4020, 1986.
Bauer et al., *Vox Sang*, 61:156-157, 1991.
Baxter et al., *Micro. Res.*, 41(1):5-23, 1991.
Bevilacqua et al., *Proc. Natl. Acad. Sci. USA*, 84:9238-9242, 1987.
Bhagwa et al., *Nature*, 316:511-513, 1985.
Bhattacharya et al., *Hybridoma*, 4:153, 1985.
Bhattacharya et al., *Cancer Res.*, 44:4528, 1984.
Bicknell and Harris, *Seminars in Cancer Biology*, 3:399-407, 1992.
Bikfalvi et al., *Exp. Cell Res.*, 181:75-84, 1989.
Birembaut et al., *J. Pathology*, 145:283-296, 1985.
Bittner et al., *Methods in Enzymol.*, 153:516-544, 1987.
Bjorndahl et al., *Eur. J. Immunol.*, 19:881-887, 1989.
Blakey et al., *Biochem Biophys ACTA*, 923Y(1):59-65, 1987b.
Blakey et al., *Cancer Res.*, 47:947-952, 1987a.
Bolhuis et al., *J. Immunol.*, 149:1840-1846, 1992.
Borden et al., *Cancer*, 65:800-814, 1990.
Brennan et al., *Science*, 229:81-83, 1985.
Brinkmann et al., *Proc. Natl. Acad. Sci.*, 88(19):8616-20, 1991.
Brooks et al., *Cell*, 79:1157-1164, 1994.
Brooks et al., *Science*, 264:569-571, 1994.
Brown et al., *J. Exp. Med.*, 176:1375-1379, 1992.
Brown et al., *PNAS*, 78:539, 1981a.
Brown et al., *J. Immunol.*, 127:539, 1981b.
Brown et al., *Cancer Res.*, 53:4727-4735, 1993.

Broze, *Seminars in Hematol.*, 29:159-169, 1992.
Bruland et al., *Cancer Research*, 48:5302-5309, 1988.
Bruland et al., *Int. J. Cancer*, 38(1):27-31, 1986.
Buhring et al., *Leukemia*, 5:841-847, 1991.
Burchell et al., *J. Immunol.*, 131(1):508-13, 1983.
Burrows, & Thorpe, *PNAS*, 90:8996-9000, 1993.
Burrows et al., *Cancer Res*, 52:5954-5962, 1992.
Burrows et al., *Cancer Res.*, 51:4768-4775, 1991.
Burrows et al., *Clin. Cancer Res.*, 1995 (in press).
Burtin et al., *Cancer*, 31:719-726, 1983.
Byers & Baldwin, *Immunol*, 65:329-335, 1988.
Byers et al., *Cancer Res.*, 49:6153-6160, 1989.
Byers et al., 2nd Int. Conf. Mab Immunocon., *Cancer*, 41:1987.
Campbell, In: *Monoclonal Antibody Technology, Laboratory Techniques in Biochemistry and Molecular Biology*, Vol. 13, Burden & Von Knippenberg (Eds.), Elseview, Amsterdam, pp. 75-83, 1984
Carnemolla et al., *J. Cell Biol.*, 108:1139-1148, 1989.
Carnemolla et al., *J. Biol. Chem.*, 267(34):24689-24692, 1992.
Carrel et al., *Hybridoma*, 1:387, 1982.
Cavenagh et al., *Br J Haematol*, 85(2):285-91, 1993.
Chapman et al., *Arthritis Rheum*, 37(12):1752-6, 1994.
Chee et al., *Cancer Res.*, 43:3142, 1982.
Chen et al., *J. Immunol*, 145:8-12, 1990.
Cherwinski et al., *J. Exp. Med.*, 166:1229-1244, 1989.
Cheung et al., *Proc. AACR*, 27:318, 1986.
Clark et al., *Biochim. Biophys. ACTA*, 867:244-251, 1986.
Clark et al., *Cancer Res.*, 51:944-948, 1991.
Clark et al., *Int. J. Cancer*, 2:15-17, 1988.
Clauss et al., *J. Exp. Med.*, 172:1535-1545, 1990.
Cohn et al., *Arch. Surg.*, 122:1425, 1987.
Colberre-Garapin et al., *J. Mol. Biol.*, 150:1, 1981.
Colcher et al., *Cancer Invest*, 1:127, 1983.
Colcher et al., *Cancer Res.*, 47:1185 and 4218, 1987.
Colcher et al., *PNAS*, 78:3199, 1981.
Collins et al., *Proc. Natl. Acad. Sci. U.S.A.*, 81:4917-4921, 1984.
Conn et al., *Proc. Natl. Acad. Sci. USA*, 87:2628-2632, 1990.
Connolly et al., *J. Biol. Chem.*, 264(33):20017-20024, 1989.
Corgon-Cardo et al., *Laboratory Investigation*, 63(6):832-840, 1990.
Corvalen, *Cancer Immuno.*, 24:133, 1987.
Cotran et al., *J. Exp. Med.*, 164:661-666, 1986.
Crea et al., *Proc. Natl. Acad. Sci. U.S.A* 75:5765, 1978.
Croghan et al., *Cancer Res.*, 43:4980, 1983.
Croghan et al., *Cancer Res.*, 44:1954, 1984.
Daar et al., *Transplantation*, 38(3):293-298, 1984.
Davies and Wlodawer, *FASEB J.*, 9:50-56, 1995.
Davis & Preston, *Analytical Biochemistry*, 116(2):402-407, 1981.
de Krester et al., *Int. J. Cancer*, 37:705, 1986.
De Vries et al., *Science*, 255:989-991, 1992.
DeFranco, *Nature*, 352:754-755, 1991.
deLeij et al., *Bispecific antibodies and targeted cellular cytotoxicity*, Romet-Lemonne et al., p. 249, 1991.
Denekamp, et al., *Brit. J. Cancer*, 461:711-720, 1982.
Denekamp, *Cancer Meta. Rev.*, 9:267-282, 1990.
Denekamp, *Prog. Appl. Microcirc.*, 4:28-38, 1984.
Detmar et al., *J. Exp. Med.*, 180:1141-1146, 1994.
Dewerchin et al., *Blood*, 78(4):1005-1018, 1991.
Di Scipio et al., *Biochemistry*, 16:5253-5260, 1977.
Dillman et al., *Antibody, Immunocon. Radiopharm.*, 1:65-77, 1988.
Dippold et al., *PNAS*, 77:6115, 1980.
Dixon et al., *Mol. & Cell Biol.*, 7:4896-4902, 1989.
Duijvestijn et al., *J. Immunol.*, 138:713-719, 1987.
Dunham & Stewart, i J. Natl. Cancer Inst., 13:1299-1377, 1953.
Dustin et al., *J. Immunol.*, 137:245-254, 1986.
Dvorak et al., *J. Exp. Med.*, 174:1275-1278, 1991.
Dvorak et al., *Cancer Cells*, 3(3):77-85, 1991.
Edelman et al., *Proc. Natl. Acad. Sci. USA*, 90:1513-1517, 1993.
Edgington et al., *Thrombosis and Haemostasis*, 66(1):67-79, 1991.
Ellis et al., *Histopathol.*, 8:501, 1984.
Embleton et al., *Br. J. Cancer*, 63(5):670-674, 1991.
Epenetos et al., *Cancer Res.*, 46:3183-3191, 1986.
Epenetos et al., *Lancet*, Nov. 6, 2:1000-1004, 1982.
Fair et al., *J. Biol. Chem.*, 262, 11692-11698, 1987.
Farrans et al., *Lancet*, 2:397, 1982.
Febbraio and Silverstein, *J. Biol. Chem.*, 265(30):18531-18537, 1990.
Ferrara et al., *J. Cell. Biochem.*, 47:211-218, 1991.
Ferrara et al., *Endocrine Reviews*, 13(1):18-32, 1992.
Fisher et al., *Thrombosis Research*, 48:89-99, 1987.
Flavell et al., *Br. J. Cancer*, 65:545-551, 1992.
Flavell et al., *Br. J. Cancer*, 64(2):274-280, 1991.
Folkman, *Adv. Cancer Res.*, 43:175-230, 1985a.
Folkman et al., *Ann. Surg.*, 214(4):414-427, 1991.
Folkman, In: *Important Advances in Oncology, Part I*, DeVita et al. (Eds.), J B Lippincott, Philadelphia, pp. 42-62, 1985b.
Foster et al., *Virchows Arch. (Pathol. Anat. Histophatol.)*, 394:295, 1982.
Foster et al., *Human Pathol.*, 15:502 1984.
Fox, et al., *J. Biol. Resp.*, 9:499-511, 1990.
Frelinger III et al., *J. Biol. Chem.*, 266(26):17106-17111, 1991.
Frelinger III et al., *J. Biol. Chem.*, 265(11):6346-6352, 1990.
French et al., *Cancer Res.*, 51:2358-2361, 1991.
Gailani and Broze, Jr., *Science*, 253:909-912, 2991.
Galfre et al., *Methods Enzymol.*, 73:1-46, 1981.
Gallagher et al., *J. Surg. Res.*, 40:159, 1986.
Galland et al., *???????*, 1233-1240, 1993.
Gangopadhyay et al., *Cancer Res.*, 45:1744, 1985.
Gefter et al., *Somatic Cell Genet.*, 3:231-236, 1977.
Geppert et al., *Immunological Reviews*, 117:5-66, 1990.
Ghetie et al., *Cancer Res.*, 51:5876-5880, 1991.
Ghose, *CRC Critical Review in Therapeutic Drug Carrier Systems*, 3:262-359, 1982.
Ghose & Blair, *CRC Critical Reviews in Therapeutic Drug Carrier Systems*, 3:262-359, 1987.
Gibbons, In: *J. D. Gibbons* (ed.), "Nonparametric methods for quantitative analysis," pp. 160, New York: Holt, Rinehart and Winston. 1976.
Gitoy-Goren et. al., Biochem. Biophys. Res. Comm., 190: 702-, 1993
Glassy et al., *PNAS*, 80:63227, 1983.
Glennie et al., *J. Immunol.*, 141(10):3662-3670, 1988.
Glennie et al., *J. Immunol.*, 139:2367-2375, 1987.
Goding, In: *Monoclonal Antibodies: Principles and Practice*, 2d ed., Academic Press, Orlando, Fla., pp. 60-61, 65-66, 71-74, 1986.
Gomez-Pinilla and Cotman, *Neuroscience*, 49:771-780, 1992.
Gosset et al., *Int Arch Allergy Immunol*, 106(1):69-77, 1995.
Gougos et al., *Int. Immunol.*, 4:83-92, 1992.
Gougos & Letarte, *J. Immunol.*, 141:1925-1933, 1988.
Griffin et al., *Treat. Res.*, 37:433-455, 1988b.
Griffin et al., *Proc. 2nd Conf. on Radioimmunodetection & Therapy of Cancer*, 82, 1988a.
Groenewegen et al., *Nature*, 316:361-363, 1985.

Groves et al., *Br J Dermatol*, 124(2):117-23, 1991.
Gusterson et al., *Br. J. Cancer*, 58:453, 1988.
Hagemeier et al., *Int. J. Cancer*, 38:481-488, 1986.
Hakkert et al., *Blood*, 78(10):2721-6, 1991.
Hammerling, *Transplant. Rev.*, 30:64-82, 1976.
Hattey et al., *Thrombosis Research*, 45(5):485-495, 1987.
Hayes et al., *J. Clin. Invest.*, 75:1671, 1985.
Hayward et al., *Biological Chemistry*, 266(11):7114-7120, 1991.
Hendler et al., *Trans. Assoc. Am. Physicians*, 94:217, 1981.
Herblin and Gross, *Angiogenesis: Key Principles—Science—Technology—Medicine*, 214-218, 1992.
Hess et al., *Transplantation*, 6:1232-1240, 1991.
Heynen et al., *J. Clin. Invest.*, 94:1098-1112, 1994.
Horan Hand et al., *Cancer Res.*, 45:2713, 1985.
Howard et al., *Developmental Biology*, 146:325-338, 1991.
Huang et al., *Anticancer Research*, 13:887-890, 1993.
Imai et al., *JNCI*, 68:761, 1982.
Imam et al., J. Immunobiol, 1984.
Inouye et al., *Nucleic Acids Res.*, 13:3101-3109, 1985.
Jain, *Cancer Meta. Rev.*, 9(3):253-266, 1990.
Jakeman et al., *J. Clin. Invest.*, 89:244-253, 1992.
Johnson & Reithmuller, Hybridoma, 1:381, 1982.
Johnson et al., *Am. J. Reprod. Immunol.*, 1:246, 1981
June et al., *Molecular Cell Biology*, 12:4472-4481, 1987.
June et al., *Immunology Today*, 11(6) :211-216, 1990.
Jutila et al., *J Exp Med.* 175(6) :1565-73, 1992.
Juweid et al., *Cancer Res.*, 52:5144-5153, 1992.
Kabawat et al., *Int. J. Gynecol. Pathol.*, 4:245, 1985.
Kabawat et al., *Int. J. Gynecol. Pathol.*, 4:265, 1983.
Kandel et al., *Cell*, 66:1095-1104, 1991.
Kantor et al., *Hybridoma*, 1:473, 1982.
Karasek, *J. Invest. Derm.*, 93(2):335-385, 1989.
Keelan et al., *Am J Physiol*, 266(1 Pt 2) pH278-90, January 1994a.
Keelan et al., *J Nucl Med*, 35(2):276-81, Februart 1994b.
Kennel et al., *Cancer Res.*, 51:1529-1536, 1991.
Kim et. al., *Growth Factors*, 7:53-64, 1992.
Kim et al., *Nature*, 362:841-844, 1993.
Kimura et al., *Immunogenetics*, 11:373-381, 1983.
Kinsel et al., *Cancer Res.*, 49:1052, 1989.
Kishimoto et al., *Blood*, 78(3):805-11, 1991.
Kisiel, *J. Biol. Chem.*, 254(23):12230-12234, 1979.
Kjeldsen et al., *2nd Int. Wkshop of MAbs & Breast Cancer*, San Fran., November, 1986.
Klagsbrun & Folkman, *Angiogenesis Handook of Experimental Pharmacology*, Vol. 95, Sporn & Roberts, Springer-Verlag, Berlin, pp. 549-586, 1990.
Kohler & Milstein, *Nature*, 256:495-497, 1975.
Kohler & Milstein, *Eur. J. Immunol.*, 6:511-519, 1976.
Kondo et al., *Biochem. and Biophys. Res. Comm.*, 194(3): 1234-1241, 1993.
Krishnaswamy et al., *J. Biol. Chem.*, 267(36):26110-26120, 1992.
Krishnaswamy et al., *J. Biol. Chem.*, 267(33):23696-23706, 1992.
Kufe et al., *Hybridoma*, 3:223, 1984.
Lan et al., *Cancer Res.*, 44:1954, 1984.
Lan et al., *Cancer Res.*, 45:305, 1985.
Lee et al., *Methods in Enzymology*, 237:146-164, 1994.
Leith et al., *British J. Cancer*, 66(2)-:345-8, 1992.
Lemkin et al., *Proc. Am. Soc. Clin. Oncol.*, 3:47, 1984.
Leung et al., Science, 246:1306-1309, 1989.
Leydem et al., *Cancer*, 57:1135, 1986.
LoBuglio et al., JNCI, 80:932, 1988.
Logan et al., *Proc. Natl. Acad. Sci. USA*, 81:3655-3659, 1984.
Loop et al., Int. J. Cancer, 27:775, 1981.
Lord et al., In: *Genetically Engineered Toxins*, Frank (Ed.), M. Dekker Publ., p. 183, 1992.
Lowder et al., *Blood*, 69:199-210, 1987.
Lowe et al., *Immunol Lett.*, 12:263-269, 1986.
Lowy et al., *Cell*, 22:817, 1980.
Maeda et al., *J. Invest. Derm.*, 97:183-189, 1991.
Manabe et al., *J. Lab. Clin. Med.*, 104(3):445-454, 1984.
Mandeville et al., *Cancer Detect. Prev.*, 10:89, 1987.
Mann, *TIBS* 12, 229-233, 1987.
Mason & Williams, *Biochem J*, 187:1-20, 1980.
Massoglia et al., *J. Cell. Phys.*, 132:531-537, 1987.
Masuko et al., *Cancer Res.*, 44:2813, 1984.
Mattes et al., *PNAS*, 81:568, 1984.
Mazzocchi et al., *Cancer Immunol. Immunother.*, 32:13-21, 1990.
McDicken et al., *Br. J. Cancer*, 52:59, 1985.
Menard et al., *Cancer Res.*, 63:1295, 1983.
Messing et al., Third Cleveland Symposium on Macromoleculesand Recombinant DNA, Editor A. Walton, Elsevier, Amsterdam, 1981.
Metzelaar et al., *Blood*, 79(2):372-379, 1992.
Metzelaar et al., *J. Biol. Chem.*, 266(5):3239-3245, 1991.
Mignatti et al., *J. Cell. Biol.*, 113:1193-1201, 1991.
Millauer et al., *Cell*, 72:835-846, 1993.
Miotti et al., *Cancer Res.*, 65:826, 1985.
Miotti et al., *Int. J. Cancer*, 39:297, 1987.
Montefort et al., *Eur Respir J.* 5(7):815-23, 1992.
Moroi and Aoki, *J. Biol. Chem.*, 251(19):5956-5965, 1976.
Morrissey et al., *Blood*, 81:734-744, 1993.
Morrissey et al., *Cell*, 50:129-135, 1987.
Morrissey et al., *Thrombosis Res.*, 52:247-261, 1988.
Moughal et al., *J Periodontal Res*, 27(6):623-30, 1992.
Mulligan et al., *Proc. Natl. Acad. Sci. USA*, 78:2072, 1981.
Mulligan et al., *J. Clin. Invest.*, 88:1396-1406, 1991
Munz et al., *J. Nucl, Med.*, 27:1739, 1986.
Murray et al., *Radio. Onc.*, 16:221-234, 1989.
Nabel et al., *Nature*, 362:844-846, 1993.
Nakamura, *Prog. Growth Factor Res.*, 3:67-86, 1991.
Nelson, 1991.
Nemerson, *Blood*, 71(1):1-8, 1988.
Neumann et al., *Arch Dermatol*, 130(7):879-83, 1994.
Nieuwenhuis et al., *Blood*, 70(3):838-845, 1987.
Nishikawa et al., *Advances in Experimental Medicine and Biology*, 324:131-139, 1992.
Nitta et al., *Lancet*, 335:368-371, 1990.
Nolan & Kennedy, *Biochemica et Biophysica Acta*, 1040:1-11, 1990.
Norton et al., *Biochem Biophys Res Commun*, 195(1):250-8, 1993.
O'Connell et al., *Clin. Exp. Immunol.*, 90:154-159, 1992.
O'Connell et al., *J. Immunol.*, 144(2):521-525, 1990.
O'Hare et al., *Proc. Natl. Acad. Sci. USA*, 78:1527, 1981.
Ogawa et al., *British J. Haematology*, 75:517-524, 1990.
Ohuchida et al. *J. Am. Chem. Soc.*, 103(15):4597-4599, 1981.
Oi & Morrison, *Mt. Sinai J. Med.*, 53(3):175-180, 1986.
Olander et al., *Biochem. and Biophys. Res. Comm.*, 175(1): 68-76, 1991.
Olofsson et al., *Blood*, 84(8):2749-58, 1994.
Osborn et al., *Cell*, 59:1203-1211, 1989.
Osterud et al., *Thrombosis Res.*, 42:323-329, 1986.
Paborsky et al., *J. Biol. Chem.*, 266(32):21911-21916, 1991.
Palleroni et al., *Int. J. Cancer*, 49:296-302, 1991.
Patt et al., *Cancer Bull.*, 40:218, 1988.
Paul et al., *Hybridoma*, 5:171, 1986.
Paulus, *Behrini Inst. Mitt.*, 78:118-132, 1985.
Perez et al., *J. Exp. Med.*, 163:166-178, 1986.
Perez et al., *J. Immunol.*, 137:2069-2072, 1986.

Perez et al., *Nature*, 316:354-356, 1985.
Perkins et al., *Eur. J. Nucl. Med.*, 10:296, 1985.
Pietersz et al., *Antibody, Immunoconj. Radiopharm.*, 1:79-103, 1988.
Pimm et al., *J. Cancer Res. Clin. Oncol.*, 118:367-370, 1992.
Plate et al., *Cancer Res.*, 53:5822-5827, 1993.
Plate et al., *Nature*, 359:845-848, 1992.
Pober et al., *J. Exp. Med.*, 157:1339-1353, 1991.
Poels et al., *J. Natl. Cancer Res.*, 44:4528, 1984.
Poels et al., *J. Natl. Cancer*, 76:781, 1986.
Pukrittayakamee et al., *Mol. Biol. Med.*, 1:123-135, 1983.
Qian et al., *Cancer Res.*, 140:3250, 1991.
Rao and Rapaport, *Biochemistry*, 85:6687-6691, 1988.
Rasmussen et al., *Breast Cancer Res. Treat.*, 2:401, 1982.
Rehemtulla et al., *Thrombosis and Haemostasis*, 65(5):521-527, 1991.
Reilly et al., *Biochem. Biophys. Res. Commun.*, 164:736-743, 1989.
Reisfeld et al., *Melanoma Antigens and Antibodies*, p. 317, 1982.
*Remington's Pharmaceutical Sciences*, 16th Ed., Mack Publishing Company, 1980.
Rettig et al., *Proc. Natl. Acad. Sci. USA*, 89:10832-10836, 1992.
Riva et al., *Int. J. Cancer*, 2:114, 1988
Rivoltini et al., *3rd Int. Conf. Bispecific Antibodies and Targeted Cellular Cytotoxicity*, 1992.
Rowinksy, *Clinical Investigation*, Abstracts from Chemotherapy foundation symposium X. Innovative cancer chemotherapy for tomorrow, pp. 6-9, 1992.
Ruco et al., *Am. J Pathol.*, 137(5):1163-1171, 1990.
Ruf and Edgington, *Thrombosis and Haemostasis*, 66(5):529-533, 1991.
Ruf et al., *J. Biol. Chem.*, 266(24):15719-15725, 1991.
Ruf et al., *J. Biol. Chem.*, 266(4):2158-2166, 1991.
Ruf et al., *JBC*, 266:2158-2166, 1991.
Ruf & Edgington, *FASEB J.*, 8:385-390, 1994.
Ruther et al., *EMBO J.*, 2:1791, 1983.
Safran et al., *Oncogene*, 5:635-643, 1990.
Sainsbury et al., *Lancet*, 1:364, 1985.
Sambrook et al., *Molecular Cloning, A Laboratory Manual*, Cold Spring Harbor Laboratory, N.Y., 1989.
Sands, *Immunoconjugates and Radiopharmaceuticals*, 1:213-226, 1988.
Santerre et al., *Gene*, 30:147, 1984.
Saxton et al., *Hybridoma*, 1:433, 1982.
Scarpati et al., *Biochemistry*, 26:5234-5238, 1987.
Schlingemann et al., *Lab. Invest.*, 52:71-76, 1985.
Schlingemann et al., *Lab. Invest.*, 62:690-696, 1990.
Schlom et al., *Adv. Cancer Res.*, 43:143, 1985.
Schutt et al., *Immunol. Lett.*, 19:321-328, 1988.
Schweigerer et al., *Nature*, 325:257-259, 1987.
Sedmak et al., *Transplantation*, 58(12):1379-85, 1994.
Segal et al., 1992.
Senger et al., *Cancer and Metastasis Reviews*, 12:303-324, 1993.
Senger et al., *Cancer Research*, 50:1774-1778, 1990.
Shankar et al., *J. Biol. Chem.*, 269(19):13936-13941, 1994.
Shen and Tai, *J. Biol. Chem.*, 261(25):11585-11591, 1986.
Shepard et al., *J. Clin. Immunol.*, 11:117-127, 1991.
Shockley et al., *Ann. N.Y. Acad. Sci.*, 617:367-382, 1991.
Shrestha et. al., *Eur. J. Cancer B. Oral. Oncol.*, 30B(6):393-9, 1994.
Shweiki et al., *Nature*, 359:843-847, 1992.
Silber et al., *J Clin Invest*, 93(4):1554-63, 1994.
Silverstein and Febbraio, *Blood*, 80(6):1470-1475, 1992.
Sioussat et al., *Arch. Biochem. Biophys.*, 301(1):15-20, 1993.
Sloane, *Cancer*, 17:1786, 1981.
Smith et al., *J. Virol.*, 46:584, 1983.
Smith et al., 1989.
Smith et al., *Proc. Am. Soc. Clin. O. col.*, 6:250, 1987.
Soule et al., *PNAS*, 80:1332, 1983
Span et al., *Immunology*, 72(3):355-60, 1991.
Spicer et al., *Proc. Natl. Acad. Sci. USA*, 84:5148-5152, 1987.
Sporn et al., *Blood*, 81(9):2406-12, 1993.
Staerz et al., *Nature*, 314(6012):628-631, 1985.
Stavrou, *Neurosurg. Rev.*, 13:7, 1990.
Stefanik et al., *Cancer Research*, 51:5760-5765, 1991.
Steinberg et al., *J Heart Lung Transplant*, 13(2):306-18, March-April 1994.
Stern et al., *Proc. Natl. Acad. Sci. USA*, 80:4119-4123, 1982.
Stern et al., *J. Biol. Chem.*, 260(11):6717-6722, 1985.
Stevenson et al., *Chem. Immunol.*, 48:126-166, 1990.
Street et al., *Cell. Immunol.*, 120:75-81, 1989.
Stuhlmiller et al., *Hybridoma*, 1:447, 1982.
Sugama et al., *J. Cell Biol.*, 119(4):935-944, 1992.
Sunderland et al., *Cancer Res.*, 44:4496, 1984.
Szybalska et al., *Proc. Natl. Acad. Sci. USA*, 48:2026, 1962.
Szymendera, *Tumour Biology*, 7:333, 1986.
Takahashi et al., *Cancer*, 61:881, 1988.
Teramoto et al., *Cancer*, 50:241, 1982.
Tessler et al., *J. Biol. Chem.*, 269(17):12456-12461, 1994.
Thieme et al., *Diabetes*, 44(1):98-103, 1995.
Thompson et al., *J. Natl. Cancer Inst.*, 70:409, 1983.
Thor et al., *Cancer Res.*, 46:3118, 1986
Thorpe et al., *Cancer Res.*, 48:6396-6403, 1988.
Ting et al., *J. Immunol.*, 141:741-748, 1988.
Tischer et al., *Biochem. and Biophys. Res. Comm.*, 165(3):1198-1206, 1989.
Tischer et al., *J. Biol. Chem.*, 266(18):11947-11954, 1991.
Titus et al., *J. Immunol.*, 138:4018-4022, 1987.
Tomiyama et al., *Blood*, 79(9):2303-2312, 1992.
Tone et al., *J. Biochem.*, 102(5):1033-1941, 1987.
Tsuji et al., *Cancer Res.*, 45:2358, 1985.
Tuominen and Kallioinen, *J. Cutan. Pathol.* 21(5):424-9, 1994.
Tutt et al., *Eur. J. Immunol.*, 21:1351-1358, 1991.
Ugarova et al., *J. Biol. Chem.*, 268(28):21080-21087, 1993.
Ulich et al., *Inflammation*, 18(4):389-98, 1994.
Vaickus et al., *Cancer Invest.*, 9:195-209, 1991.
Vaisman et al., *J. Biol. Chem.*, 265(32):19461-19466, 1990.
Van Heeke et al., *J. Biol. Chem.*, 264:5503-5509, 1989.
Van Duk et al., *Int. J. Cancer*, 43:344-349, 1989.
Veale et al., *Arthritis Rheum*, 36(7):893-900, 1993.
Venkateswaran et al., *Hybridoma*, 11(6):729-739, 1992.
Vitetta et al., *Cancer Res.*, 15:4052-4058, 1991.
von Asmuth et al., *Eur J Immunol*, 22(10):2519-26, 1992.
Wagener et al., *Int. J. Cancer*, 33:469, 1984.
Wang et al., *Int. J. Cancer*, 54:363-370, 1993.
Wang et al., *Biochem. and Biophys. Res. Comm.*, 177(1):286-291, 1991.
Warr et al., *Blood*, 75:1481-1489, 1990.
Watanabe et al., *Proc. Natl. Acad. Sci. USA*, 86:9456-9460, 1989.
Wawrzynczak & Thorpe, "Methods for preparing immunotoxins: effect of the linkage on activity and stability", in: *Immunoconjugates,: Antibody conjugates in radioimaging and therapy of cancer*, Vogel (ed), New York, Oxfod University Press, pp. 28-55, 1987.
Weiner et al., *Cancer Res.*, 49:4062-4067, 1989.
Weiss et al., *Blood*, 73:968-975, 1989.
Whittle et al., *Nature*, 292:472-474, 1981.
Wigler et al., *Proc. Natl. Acad. Sci. USA*, 77:3567, 1980.
Wigler et al., *Cell*, 11:223, 1977.

Wildgoose et al., *Blood,* 80:25-28, 1992.
Williams and Esnouf, *Biochem. J.,* 84:52-62, 1962.
Wilson et al., *Int. J. Cancer,* 28:293, 1981.
Wiman and Collen, *Eur. J. Biochem.,* 78:19-26, 1977.
Wiman, *Biochem. J.,* 191:229-232, 1980.
Winter & Milstein, *Nature,* 349:293-299, 1991.
Woodbury et al., *PNAS,* 77:2183, 1980.
Wu et al., *Int. J. Pharm.,* 12:235-239, 1990.
Xu et al., *J. Biol. Chem.,* 267(25):17792-17803, 1992.
Yamaguchi et al., *Proc. Natl. Acad. Sci. USA,* 91:484-488, 1994.
Yamaue et al., *Biotherapy,* 2:247-259, 1990.
Zamarron et al., *J. Biol. Chem.,* 266(24):16193-16199, 1991.
Zhang et al., *Int J Cancer,* 59(6):823-9, 1994.

---

What is claimed is:

1. A method for treating cancer, comprising administering to an animal with a vascularized tumor a therapeutically effective amount of:
   (a) at least one binding ligand that comprises a first binding region that binds to a component expressed, accessible to binding or localized on the surface of a tumor cell, intratumoral vasculature or tumor stroma; wherein said first binding region is operatively linked to a mutant Tissue Factor, truncated Tissue Factor, dimeric Tissue Factor or polymeric Tissue Factor or to an antibody, or antigen binding region thereof, that binds to a mutant Tissue Factor, truncated Tissue Factor, dimeric Tissue Factor or polymeric Tissue Factor; and
   (b) treating said animal with radiotherapy or chemotherapy.

2. The method of claim 1, wherein said animal is a human patient.

3. The method of claim 1, wherein said animal is treated with radiotherapy.

4. The method of claim 1, wherein said animal is treated with chemotherapy.

5. The method of claim 1, wherein said animal is treated with one or more chemotherapeutic agents.

6. The method of claim 1, wherein said first binding region comprises an antibody or antigen binding region thereof.

7. The method of claim 6, wherein said first binding region comprises a monoclonal antibody or antigen binding region thereof.

8. The method of claim 6, wherein said first binding region comprises a human or humanized antibody or antigen binding region thereof.

9. The method of claim 6, wherein said first binding region comprises an scFv, Fv, Fab', Fab or F(ab')$_2$ antigen binding region of an antibody.

10. The method of claim 1, wherein said first binding region binds to a surface-expressed, surface-accessible or surface-localized component of intratumoral vasculature.

11. The method of claim 10, wherein said first binding region binds to an MHC Class II protein, a VEGF/VPF receptor, an FGF receptor, a TGFβ receptor, a TIE, VCAM-1, ICAM-1, P-selectin, E-selectin, $\alpha_v\beta_3$ integrin, pleiotropin, endosialin or endoglin.

12. The method of claim 11, wherein said first binding region binds to a VEGF/VPF receptor.

13. The method of claim 11, wherein said first binding region binds to VCAM-1.

14. The method of claim 11, wherein said first binding region binds to E-selectin.

15. The method of claim 11, wherein said first binding region binds to endoglin.

16. The method of claim 10, wherein said first binding region binds to FGF, TGFβ, a ligand that binds to a TIE, a tumor-associated fibronectin isoform, scatter factor, hepatocyte growth factor (HGF), platelet factor 4 (PF4), PDGF or TIMP.

17. The method of claim 10, wherein said first binding region comprises a ligand that binds to a cell surface receptor of intratuinoral vasculature.

18. The method of claim 17, wherein said first binding region comprises VEGF.

19. The method of claim 1, wherein said first binding region binds to a surface-expressed, surface-accessible or surface-localized component of tumor stroma.

20. The method of claim 19, wherein said first binding region comprises an antibody, or antigen binding region thereof, that binds to tenascin.

21. The method of claim 19, wherein said first binding region comprises an antibody, or antigen binding region thereof, that binds to a basement membrane component.

22. The method of claim 19, wherein said first binding region comprises an antibody, or antigen binding region thereof, that binds to an activated platelet.

23. The method of claim 19, wherein said first binding region comprises an antibody, or antigen binding region thereof, that binds to an inducible tumor stroma component.

24. The method of claim 23, wherein said first binding region comprises an antibody, or antigen binding region thereof, that binds to a tumor stroma component inducible by a coagulant.

25. The method of claim 24, wherein said first binding region comprises an antibody, or antigen binding region thereof, that binds to a tumor stroma component inducible by thrombin.

26. The method of claim 25, wherein said first binding region comprises an antibody, or antigen binding region thereof, that binds to RIBS.

27. The method of claim 1, wherein said first binding region is operatively linked to a human mutant Tissue Factor, human truncated Tissue Factor, human dimeric Tissue Factor or human polymeric Tissue Factor or to an antibody, or antigen binding region thereof, that binds to a human mutant Tissue Factor, human truncated Tissue Factor, human dimeric Tissue Factor or human polymeric Tissue Factor.

28. The method of claim 1, wherein said first binding region is operatively linked to a mutant Tissue Factor, or to an antibody, or antigen binding region thereof, that binds to a mutant Tissue Factor.

29. The method of claim 1, wherein said first binding region is operatively linked to a dimeric or polymeric Tissue Factor, or to an antibody, or antigen binding region thereof, that binds to a dimeric or polymeric Tissue Factor.

30. The method of claim 1, wherein said first binding region is operatively linked to a truncated Tissue Factor, or to an antibody, or antigen binding region thereof, that binds to a truncated Tissue Factor.

31. The method of claim 30, wherein said first binding region is operatively linked to a truncated Tissue Factor that has the amino acid sequence of SEQ ID NO:23, or to an antibody, or antigen binding region thereof, that binds to said truncated Tissue Factor.

32. A method for treating cancer, comprising administering to an animal with a vascularized tumor a therapeutically effective amount of:

(a) at least one binding ligand that comprises a first binding region that binds to a surface-expressed, surface-accessible or surface-localized component of intratumoral vasculature; wherein said first binding region binds to a VEGF/VPF receptor, E-selectin, FGF, TGFβ, a ligand that binds to a TIE, a tumor-associated fibronectin isoform, scatter factor, hepatocyte growth factor (HGF), platelet factor 4 (PF4), PDGF or TIMP; and wherein said first binding region is operatively linked to a coagulation factor or to an antibody, or antigen binding region thereof, that binds to a coagulation factor; and (b) treating said animal with radiotherapy or chemotherapy.

33. The method of claim 1, wherein said at least one binding ligand comprises a first binding region that is operatively linked to said mutant Tissue Factor, truncated Tissue Factor, dimeric Tissue Factor or polymeric Tissue Factor.

34. The method of claim 1, wherein said at least one binding ligand comprises a first binding region that is operatively linked to an antibody, or antigen binding region thereof, that binds to said mutant Tissue Factor, truncated Tissue Factor, dimeric Tissue Factor or polymeric Tissue Factor.

35. The method of claim 34, wherein said at least one binding ligand comprises a first binding region that is operatively linked to an scFv, Fv, Fab', Fab or F(ab')$_2$ fragment of an antibody that binds to said mutant Tissue Factor, truncated Tissue Factor, dimeric Tissue Factor or polymeric Tissue Factor.

36. The method of claim 34, wherein said at least one binding ligand further comprises a mutant Tissue Factor, truncated Tissue Factor, dimeric Tissue Factor or polymeric Tissue Factor bound to said antibody, or antigen binding region thereof.

37. The method of claim 1, wherein said at least one binding ligand is a fusion protein prepared by expressing a recombinant vector in a host cell, wherein said vector comprises, in the same reading frame, a DNA segment encoding said first binding region operatively linked to a DNA segment encoding said mutant Tissue Factor, truncated Tissue Factor, dimeric Tissue Factor or polymeric Tissue Factor or said antibody, or antigen binding region thereof, that binds to said mutant Tissue Factor, truncated Tissue Factor, dimeric Tissue Factor or polymeric Tissue Factor.

38. The method of claim 5, wherein said one or more chemotherapeutic agents comprise one or more chemotherapeutic agents selected from the group consisting of doxorubicin, daunomycin, methotrexate and vinblastine.

39. The method of claim 37, wherein said first binding region comprises an antibody or antigen binding region thereof.

40. The method of claim 37, wherein said first binding region comprises a monoclonal, human or humanized antibody or antigen binding region thereof.

41. The method of claim 37, wherein said first binding region comprises an scFv, Fv, Fab', Fab or F(ab')$_2$ antigen binding region of an antibody.

42. The method of claim 37, wherein said first binding region binds to a surface-expressed, surface-accessible or surface-localized component of intratumoral vasculature.

43. The method of claim 42, wherein said first binding region binds to an MHC Class II protein, a VEGF/VPF receptor, an FGF receptor, a TGFβ receptor, a TIE, VCAM-1, ICAM-1, P-selectin, E-selectin, $\alpha_v\beta_3$ integrin, pleiotropin, endosialin, endoglin, FGF, TGFβ, a ligand that binds to a TIE, a tumor-associated fibronectin isoform, scatter factor, hepatocyte growth factor (HGF), platelet factor 4 (PF4), PDGF or TIMP.

44. The method of claim 17, wherein said at least one binding ligand is a fusion protein prepared by expressing a recombinant vector in a host cell, wherein said vector comprises, in the same reading frame, a DNA segment encoding said first binding region operatively linked to a DNA segment encoding said mutant Tissue Factor, truncated Tissue Factor, dimeric Tissue Factor or polymeric Tissue Factor or said antibody, or antigen binding region thereof, that binds to said mutant Tissue Factor, truncated Tissue Factor, dimeric Tissue Factor or polymeric Tissue Factor.

45. The method of claim 44, wherein said first binding region comprises VEGF.

46. The method of claim 37, wherein said first binding region binds to a surface-expressed, surface-accessible or surface-localized component of tumor stroma.

47. The method of claim 46, wherein said first binding region comprises an antibody, or antigen binding region thereof, that binds to tenascin, a basement membrane component, an activated platelet or an inducible tumor stroma component.

48. The method of claim 46, wherein said first binding region comprises an antibody, or antigen binding region thereof, that binds to RIBS.

49. A method for treating cancer, comprising administering to an animal with a vascularized tumor at least one binding ligand in an amount effective to promote blood coagulation in said vascularized tumor, wherein said binding ligand:
(a) comprises a first binding region that binds to a surface-expressed, surface-accessible or surface-localized component of a tumor cell, intratumoral vasculature or tumor-associated stroma; the first binding region operatively linked to a coagulation factor or to an antibody, or antigen binding region thereof, that binds to a coagulation factor; and
(b) treating said animal with radiotherapy or chemotherapy.

50. A method for treating cancer, comprising administering to an animal with a vascularized tumor a therapeutically effective amount of:
(a) at least one binding ligand that comprises a first binding region that binds to a component expressed, accessible to binding or localized on the surface of a tumor cell, intratumoral vasculature or tumor stroma; the first binding region operatively linked to a coagulation factor or to an antibody, or antigen binding region thereof, that binds to a coagulation factor; and
(b) treating said animal with radiotherapy.

51. A method for treating cancer, comprising administering to a human patient with a vascularized tumor a therapeutically effective amount of:
(a) at least one binding ligand that comprises a first binding region that binds to a component expressed, accessible to binding or localized on the surface of a tumor cell, intratumoral vasculature or tumor stroma; the first binding region operatively linked to Tissue Factor or to an antibody, or antigen binding region thereof, that binds to Tissue Factor; and
(b) treating said patient with radiotherapy or chemotherapy.

52. A method for treating cancer, comprising administering to an animal with a vascularized tumor a therapeutically effective amount of:
(a) at least one binding ligand that comprises a first binding region that binds to a component expressed, accessible to binding or localized on the surface of a tumor cell, intratumoral vasculature or tumor stroma; the first binding region operatively linked to Tissue Factor or to an antibody, or antigen binding region thereof, that binds to Tissue Factor; and
(b) treating said animal with radiotherapy or chemotherapy.

53. The method of claim 17, wherein said animal is a human patient.

54. The method of claim 17, wherein said animal is treated with radiotherapy.

55. The method of claim 17, wherein said animal is treated with chemotherapy.

56. The method of claim 17, wherein said first binding region is operatively linked to a human mutant Tissue Factor, human truncated Tissue Factor, human dimeric Tissue Factor or human polymeric Tissue Factor or to an antibody, or antigen binding region thereof, that binds to a human mutant Tissue Factor, human truncated Tissue Factor, human dimeric Tissue Factor or human polymeric Tissue Factor.

57. The method of claim 17, wherein said first binding region is operatively linked to a mutant Tissue Factor, or to an antibody, or antigen binding region thereof, that binds to a mutant Tissue Factor.

58. The method of claim 17, wherein said first binding region is operatively linked to a truncated Tissue Factor, or to an antibody, or antigen binding region thereof, that binds to a truncated Tissue Factor.

59. The method of claim 32, wherein said first binding region is operatively linked to Factor II/IIa, Factor VII/VIIa, Factor IX/IXa, Factor X/Xa, a vitamin K-dependent coagulation factor lacking the Gla modification, Russell's viper venom Factor X activator, thromboxane A$_2$, thromboxane A$_2$ synthase or α2-antiplasmin, or to an antibody, or antigen binding region thereof, that binds to Factor II/IIa, Factor VII/VIIa, Factor IX/IXa, Factor X/Xa, a vitamin K-dependent coagulation factor lacking the Gla modification, Russell's viper venom Factor X activator, thromboxane A$_2$, thromboxane A$_2$ synthase or α2-antiplasin.

60. The method of claim 32, wherein said first binding region binds to a VEGF/VPF receptor.

61. The method of claim 32, wherein said first binding region binds to E-selectin.

62. The method of claim 32, wherein said first binding region binds to FGF, TGFβ, a ligand that binds to a TIE, a tumor-associated fibronectin isoform, scatter factor, hepatocyte growth factor (HGF), platelet factor 4 (PF4), PDGF or TIMP.

63. A method for treating cancer, comprising administering to an animal with a vascularized tumor a therapeutically effective amount of:
  (a) at least one binding ligand that comprises a first binding region that binds to a surface-expressed, surface-accessible or surface-localized component of tumor stroma; wherein said first binding region comprises an antibody, or antigen binding region thereof, that binds to tenascin, a basement membrane component, an activated platelet or an inducible tumor stroma component; and wherein said first binding region is operatively linked to a coagulation factor or to an antibody, or antigen binding region thereof, that binds to a coagulation factor; and
  (b) treating said animal with radiotherapy or chemotherapy.

64. The method of claim 63, wherein said first binding region comprises an antibody, or antigen binding region thereof, that binds to tenascin.

65. The method of claim 63, wherein said first binding region comprises an antibody, or antigen binding region thereof, that binds to a basement membrane component.

66. The method of claim 63, wherein said first binding region comprises an antibody, or antigen binding region thereof, that binds to an activated platelet.

67. The method of claim 63, wherein said first binding region comprises an antibody, or antigen binding region thereof, that binds to an inducible tumor stroma component.

68. A method for treating cancer, comprising administering to an animal with a vascularized tumor a therapeutically effective amount of:
  (a) at least one binding ligand that comprises a first binding region that binds to a surface-expressed, surface-accessible or surface-localized component of tumor stroma; wherein said first binding region comprises an antibody, or antigen binding region thereof, that binds to a tumor stroma component inducible by thrombin; and wherein said first binding region is operatively linked to a coagulation factor or to an antibody, or antigen binding region thereof, that binds to a coagulation factor; and
  (b) treating said animal with radiotherapy or chemotherapy.

69. The method of claim 68, wherein said first binding region comprises an antibody, or antigen binding region thereof, that binds to RIBS.

* * * * *

UNITED STATES PATENT AND TRADEMARK OFFICE
CERTIFICATE OF CORRECTION

PATENT NO. : 7,691,380 B2
APPLICATION NO. : 10/375716
DATED : April 6, 2010
INVENTOR(S) : Philip E. Thorpe et al.

It is certified that error appears in the above-identified patent and that said Letters Patent is hereby corrected as shown below:

Title Page, Item [73], column 1, insert --The Scripps Research Institute, La Jolla, CA (US)--.

In claim 17, at column 143, lines 41, delete "intratuinoral" and insert --intratumoral-- therefor.

In claim 59, at column 146, lines 67, delete "α2-antiplasin" and insert --α2-antiplasmin-- therefor.

Signed and Sealed this

Eighth Day of June, 2010

David J. Kappos
*Director of the United States Patent and Trademark Office*

SEQUENCE LISTING

<160> NUMBER OF SEQ ID NOS: 38

<210> SEQ ID NO 1
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 1
gtcatgccat ggcctcaggc actacaa                                        27

<210> SEQ ID NO 2
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 2
tgacaagctt attctctgaa ttcccccttt ct                                  32

<210> SEQ ID NO 3
<211> LENGTH: 47
<212> TYPE: DNA
<213> ORGANISM: Artificial
<220> FEATURE:
<223> OTHER INFORMATION: Synthetic Oligonucleotide

<400> SEQUENCE: 3
gtcatgccat ggccctggtg cctcgtgctt ctggcactac aaatact                  47

<210> SEQ ID NO 4
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 4
gtcatgccat ggcctgctca ggcactacaa atactgtg                            38

<210> SEQ ID NO 5
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 5
gtcatgccat ggccctggtg cctcgtggtt cttgcggcac tacaaatact               50

<210> SEQ ID NO 6
<211> LENGTH: 35
<212> TYPE: DNA
<213> ORGANISM: Artificial

```
<220> FEATURE:
<223> OTHER INFORMATION: Synthetic Oligonucleotide

<400> SEQUENCE: 6
tgacaagctt agcattctct gaattccccc tttct                              35

<210> SEQ ID NO 7
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 7
gtcatgccat ggccctggtg cctcgtggtt gcggaggcgg tggatcaggc              50

<210> SEQ ID NO 8
<211> LENGTH: 36
<212> TYPE: DNA
<213> ORGANISM: Artificial
<220> FEATURE:
<223> OTHER INFORMATION: Synthetic Oligonucleotide

<400> SEQUENCE: 8
agtatttgta gtgcctgagg atccgccacc tccact                             36

<210> SEQ ID NO 9
<211> LENGTH: 45
<212> TYPE: DNA
<213> ORGANISM: Artificial
<220> FEATURE:
<223> OTHER INFORMATION: Synthetic Oligonucleotide

<400> SEQUENCE: 9
ggaggcggtg gatcaggcgg tggaggtagt ggaggtggcg gatcc                   45

<210> SEQ ID NO 10
<211> LENGTH: 17
<212> TYPE: DNA
<213> ORGANISM: Artificial
<220> FEATURE:
<223> OTHER INFORMATION: Synthetic Oligonucleotide

<400> SEQUENCE: 10
gtcatgccat ggccctg                                                  17

<210> SEQ ID NO 11
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 11
tgacaagctt attctctgaa ttccccctttt ct                                32

<210> SEQ ID NO 12
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 12
gtcatgccat ggccctggtg cctcgtggtt cttgcggcac tacaaatact              50
```

<210> SEQ ID NO 13
<211> LENGTH: 53
<212> TYPE: DNA
<213> ORGANISM: Artificial
<220> FEATURE:
<223> OTHER INFORMATION: Synthetic Oligonucleotide

<400> SEQUENCE: 13
cgcggatcca ccgccaccag atccaccgcc tccttctctg aattcccctt tct      53

<210> SEQ ID NO 14
<211> LENGTH: 44
<212> TYPE: DNA
<213> ORGANISM: Artificial
<220> FEATURE:
<223> OTHER INFORMATION: Synthetic Oligonucleotide

<400> SEQUENCE: 14
cgcggatccg gcggtggagg ctcttcaggc actacaaata ctgt                 44

<210> SEQ ID NO 15
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 15
tgacaagctt attctctgaa ttccccttc t                                31

<210> SEQ ID NO 16
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 16
gtcatgccat ggccctggtg cctcgtggtt cttgcggcac tacaaatact            50

<210> SEQ ID NO 17
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 17
tgacaagctt attctctgaa ttccccttc t                                31

<210> SEQ ID NO 18
<211> LENGTH: 44
<212> TYPE: DNA
<213> ORGANISM: Artificial
<220> FEATURE:
<223> OTHER INFORMATION: Synthetic Oligonucleotide

<400> SEQUENCE: 18
gtcatgccat ggccctggtg cctcgtggtt gcactacaaa tact                  44

<210> SEQ ID NO 19
<211> LENGTH: 34
<212> TYPE: DNA
<213> ORGANISM: Artificial
<220> FEATURE:
<223> OTHER INFORMATION: Synthetic Oligonucleotide

<400> SEQUENCE: 19
tgacaagctt agcattctct gaattcccct ttct                                    34

<210> SEQ ID NO 20
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 20
caagttcagc caagaaaac                                                     19

<210> SEQ ID NO 21
<211> LENGTH: 36
<212> TYPE: DNA
<213> ORGANISM: Artificial
<220> FEATURE:
<223> OTHER INFORMATION: Synthetic Oligonucleotide

<400> SEQUENCE: 21
acactttatt atcggaaatc ttcagcttca ggaaag                                  36

<210> SEQ ID NO 22
<211> LENGTH: 657
<212> TYPE: DNA
<213> ORGANISM: Homo sapiens

<400> SEQUENCE: 22
tcaggcacta caaatactgt ggcagcatat aatttaactt ggaaatcaac taatttcaag         60
acaattttgg agtgggaacc caaacccgtc aatcaagtct acactgttca ataagcact         120
aagtcaggag attggaaaag caaatgcttt tacacaacag acacagagtg tgacctcacc        180
gacgagattg tgaaggatgt gaagcagacg tacttggcac gggtcttctc ctacccggca        240
gggaatgtgg agagcaccgg ttctgctggg gagcctctgt atgagaactc cccagagttc        300
acaccttacc tggagacaaa cctcggacag ccaacaattc agagttttga acaggtggga        360
acaaaagtga atgtgaccgt agaagatgaa cggactttag tcagaaggaa caacactttc        420
ctaagcctcc gggatgtttt tggcaaggac ttaatttata cacttttatta ttggaaatct       480
tcaagttcag gaaagaaaac agccaaaaca acactaatg agttttgat tgatgtggat         540
aaaggagaaa actactgttt cagtgttcaa gcagtgattc cctcccgaac agttaaccgg        600
aagagtacag acagcccggt agagtgtatg ggccaggaga aggggaatt cagagaa            657

<210> SEQ ID NO 23
<211> LENGTH: 219
<212> TYPE: PRT
<213> ORGANISM: Homo sapiens

<400> SEQUENCE: 23

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

-continued

```
Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

```
<210> SEQ ID NO 24
<211> LENGTH: 1947
<212> TYPE: DNA
<213> ORGANISM: Homo sapiens

<400> SEQUENCE: 24
tgcagctgcc tggctgcctg gccctggctg ccctgtgtag ccttgtgcac agccagcatg    60
tgttcctggc tcctcagcaa gcacggtcgc tgctccagcg ggtccggcga gccaacacct   120
tcttggagga ggtgcgcaag ggcaacctag agcgagagtg cgtggaggag acgtgcagct   180
acgaggaggc cttcgaggct ctggagtcct ccacggctac ggatgtgttc tgggccaagt   240
acacagcttg tgagacagcg aggacgcctc gagataagct tgctgcatgt ctggaaggta   300
actgtgctga gggtctgggt acgaactacc gagggcatgt gaacatcacc cggtcaggca   360
ttgagtgcca gctatggagg agtcgctacc cacataagcc tgaaatcaac tccactaccc   420 atcctgggc cgacctacag gagaatttct gccgcaaccc cgacagcagc aacacgggac   480
cctggtgcta cactacagac cccaccgtga ggaggcagga atgcagcatc cctgtctgtg   540
gccaggatca agtcactgta gcgatgactc cacgctccga aggctccagt gtgaatctgt   600
cacctccatt ggagcagtgt gtccctgatc gggggcagca gtaccagggg cgcctggcgg   660
tgaccacaca tgggctcccc tgcctggcct gggcagcgc acaggccaag gccctgagca   720
agcaccagga cttcaactca gctgtgcagc tggtggagaa cttctgccgc aacccagacg   780
gggatgagga gggcgtgtgg tgctatgtgg ccgggaagcc tggcgacttt gggtactgcg   840
acctcaacta ttgtgaggag gccgtggagg aggagacagg agatgggctg gatgaggact   900
cagacagggc catcgaaggg cgtaccgcca agtgagta ccagactttc ttcaatccga   960
ggacctttgg ctcgggagag gcagactgtg gctgcgacc tctgttcgag aagaagtcgc   1020
tggaggacaa aaccgaaaga gagctcctgg aatcctacat cgacgggcgc attgtggagg  1080
gctcggatgc agagatcggc atgtcacctt ggcaggtgat gcttttccgg aagagtcccc  1140
aggagctgct gtgtgggcc agcctcatca gtgaccgctg gtcctcacc gccgcccact   1200 gcctcctgta cccgcccgtgg gacaagaact tcaccgagaa tgaccttctg gtgcgcattg  1260
```

| | | | | |
|---|---|---|---|---|
| gcaagcactc | ccgcaccagg | tacgagcgaa | acattgaaaa | gatatccatg ttggaaaaga | 1320 |
| tctacatcca | ccccaggtac | aactggcggg | agaacctgga | ccgggacatt gccctgatga | 1380 |
| agctgaagaa | gcctgttgcc | ttcagtgact | acattcaccc | tgtgtgtctg cccgacaggg | 1440 |
| agacggcagc | cagcttgctc | caggctggat | acaaggggcg | ggtgacaggc tggggcaacc | 1500 |
| tgaaggagag | gtggacagcc | aacgttggta | aggggcagcc | cagtgtcctg caggtggtga | 1560 |
| acctgcccat | tgtggagcgg | ccggtctgca | aggactccac | ccggatccgc atcactgaca | 1620 |
| acatgttctg | tgctggttac | aagcctgatg | aagggaaacg | aggggatgcc tgtgaaggtg | 1680 |
| acagtggggg | acccttgtc | atgaagagcc | cctttaacaa | ccgctggtat caaatgggca | 1740 |
| tcgtctcatg | gggtgaaggc | tgtgaccggg | atgggaaata | tggcttctac acacatgtgt | 1800 |
| tccgcctgaa | gaagtggata | cagaaggtca | ttgatcagtt | tggagagtag ggggccactc | 1860 |
| atattctggg | ctcctggaac | caatcccgtg | aaagaattat | ttttgtgttt ctaaaactat | 1920 |
| ggttcccaat | aaaagtgact | ctcagcg | | | 1947 |

<210> SEQ ID NO 25
<211> LENGTH: 2462
<212> TYPE: DNA
<213> ORGANISM: Homo sapiens

<400> SEQUENCE: 25

| | | | | |
|---|---|---|---|---|
| tcaacaggca | ggggcagcac | tgcagagatt | tcatcatggt | ctcccaggcc ctcaggctcc | 60 |
| tctgccttct | gcttgggctt | cagggctgcc | tggctgcagg | cggggtcgct aaggcctcag | 120 |
| gaggagaaac | acgggacatg | ccgtggaagc | cggggcctca | cagagtcttc gtaacccagg | 180 |
| aggaagccca | cggcgtcctg | caccggcgcc | ggcgcgccaa | cgcgttcctg gaggagctgc | 240 |
| ggccgggctc | cctggagagg | gagtgcaagg | aggagcagtg | ctccttcgag gaggcccggg | 300 |
| agatcttcaa | ggacgcggag | aggacgaagc | tgttctggat | tcttacagt gatggggacc | 360 |
| agtgtgcctc | aagtccatgc | cagaatgggg | gctcctgcaa | ggaccagctc cagtcctata | 420 |
| tctgcttctg | cctccctgcc | ttcgagggcc | ggaactgtga | gacgcacaag gatgaccagc | 480 |
| tgatctgtgt | gaacgagaac | ggcggctgtg | agcagtactg | cagtgaccac acgggcacca | 540 |
| agcgctcctg | tcggtgccac | gagggggtact | ctctgctggc | agacggggtg tcctgcacac | 600 |
| ccacagttga | atatccatgt | ggaaaaatac | ctattctaga | aaaagaaat gccagcaaac | 660 |
| cccaaggccg | aattgtgggg | ggcaaggtgt | gccccaaagg | ggagtgtcca tggcaggtcc | 720 |
| tgttgttggt | gaatggagct | cagttgtgtg | ggggaccct | gatcaacacc atctgggtgg | 780 |
| tctccgcggc | ccactgttc | gacaaaatca | agaactggag | gaacctgatc gcggtgctgg | 840 |
| gcgagcacga | cctcagcgag | cacgacgggg | atgagcagag | ccggcgggtg gcgcaggtca | 900 |
| tcatccccag | cacgtacgtc | ccgggcacca | ccaaccacga | tatcgcgctg ctccgcctgc | 960 |
| accagcccgt | ggtcctcact | gaccatgtgg | tgcccctctg | cctgcccgaa cggacgttct | 1020 |
| ctgagaggac | gctggccttc | gtgcgcttct | cattggtcag | cggctggggc cagctgctgg | 1080 |
| accgtggcgc | cacggccctg | gagctcatgg | tgctcaacgt | gccccggctg atgacccagg | 1140 |
| actgcctgca | gcagtcacgg | aaggtgggag | actccccaaa | tatcacggag tacatgttct | 1200 |
| gtgccggcta | ctcggatggc | agcaaggact | cctgcaaggg | ggacagtgga ggcccacatg | 1260 |
| ccacccacta | ccggggcacg | tggtacctga | cgggcatcgt | cagctggggc cagggctgcg | 1320 |
| caaccgtggg | ccactttggg | gtgtacacca | gggtctccca | gtacatcgag tggctgcaaa | 1380 |

```
agctcatgcg ctcagagcca cgcccaggag tcctcctgcg agcccatttt ccctagccca      1440
gcagccctgg cctgtggaga gaaagccaag gctgcgtcga actgtcctgg caccaaatcc      1500
catatattct tctgcagtta atggggtaga ggagggcatg ggaggagggg agaggtgggg      1560
agggagacag agacagaaac agagagagac agagacagag agagactgag ggagagactc      1620
tgaggacatg gagagagact caaagagact ccaagattca aagagactaa tagagacaca      1680
gagatggaat agaaaagatg agaggcagag gcagacaggc gctggacaga ggggcagggg      1740
agtgccaagg ttgtcctgga ggcagacagc ccagctgagc ctccttacct cccttcagcc      1800
aagccccacc tgcacgtgat ctgctggccc tcaggctgct gctctgcctt cattgctgga      1860
gacagtagag gcatgaacac acatggatgc acacacacac acgccaatgc acacacacag      1920
agatatgcac acacacggat gcacacacag atggtcacac agagatacgc aaacacaccg      1980
atgcacacgc acatagagat atgcacacac agatgcacac acagatatac acatggatgc      2040
acgcacatgc caatgcacgc acacatcagt gcacacggat gcacagagat atgcacacac      2100
cgatgtgcgc acacacagat atgcacacac atggatgagc acacacacac caagtgcgca      2160
cacacaccga tgtacacaca cagatgcaca cacagatgca cacacaccga tgctgactcc      2220
atgtgtgctg tcctctgaag gcggttgttt agctctcact tttctggttc ttatccatta      2280
tcatcttcac ttcagacaat tcagaagcat caccatgcat ggtggcgaat gcccccaaac      2340
tctcccccaa atgtatttct cccttcgctg ggtgccgggc tgcacagact attccccacc      2400
tgcttcccag cttcacaata aacggctgcg tctcctccgc acacctgtgg tgcctgccac      2460
cc                                                                    2462

<210> SEQ ID NO 26
<211> LENGTH: 1437
<212> TYPE: DNA
<213> ORGANISM: Homo sapiens

<400> SEQUENCE: 26
atgcagcgcg tgaacatgat catggcagaa tcaccaagcc tcatcaccat ctgcctttta       60
ggatatctac tcagtgctga atgtacagtt tttcttgatc atgaaaacgc caacaaaatt      120
ctgaatcggc caaagaggta taattcaggt aaattggaag agtttgttca agggaacctt      180
gagagagaat gtatggaaga aaagtgtagt tttgaagaac cacgagaagt ttttgaaaac      240
actgaaaaga caactgaatt ttggaagcag tatgttgatg gagatcagtg tgagtccaat      300
ccatgtttaa atggcggcag ttgcaaggat gacattaatt cctatgaatg ttggtgtccc      360
tttggatttg aaggaaagaa ctgtgaatta gatgtaacat gtaacattaa gaatggcaga      420
tgcgagcagt tttgtaaaaa tagtgctgat aacaaggtgg tttgctcctg tactgaggga      480
tatcgacttg cagaaaacca gaagtcctgt gaaccagcag tgccatttcc atgtggaaga      540
gtttctgttt cacaaacttc taagctcacc cgtgctgagg ctgttttttcc tgatgtggac      600 tatgtaaatc ctactgaagc tgaaaccatt ttggataaca tcactcaagg cacccaatca      660
tttaatgact tcactcgggt tgttggtgga gaagatgcca aaccaggtca attcccttgg      720
caggttgttt tgaatggtaa agttgatgca ttctgtggag gctctatcgt taatgaaaaa      780
tggattgtaa ctgctgccca ctgtgttgaa actggtgtta aaattacagt tgtcgcaggt      840
gaacataata ttgaggagac agaacataca gagcaaaagc gaaatgtgat tcgagcaatt      900
attcctcacc acaactacaa tgcagctatt aataagtaca accatgacat tgcccttctg      960
gaactggacg aacccttagt gctaaacagc tacgttacac ctatttgcat tgctgacaag     1020
```

```
gaatacacga acatcttcct caaatttgga tctggctatg taagtggctg ggcaagagtc      1080
ttccacaaag ggagatcagc tttagttctt cagtaccttα gagttccact tgttgaccga      1140
gccacatgtc ttcgatctac aaagttcacc atctataaca acatgttctg tgctggcttc      1200
catgaaggag gtagagattc atgtcaagga gatagtgggg acccccatgt tactgaagtg      1260
gaagggacca gtttcttaac tggaattatt agctggggtg aagagtgtgc aatgaaaggc      1320
aaatatggaa tatataccaa ggtatcccgg tatgtcaact ggattaagga aaaaacaaag      1380
ctcacttaat gaaagatgga tttccaaggt taattcattg gaattgaaaa ttaacag        1437

<210> SEQ ID NO 27
<211> LENGTH: 1126
<212> TYPE: DNA
<213> ORGANISM: Homo sapiens

<400> SEQUENCE: 27
ggattcgaag gcaaaaactg tgaattattc acacggaagc tctgcagcct ggacaacggg       60
gactgtgacc agttctgcca cgaggaacag aactctgtgg tgtgctcctg cgcccgcggg      120
tacaccctgg ctgacaacgg caaggcctgc attcccacag ggccctaccc ctgtgggaaa      180
cagaccctgg aacgcaggaa gaggtcagtg gcccaggcca ccagcagcag cggggaggcc      240
cctgacagca tcacatggaa gccatatgat gcagccgacc tggaccccac cgagaacccc      300
ttcgacctgc ttgacttcaa ccagacgcag cctgagaggg gcgacaacaa cctcaccagg      360
atcgtgggag gccaggaatg caaggacggg gagtgtccct ggcaggccct gctcatcaat      420
gaggaaaacg agggtttctg tggtggaacc attctgagcg agttctacat cctaacggca      480
gcccactgtc tctaccaagc caagagattc gaagggacc ggaacacgga gcaggaggag      540
ggcggtgagg cggtgcacga ggtggaggtg gtcatcaagc acaaccggtt cacaaaggag      600
acctatgact tcgacatcgc cgtgctccgg ctcaagaccc ccatcacctt ccgcatgaac      660
gtggcgcctg cctgcctccc cgagcgtgac tgggccgagt ccacgctgat gacgcagaag      720
acggggattg tgagcggctt cgggcgcacc cacgagaagg gccggcagtc caccaggctc      780
aagatgctgg aggtgcccta cgtggaccgc aacagctgca gctgtccag cagcttcatc      840 atcacccaga acatgttctg tgccggctac gacaccaagc aggaggatgc ctgccagggg      900
gacagcgggg gcccgcacgt cacccgcttc aaggacacct acttcgtgac aggcatcgtc      960
agctggggag agggctgtgc ccgtaagggg aagtacggga tctacaccaa ggtcaccgcc     1020
ttcctcaagt ggatcgacag gtccatgaaa accagggget tgcccaaggc caagagccat     1080
gccccggagg tcataacgtc ctctccatta aagtgagatc ccactc                    1126

<210> SEQ ID NO 28
<211> LENGTH: 45
<212> TYPE: DNA
<213> ORGANISM: Artificial
<220> FEATURE:
<223> OTHER INFORMATION: Synthetic Oligonucleotide

<400> SEQUENCE: 28
gaagaaggga tcctggtgcc tcgtggttct ggcactacaa atact                       45

<210> SEQ ID NO 29
<211> LENGTH: 30
<212> TYPE: DNA
<213> ORGANISM: Artificial
<220> FEATURE:
```

<223> OTHER INFORMATION: Synthetic Oligonucleotide

<400> SEQUENCE: 29
ctggcctcaa gcttaacgga attcaccttt                                      30

<210> SEQ ID NO 30
<211> LENGTH: 25
<212> TYPE: PRT
<213> ORGANISM: Cavia porcellus

<400> SEQUENCE: 30

Ala Pro Met Ala Glu Gly Glu Gln Lys Pro Arg Glu Val Val Lys Phe
1               5                   10                  15

Met Asp Val Tyr Lys Arg Ser Tyr Cys
            20                  25

<210> SEQ ID NO 31
<211> LENGTH: 26
<212> TYPE: PRT
<213> ORGANISM: Homo sapiens

<400> SEQUENCE: 31

Ala Pro Met Ala Glu Gly Gly Gly Gln Asn His His Glu Val Val Lys
1               5                   10                  15

Phe Met Asp Val Tyr Gln Arg Ser Tyr Cys
            20                  25

<210> SEQ ID NO 32
<211> LENGTH: 25
<212> TYPE: PRT
<213> ORGANISM: Cavia porcellus

<400> SEQUENCE: 32

Met Ala Ala Gly Ser Ile Thr Thr Leu Pro Ala Leu Pro Glu Gly Gly
1               5                   10                  15

Asp Gly Gly Ala Phe Ala Pro Gly Cys
            20                  25

<210> SEQ ID NO 33
<211> LENGTH: 6
<212> TYPE: PRT
<213> ORGANISM: Artificial
<220> FEATURE:
<223> OTHER INFORMATION: Synthetic Peptide

<400> SEQUENCE: 33

His His His His His His
1               5

<210> SEQ ID NO 34
<211> LENGTH: 229
<212> TYPE: PRT
<213> ORGANISM: Artificial
<220> FEATURE:
<223> OTHER INFORMATION: Synthetic Peptide

<400> SEQUENCE: 34

His His His His His His Ala Met Ala Cys Ser Gly Thr Thr Asn Thr
1               5                   10                  15

Val Ala Ala Tyr Asn Leu Thr Trp Lys Ser Thr Asn Phe Lys Thr Ile
            20                  25                  30

Leu Glu Trp Glu Pro Lys Pro Val Asn Gln Val Tyr Thr Val Gln Ile
        35                  40                  45

```
Ser Thr Lys Ser Gly Asp Trp Lys Ser Lys Cys Phe Tyr Thr Thr Asp
    50                  55                  60

Thr Glu Cys Asp Leu Thr Asp Glu Ile Val Lys Asp Val Lys Gln Thr
65                  70                  75                  80

Tyr Leu Ala Arg Val Phe Ser Tyr Pro Ala Gly Asn Val Glu Ser Thr
                85                  90                  95

Gly Ser Ala Gly Glu Pro Leu Tyr Glu Asn Ser Pro Glu Phe Thr Pro
            100                 105                 110

Tyr Leu Glu Thr Asn Leu Gly Gln Pro Thr Ile Gln Ser Phe Glu Gln
            115                 120                 125

Val Gly Thr Lys Val Asn Val Thr Val Glu Asp Glu Arg Thr Leu Val
    130                 135                 140

Arg Arg Asn Asn Thr Phe Leu Ser Leu Arg Asp Val Phe Gly Lys Asp
145                 150                 155                 160

Leu Ile Tyr Thr Leu Tyr Tyr Trp Lys Ser Ser Ser Gly Lys Lys
                165                 170                 175

Thr Ala Lys Thr Asn Thr Asn Glu Phe Leu Ile Asp Val Asp Lys Gly
            180                 185                 190

Glu Asn Tyr Cys Phe Ser Val Gln Ala Val Ile Pro Ser Arg Thr Val
            195                 200                 205

Asn Arg Lys Ser Thr Asp Ser Pro Val Glu Cys Met Gly Gln Glu Lys
    210                 215                 220

Gly Glu Phe Arg Glu
225
```

<210> SEQ ID NO 35
<211> LENGTH: 237
<212> TYPE: PRT
<213> ORGANISM: Artificial
<220> FEATURE:
<223> OTHER INFORMATION: Synthetic Peptide

<400> SEQUENCE: 35

```
Gly Ser Cys Gly Gly Gly Ser Gly Gly Gly Ser Gly Gly Gly
1               5                   10                  15

Gly Ser Ser Gly Thr Thr Asn Thr Val Ala Ala Tyr Asn Leu Thr Trp
            20                  25                  30

Lys Ser Thr Asn Phe Lys Thr Ile Leu Glu Trp Glu Pro Lys Pro Val
            35                  40                  45

Asn Gln Val Tyr Thr Val Gln Ile Ser Thr Lys Ser Gly Asp Trp Lys
    50                  55                  60

Ser Lys Cys Phe Tyr Thr Thr Asp Thr Glu Cys Asp Leu Thr Asp Glu
65                  70                  75                  80

Ile Val Lys Asp Val Lys Gln Thr Tyr Leu Ala Arg Val Phe Ser Tyr
                85                  90                  95

Pro Ala Gly Asn Val Glu Ser Thr Gly Ser Ala Gly Glu Pro Leu Tyr
            100                 105                 110

Glu Asn Ser Pro Glu Phe Thr Pro Tyr Leu Glu Thr Asn Leu Gly Gln
            115                 120                 125

Pro Thr Ile Gln Ser Phe Glu Gln Val Gly Thr Lys Val Asn Val Thr
    130                 135                 140

Val Glu Asp Glu Arg Thr Leu Val Arg Arg Asn Asn Thr Phe Leu Ser
145                 150                 155                 160

Leu Arg Asp Val Phe Gly Lys Asp Leu Ile Tyr Thr Leu Tyr Tyr Trp
                165                 170                 175
```

```
Lys Ser Ser Ser Ser Gly Lys Lys Thr Ala Lys Thr Asn Thr Asn Glu
            180                 185                 190

Phe Leu Ile Asp Val Asp Lys Gly Glu Asn Tyr Cys Phe Ser Val Gln
            195                 200                 205

Ala Val Ile Pro Ser Arg Thr Val Asn Arg Lys Ser Thr Asp Ser Pro
            210                 215                 220

Val Glu Cys Met Gly Gln Glu Lys Gly Glu Phe Arg Glu
225                 230                 235
```

<210> SEQ ID NO 36
<211> LENGTH: 454
<212> TYPE: PRT
<213> ORGANISM: Artificial
<220> FEATURE:
<223> OTHER INFORMATION: Synthetic Peptide

<400> SEQUENCE: 36

```
Gly Ser Gly Thr Thr Asn Thr Val Ala Ala Tyr Asn Leu Thr Trp Lys
1               5                   10                  15

Ser Thr Asn Phe Lys Thr Ile Leu Glu Trp Glu Pro Lys Pro Val Asn
            20                  25                  30

Gln Val Tyr Thr Val Gln Ile Ser Thr Lys Ser Gly Asp Trp Lys Ser
            35                  40                  45

Lys Cys Phe Tyr Thr Thr Asp Thr Glu Cys Asp Leu Thr Asp Glu Ile
    50                  55                  60

Val Lys Asp Val Lys Gln Thr Tyr Leu Ala Arg Val Phe Ser Tyr Pro
65                  70                  75                  80

Ala Gly Asn Val Glu Ser Thr Gly Ser Ala Gly Glu Pro Leu Tyr Glu
                85                  90                  95

Asn Ser Pro Glu Phe Thr Pro Tyr Leu Glu Thr Asn Leu Gly Gln Pro
            100                 105                 110

Thr Ile Gln Ser Phe Glu Gln Val Gly Thr Lys Val Asn Val Thr Val
            115                 120                 125

Glu Asp Glu Arg Thr Leu Val Arg Arg Asn Asn Thr Phe Leu Ser Leu
130                 135                 140

Arg Asp Val Phe Gly Lys Asp Leu Ile Tyr Thr Leu Tyr Tyr Trp Lys
145                 150                 155                 160

Ser Ser Ser Ser Gly Lys Lys Thr Ala Lys Thr Asn Thr Asn Glu Phe
                165                 170                 175

Leu Ile Asp Val Asp Lys Gly Glu Asn Tyr Cys Phe Ser Val Gln Ala
            180                 185                 190

Val Ile Pro Ser Arg Thr Val Asn Arg Lys Ser Thr Asp Ser Pro Val
            195                 200                 205

Glu Cys Met Gly Gln Glu Lys Gly Glu Phe Arg Glu Gly Gly Gly Gly
    210                 215                 220

Ser Gly Gly Gly Gly Ser Gly Gly Gly Gly Ser Ser Gly Thr Thr Asn
225                 230                 235                 240

Thr Val Ala Ala Tyr Asn Leu Thr Trp Lys Ser Thr Asn Phe Lys Thr
                245                 250                 255

Ile Leu Glu Trp Glu Pro Lys Pro Val Asn Gln Val Tyr Thr Val Gln
            260                 265                 270

Ile Ser Thr Lys Ser Gly Asp Trp Lys Ser Lys Cys Phe Tyr Thr Thr
            275                 280                 285

Asp Thr Glu Cys Asp Leu Thr Asp Glu Ile Val Lys Asp Val Lys Gln
290                 295                 300
```

```
Thr Tyr Leu Ala Arg Val Phe Ser Tyr Pro Ala Gly Asn Val Glu Ser
305                 310                 315                 320

Thr Gly Ser Ala Gly Glu Pro Leu Tyr Glu Asn Ser Pro Glu Phe Thr
            325                 330                 335

Pro Tyr Leu Glu Thr Asn Leu Gly Gln Pro Thr Ile Gln Ser Phe Glu
            340                 345                 350

Gln Val Gly Thr Lys Val Asn Val Thr Val Glu Asp Glu Arg Thr Leu
            355                 360                 365

Val Arg Arg Asn Asn Thr Phe Leu Ser Leu Arg Asp Val Phe Gly Lys
            370                 375                 380

Asp Leu Ile Tyr Thr Leu Tyr Tyr Trp Lys Ser Ser Ser Gly Lys
385                 390                 395                 400

Lys Thr Ala Lys Thr Asn Thr Asn Glu Phe Leu Ile Asp Val Asp Lys
            405                 410                 415

Gly Glu Asn Tyr Cys Phe Ser Val Gln Ala Val Ile Pro Ser Arg Thr
            420                 425                 430

Val Asn Arg Lys Ser Thr Asp Ser Pro Val Glu Cys Met Gly Gln Glu
            435                 440                 445

Lys Gly Glu Phe Arg Glu
            450

<210> SEQ ID NO 37
<211> LENGTH: 455
<212> TYPE: PRT
<213> ORGANISM: Artificial
<220> FEATURE:
<223> OTHER INFORMATION: Synthetic Peptide

<400> SEQUENCE: 37

Ser Gly Cys Gly Thr Thr Asn Thr Val Ala Ala Tyr Asn Leu Thr Trp
1               5                   10                  15

Lys Ser Thr Asn Phe Lys Thr Ile Leu Glu Trp Glu Pro Lys Pro Val
            20                  25                  30

Asn Gln Val Tyr Thr Val Gln Ile Ser Thr Lys Ser Gly Asp Trp Lys
        35                  40                  45

Ser Lys Cys Phe Tyr Thr Thr Asp Thr Glu Cys Asp Leu Thr Asp Glu
    50                  55                  60

Ile Val Lys Asp Val Lys Gln Thr Tyr Leu Ala Arg Val Phe Ser Tyr
65                  70                  75                  80

Pro Ala Gly Asn Val Glu Ser Thr Gly Ser Ala Gly Glu Pro Leu Tyr
                85                  90                  95

Glu Asn Ser Pro Glu Phe Thr Pro Tyr Leu Glu Thr Asn Leu Gly Gln
            100                 105                 110

Pro Thr Ile Gln Ser Phe Glu Gln Val Gly Thr Lys Val Asn Val Thr
        115                 120                 125

Val Glu Asp Glu Arg Thr Leu Val Arg Arg Asn Asn Thr Phe Leu Ser
130                 135                 140

Leu Arg Asp Val Phe Gly Lys Asp Leu Ile Tyr Thr Leu Tyr Tyr Trp
145                 150                 155                 160

Lys Ser Ser Ser Gly Lys Lys Thr Ala Lys Thr Asn Thr Asn Glu
                165                 170                 175

Phe Leu Ile Asp Val Asp Lys Gly Glu Asn Tyr Cys Phe Ser Val Gln
            180                 185                 190

Ala Val Ile Pro Ser Arg Thr Val Asn Arg Lys Ser Thr Asp Ser Pro
        195                 200                 205
```

Val Glu Cys Met Gly Gln Glu Lys Gly Glu Phe Arg Glu Gly Gly Gly
210                 215                 220

Gly Ser Gly Gly Gly Ser Gly Gly Gly Ser Ser Gly Thr Thr
225                 230                 235                 240

Asn Thr Val Ala Ala Tyr Asn Leu Thr Trp Lys Ser Thr Asn Phe Lys
            245                 250                 255

Thr Ile Leu Glu Trp Glu Pro Lys Pro Val Asn Gln Val Tyr Thr Val
                260                 265                 270

Gln Ile Ser Thr Lys Ser Gly Asp Trp Lys Ser Lys Cys Phe Tyr Thr
        275                 280                 285

Thr Asp Thr Glu Cys Asp Leu Thr Asp Glu Ile Val Lys Asp Val Lys
    290                 295                 300

Gln Thr Tyr Leu Ala Arg Val Phe Ser Tyr Pro Ala Gly Asn Val Glu
305                 310                 315                 320

Ser Thr Gly Ser Ala Gly Glu Pro Leu Tyr Glu Asn Ser Pro Glu Phe
                325                 330                 335

Thr Pro Tyr Leu Glu Thr Asn Leu Gly Gln Pro Thr Ile Gln Ser Phe
            340                 345                 350

Glu Gln Val Gly Thr Lys Val Asn Val Thr Val Glu Asp Glu Arg Thr
        355                 360                 365

Leu Val Arg Arg Asn Asn Thr Phe Leu Ser Leu Arg Asp Val Phe Gly
    370                 375                 380

Lys Asp Leu Ile Tyr Thr Leu Tyr Tyr Trp Lys Ser Ser Ser Ser Gly
385                 390                 395                 400

Lys Lys Thr Ala Lys Thr Asn Thr Asn Glu Phe Leu Ile Asp Val Asp
                405                 410                 415

Lys Gly Glu Asn Tyr Cys Phe Ser Val Gln Ala Val Ile Pro Ser Arg
            420                 425                 430

Thr Val Asn Arg Lys Ser Thr Asp Ser Pro Val Glu Cys Met Gly Gln
        435                 440                 445

Glu Lys Gly Glu Phe Arg Glu
    450                 455

<210> SEQ ID NO 38
<211> LENGTH: 454
<212> TYPE: PRT
<213> ORGANISM: Artificial
<220> FEATURE:
<223> OTHER INFORMATION: Synthetic Peptide

<400> SEQUENCE: 38

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

-continued

```
Ile Gln Ser Phe Glu Gln Val Gly Thr Lys Val Asn Val Thr Val Glu
        115                 120                 125
Asp Glu Arg Thr Leu Val Arg Arg Asn Asn Thr Phe Leu Ser Leu Arg
        130                 135                 140
Asp Val Phe Gly Lys Asp Leu Ile Tyr Thr Leu Tyr Tyr Trp Lys Ser
145                 150                 155                 160
Ser Ser Ser Gly Lys Lys Thr Ala Lys Thr Asn Thr Asn Glu Phe Leu
                165                 170                 175
Ile Asp Val Asp Lys Gly Glu Asn Tyr Cys Phe Ser Val Gln Ala Val
                180                 185                 190
Ile Pro Ser Arg Thr Val Asn Arg Lys Ser Thr Asp Ser Pro Val Glu
                195                 200                 205
Cys Met Gly Gln Glu Lys Gly Glu Phe Arg Glu Gly Gly Gly Gly Ser
        210                 215                 220
Gly Gly Gly Gly Ser Gly Gly Gly Ser Ser Gly Thr Thr Asn Thr
225                 230                 235                 240
Val Ala Ala Tyr Asn Leu Thr Trp Lys Ser Thr Asn Phe Lys Thr Ile
                245                 250                 255
Leu Glu Trp Glu Pro Lys Pro Val Asn Gln Val Tyr Thr Val Gln Ile
                260                 265                 270
Ser Thr Lys Ser Gly Asp Trp Lys Ser Lys Cys Phe Tyr Thr Thr Asp
                275                 280                 285
Thr Glu Cys Asp Leu Thr Asp Glu Ile Val Lys Asp Val Lys Gln Thr
        290                 295                 300
Tyr Leu Ala Arg Val Phe Ser Tyr Pro Ala Gly Asn Val Glu Ser Thr
305                 310                 315                 320
Gly Ser Ala Gly Glu Pro Leu Tyr Glu Asn Ser Pro Glu Phe Thr Pro
                325                 330                 335
Tyr Leu Glu Thr Asn Leu Gly Gln Pro Thr Ile Gln Ser Phe Glu Gln
                340                 345                 350
Val Gly Thr Lys Val Asn Val Thr Val Glu Asp Glu Arg Thr Leu Val
                355                 360                 365
Arg Arg Asn Asn Thr Phe Leu Ser Leu Arg Asp Val Phe Gly Lys Asp
        370                 375                 380
Leu Ile Tyr Thr Leu Tyr Tyr Trp Lys Ser Ser Ser Ser Gly Lys Lys
385                 390                 395                 400
Thr Ala Lys Thr Asn Thr Asn Glu Phe Leu Ile Asp Val Asp Lys Gly
                405                 410                 415
Glu Asn Tyr Cys Phe Ser Val Gln Ala Val Ile Pro Ser Arg Thr Val
                420                 425                 430
Asn Arg Lys Ser Thr Asp Ser Pro Val Glu Cys Met Gly Gln Glu Lys
        435                 440                 445
Gly Glu Phe Arg Glu Cys
        450
```